US010155716B2

(12) United States Patent
Chambournier et al.

(10) Patent No.: US 10,155,716 B2
(45) Date of Patent: Dec. 18, 2018

(54) AMINE SALTS OF A PROSTACYCLIN ANALOG

(71) Applicant: CAYMAN CHEMICAL COMPANY INCORPORATED, Ann Arbor, MI (US)

(72) Inventors: Gilles Chambournier, Ann Arbor, MI (US); Gregory William Endres, Saline, MI (US); Kirk William Hering, Canton, MI (US); Victor Fedij, Ypsilanti, MI (US); Hussein Mahmoud Mahmoud, Ann Arbor, MI (US)

(73) Assignee: Cayman Chemical Company Incorporated, Ann Arbor, MI (US)

( * ) Notice: Subject to any disclaimer, the term of this patent is extended or adjusted under 35 U.S.C. 154(b) by 0 days.

(21) Appl. No.: 15/852,922

(22) Filed: Dec. 22, 2017

(65) Prior Publication Data

US 2018/0118656 A1 May 3, 2018

Related U.S. Application Data

(62) Division of application No. 15/036,219, filed as application No. PCT/US2014/064519 on Nov. 7, 2014, now Pat. No. 9,890,104.

(60) Provisional application No. 61/903,730, filed on Nov. 13, 2013.

(51) Int. Cl.
| | |
|---|---|
| C07C 29/09 | (2006.01) |
| C07C 59/72 | (2006.01) |
| C07F 7/18 | (2006.01) |
| C07C 41/26 | (2006.01) |
| C07C 51/09 | (2006.01) |
| C07C 51/347 | (2006.01) |
| C07C 51/41 | (2006.01) |
| C07C 45/29 | (2006.01) |
| C07C 51/00 | (2006.01) |

(52) U.S. Cl.
CPC .............. *C07C 59/72* (2013.01); *C07C 29/09* (2013.01); *C07C 41/26* (2013.01); *C07C 45/298* (2013.01); *C07C 51/00* (2013.01); *C07C 51/09* (2013.01); *C07C 51/347* (2013.01); *C07C 51/412* (2013.01); *C07F 7/1804* (2013.01); *C07F 7/1836* (2013.01); *C07F 7/1844* (2013.01); *C07C 2603/14* (2017.05)

(58) Field of Classification Search
None
See application file for complete search history.

(56) References Cited

U.S. PATENT DOCUMENTS

| 6,441,245 B1 | 8/2002 | Moriarty et al. |
| 2002/0087025 A1 | 7/2002 | Moriarty et al. |
| 2009/0163738 A1 | 6/2009 | Batra et al. |

FOREIGN PATENT DOCUMENTS

CN 106038570 A 10/2016

OTHER PUBLICATIONS

Moriarty et al. "The Intramolecular Asymmetric Pauson-Khand Cyclization as a Novel and General Stereoselective Route to Benzindene Prostacyclins: Synthesis of UT-15 (Treprostinil)", J. Org. Chem., 69:1890-1902, 2004.
PCT International Search Report, PCT/US2014/064519, dated Feb. 17, 2015 (4 pages).
Chinese Search Report, CN 2014800623284, dated May 12, 2017 (2 pages).

*Primary Examiner* — Sudhakar Katakam
*Assistant Examiner* — Jennifer C Sawyer
(74) *Attorney, Agent, or Firm* — Honigman Miller Schwartz and Cohn LLP; Fernando Alberdi; Jonathan P. O'Brien

(57) ABSTRACT

The present invention provides amine salts of the prostacyclin analogue of Formula I

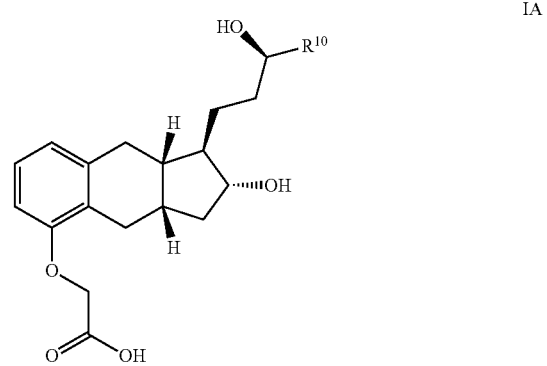

and processes for generating these amine salts.

99 Claims, No Drawings

AMINE SALTS OF A PROSTACYCLIN ANALOG

CROSS-REFERENCE TO RELATED APPLICATIONS

This application is a divisional of U.S. application Ser. No. 15/036,219, filed May 12, 2016, which is a 35 U.S.C. § 371(c) United States National Phase filing of International Application Serial No. PCT/US2014/064519, filed Nov. 7, 2014, which claims the benefit of priority to U.S. Provisional Application Ser. No. 61/903,730, filed Nov. 13, 2013, the disclosures of which are incorporated herein by reference in their entirety.

TECHNICAL FIELD OF THE INVENTION

The present invention relates to novel amine salts of a prostacyclin analog that are useful for treating hypertension and other diseases. Furthermore, this invention relates to methods of synthesizing such salts.

BACKGROUND

Prostacyclin derivatives and analogs are useful pharmaceutical compounds possessing activities such as platelet aggregation inhibition, gastric secretion reduction, lesion inhibition, vasodilation, and bronchodilation.

Treprostinil is a synthetic prostacyclin derivative currently marketed as an active pharmaceutical ingredient (API) for its ability to inhibit pulmonary arterial hypertension under the trade name Remodulin®. Treprostinil was first described in U.S. Pat. No. 4,306,075.

Prostacyclin derivatives are traditionally synthesized using a variety of methods that are described in *J. Org. Chem.* 2004, 69, 1890-1902, Drug of the Future, 2001, 26(4), 364-374, U.S. Pat. Nos. 4,306,075; 6,441,245; 6,528,688; 6,700,025; 6,765,117; 6,809,223 and U.S. patent application publication nos. 2009/0163738, 2011/0319641 A1, as well as Canadian patent application publication no. 2710726 A1. The entire teachings of these documents are incorporated herein by reference in their entireties. Also disclosed in these publications are processes and intermediates useful for the preparation of Treprostinil. However, the methods of these teachings suffer from one or more problems including toxic oxidation reagents, reduced yields, elevated levels of impurities, poor scalability, and numerous chromatography steps to purify intermediates and final products. Thus, there remains a need for safe, scalable, efficient, and economical processes for the preparation of Treprostinil.

SUMMARY OF THE INVENTION

As described herein, the present invention provides novel amine salts of the compound of Formula IA

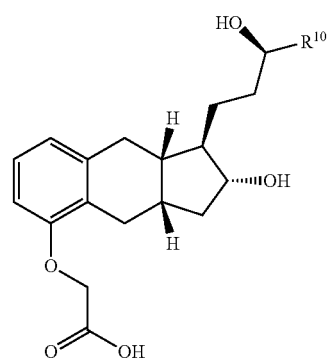

IA wherein $R^{10}$ is a linear or branched $C_{1-6}$ alkyl.

For example, the present invention provides an N-methyldiethanolamine salt of the compound of Formula IA

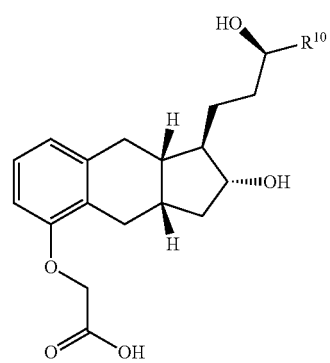

IA wherein $R^{10}$ is a linear or branched $C_{1-6}$ alkyl.

In another example, the compound of Formula IA is a compound of Formula I

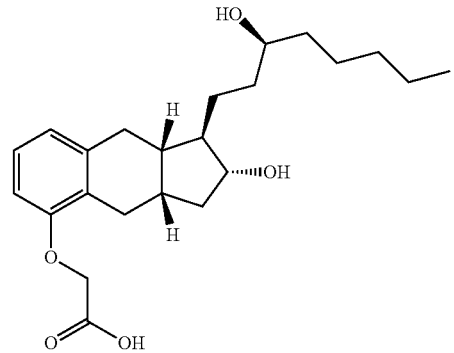

I

The present invention also provides processes for preparing an N-methyldiethanolamine salt of the prostacyclin analogue of Formula IA:

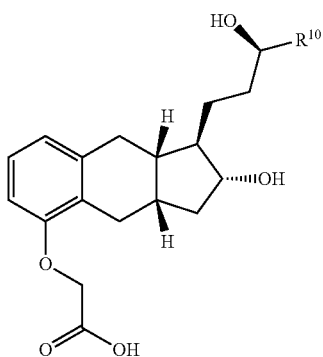

wherein $R^{10}$ is a linear or branched $C_{1-6}$ alkyl.

The processes of the present invention comprise steps that generate improved yields and fewer byproducts than traditional methods. The processes of the present invention employ reagents (e.g., the oxidizing reagent) that are less toxic than those used in the traditional methods (e.g., oxalyl chloride). Many of the processes of the present invention do not require additional chromatography for purification of intermediates and generate intermediates with improved e.e. and chemical purity. And, the processes of the present invention are scalable to generate commercial quantities of the final compound.

One aspect of the present invention provides a method of generating an N-methyldiethanolamine salt of the compound of Formula I

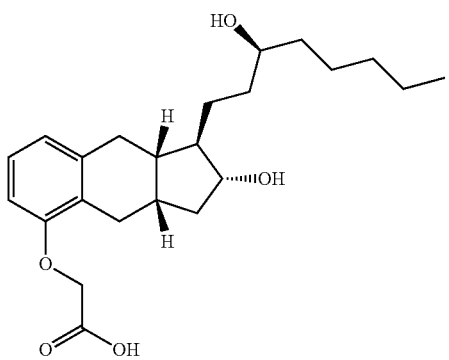

comprising the steps of: i) reacting a compound of Formula 9 with an oxidizing agent in the presence of an organic solvent to generate a compound of Formula 10

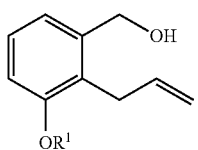

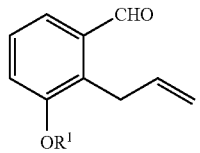

wherein $R^1$ is $C_{1-6}$ alkyl and the oxidizing agent comprises $MnO_2$ or Dess-Martin periodinane; ii) reacting the compound of Formula 10 with a compound of Formula 5 in the presence of a base and an organic solvent to generate a compound of Formula 11, wherein each $R^2$ is independently selected from $C_{1-6}$ alkyl or phenyl; and

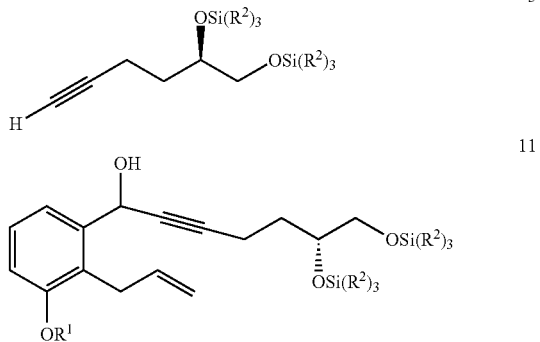

iii) converting the compound of Formula 11 to the N-methyldiethanolamine salt of the compound of Formula I.

In some implementations, the organic solvent of step i) comprises a halogenated organic solvent. For example, the organic solvent of step i) comprises dichloromethane, chloroform, or any combination thereof.

In some implementations, the base of step ii) comprises an alkyllithium reagent. For example, the base of step ii) comprises sec-butyllithium.

In some implementations, the organic solvent of step ii) comprises pentane, hexane, cyclohexane, heptane, tetrahydrofuran, 1,4-dioxane, diethyl ether, petro ether, methyl-tert-butylether, or any combination thereof. For example, the organic solvent of step ii) comprises methyl-tert-butylether.

Some methods further comprise the steps of: iv) refluxing the compound of Formula 1a in the presence of methanol to generate a compound of Formula 1 having an e.e. of greater than about 98%;

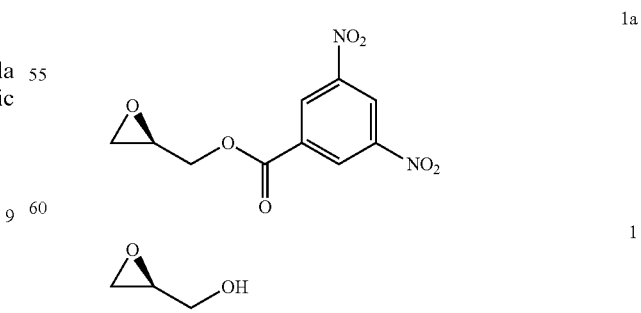

v) reacting the compound of Formula 1 with $SiCl(R^2)_3$ under basic conditions to generate the compound of Formula 2;

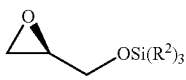

2 vi) reacting the compound of Formula 2 with 1-TMS-1-propyne to generate the compound of Formula 3; and

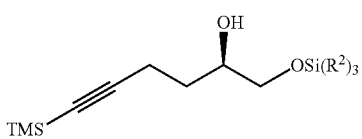

3 vii) converting the compound of Formula 3 to the compound of Formula 5.

Another aspect of the present invention provides a method of generating an N-methyldiethanolamine salt of the compound of Formula I

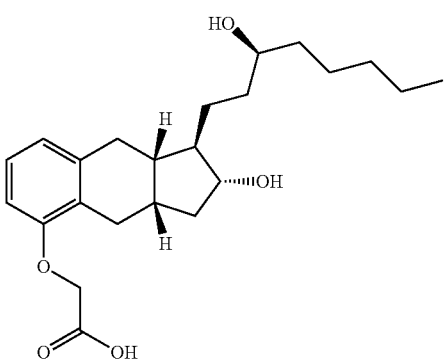

I comprising the steps of: viii) reacting a compound of Formula 11 with an oxidizing agent in the presence of an organic solvent to generate a compound of Formula 12

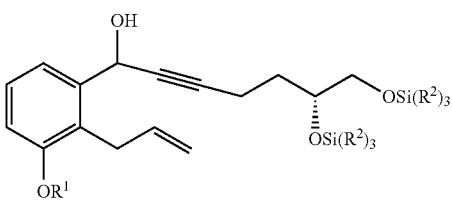

11

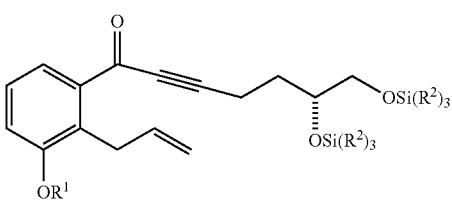

12 wherein $R^1$ is $C_{1-6}$ alkyl, each $R^2$ is independently selected from $C_{1-6}$ alkyl or phenyl, and the oxidizing agent comprises $MnO_2$; and ix) converting the compound of Formula 12 to the N-methyldiethanolamine salt of the compound of Formula I.

In some implementations, each of the —$OSi(R^2)_3$ groups in the compounds of Formulae 11 and 12 is independently selected from

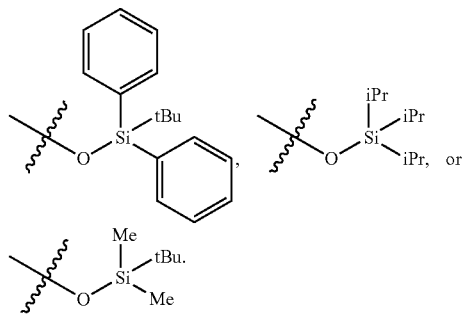

In some implementations, the organic solvent of step viii) comprises a halogenated organic solvent. In some examples, the halogenated organic solvent of step viii) comprises dichloromethane, chloroform, or any combination thereof.

Some methods further comprise the steps of: i) reacting a compound of Formula 9 with an oxidizing agent in the presence of an organic solvent to generate a compound of Formula 10

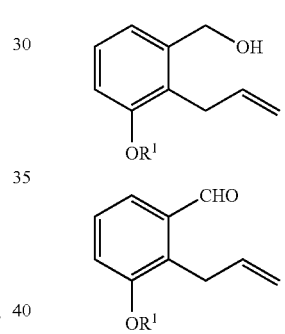

9

10 wherein $R^1$ is $C_{1-6}$ alkyl and the oxidizing agent comprises $MnO_2$ or Dess-Martin periodinane; and ii) reacting the compound of Formula 10 with a compound of Formula 5

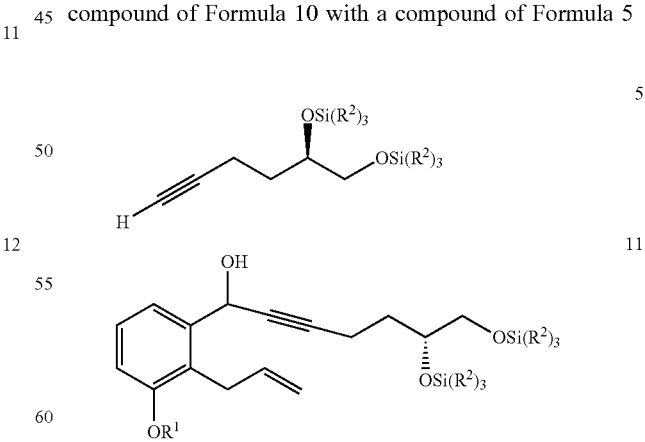

5

11 in the presence of a base and an organic solvent to generate a compound of Formula 11.

In some implementations, the base of step ii) comprises an alkyllithium reagent. For example, the alkyllithium reagent of step ii) comprises sec-butyllithium.

In some implementations, the organic solvent of step ii) comprises pentane, hexane, cyclohexane, heptane, tetrahydrofuran, 1,4-dioxane, diethyl ether, petro ether, methyl-tert-butylether, or any combination thereof. For example, the organic solvent of step ii) comprises methyl-tert-butylether.

Another aspect of the present invention provides a method of generating an N-methyldiethanolamine salt of the compound of Formula I

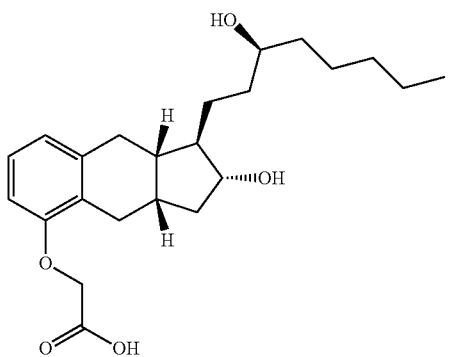

I comprising the steps of: x) reacting a compound of Formula 12 with a reducing agent in the presence of an organic solvent to generate a compound of Formula 13

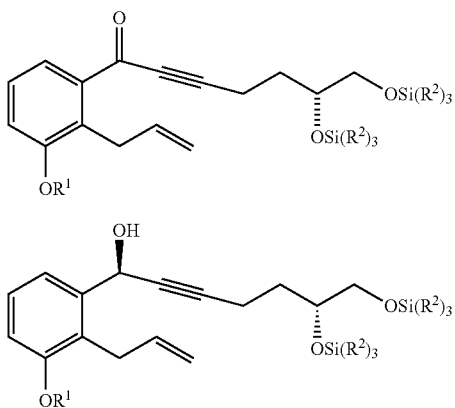

12

13 wherein the organic solvent comprises THF, $R^1$ is $C_{1-6}$ alkyl, and each $R^2$ is independently $C_{1-6}$ alkyl or phenyl; and xi) converting the compound of Formula 13 to the N-methyldiethanolamine salt of the compound of Formula I.

In some implementations, the reducing agent of step x) comprises a chiral borane compound. And, in some examples, the chiral borane compound is selected from (R)-1-methyl-3,3-diphenylhexahydropyrrolo[1,2-c][1,3,2]oxazaborole, (R)-3,3-diphenylhexahydropyrrolo[1,2-c][1,3,2]oxazaborole, (R)-1-butyl-3,3-diphenylhexahydropyrrolo[1,2-c][1,3,2]oxazaborole, (R)-tetrahydro-1,3,3-triphenyl-1H,3H-pyrrolo[1,2-c][1,3,2]oxaborole, (4S)-2-methyl-4,5,5-triphenyl-1,3,2-oxazaborolidine, or any combination thereof.

In some implementations, the organic solvent of step x) further comprises toluene.

Some methods further comprise the step of: viii) reacting a compound of Formula 11 with an oxidizing agent to generate the compound of Formula 12, wherein the oxidizing agent comprises $MnO_2$

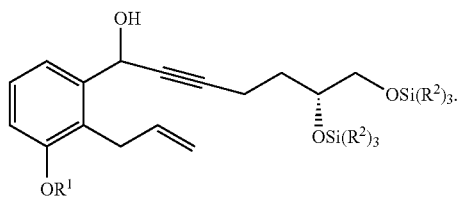

11

Some methods further comprise the steps of: i) reacting a compound of Formula 9 with an oxidizing agent to generate a compound of Formula 10; and

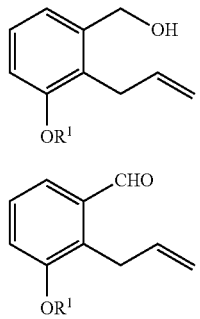

9

10 ii) reacting the compound of Formula 10 with a compound of Formula 5 in the presence of a base and an organic solvent to generate a compound of Formula 11

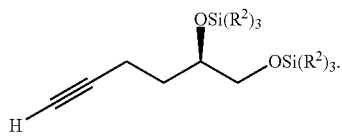

5

In some implementations, the oxidizing agent comprises $MnO_2$ or Dess-Martin periodinane.

In some implementations, the base of step ii) comprises an alkyllithium reagent. For example, the alkyllithium reagent of step ii) comprises sec-butyllithium.

In some implementations, the organic solvent of step ii) comprises pentane, hexane, cyclohexane, heptane, tetrahydrofuran, 1,4-dioxane, diethyl ether, petro ether, methyl-tert-butylether, or any combination thereof. For example, the organic solvent of step ii) comprises methyl-tert-butylether.

Some methods further comprise the steps of: iv) refluxing the compound of Formula 1a in the presence of methanol to generate a compound of Formula 1 having an e.e. of greater than about 98%;

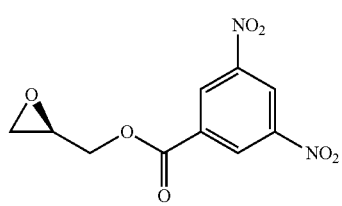

1a

-continued

1
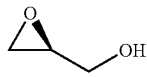

v) reacting the compound of Formula 1 with SiCl(R²)₃ under basic conditions to generate the compound of Formula 2;

2
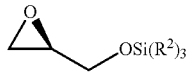

vi) reacting the compound of Formula 2 with 1-TMS-1-propyne to generate the compound of Formula 3; and 3
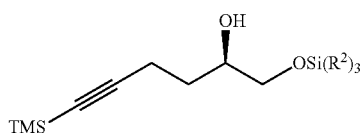

vii) converting the compound of Formula 3 to the compound of Formula 5.

Another aspect of the present invention provides a method of generating an N-methyldiethanolamine salt of the compound of Formula I I
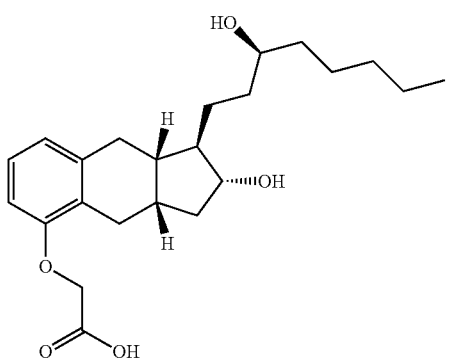

comprising the steps of: xii) hydrogenating a compound of Formula 15 in the presence of an organic solvent (e.g., an alcohol (e.g., methanol, ethanol, or any combination thereof), an optionally substituted THF (e.g., 2-methyl-THF or THF), EtOAc, or any combination thereof) to generate the compound of Formula 16

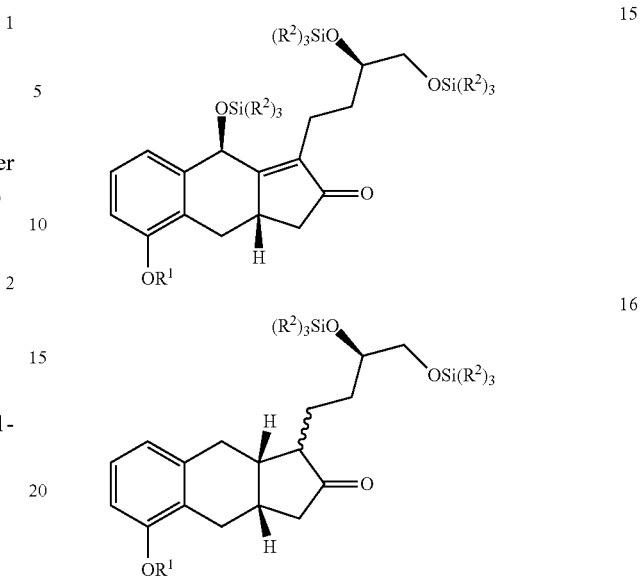

wherein $R^1$ is $C_{1-6}$ alkyl and each $R^2$ is independently selected from $C_{1-6}$ alkyl or phenyl; and xiii) converting the compound of Formula 16 to the N-methyldiethanolamine salt of the compound of Formula I.

Some methods further comprise the steps of: x) reacting a compound of Formula 12 with a reducing agent in the presence of an organic solvent to generate a compound of Formula

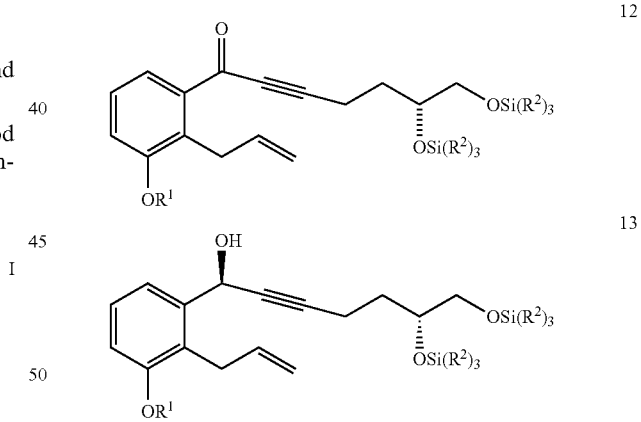

wherein the organic solvent comprises THF; and xiv) converting the compound of Formula 13 to the compound of Formula 15.

In some implementations, the reducing agent of step x) comprises a chiral borane compound. And, in some examples, the chiral borane compound is selected from (R)-1-methyl-3,3-diphenylhexahydropyrrolo[1,2-c][1,3,2]oxazaborole, (R)-3,3-diphenylhexahydropyrrolo[1,2-c][1,3,2]oxazaborole, (R)-1-butyl-3,3-diphenylhexahydropyrrolo[1,2-c][1,3,2]oxazaborole, (R)-tetrahydro-1,3,3-triphenyl-1H,3H-pyrrolo[1,2-c][1,3,2]oxazaborole, (4S)-2-methyl-4,5,5-triphenyl-1,3,2-oxazaborolidine, or any combination thereof.

Some methods further comprise the steps of: viii) reacting a compound of Formula 11 with an oxidizing agent to generate the compound of Formula 12, wherein the oxidizing agent comprises MnO$_2$

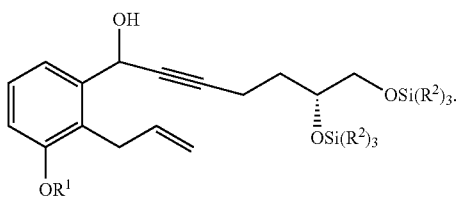

11

Some methods further comprise the steps of: i) reacting a compound of Formula 9 with an oxidizing agent to generate a compound of Formula 10; and

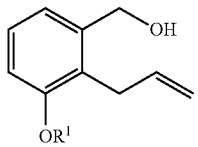

9

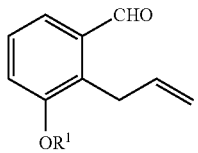

10 ii) reacting the compound of Formula 10 with a compound of Formula 5 in the presence of a base and an organic solvent to generate a compound of Formula 11

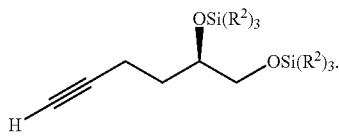

5

In some implementations, the oxidizing agent of step i) comprises MnO$_2$ or Dess-Martin periodinane.

In some implementations, the base of step ii) comprises an alkyllithium reagent. For example, the alkyllithium reagent of step ii) comprises sec-butyllithium.

In some implementations, the organic solvent of step ii) comprises pentane, hexane, cyclohexane, heptane, tetrahydrofuran, 1,4-dioxane, diethyl ether, petro ether, methyl-tert-butylether, or any combination thereof. For example, the organic solvent of step ii) comprises methyl-tert-butylether.

Some methods further comprise the steps of: iv) refluxing the compound of Formula 1a in the presence of methanol to generate a compound of Formula 1 having an e.e. of greater than about 98%;

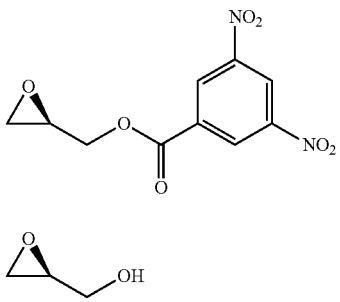

1a

1 v) reacting the compound of Formula 1 with SiCl(R$^2$)$_3$ under basic conditions to generate the compound of Formula 2;

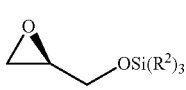

2 vi) reacting the compound of Formula 2 with 1-TMS-1-propyne to generate the compound of Formula 3; and

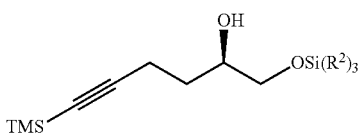

3 vii) converting the compound of Formula 3 to the compound of Formula 5.

Another aspect of the present invention provides a method of generating an N-methyldiethanolamine salt of the compound of Formula I

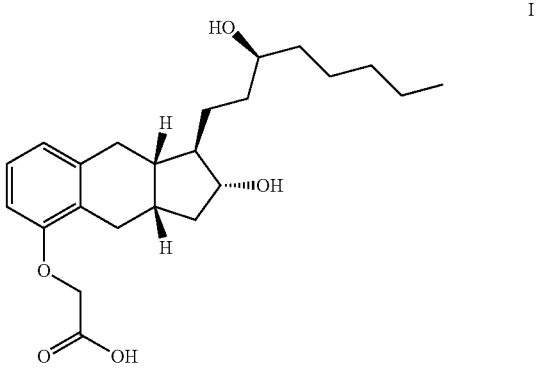 [SMILES: CCCCC[C@H](O)CC[C@@H]1[C@H]2Cc3cccc(OCC(=O)O)c3C[C@H]2C[C@H]1O]

I comprising the steps of: xv) reacting a compound of Formula 21 with n-butyllithium in the presence of an organic solvent and a transition metal catalyst to generate a compound of Formula 22

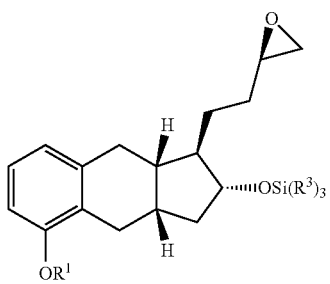

21

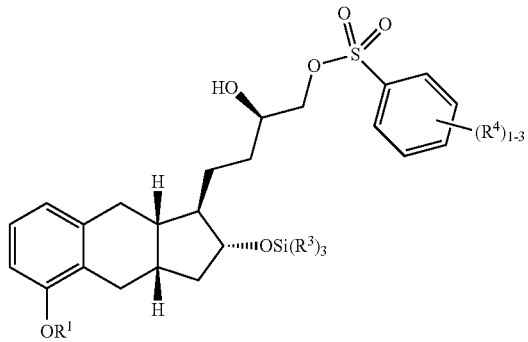

20 xviii) reacting the compound of Formula 20 with methanol under basic conditions to generate the compound of Formula 21.

Some methods further comprise the steps of: xix) reacting a compound of Formula 16 with a reducing agent to generate a compound of Formula 17;

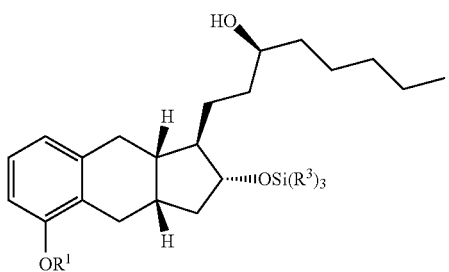

22

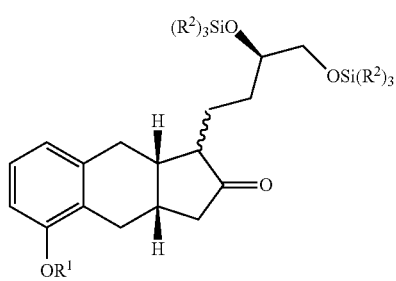

16 wherein $R^3$ is $C_{1-6}$ alkyl or phenyl; and xvi) converting the compound of Formula 22 to the N-methyldiethanolamine salt of the compound of Formula I.

In some implementations, the transition metal catalyst of step xv) comprises a compound or complex either of which comprises Cu having a +1 oxidation state. For example, the transition metal catalyst of step xv) comprises CuX, wherein X is selected from halogen, acetate, benzoate, cyanide, hydroxide, nitrate, or any combination thereof. In other examples, the transition metal catalyst of step xv) comprises CuI.

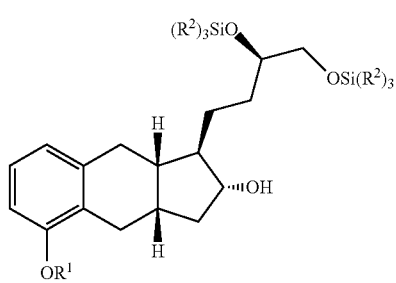

17

Some methods further comprise the steps of: xvii) reacting a compound of Formula 19 with $R^4$-substituted benzenesulfonyl chloride under basic conditions to generate a compound of Formula 20, wherein each $R^4$ is independently selected from —H or $C_{1-3}$ alkyl; and xx) reacting the compound of claim 17 with $Si(R^3)_3Cl$ under basic conditions to generate a compound of Formula 18; and

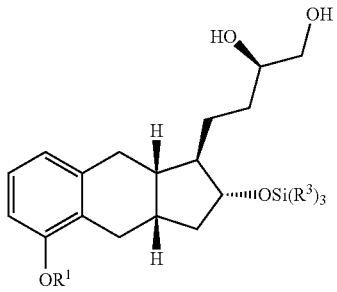

19

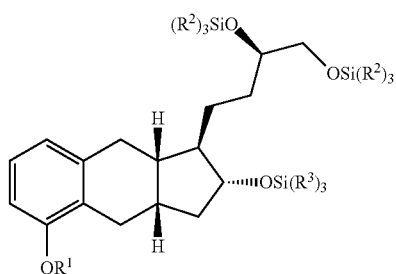

18 xxi) selectively deprotecting the compound of Formula 18 to generate the compound of Formula 19.

Some methods further comprise the steps of: xii) hydrogenating a compound of Formula 15

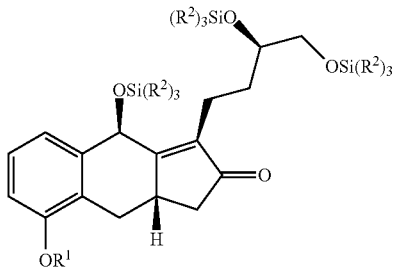

15 in the presence of an organic solvent (e.g., an alcohol (e.g., methanol, ethanol, or any combination thereof), an optionally substituted THF (e.g., 2-methyl-THF or THF), EtOAc, or any combination thereof) to generate the compound of Formula 16.

In some implementations, the hydrogenation of the compound of Formula 15 also occurs in the presence of a base (e.g., potassium carbonate or potassium bicarbonate).

Some methods further comprise the steps of: x) reacting a compound of Formula 12 with a reducing agent to generate a compound of Formula 13; and

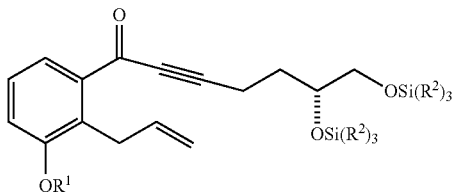

12

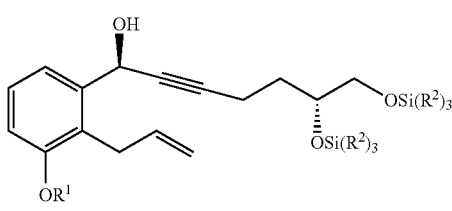

13 xiv) converting the compound of Formula 13 to the compound of Formula 15.

In some implementations, the reducing agent of step x) comprises a chiral borane compound. And, in some examples, the chiral borane compound is selected from (R)-1-methyl-3,3-diphenylhexahydropyrrolo[1,2-c][1,3,2]oxazaborole, (R)-3,3-diphenylhexahydropyrrolo[1,2-c][1,3,2]oxazaborole, (R)-1-butyl-3,3-diphenylhexahydropyrrolo[1,2-c][1,3,2]oxazaborole, (R)-tetrahydro-1,3,3-triphenyl-1H,3H-pyrrolo[1,2-c][1,3,2]oxaborole, (4S)-2-methyl-4,5,5-triphenyl-1,3,2-oxazaborolidine, or any combination thereof.

Some methods further comprise the step of: viii) reacting a compound of Formula 11

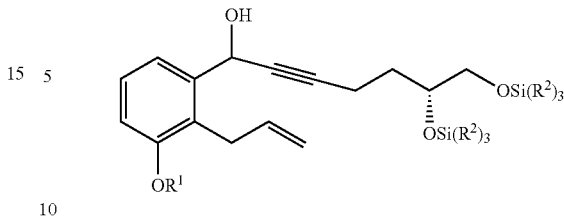

11 with an oxidizing agent to generate the compound of Formula 12, wherein the oxidizing agent comprises $MnO_2$.

Some methods further comprise the steps of: i) reacting a compound of Formula 9 with an oxidizing agent to generate a compound of Formula 10; and

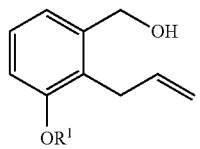

9

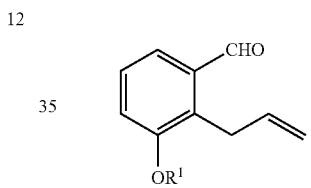

10 ii) reacting the compound of Formula 10 with a compound of Formula 5 in the presence of a base and an organic solvent to generate a compound of Formula 11

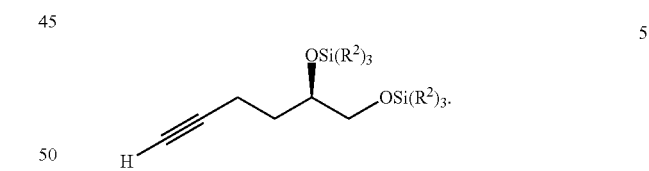

5

In some implementations, the oxidizing agent of step i) comprises $MnO_2$ or Dess-Martin periodinane.

In some implementations, the base of step ii) comprises an alkyllithium reagent. For example, the alkyllithium reagent of step ii) comprises sec-butyllithium.

In some implementations, the organic solvent of step ii) comprises pentane, hexane, cyclohexane, heptane, tetrahydrofuran, 1,4-dioxane, diethyl ether, petro ether, methyl-tert-butylether, or any combination thereof. For example, the organic solvent of step ii) comprises methyl-tert-butylether.

Some methods further comprise the steps of: iv) refluxing the compound of Formula 1a in the presence of methanol to generate a compound of Formula 1 having greater than about 99% e.e.;

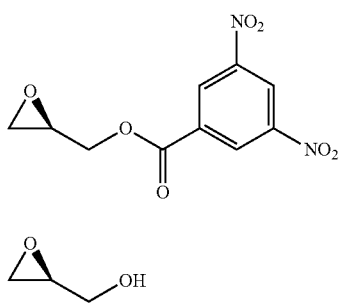

1a

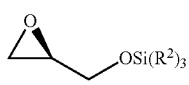

1 v) reacting the compound of Formula 1 with SiCl(R²)₃ under basic conditions to generate the compound of Formula 2;

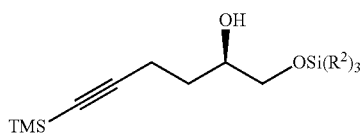

2 vi) reacting the compound of Formula 2 with 1-TMS-1-propyne to generate the compound of Formula 3; and

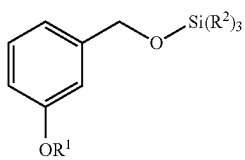

3 vii) converting the compound of Formula 3 to the compound of Formula 5.

Some methods further comprise the steps of: xxii) reacting a compound of Formula 7 with a 3-haloprop-1-ene in the presence of a base and an organic solvent to generate a compound of Formula 8; and

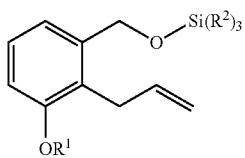

7

8 xxiii) deprotecting the compound of Formula 8 to generate the compound of Formula 9.

Another aspect of the present invention provides a method of generating an N-methyldiethanolamine salt of the compound of Formula I

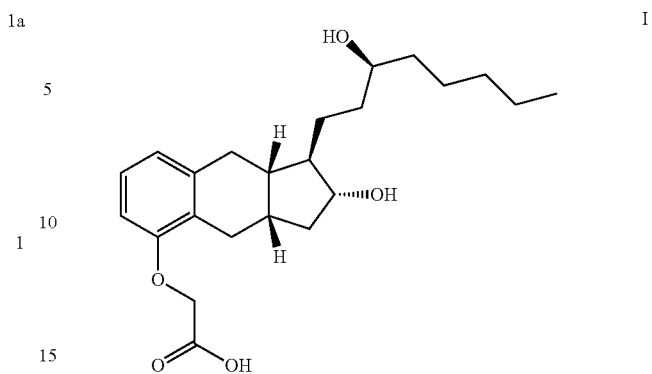

I comprising the steps of: xxii) reacting a compound of Formula 7, wherein R¹ is $C_{1-6}$ alkyl and each R² is independently selected from $C_{1-6}$ alkyl or phenyl, with a 3-haloprop-1-ene in the presence of a base and an organic solvent to generate a compound of Formula 8;

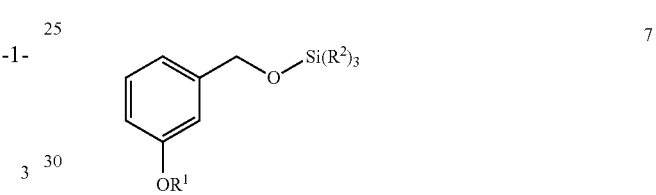

7

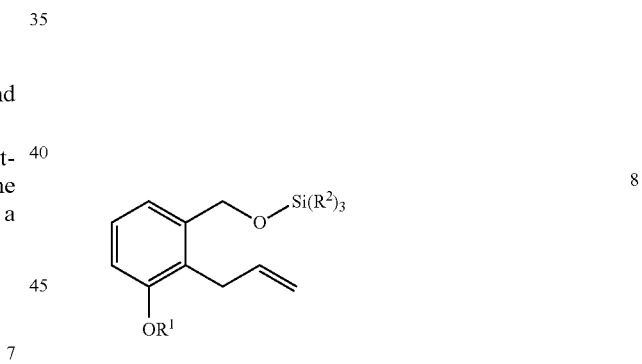

8 xxiii) deprotecting the compound of Formula 8 to generate the compound of Formula 9, and

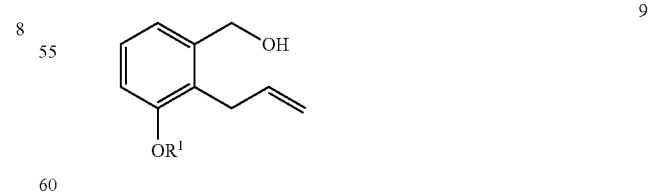

9 xxiv) converting the compound of Formula 9 to the N-methyldiethanolamine salt of the compound of Formula I, wherein the base of step xxii) comprises sec-butyl lithium.

Another aspect of the present invention provides a method of generating an N-methyldiethanolamine salt of the compound of Formula I

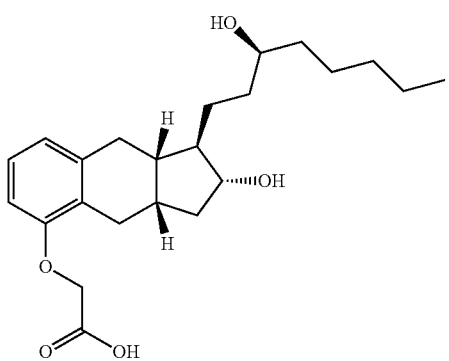

comprising the steps of: i) reacting a compound of Formula 9 with an oxidizing agent in the presence of an organic solvent to generate a compound of Formula 10

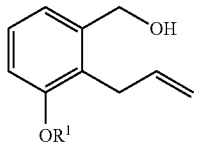

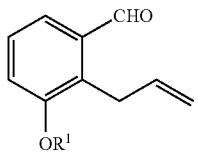

wherein $R^1$ is $C_{1-6}$ alkyl and the oxidizing agent comprises $MnO_2$ or Dess-Martin periodinane; ii) reacting the compound of Formula 10 with a compound of Formula 5a in the presence of a base and an organic solvent to generate a compound of Formula IIa; and

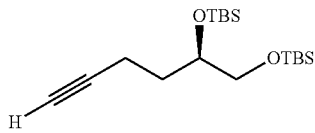

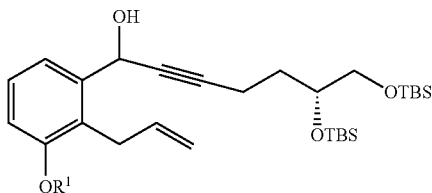

iii) converting the compound of Formula IIa to the N-methyldiethanolamine salt of the compound of Formula I.

In some implementations, the organic solvent of step i) comprises a halogenated organic solvent. For example, the organic solvent of step i) comprises dichloromethane, chloroform, or any combination thereof.

In some implementations, the base of step ii) comprises an alkyllithium reagent. For example, the base of step ii) comprises sec-butyllithium.

In some implementations, the organic solvent of step ii) comprises pentane, hexane, cyclohexane, heptane, tetrahydrofuran, 1,4-dioxane, diethyl ether, petro ether, methyl-tert-butylether, or any combination thereof. For example, the organic solvent of step ii) comprises methyl-tert-butylether.

Some methods further comprise the steps of: iv) refluxing the compound of Formula 1a in the presence of methanol to generate a compound of Formula 1 having an e.e. of greater than about 98%;

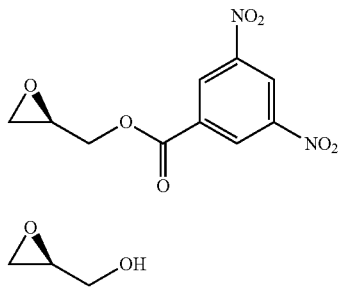

v) reacting the compound of Formula 1 with TBSCl under basic conditions to generate the compound of Formula 2a;

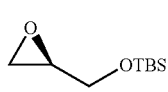

vi) reacting the compound of Formula 2a with 1-TMS-1-propyne to generate the compound of Formula 3a; and

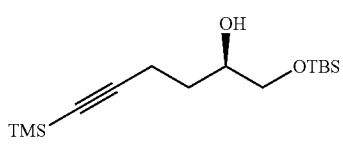

vii) converting the compound of Formula 3a to the compound of Formula 5a.

Another aspect of the present invention provides a method of generating an N-methyldiethanolamine salt of the compound of Formula I

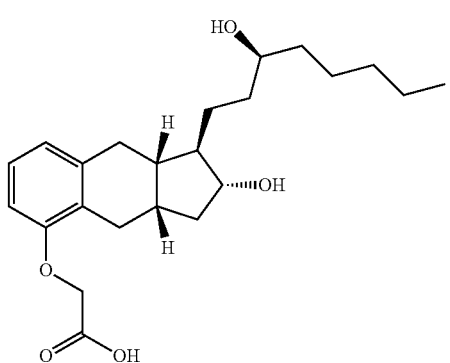

comprising the steps of: viii) reacting a compound of Formula 11a with an oxidizing agent in the presence of an organic solvent to generate a compound of Formula 12a

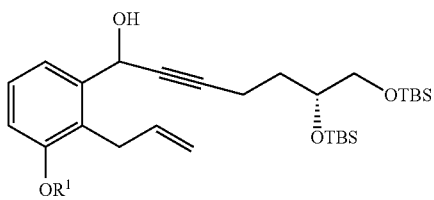

11a

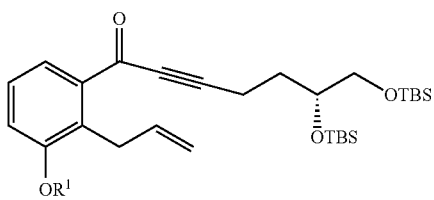

12a wherein $R^1$ is $C_{1-6}$ alkyl and the oxidizing agent comprises $MnO_2$; and ix) converting the compound of Formula 12a to the N-methyldiethanolamine salt of the compound of Formula I.

In some implementations, the organic solvent of step viii) comprises a halogenated organic solvent. For example, the halogenated organic solvent of step viii) comprises dichloromethane, chloroform, or any combination thereof.

Some methods further comprise the steps of: i) reacting a compound of Formula 9 with an oxidizing agent in the presence of an organic solvent to generate a compound of Formula 10

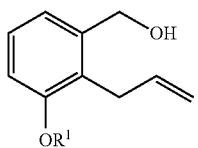

9

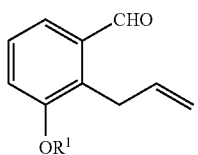

10 wherein the oxidizing agent comprises $MnO_2$ or Dess-Martin periodinane; and ii) reacting the compound of Formula 10 with a compound of Formula 5a

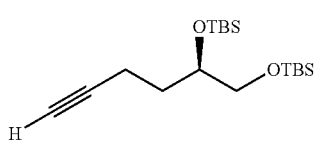

5a

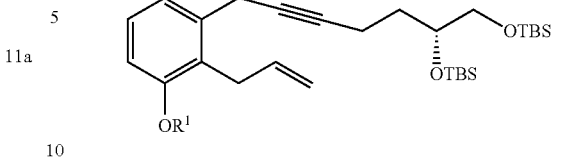

11a in the presence of a base and an organic solvent to generate a compound of Formula 11a.

In some implementations, the organic solvent of step i) comprises a halogenated organic solvent. For example, the organic solvent of step i) comprises dichloromethane, chloroform, or any combination thereof.

In some implementations, the base of step ii) comprises an alkyllithium reagent. For example, the base of step ii) comprises sec-butyllithium.

In some implementations, the organic solvent of step ii) comprises pentane, hexane, cyclohexane, heptane, tetrahydrofuran, 1,4-dioxane, diethyl ether, petro ether, methyl-tert-butylether, or any combination thereof. For example, the organic solvent of step ii) comprises methyl-tert-butylether.

Another aspect of the present invention provides a method of generating an N-methyldiethanolamine salt of the compound of Formula I

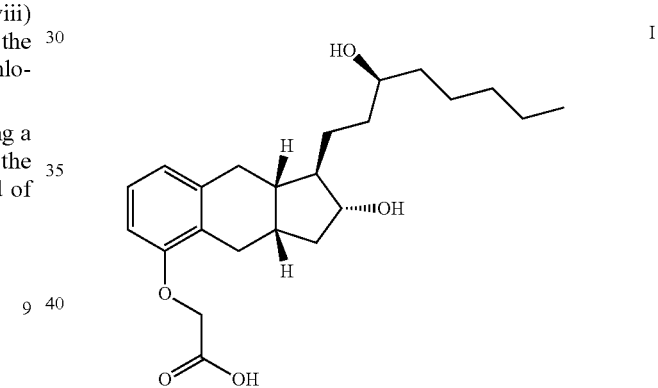

I comprising the steps of: x) reacting a compound of Formula 12a with a reducing agent in the presence of an organic solvent to generate a compound of Formula 13a

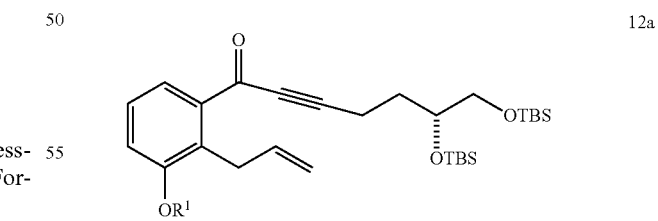

12a

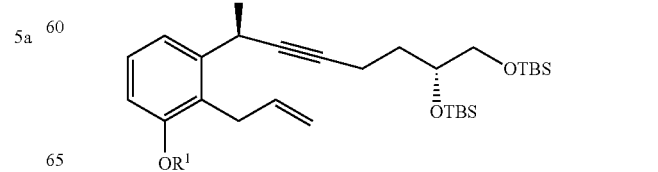

13a wherein the organic solvent comprises THF, $R^1$ is $C_{1-6}$ alkyl, and each $R^2$ is independently selected from $C_{1-6}$ alkyl or phenyl; and xi) converting the compound of Formula 13 to the N-methyldiethanolamine salt of the compound of Formula I.

In some implementations, the reducing agent of step x) comprises a chiral borane compound. And, in some examples, the chiral borane compound is selected from (R)-1-methyl-3,3-diphenylhexahydropyrrolo[1,2-c][1,3,2]oxazaborole, (R)-3,3-diphenylhexahydropyrrolo[1,2-c][1,3,2]oxazaborole, (R)-1-butyl-3,3-diphenylhexahydropyrrolo[1,2-c][1,3,2]oxazaborole, (R)-tetrahydro-1,3,3-triphenyl-1H,3H-pyrrolo[1,2-c][1,3,2]oxaborole, (4S)-2-methyl-4,5,5-triphenyl-1,3,2-oxazaborolidine, or any combination thereof.

In some implementations, the organic solvent of step x) comprises THF.

In some implementations, the organic solvent of step x) further comprises toluene.

Some methods further comprise the step of: viii) reacting a compound of Formula 11a with an oxidizing agent to generate the compound of Formula 12a, wherein the oxidizing agent comprises $MnO_2$

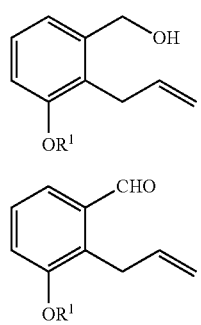

11a

Some methods further comprise the steps of: i) reacting a compound of Formula 9 with an oxidizing agent to generate a compound of Formula 10; and

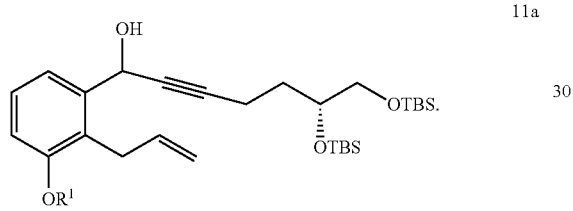

9

10 ii) reacting the compound of Formula 10 with a compound of Formula 5a in the presence of a base and an organic solvent to generate a compound of Formula 11a

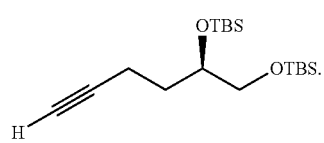

5a

In some implementations, the oxidizing agent of step i) comprises $MnO_2$ or Dess-Martin periodinane.

In some implementations, the base of step ii) comprises an alkyllithium reagent. For example, the alkyllithium reagent of step ii) comprises sec-butyllithium.

In some implementations, the organic solvent of step ii) comprises pentane, hexane, cyclohexane, heptane, tetrahydrofuran, 1,4-dioxane, diethyl ether, petro ether, methyl-tert-butylether, or any combination thereof. For example, the organic solvent of step ii) comprises methyl-tert-butylether.

Some methods further comprise the steps of: iv) refluxing the compound of Formula 1a in the presence of methanol to generate a compound of Formula 1 having an e.e. of greater than about 98%;

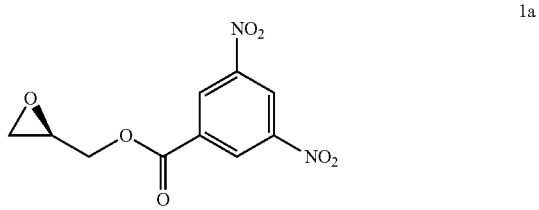

1a

1 v) reacting the compound of Formula 1 with TBSCl under basic conditions to generate the compound of Formula 2a;

2a vi) reacting the compound of Formula 2a with 1-TMS-1-propyne to generate the compound of Formula 3a; and 3a vii) converting the compound of Formula 3a to the compound of Formula 5a.

Another aspect of the present invention provides a method of generating an N-methyldiethanolamine salt of the compound of Formula I

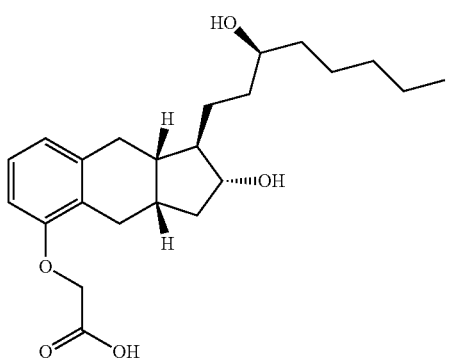

I comprising the steps of: xii) hydrogenating a compound of Formula 15a in the presence of an organic solvent (e.g., an alcohol (e.g., methanol, ethanol, or any combination thereof), an optionally substituted THF (e.g., 2-methyl-THF or THF), EtOAc, or any combination thereof) to generate the compound of Formula 16a

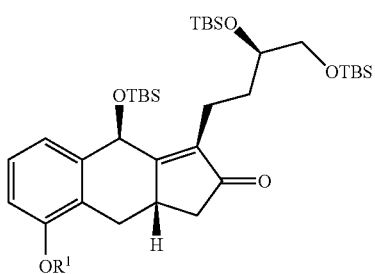

15a

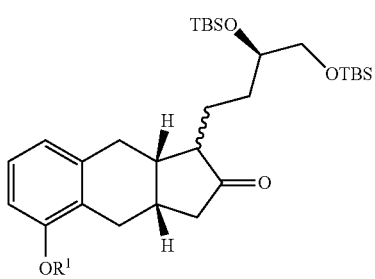

16a wherein $R^1$ is $C_{1-6}$ alkyl; and xiii) converting the compound of Formula 16a to the N-methyldiethanolamine salt of the compound of Formula I.

In some implementations, the hydrogenation of the compound of Formula 15a also occurs in the presence of a base (e.g., potassium carbonate or potassium bicarbonate).

Some methods further comprise the steps of: x) reacting a compound of Formula 12a with a reducing agent in the presence of an organic solvent to generate a compound of Formula 13a

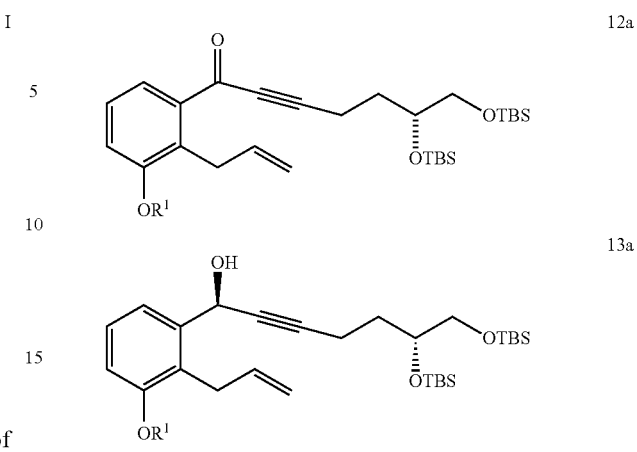

12a

13a wherein the organic solvent comprises THF; and xiv) converting the compound of Formula 13a to the compound of Formula 15a.

Some methods further comprise the steps of: viii) reacting a compound of Formula 11a with an oxidizing agent to generate the compound of Formula 12a, wherein the oxidizing agent comprises $MnO_2$

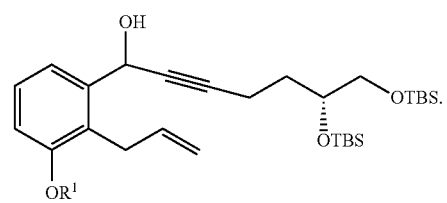

11a

Some methods further comprise the steps of: i) reacting a compound of Formula 9 with an oxidizing agent to generate a compound of Formula 10; and

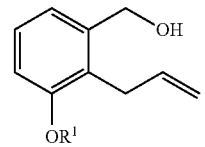

9

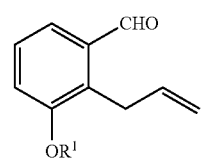

10 ii) reacting the compound of Formula 10 with a compound of Formula 5a in the presence of a base and an organic solvent to generate a compound of Formula 11a

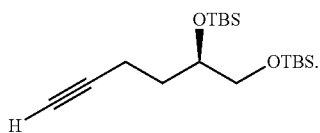
5a

Some methods further comprise the steps of: iv) refluxing the compound of Formula 1a in the presence of methanol to generate a compound of Formula 1 having an e.e. of greater than about 98%;

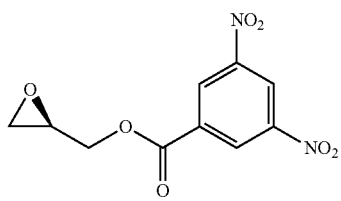
1a

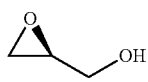
1 v) reacting the compound of Formula 1 with TBSCl under basic conditions to generate the compound of Formula 2a;

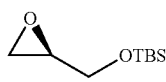
2a vi) reacting the compound of Formula 2a with 1-TMS-1-propyne to generate the compound of Formula 3a; and

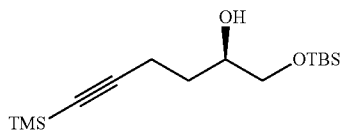
3a vii) converting the compound of Formula 3a to the compound of Formula 5a.

Another aspect of the present invention provides a method of generating an N-methyldiethanolamine salt of the compound of Formula I

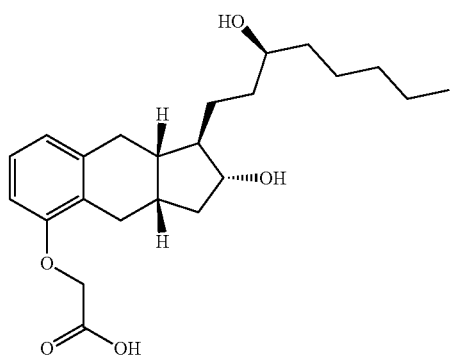
I comprising the steps of: xv) reacting a compound of Formula 21a with n-butyllithium in the presence of an organic solvent and a transition metal catalyst to generate a compound of Formula 22a

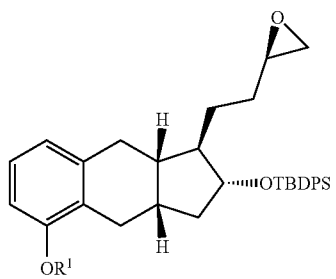
21a

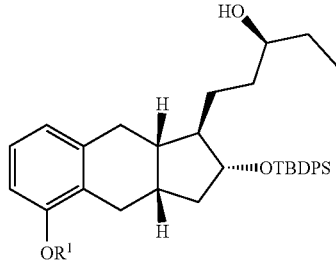
22a wherein $R^1$ is $C_{1-6}$ alkyl; and xvi) converting the compound of Formula 22a to the N-methyldiethanolamine salt of the compound of Formula I.

In some implementations, the transition metal catalyst of step xv) comprises a compound or complex either of which comprises Cu having a +1 oxidation state. For example, the transition metal catalyst of step xv) comprises CuX, wherein X is selected from halogen, acetate, benzoate, cyanide, hydroxide, nitrate, or any combination thereof. In other examples, the transition metal catalyst of step xv) comprises CuI.

Some methods further comprise the steps of: xvii) reacting a compound of Formula 19a with triisopropylbenzenesulfonyl chloride under basic conditions to generate a compound of Formula 20a; and

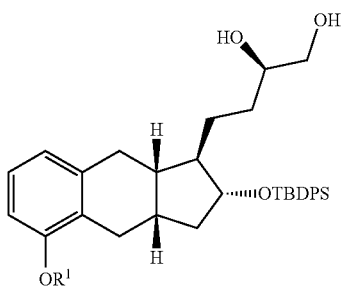

19a

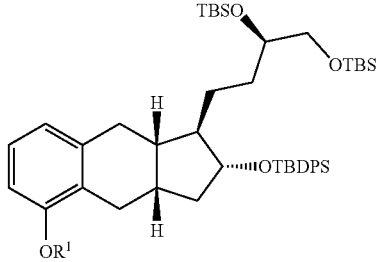

18a xxi) selectively deprotecting the compound of Formula 18a to generate the compound of Formula 19a.

Some methods further comprise the step of: xii) hydrogenating a compound of Formula 15a

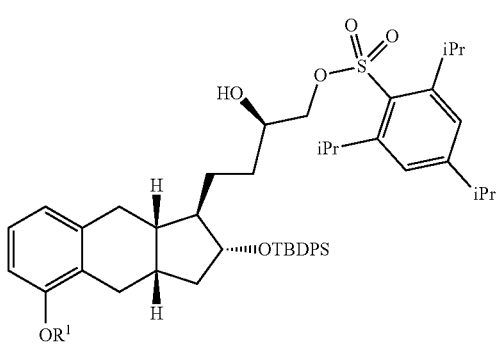

20a

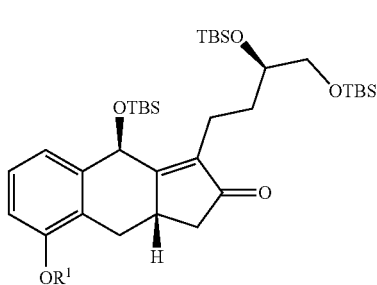

15a xviii) reacting the compound of Formula 20a with methanol under basic conditions to generate the compound of Formula 21a.

Some methods further comprise the steps of: xix) reacting a compound of Formula 16a with a reducing agent to generate a compound of Formula 17a;

in the presence of an organic solvent, (e.g., an alcohol (e.g., methanol, ethanol, or any combination thereof), an optionally substituted THF (e.g., 2-methyl-THF or THF), EtOAc, or any combination thereof) to generate the compound of Formula 16a.

In some implementations, the alcohol of step xii) is anhydrous (e.g., anhydrous methanol).

In some implementations, the hydrogenation of the compound of Formula 15a occurs in the presence of a base (e.g., potassium carbonate or potassium bicarbonate).

Some methods further comprise the steps of: x) reacting a compound of Formula 12a with a reducing agent to generate a compound of Formula 13a; and

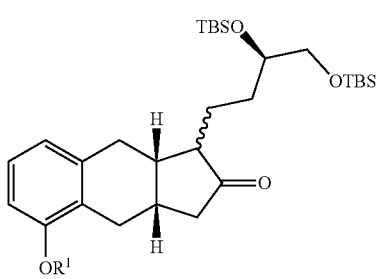

16a

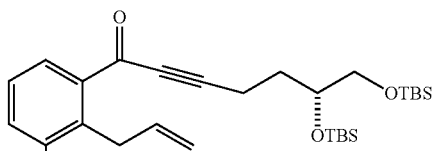

12a

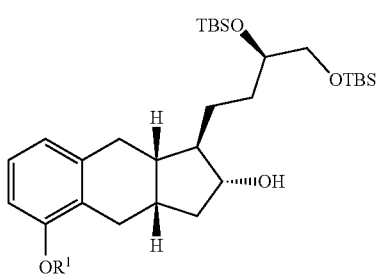

17a

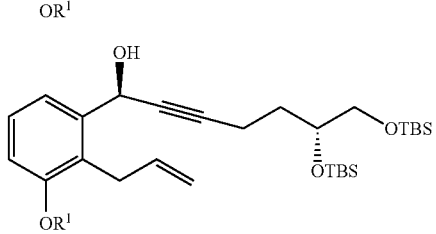

13a xx) reacting the compound of Formula 17a with TBDPSCl under basic conditions to generate a compound of Formula 18a; and xiv) converting the compound of Formula 13a to the compound of Formula 15a.

Some methods further comprise the step of: viii) reacting a compound of Formula 11a

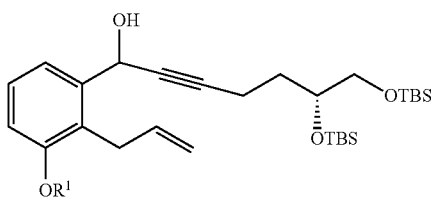

11a with an oxidizing agent to generate the compound of Formula 12a, wherein the oxidizing agent comprises MnO$_2$.

Some methods further comprise the steps of: i) reacting a compound of Formula 9 with an oxidizing agent to generate a compound of Formula 10; and

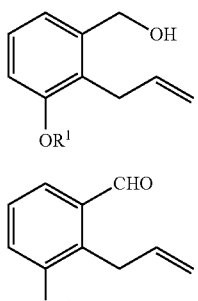

9

10 ii) reacting the compound of Formula 10 with a compound of Formula 5a in the presence of a base and an organic solvent to generate a compound of Formula 11a

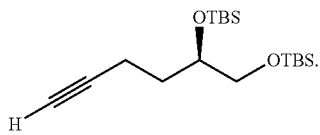

5a

Some methods further comprise the steps of: iv) refluxing the compound of Formula 1a in the presence of methanol to generate a compound of Formula 1 having an e.e. of greater than about 98%;

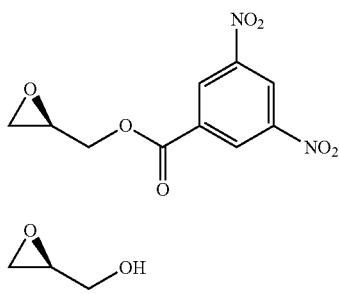

1a

1 v) reacting the compound of Formula 1 with TBSCl under basic conditions to generate the compound of Formula 2a;

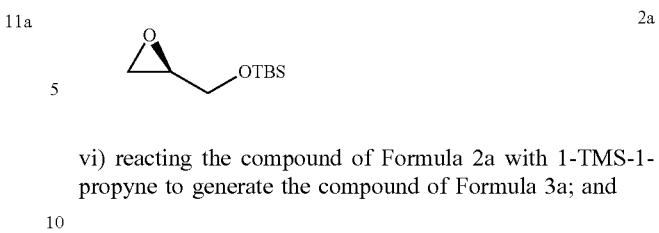

2a vi) reacting the compound of Formula 2a with 1-TMS-1-propyne to generate the compound of Formula 3a; and

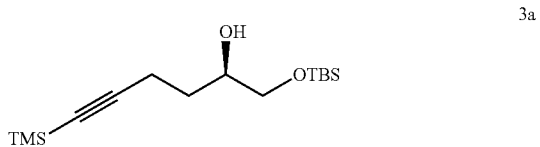 [SMILES: CC(C)(C)[Si](C)(C)OC[C@H](O)CCC#C[Si](C)(C)C]

3a vii) converting the compound of Formula 3a to the compound of Formula 5a.

Some methods further comprise the steps of: xxii) reacting a compound of Formula 7a with a 3-haloprop-1-ene in the presence of a base and an organic solvent to generate a compound of Formula 8a; and

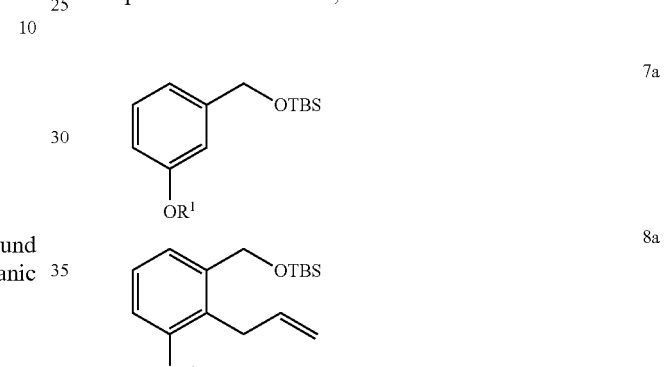

7a

8a xxiii) deprotecting the compound of Formula 8a to generate the compound of Formula 9.

Another aspect of the present invention provides a method of generating an N-methyldiethanolamine salt of the compound of Formula I

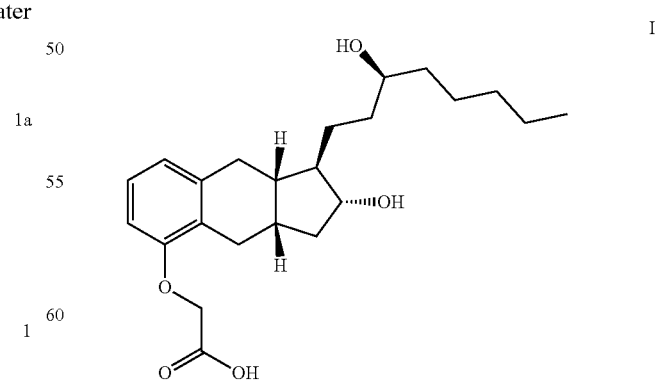

I comprising the steps of: i) reacting a compound of Formula 9 with an oxidizing agent to generate a compound of Formula 10;

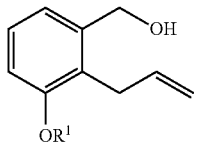

9

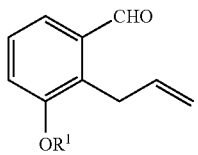

10 ii) reacting the compound of Formula 10 with a compound of Formula 5a in the presence of a base and an organic solvent to generate a compound of Formula 11a;

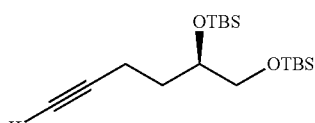

5a

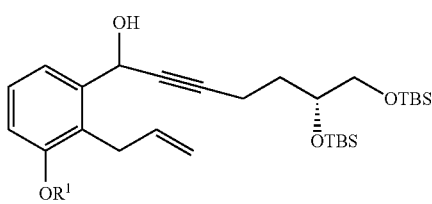

11a iv) refluxing the compound of Formula 1a in the presence of methanol to generate a compound of Formula 1 having an e.e. of greater than about 98%;

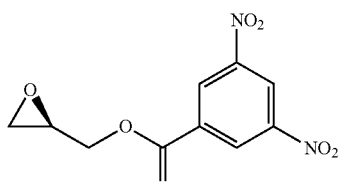

1a

1 v) reacting the compound of Formula 1 with TBSCl under basic conditions to generate the compound of Formula 2a;

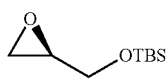

2a vi) reacting the compound of Formula 2a with 1-TMS-1-propyne to generate the compound of Formula 3a;

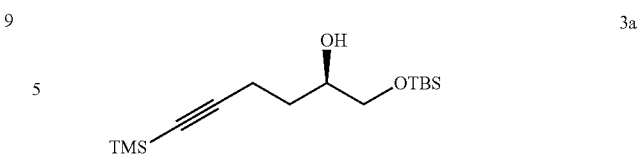

3a vii) converting the compound of Formula 3a to the compound of Formula 5a;

viii) reacting a compound of Formula 11a with an oxidizing agent to generate the compound of Formula 12a, wherein the oxidizing agent comprises $MnO_2$;

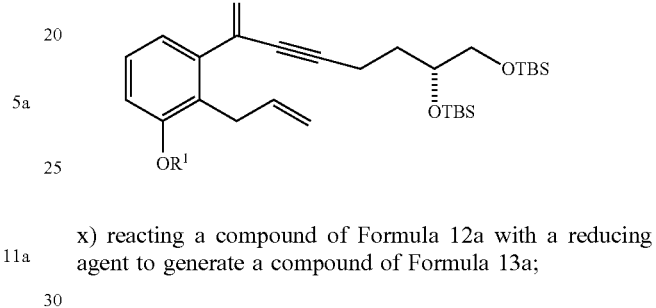

12a x) reacting a compound of Formula 12a with a reducing agent to generate a compound of Formula 13a;

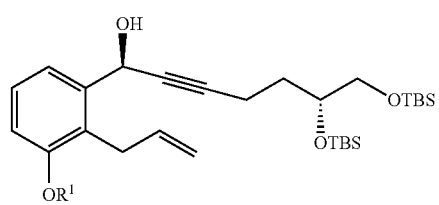

13a xiv) converting the compound of Formula 13a to the compound of Formula 15a;

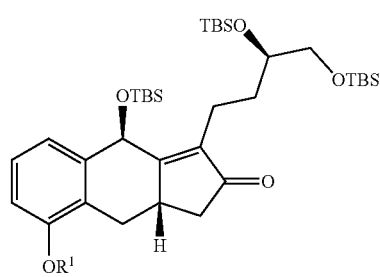

15a xii) hydrogenating a compound of Formula 15a in the presence of an organic solvent (e.g., an alcohol (e.g., methanol, ethanol, or any combination thereof), an optionally substituted THF (e.g., 2-methyl-THF or THF), EtOAc, or any combination thereof) to generate the compound of Formula 16a;

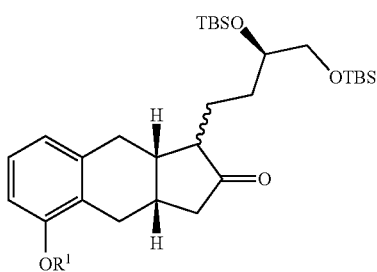

16a xix) reacting a compound of Formula 16a with a reducing agent to generate a compound of Formula 17a;

xx) reacting the compound of Formula 17a with TDPSCl under basic conditions to generate a compound of Formula 18a;

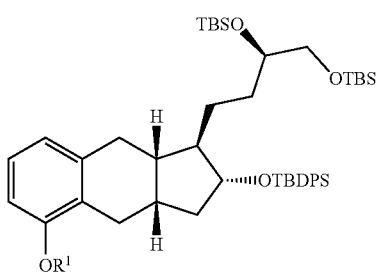

18a xxi) selectively deprotecting the compound of Formula 18a to generate the compound of Formula 19a;

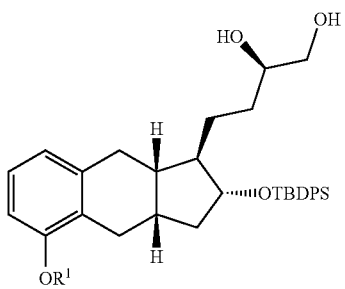

19a xvii) reacting a compound of Formula 19a with triisopropylbenzenesulfonyl chloride under basic conditions to generate a compound of Formula 20a;

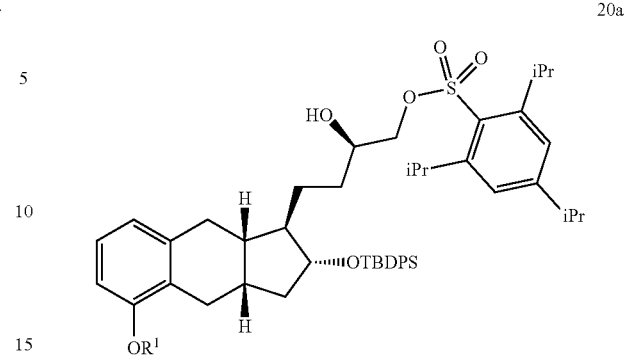

20a xviii) reacting the compound of Formula 20a with methanol under basic conditions to generate the compound of Formula 21a;

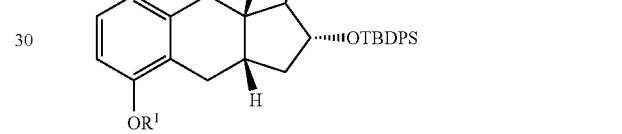

21a xv) reacting a compound of Formula 21a with n-butyllithium in the presence of an organic solvent and a transition metal catalyst to generate a compound of Formula 22a; and

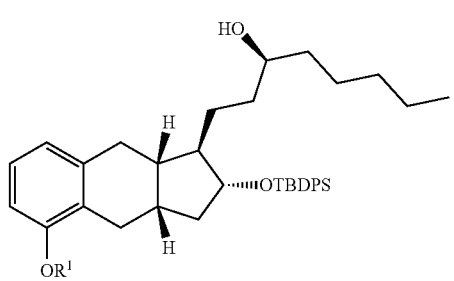

22a xvi) converting the compound of Formula 22a to the N-methyldiethanolamine salt of the compound of Formula I.

Some methods further comprise the step of: xxiv) reacting the compound of Formula I with N-methyldiethanolamine in the presence of an organic solvent to generate the N-methyldiethanolamine salt of the compound of Formula I. about 97% or greater.

DETAILED DESCRIPTION OF THE INVENTION

The present invention provides amine salts of the compound of Formula IA and methods of generating these salts

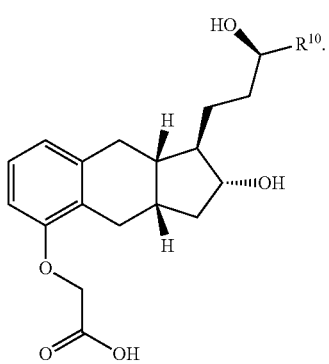

The present invention also provides novel intermediates that are useful for the synthesis of the compound of Formula I.

I. Definitions

As used herein, the following definitions shall apply unless otherwise indicated.

For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001, the entire contents of which are hereby incorporated by reference.

As used herein, the term "Treprostinil" refers to (1R,2R, 3aS,9aS)-[[2,3,3a,4,9,9a-hexahydro-2-hydroxy-1-[(3S)-3-hydroxyoctyl]-1H-benz[f]inden-5-yl]oxy]acetic acid having the chemical structure, illustrated below, of the compound of Formula I

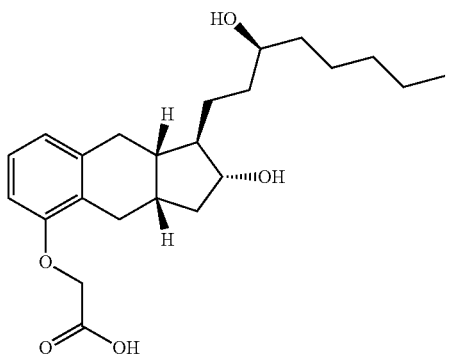

Treprostinil is a synthetic analog of prostacyclin (PGI$_2$) that is indicated for the treatment of pulmonary arterial hypertension and other diseases in patients. Treprostinil is formulated into a variety of dosage forms including forms suited for i.v. infusion and inhalation.

As used herein, the term "2-hydroxy-N-(2-hydroxyethyl)-N-methylethanaminium 2-(((1R,2R,3aS,9aS)-2-hydroxy-1-((S)-3-hydroxyoctyl)-2,3,3a,4,9,9a-hexahydro-1H-cyclopenta[b]naphthalen-5-yl)oxy)acetate" refers to the N-methyldiethanolamine salt of Treprostinil. The N-methyldiethanolamine salt of Treprostinil is also represented by the structural depiction

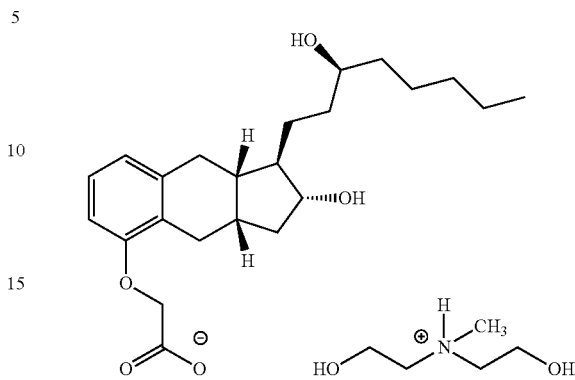

and equivalents thereof.

As described herein, compounds of the invention may optionally be substituted with one or more substituents, such as are illustrated generally above, or as exemplified by particular classes, subclasses, and species of the invention.

As used herein, the term "hydroxyl" or "hydroxy" refers to an —OH moiety.

As used herein the term "aliphatic" encompasses the terms alkyl, alkenyl, alkynyl, each of which being optionally substituted as set forth below.

As used herein, an "alkyl" group refers to a saturated aliphatic hydrocarbon group containing 1-12 (e.g., 1-8, 1-6, or 1-4) carbon atoms. An alkyl group can be straight or branched. Examples of alkyl groups include, but are not limited to, methyl, ethyl, propyl, isopropyl, butyl, isobutyl, sec-butyl, tert-butyl, n-pentyl, n-heptyl, or 2-ethylhexyl. An alkyl group can be substituted (i.e., optionally substituted) with one or more substituents such as halo, phospho, cycloaliphatic [e.g., cycloalkyl or cycloalkenyl], heterocycloaliphatic [e.g., heterocycloalkyl or heterocycloalkenyl], aryl, heteroaryl, alkoxy, aroyl, heteroaroyl, acyl [e.g., (aliphatic)carbonyl, (cycloaliphatic)carbonyl, or (heterocycloaliphatic)carbonyl], nitro, cyano, amido [e.g., (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, heteroaralkylcarbonylamino alkylaminocarbonyl, cycloalkylaminocarbonyl, heterocycloalkylaminocarbonyl, arylaminocarbonyl, or heteroarylaminocarbonyl], amino [e.g., aliphaticamino, cycloaliphaticamino, or heterocycloaliphaticamino], sulfonyl [e.g., aliphatic-SO$_2$—], sulfinyl, sulfanyl, sulfoxy, urea, thiourea, sulfamoyl, sulfamide, oxo, carboxy, carbamoyl, cycloaliphaticoxy, heterocycloaliphaticoxy, aryloxy, heteroaryloxy, aralkyloxy, heteroarylalkoxy, alkoxycarbonyl, alkylcarbonyloxy, or hydroxy. Without limitation, some examples of substituted alkyls include carboxyalkyl (such as HOOC-alkyl, alkoxycarbonylalkyl, and alkylcarbonyloxyalkyl), cyanoalkyl, hydroxyalkyl, alkoxyalkyl, acylalkyl, aralkyl, (alkoxyaryl)alkyl, (sulfonylamino)alkyl (such as (alkyl-SO$_2$-amino)alkyl), aminoalkyl, amidoalkyl, (cycloaliphatic)alkyl, or haloalkyl.

As used herein, an "alkenyl" group refers to an aliphatic carbon group that contains 2-8 (e.g., 2-12, 2-6, or 2-4) carbon atoms and at least one double bond. Like an alkyl group, an alkenyl group can be straight or branched. Examples of an alkenyl group include, but are not limited to allyl, 1- or 2-isopropenyl, 2-butenyl, and 2-hexenyl. An alkenyl group can be optionally substituted with one or more substituents such as halo, phospho, cycloaliphatic [e.g., cycloalkyl or cycloalkenyl], heterocycloaliphatic [e.g., heterocycloalkyl or heterocycloalkenyl], aryl, heteroaryl, alkoxy, aroyl, heteroaroyl, acyl [e.g., (aliphatic)carbonyl, (cycloaliphatic)carbonyl, or (heterocycloaliphatic)carbonyl], nitro, cyano, amido [e.g., (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, heteroaralkylcarbonylamino alkylaminocarbonyl, cycloalkylaminocarbonyl, heterocycloalkylaminocarbonyl, arylaminocarbonyl, or heteroarylaminocarbonyl], amino [e.g., aliphaticamino, cycloaliphaticamino, heterocycloaliphaticamino, or aliphaticsulfonylamino], sulfonyl [e.g., alkyl-$SO_2$—, cycloaliphatic-$SO_2$—, or aryl-$SO_2$—], sulfinyl, sulfanyl, sulfoxy, urea, thiourea, sulfamoyl, sulfamide, oxo, carboxy, carbamoyl, cycloaliphaticoxy, heterocycloaliphaticoxy, aryloxy, heteroaryloxy, aralkyloxy, heteroaralkoxy, alkoxycarbonyl, alkylcarbonyloxy, or hydroxy. Without limitation, some examples of substituted alkenyls include cyanoalkenyl, alkoxyalkenyl, acylalkenyl, hydroxyalkenyl, aralkenyl, (alkoxyaryl)alkenyl, (sulfonylamino)alkenyl (such as (alkyl-$SO_2$-amino)alkenyl), aminoalkenyl, amidoalkenyl, (cycloaliphatic)alkenyl, or haloalkenyl.

As used herein, an "alkynyl" group refers to an aliphatic carbon group that contains 2-8 (e.g., 2-12, 2-6, or 2-4) carbon atoms and has at least one triple bond. An alkynyl group can be straight or branched. Examples of an alkynyl group include, but are not limited to, propargyl and butynyl. An alkynyl group can be optionally substituted with one or more substituents such as aroyl, heteroaroyl, alkoxy, cycloalkyloxy, heterocycloalkyloxy, aryloxy, heteroaryloxy, aralkyloxy, nitro, carboxy, cyano, halo, hydroxy, sulfo, mercapto, sulfanyl [e.g., aliphaticsulfanyl or cycloaliphaticsulfanyl], sulfinyl [e.g., aliphaticsulfinyl or cycloaliphaticsulfinyl], sulfonyl [e.g., aliphatic-$SO_2$—, aliphaticamino-$SO_2$—, or cycloaliphatic-$SO_2$—], amido [e.g., aminocarbonyl, alkylaminocarbonyl, alkylcarbonylamino, cycloalkylaminocarbonyl, heterocycloalkylaminocarbonyl, cycloalkylcarbonylamino, arylaminocarbonyl, arylcarbonylamino, aralkylcarbonylamino, (heterocycloalkyl)carbonylamino, (cycloalkylalkyl)carbonylamino, heteroaralkylcarbonylamino, heteroarylcarbonylamino or heteroarylaminocarbonyl], urea, thiourea, sulfamoyl, sulfamide, alkoxycarbonyl, alkylcarbonyloxy, cycloaliphatic, heterocycloaliphatic, aryl, heteroaryl, acyl [e.g., (cycloaliphatic)carbonyl or (heterocycloaliphatic)carbonyl], amino [e.g., aliphaticamino], sulfoxy, oxo, carboxy, carbamoyl, (cycloaliphatic)oxy, (heterocycloaliphatic)oxy, or (heteroaryl)alkoxy.

As used herein, an "amido" encompasses both "aminocarbonyl" and "carbonylamino". These terms when used alone or in connection with another group refer to an amido group such as —N($R^X$)—C(O)—$R^Y$ or —C(O)—N($R^X$)$_2$, when used terminally, and —C(O)—N($R^X$)— or —N($R^X$)—C(O)— when used internally, wherein $R^X$ and $R^Y$ can be aliphatic, cycloaliphatic, aryl, aralphatic, heterocycloaliphatic, heteroaryl or heteroaralphatic. Examples of amido groups include alkylamido (such as alkylcarbonylamino or alkylaminocarbonyl), (heterocycloaliphatic)amido, (heteroaralkyl)amido, (heteroaryl)amido, (heterocycloalkyl)alkylamido, arylamido, aralkylamido, (cycloalkyl)alkylamido, or cycloalkylamido.

As used herein, an "amino" group refers to —$NR^XR^Y$ wherein each of $R^X$ and $R^Y$ is independently hydrogen, aliphatic, cycloaliphatic, (cycloaliphatic)aliphatic, aryl, aralphatic, heterocycloaliphatic, (heterocycloaliphatic)aliphatic, heteroaryl, carboxy, sulfanyl, sulfinyl, sulfonyl, (aliphatic)carbonyl, (cycloaliphatic)carbonyl, ((cycloaliphatic)aliphatic)carbonyl, arylcarbonyl, (aralphatic)carbonyl, (heterocycloaliphatic)carbonyl, ((heterocycloaliphatic)aliphatic)carbonyl, (heteroaryl)carbonyl, or (heteroaralphatic)carbonyl, each of which being defined herein and being optionally substituted. Examples of amino groups include alkylamino, dialkylamino, or arylamino. When the term "amino" is not the terminal group (e.g., alkylcarbonylamino), it is represented by —$NR^X$—, where $R^X$ has the same meaning as defined above.

As used herein, an "aryl" group used alone or as part of a larger moiety as in "aralkyl", "aralkoxy", or "aryloxyalkyl" refers to monocyclic (e.g., phenyl); bicyclic (e.g., indenyl, naphthalenyl, tetrahydronaphthyl, tetrahydroindenyl); and tricyclic (e.g., fluorenyl tetrahydrofluorenyl, or tetrahydroanthracenyl, anthracenyl) ring systems in which the monocyclic ring system is aromatic or at least one of the rings in a bicyclic or tricyclic ring system is aromatic. The bicyclic and tricyclic groups include benzofused 2-3 membered carbocyclic rings. For example, a benzofused group includes phenyl fused with two or more $C_4$-s carbocyclic moieties. An aryl is optionally substituted with one or more substituents including aliphatic [e.g., alkyl, alkenyl, or alkynyl]; cycloaliphatic; (cycloaliphatic)aliphatic; heterocycloaliphatic; (heterocycloaliphatic)aliphatic; aryl; heteroaryl; alkoxy; (cycloaliphatic)oxy; (heterocycloaliphatic)oxy; aryloxy; heteroaryloxy; (aralphatic)oxy; (heteroaralphatic)oxy; aroyl; heteroaroyl; amino; oxo (on a non-aromatic carbocyclic ring of a benzofused bicyclic or tricyclic aryl); nitro; carboxy; amido; acyl [e.g., (aliphatic)carbonyl; (cycloaliphatic)carbonyl; ((cycloaliphatic)aliphatic)carbonyl; (aralphatic)carbonyl; (heterocycloaliphatic)carbonyl; ((heterocycloaliphatic)aliphatic)carbonyl; or (heteroaralphatic)carbonyl]; sulfonyl [e.g., aliphatic-$SO_2$— or amino-$SO_2$—]; sulfinyl [e.g., aliphatic-S(O)— or cycloaliphatic-S(O)—]; sulfanyl [e.g., aliphatic-S—]; cyano; halo; hydroxy; mercapto; sulfoxy; urea; thiourea; sulfamoyl; sulfamide; or carbamoyl. Alternatively, an aryl can be unsubstituted.

Non-limiting examples of substituted aryls include haloaryl [e.g., mono-, di (such as p,m-dihaloaryl), and (trihalo)aryl]; (carboxy)aryl [e.g., (alkoxycarbonyl)aryl, ((aralkyl)carbonyloxy)aryl, and (alkoxycarbonyl)aryl]; (amido)aryl [e.g., (aminocarbonyl)aryl, (((alkylamino)alkyl) aminocarbonyl)aryl, (alkylcarbonyl)aminoaryl, (arylaminocarbonyl)aryl, and (((heteroaryl)amino)carbonyl)aryl]; aminoaryl [e.g., ((alkylsulfonyl)amino)aryl or ((dialkyl)amino)aryl]; (cyanoalkyl)aryl; (alkoxy)aryl; (sulfamoyl)aryl [e.g., (aminosulfonyl)aryl]; (alkylsulfonyl)aryl; (cyano)aryl; (hydroxyalkyl)aryl; ((alkoxy)alkyl)aryl; (hydroxy)aryl, ((carboxy)alkyl)aryl; (((dialkyl)amino)alkyl)aryl; (nitroalkyl)aryl; (((alkylsulfonyl)amino)alkyl)aryl; ((heterocycloaliphatic)carbonyl)aryl; ((alkylsulfonyl)alkyl)aryl; (cyanoalkyl)aryl; (hydroxyalkyl)aryl; (alkylcarbonyl)aryl; alkylaryl; (trihaloalkyl)aryl; p-amino-m-alkoxycarbonylaryl; p-amino-m-cyanoaryl; p-halo-m-aminoaryl; or (m-(heterocycloaliphatic)-o-(alkyl))aryl.

As used herein, an "aralphatic" such as an "aralkyl" group refers to an aliphatic group (e.g., a $C_{1-4}$ alkyl group) that is substituted with an aryl group. "Aliphatic," "alkyl," and "aryl" are defined herein. An example of an aralphatic such as an aralkyl group is benzyl.

As used herein, an "aralkyl" group refers to an alkyl group (e.g., a $C_{1-4}$ alkyl group) that is substituted with an aryl group. Both "alkyl" and "aryl" have been defined above. An example of an aralkyl group is benzyl. An aralkyl is optionally substituted with one or more substituents such as aliphatic [e.g., alkyl, alkenyl, or alkynyl, including carboxyalkyl, hydroxyalkyl, or haloalkyl such as trifluoromethyl], cycloaliphatic [e.g., cycloalkyl or cycloalkenyl], (cycloalkyl)alkyl, heterocycloalkyl, (heterocycloalkyl)alkyl, aryl, heteroaryl, alkoxy, cycloalkyloxy, heterocycloalkyloxy, aryloxy, heteroaryloxy, aralkyloxy, heteroaralkyloxy, aroyl, heteroaroyl, nitro, carboxy, alkoxycarbonyl, alkylcarbonyloxy, amido [e.g., aminocarbonyl, alkylcarbonylamino, cycloalkylcarbonylamino, (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, or heteroaralkylcarbonylamino], cyano, halo, hydroxy, acyl, mercapto, alkylsulfanyl, sulfoxy, urea, thiourea, sulfamoyl, sulfamide, oxo, or carbamoyl.

As used herein, a "bicyclic ring system" includes 6-12 (e.g., 8-12 or 9, 10, or 11) membered structures that form two rings, wherein the two rings have at least one atom in common (e.g., 2 atoms in common). Bicyclic ring systems include bicycloaliphatics (e.g., bicycloalkyl or bicycloalkenyl), bicycloheteroaliphatics, bicyclic aryls, and bicyclic heteroaryls.

As used herein, a "cycloaliphatic" group encompasses a "cycloalkyl" group and a "cycloalkenyl" group, each of which being optionally substituted as set forth below.

As used herein, a "cycloalkyl" group refers to a saturated carbocyclic mono- or bicyclic (fused or bridged) ring of 3-10 (e.g., 5-10) carbon atoms. Examples of cycloalkyl groups include cyclopropyl, cyclobutyl, cyclopentyl, cyclohexyl, cycloheptyl, adamantyl, norbornyl, cubyl, octahydroindenyl, decahydro-naphthyl, bicyclo[3.2.1]octyl, bicyclo[2.2.2]octyl, bicyclo[3.3.1]nonyl, bicyclo[3.3.2.]decyl, bicyclo[2.2.2]octyl, adamantyl, or ((aminocarbonyl)cycloalkyl)cycloalkyl.

A "cycloalkenyl" group, as used herein, refers to a non-aromatic carbocyclic ring of 3-10 (e.g., 4-8) carbon atoms having one or more double bonds. Examples of cycloalkenyl groups include cyclopentenyl, 1,4-cyclohexa-di-enyl, cycloheptenyl, cyclooctenyl, hexahydro-indenyl, octahydro-naphthyl, cyclohexenyl, bicyclo[2.2.2]octenyl, or bicyclo[3.3.1]nonenyl.

A cycloalkyl or cycloalkenyl group can be optionally substituted with one or more substituents such as phospho, aliphatic [e.g., alkyl, alkenyl, or alkynyl], cycloaliphatic, (cycloaliphatic) aliphatic, heterocycloaliphatic, (heterocycloaliphatic) aliphatic, aryl, heteroaryl, alkoxy, (cycloaliphatic)oxy, (heterocycloaliphatic)oxy, aryloxy, heteroaryloxy, (araliphatic)oxy, (heteroaraliphatic)oxy, aroyl, heteroaroyl, amino, amido [e.g., (aliphatic)carbonylamino, (cycloaliphatic)carbonylamino, ((cycloaliphatic)aliphatic)carbonylamino, (aryl)carbonylamino, (araliphatic)carbonylamino, (heterocycloaliphatic)carbonylamino, ((heterocycloaliphatic)aliphatic)carbonylamino, (heteroaryl)carbonylamino, or (heteroaraliphatic)carbonylamino], nitro, carboxy [e.g., HOOC—, alkoxycarbonyl, or alkylcarbonyloxy], acyl [e.g., (cycloaliphatic)carbonyl, ((cycloaliphatic) aliphatic)carbonyl, (araliphatic)carbonyl, (heterocycloaliphatic)carbonyl, ((heterocycloaliphatic)aliphatic)carbonyl, or (heteroaraliphatic)carbonyl], cyano, halo, hydroxy, mercapto, sulfonyl [e.g., alkyl-$SO_2$— and aryl-$SO_2$—], sulfinyl [e.g., alkyl-S(O)—], sulfanyl [e.g., alkyl-S—], sulfoxy, urea, thiourea, sulfamoyl, sulfamide, oxo, or carbamoyl.

As used herein, the term "heterocycloaliphatic" encompasses heterocycloalkyl groups and heterocycloalkenyl groups, each of which being optionally substituted as set forth below.

As used herein, a "heterocycloalkyl" group refers to a 3-10 membered mono- or bicyclic (fused or bridged) (e.g., 5- to 10-membered mono- or bicyclic) saturated ring structure, in which one or more of the ring atoms is a heteroatom (e.g., N, O, S, or combinations thereof). Examples of a heterocycloalkyl group include piperidyl, piperazyl, tetrahydropyranyl, tetrahydrofuryl, 1,4-dioxolanyl, 1,4-dithianyl, 1,3-dioxolanyl, oxazolidyl, isoxazolidyl, morpholinyl, thiomorpholyl, octahydrobenzofuryl, octahydrochromenyl, octahydrothiochromenyl, octahydroindolyl, octahydropyrindinyl, decahydroquinolinyl, octahydrobenzo[b]thiopheneyl, 2-oxa-bicyclo[2.2.2]octyl, 1-aza-bicyclo[2.2.2]octyl, 3-aza-bicyclo[3.2.1]octyl, and 2,6-dioxa-tricyclo[3.3.1.0$^{3,7}$]nonyl. A monocyclic heterocycloalkyl group can be fused with a phenyl moiety to form structures, such as tetrahydroisoquinoline, which would be categorized as heteroaryls.

A "heterocycloalkenyl" group, as used herein, refers to a mono- or bicyclic (e.g., 5- to 10-membered mono- or bicyclic) non-aromatic ring structure having one or more double bonds, and wherein one or more of the ring atoms is a heteroatom (e.g., N, O, or S). Monocyclic and bicyclic heterocycloaliphatics are numbered according to standard chemical nomenclature.

A heterocycloalkyl or heterocycloalkenyl group can be optionally substituted with one or more substituents such as phospho, aliphatic [e.g., alkyl, alkenyl, or alkynyl], cycloaliphatic, (cycloaliphatic)aliphatic, heterocycloaliphatic, (heterocycloaliphatic)aliphatic, aryl, heteroaryl, alkoxy, (cycloaliphatic)oxy, (heterocycloaliphatic)oxy, aryloxy, heteroaryloxy, (araliphatic)oxy, (heteroaraliphatic)oxy, aroyl, heteroaroyl, amino, amido [e.g., (aliphatic)carbonylamino, (cycloaliphatic)carbonylamino, ((cycloaliphatic) aliphatic) carbonylamino, (aryl)carbonylamino, (araliphatic)carbonylamino, (heterocycloaliphatic)carbonylamino, ((heterocycloaliphatic) aliphatic)carbonylamino, (heteroaryl) carbonylamino, or (heteroaraliphatic)carbonylamino], nitro, carboxy [e.g., HOOC—, alkoxycarbonyl, or alkylcarbonyloxy], acyl [e.g., (cycloaliphatic)carbonyl, ((cycloaliphatic) aliphatic)carbonyl, (araliphatic)carbonyl, (heterocycloaliphatic)carbonyl, ((heterocycloaliphatic)aliphatic)carbonyl, or (heteroaraliphatic)carbonyl], nitro, cyano, halo, hydroxy, mercapto, sulfonyl [e.g., alkylsulfonyl or arylsulfonyl], sulfinyl [e.g., alkylsulfinyl], sulfanyl [e.g., alkylsulfanyl], sulfoxy, urea, thiourea, sulfamoyl, sulfamide, oxo, or carbamoyl.

A "heteroaryl" group, as used herein, refers to a monocyclic, bicyclic, or tricyclic ring system having 4 to 15 ring atoms wherein one or more of the ring atoms is a heteroatom (e.g., N, O, S, or combinations thereof) and in which the monocyclic ring system is aromatic or at least one of the rings in the bicyclic or tricyclic ring systems is aromatic. A heteroaryl group includes a benzofused ring system having 2 to 3 rings. For example, a benzofused group includes benzo fused with one or two 4 to 8 membered heterocycloaliphatic moieties (e.g., indolizyl, indolyl, isoindolyl, 3H-indolyl, indolinyl, benzo[b]furyl, benzo[b]thiophene-yl, quinolinyl, or isoquinolinyl). Some examples of heteroaryl are azetidinyl, pyridyl, 1H-indazolyl, furyl, pyrrolyl, thienyl, thiazolyl, oxazolyl, imidazolyl, tetrazolyl, benzofuryl, isoquinolinyl, benzthiazolyl, xanthene, thioxanthene, phenothiazine, dihydroindole, benzo[1,3]dioxole, benzo[b]furyl, benzo[b]thiophenyl, indazolyl, benzimidazolyl, benzthiazolyl, puryl, cinnolyl, quinolyl, quinazolyl, cinnolyl, phthalazyl, quinazolyl, quinoxalyl, isoquinolyl, 4H-quinolizyl, benzo-1,2,5-thiadiazolyl, or 1,8-naphthyridyl.

Without limitation, monocyclic heteroaryls include furyl, thiophene-yl, 2H-pyrrolyl, pyrrolyl, oxazolyl, thazolyl, imidazolyl, pyrazolyl, isoxazolyl, isothiazolyl, 1,3,4-thiadiazolyl, 2H-pyranyl, 4-H-pranyl, pyridyl, pyridazyl, pyrimidyl, pyrazolyl, pyrazyl, or 1,3,5-triazinyl. Monocyclic heteroaryls are numbered according to standard chemical nomenclature.

Without limitation, bicyclic heteroaryls include indolizyl, indolyl, isoindolyl, 3H-indolyl, indolinyl, benzo[b]furyl, benzo[b]thiophenyl, quinolinyl, isoquinolinyl, indolizyl, isoindolyl, indolyl, benzo[b]furyl, benzo[b]thiophenyl, indazolyl, benzimidazyl, benzthiazolyl, purinyl, 4H-quinolizyl, quinolyl, isoquinolyl, cinnolyl, phthalazyl, quinazolyl, quinoxalyl, 1,8-naphthyridyl, or pteridyl. Bicyclic heteroaryls are numbered according to standard chemical nomenclature.

A heteroaryl is optionally substituted with one or more substituents such as aliphatic [e.g., alkyl, alkenyl, or alkynyl]; cycloaliphatic; (cycloaliphatic)aliphatic; heterocycloaliphatic; (heterocycloaliphatic)aliphatic; aryl; heteroaryl; alkoxy; (cycloaliphatic)oxy; (heterocycloaliphatic)oxy; aryloxy; heteroaryloxy; (araliphatic)oxy; (heteroaraliphatic) oxy; aroyl; heteroaroyl; amino; oxo (on a non-aromatic carbocyclic or heterocyclic ring of a bicyclic or tricyclic heteroaryl); carboxy; amido; acyl [e.g., aliphaticcarbonyl; (cycloaliphatic)carbonyl; ((cycloaliphatic)aliphatic)carbonyl; (araliphatic)carbonyl; (heterocycloaliphatic)carbonyl; ((heterocycloaliphatic)aliphatic)carbonyl; or (heteroaraliphatic)carbonyl]; sulfonyl [e.g., aliphaticsulfonyl or aminosulfonyl]; sulfinyl [e.g., aliphaticsulfinyl]; sulfanyl [e.g., aliphaticsulfanyl]; nitro; cyano; halo; hydroxy; mercapto; sulfoxy; urea; thiourea; sulfamoyl; sulfamide; or carbamoyl. Alternatively, a heteroaryl can be unsubstituted.

Non-limiting examples of substituted heteroaryls include (halo)heteroaryl [e.g., mono- and di-(halo)heteroaryl]; (carboxy)heteroaryl [e.g., (alkoxycarbonyl)heteroaryl]; cyanoheteroaryl; aminoheteroaryl [e.g., ((alkylsulfonyl)amino) heteroaryl and ((dialkyl)amino)heteroaryl]; (amido) heteroaryl [e.g., aminocarbonylheteroaryl, ((alkylcarbonyl) amino)heteroaryl, ((((alkyl)amino)alkyl)aminocarbonyl) heteroaryl, (((heteroaryl)amino)carbonyl)heteroaryl, ((heterocycloaliphatic)carbonyl)heteroaryl, and ((alkylcarbonyl)amino)heteroaryl]; (cyanoalkyl)heteroaryl; (alkoxy) heteroaryl; (sulfamoyl)heteroaryl [e.g., (aminosulfonyl)heteroaryl]; (sulfonyl)heteroaryl [e.g., (alkylsulfonyl) heteroaryl]; (hydroxyalkyl)heteroaryl; (alkoxyalkyl) heteroaryl; (hydroxy)heteroaryl; ((carboxy)alkyl)heteroaryl; (((dialkyl)amino)alkyl]heteroaryl; (heterocycloaliphatic) heteroaryl; (cycloaliphatic)heteroaryl; (nitroalkyl)heteroaryl; (((alkylsulfonyl)amino)alkyl)heteroaryl; ((alkylsulfonyl)alkyl)heteroaryl; (cyanoalkyl)heteroaryl; (acyl) heteroaryl [e.g., (alkylcarbonyl)heteroaryl]; (alkyl) heteroaryl; or (haloalkyl)heteroaryl [e.g., trihaloalkylheteroaryl].

A "heteroaraliphatic (such as a heteroaralkyl group) as used herein, refers to an aliphatic group (e.g., a $C_{1-4}$ alkyl group) that is substituted with a heteroaryl group. "Aliphatic," "alkyl," and "heteroaryl" have been defined above.

A "heteroaralkyl" group, as used herein, refers to an alkyl group (e.g., a $C_{1-4}$ alkyl group) that is substituted with a heteroaryl group. Both "alkyl" and "heteroaryl" have been defined above. A heteroaralkyl is optionally substituted with one or more substituents such as alkyl (including carboxyalkyl, hydroxyalkyl, and haloalkyl such as trifluoromethyl), alkenyl, alkynyl, cycloalkyl, (cycloalkyl)alkyl, heterocycloalkyl, (heterocycloalkyl)alkyl, aryl, heteroaryl, alkoxy, cycloalkyloxy, heterocycloalkyloxy, aryloxy, heteroaryloxy, aralkyloxy, heteroaralkyloxy, aroyl, heteroaroyl, nitro, carboxy, alkoxycarbonyl, alkylcarbonyloxy, aminocarbonyl, alkylcarbonylamino, cycloalkylcarbonylamino, (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, heteroaralkylcarbonylamino, cyano, halo, hydroxy, acyl, mercapto, alkylsulfanyl, sulfoxy, urea, thiourea, sulfamoyl, sulfamide, oxo, or carbamoyl.

As used herein, "cyclic moiety" and "cyclic group" refer to mono-, bi-, and tri-cyclic ring systems including cycloaliphatic, heterocycloaliphatic, aryl, or heteroaryl, each of which has been previously defined.

As used herein, a "bridged bicyclic ring system" refers to a bicyclic heterocyclicalipahtic ring system or bicyclic cycloaliphatic ring system in which the rings are bridged. Examples of bridged bicyclic ring systems include, but are not limited to, adamantanyl, norbomanyl, bicyclo[3.2.1] octyl, bicyclo[2.2.2]octyl, bicyclo[3.3.1]nonyl, bicyclo [3.3.2]decyl, 2-oxabicyclo[2.2.2]octyl, 1-azabicyclo[2.2.2] octyl, 3-azabicyclo[3.2.1]octyl, and 2,6-dioxa-tricyclo [3.3.1.0$^{3,7}$]nonyl. A bridged bicyclic ring system can be optionally substituted with one or more substituents such as alkyl (including carboxyalkyl, hydroxyalkyl, and haloalkyl such as trifluoromethyl), alkenyl, alkynyl, cycloalkyl, (cycloalkyl)alkyl, heterocycloalkyl, (heterocycloalkyl)alkyl, aryl, heteroaryl, alkoxy, cycloalkyloxy, heterocycloalkyloxy, aryloxy, heteroaryloxy, aralkyloxy, heteroaralkyloxy, aroyl, heteroaroyl, nitro, carboxy, alkoxycarbonyl, alkylcarbonyloxy, aminocarbonyl, alkylcarbonylamino, cycloalkylcarbonylamino, (cycloalkylalkyl)carbonylamino, arylcarbonylamino, aralkylcarbonylamino, (heterocycloalkyl) carbonylamino, (heterocycloalkylalkyl)carbonylamino, heteroarylcarbonylamino, heteroaralkylcarbonylamino, cyano, halo, hydroxy, acyl, mercapto, alkylsulfanyl, sulfoxy, urea, thiourea, sulfamoyl, sulfamide, oxo, or carbamoyl.

As used herein, an "acyl" group refers to a formyl group or $R^X$—C(O)— (such as alkyl-C(O)—, also referred to as "alkylcarbonyl") where $R^X$ and "alkyl" have been defined previously. Acetyl and pivaloyl are examples of acyl groups.

As used herein, an "aroyl" or "heteroaroyl" refers to an aryl-C(O)— or a heteroaryl-C(O)—. The aryl and heteroaryl portion of the aroyl or heteroaroyl is optionally substituted as previously defined.

As used herein, an "alkoxy" group refers to an alkyl-O— group where "alkyl" has been defined previously.

As used herein, a "carbamoyl" group refers to a group having the structure —O—CO—NR$^X$R$^Y$ or —NR$^X$—CO—O—R$^Z$, wherein R$^X$ and R$^Y$ have been defined above and R$^Z$ can be aliphatic, aryl, aralphatic, heterocycloaliphatic, heteroaryl, or heteroaraliphatic.

As used herein, a "carboxy" group refers to —COOH, —COOR$_X$, —OC(O)H, —OC(O)R$^X$, when used as a terminal group; or —OC(O)— or —C(O)O— when used as an internal group.

As used herein, a "haloaliphatic" group refers to an aliphatic group substituted with 1-3 halogen. For instance, the term haloalkyl includes the group —CF$_3$.

As used herein, a "mercapto" group refers to —SH.

As used herein, a "sulfo" group refers to —SO$_3$H or —SO$_3$R$^X$ when used terminally or —S(O)$_3$— when used internally.

As used herein, a "sulfamide" group refers to the structure —NR$^X$—S(O)$_2$—NR$^Y$R$^Z$ when used terminally and —NR$^X$—S(O)$_2$—NR$^Y$— when used internally, wherein R$^X$, R$^Y$, and R$^Z$ have been defined above.

As used herein, a "sulfamoyl" group refers to the structure —O—S(O)$_2$—NR$^Y$R$^Z$ wherein R$^Y$ and R$^Z$ have been defined above.

As used herein, a "sulfonamide" group refers to the structure —S(O)$_2$—NR$^X$R$^Y$ or —NR$^X$—S(O)$_2$—R$^Z$ when used terminally; or —S(O)$_2$—NR$^X$— or —NR$^X$—S(O)$_2$— when used internally, wherein R$^X$, R$^Y$, and R$^Z$ are defined above.

As used herein a "sulfanyl" group refers to —S—R$^X$ when used terminally and —S— when used internally, wherein R$^X$ has been defined above. Examples of sulfanyls include aliphatic-S—, cycloaliphatic-S—, aryl-S—, or the like.

As used herein a "sulfinyl" group refers to —S(O)—R$^X$ when used terminally and —S(O)— when used internally, wherein R$^X$ has been defined above. Exemplary sulfinyl groups include aliphatic-S(O)—, aryl-S(O)—, (cycloaliphatic(aliphatic))-S(O)—, cycloalkyl-S(O)—, heterocycloaliphatic-S(O)—, heteroaryl-S(O)—, or the like.

As used herein, a "sulfonyl" group refers to —S(O)$_2$—R$^X$ when used terminally and —S(O)$_2$— when used internally, wherein R$^X$ has been defined above. Exemplary sulfonyl groups include aliphatic-S(O)$_2$—, aryl-S(O)$_2$—, (cycloaliphatic(aliphatic))-S(O)$_2$—, cycloaliphatic-S(O)$_2$—, heterocycloaliphatic-S(O)$_2$—, heteroaryl-S(O)$_2$—, (cycloaliphatic (amido(aliphatic)))-S(O)$_2$— or the like.

As used herein, a "sulfoxy" group refers to —O—S(O)—R$^X$ or —S(O)—O—R$^X$, when used terminally and —O—S(O)— or —S(O)—O— when used internally, where R$^X$ has been defined above.

As used herein, a "halogen" or "halo" group refers to fluorine, chlorine, bromine or iodine.

As used herein, an "alkoxycarbonyl," which is encompassed by the term carboxy, used alone or in connection with another group refers to a group such as alkyl-O—C(O)—.

As used herein, an "alkoxyalkyl" refers to an alkyl group such as alkyl-O-alkyl-, wherein alkyl has been defined above.

As used herein, a "carbonyl" refer to —C(O)—.

As used herein, an "oxo" refers to =O.

As used herein, the term "phospho" refers to phosphinates and phosphonates. Examples of phosphinates and phosphonates include —P(O)(R$^P$)$_2$, wherein R$^P$ is aliphatic, alkoxy, aryloxy, heteroaryloxy, (cycloaliphatic)oxy, (heterocycloaliphatic)oxy aryl, heteroaryl, cycloaliphatic or amino.

As used herein, an "aminoalkyl" refers to the structure (R$^X$)$_2$N-alkyl-.

As used herein, a "cyanoalkyl" refers to the structure (NC)-alkyl-.

As used herein, a "urea" group refers to the structure —NR$^X$—CO—NR$^Y$R$^Z$ and a "thiourea" group refers to the structure —NR$^X$—CS—NR$^Y$R$^Z$ when used terminally and —NR$^X$—CO—NR$^Y$— or —NR$^X$—CS—NR$^Y$— when used internally, wherein R$^X$, R$^Y$, and R$^Z$ have been defined above.

As used herein, a "guanidine" group refers to the structure —N=C(N(R$^X$R$^Y$))N(R$^X$R$^Y$) or —NR$^X$—C(=NR$^X$)NR$^X$R$^Y$ wherein R$^X$ and R$^Y$ have been defined above.

As used herein, the term "amidino" group refers to the structure —C=(NR$^X$)N(R$^X$R$^Y$) wherein R$^X$ and R$^Y$ have been defined above.

In general, the term "vicinal" refers to the placement of substituents on a group that includes two or more carbon atoms, wherein the substituents are attached to adjacent carbon atoms.

In general, the term "geminal" refers to the placement of substituents on a group that includes two or more carbon atoms, wherein the substituents are attached to the same carbon atom.

The terms "terminally" and "internally" refer to the location of a group within a substituent. A group is terminal when the group is present at the end of the substituent not further bonded to the rest of the chemical structure. Carboxyalkyl, i.e., R$^X$O(O)C-alkyl is an example of a carboxy group used terminally. A group is internal when the group is present in the middle of a substituent of the chemical structure. Alkylcarboxy (e.g., alkyl-C(O)O— or alkyl-OC (O)—) and alkylcarboxyaryl (e.g., alkyl-C(O)O-aryl- or alkyl-O(CO)-aryl-) are examples of carboxy groups used internally.

As used herein, an "aliphatic chain" refers to a branched or straight aliphatic group (e.g., alkyl groups, alkenyl groups, or alkynyl groups). A straight aliphatic chain has the structure —[CH$_2$]$_v$—, where v is 1-12. A branched aliphatic chain is a straight aliphatic chain that is substituted with one or more aliphatic groups. A branched aliphatic chain has the structure —[CQQ]$_v$- where Q is independently a hydrogen or an aliphatic group; however, Q shall be an aliphatic group in at least one instance. The term aliphatic chain includes alkyl chains, alkenyl chains, and alkynyl chains, where alkyl, alkenyl, and alkynyl are defined above.

As used herein, "Dess-Martin periodinane" and its abbreviation "DMP" are used interchangeably. DMP refers to 1,1,1-triacetoxy-1,1-dihydro-1,2-benziodoxol-3(1H)-one having the structure

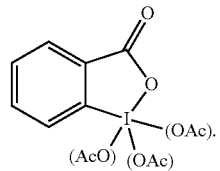

The phrase "optionally substituted" is used interchangeably with the phrase "substituted or unsubstituted." As described herein, compounds of the invention can optionally be substituted with one or more substituents, such as are illustrated generally above, or as exemplified by particular classes, subclasses, and species of the invention. As described herein, the variables R$^1$, R$^2$, R$^3$, R$^4$, R$^{10}$, and other variables contained in Formulae IA and I described herein encompass specific groups, such as alkyl and aryl. Unless otherwise noted, each of the specific groups for the variables R$^1$, R$^2$, R$^3$, R$^4$, R$^{10}$, and other variables contained therein can be optionally substituted with one or more substituents described herein. Each substituent of a specific group is further optionally substituted with one to three of halo, cyano, oxo, alkoxy, hydroxy, amino, nitro, aryl, cycloaliphatic, heterocycloaliphatic, heteroaryl, haloalkyl, and alkyl. For instance, an alkyl group can be substituted with alkylsulfanyl and the alkylsulfanyl can be optionally substituted with one to three of halo, cyano, oxo, alkoxy, hydroxy, amino, nitro, aryl, haloalkyl, and alkyl. As an additional example, the cycloalkyl portion of a (cycloalkyl) carbonylamino can be optionally substituted with one to three of halo, cyano, alkoxy, hydroxy, nitro, haloalkyl, and alkyl. When two alkoxy groups are bound to the same atom or adjacent atoms, the two alkoxy groups can form a ring together with the atom(s) to which they are bound.

In general, the term "substituted," whether preceded by the term "optionally" or not, refers to the replacement of hydrogen atoms in a given structure with the radical of a specified substituent. Specific substituents are described above in the definitions and below in the description of compounds and examples thereof. Unless otherwise indicated, an optionally substituted group can have a substituent at each substitutable position of the group, and when more than one position in any given structure can be substituted with more than one substituent selected from a specified group, the substituent can be either the same or different at every position. A ring substituent, such as a heterocycloalkyl, can be bound to another ring, such as a cycloalkyl, to form a spiro-bicyclic ring system, e.g., both rings share one common atom. As one of ordinary skill in the art will recognize, combinations of substituents envisioned by this invention are those combinations that result in the formation of stable or chemically feasible compounds.

The phrase "stable or chemically feasible," as used herein, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

As used herein, "chemical purity" refers to the degree to which a substance, i.e., the desired product or intermediate, is undiluted or unmixed with extraneous material such as chemical byproducts.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}C$- or $^{14}C$-enriched carbon are within the scope of this invention. Such compounds are useful, for example, as analytical tools or probes in biological assays, or as therapeutic agents.

Chemical structures and nomenclature are derived from ChemDraw, version 11.0.1, Cambridge, Mass.

It is noted that the use of the descriptors "first", "second", "third", or the like is used to differentiate separate elements (e.g., solvents, reaction steps, processes, reagents, or the like) and may or may not refer to the relative order or relative chronology of the elements described.

II. Commonly Used Abbreviations

The following abbreviations are used:
PG protecting group
LG leaving group
DCM dichloromethane
Ac acetyl
THF tetrahydrofuran
TMS trimethylsilyl
TBS tert-butyldimethylsilyl
TIPS tri-iso-propylsilyl
TBDPS tert-butyldiphenylsilyl
TOM tri-iso-propylsilyloxymethyl
DMP Dess-Martin periodinane
IBX 2-iodoxybenzoic acid
DMF dimethylformamide
MTBE methyl-tert-butylether
TBAF tetra-n-butylammonium fluoride
d.e. diastereomeric excess
e.e. enantiomeric excess
EtOAc ethyl acetate
DMSO dimethyl sulfoxide
MeCN acetonitrile
TCA trichloroacetic acid
ATP adenosine triphosphate
EtOH ethanol
Ph phenyl
Me methyl
Et ethyl
Bu butyl
iPr isopropyl
tBu tertbutyl
DEAD diethylazodicarboxylate
HEPES 4-(2-hydroxyethyl)-1-piperazineethanesulfonic acid
DTT dithiothreitol
MOPS 4-morpholinepropanesulfonic acid
NMR nuclear magnetic resonance
HPLC high performance liquid chromatography
LCMS liquid chromatography-mass spectrometry
TLC thin layer chromatography
Rt retention time
HOBt hydroxybenzotriazole
Ms mesyl
Ts tosyl
Tf triflyl
Bs besyl
Ns nosyl
Cbz carboxybenzyl
Moz p-methoxybenzyl carbonyl
Boc tert-butyloxycarbonyl
Fmoc 9-fluorenylmethyloxycarbonyl
Bz benzoly
Bn benzyl
PMB p-methoxybenzyl
DMPM 3,4-dimethoxybenzyl
PMP p-methoxyphenyl

III. Amine Salts

It is noted that the steps recited herein may be performed in any chronological order without regard to step number. For example, step ii) may precede or follow step i), step iii), or step iv).

In one aspect, the present invention provides novel amine salts of the compound of Formula IA

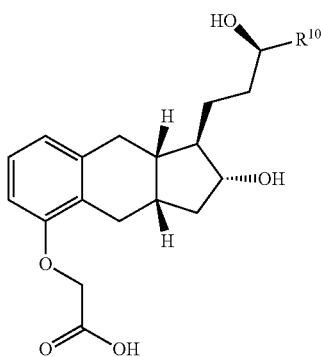

IA wherein R¹⁰ is a linear or branched C₁₋₆ alkyl.

For example, the present invention provides an N-methyldiethanolamine salt of the compound of Formula IA

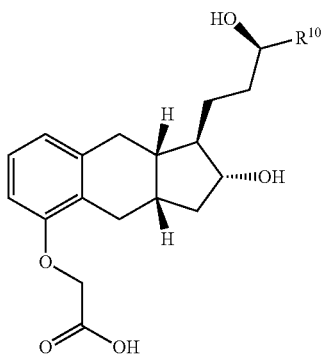

IA wherein R¹⁰ is a linear or branched C₁₋₆ alkyl.

In another example, the compound of Formula IA is a compound of Formula I

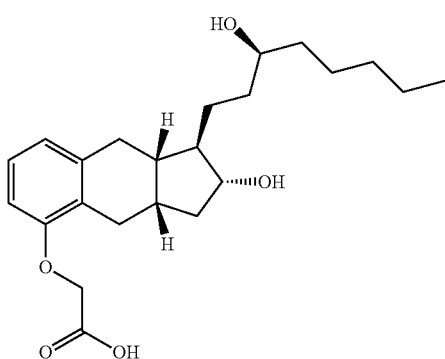

I

IV. Methods of Synthesis

Another aspect of the present invention provides a method of generating an N-methyldiethanolamine salt of the compound of Formula I

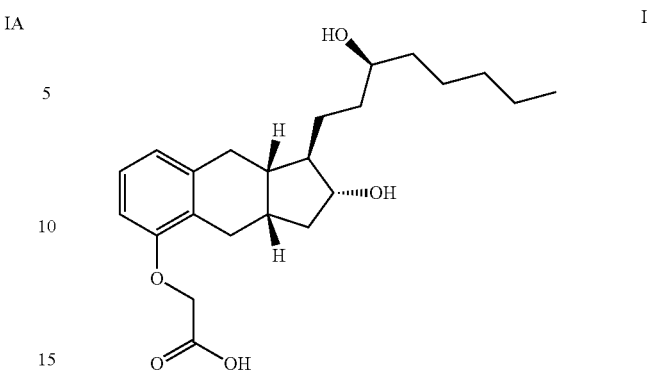

comprising the steps of: i) reacting a compound of Formula 9 with an oxidizing agent in the presence of an organic solvent to generate a compound of Formula 10

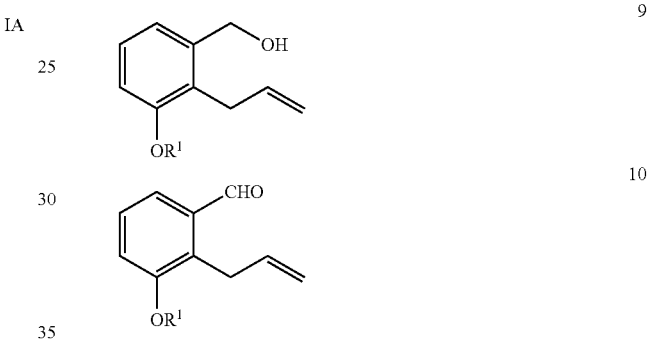

wherein R¹ is C₁₋₆ alkyl and the oxidizing agent comprises MnO₂ or Dess-Martin periodinane; ii) reacting the compound of Formula 10 with a compound of Formula 5 in the presence of a base and an organic solvent to generate a compound of Formula 11, wherein each R² is independently selected from C₁₋₆ alkyl or phenyl; and

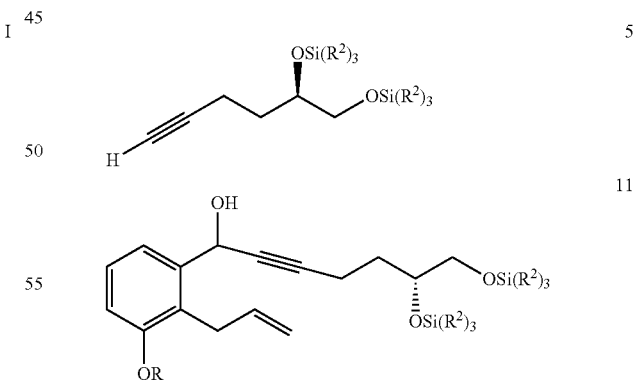

iii) converting the compound of Formula 11 to the N-methyldiethanolamine salt of the compound of Formula I.

A. Step i)

Step i) comprises reacting a compound of Formula 9 with an oxidizing agent in the presence of an organic solvent to generate a compound of Formula 10

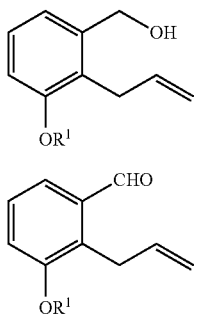

wherein R¹ is C$_{1-6}$ alkyl.

In some implementations, R¹ is methyl, ethyl, propyl, iso-propyl, butyl, sec-butyl, or tert-butyl. For example, R¹ is methyl.

In some implementations, the oxidizing agent of step i) comprises manganese(IV)oxide, i.e., MnO$_2$, DMP, or IBX. For example, the oxidizing agent comprises MnO$_2$ or DMP. And, in some instances, the oxidizing agent comprises MnO$_2$.

The organic solvent of step i) is any suitable solvent that is capable of substantially dissolving the compound of Formula 9 and is substantially inert when combined with the oxidizing agent and the compound of Formula 9. In some implementations, the organic solvent of step i) comprises a halogenated organic solvent. For example, the halogenated organic solvent comprises dichloromethane, i.e., methylene chloride, chloroform, or any combination thereof. In other implementations, the organic solvent (e.g., dichloromethane) is anhydrous.

In some implementations, the reaction of step i) is performed at a temperature from about 10° C. to about 40° C. For example, the reaction of step i) is performed at room temperature.

In other implementations, the reaction of step i) is performed under agitation, e.g., stirring.

In some implementations, the reaction of step i) is performed under an inert gas (e.g., nitrogen gas).

In other implementations, the reaction of step i) is about 99% complete (e.g., from about 95% to about 99.9% complete after about 15 hrs (e.g. from about 14 to about 18 hrs).

In some implementations, step i) generates the compound of Formula 10, having a yield of greater than about 95% (e.g., from about 95% to about 99.9% or about 99%).

B. Step ii)

Step ii) comprises reacting the compound of Formula 10 with a compound of Formula 5 in the presence of a base and an organic solvent to generate a compound of Formula 11, wherein each R² is independently selected from C$_{1-6}$ alkyl or phenyl.

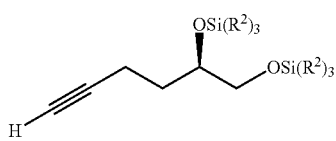

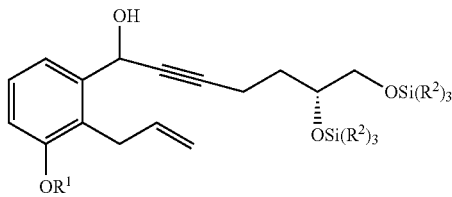

In some implementations, the base comprises an alkyllithium reagent. Examples of alkyllithium reagents include butyllithium, hexyllithium, sec-butyllithium, and methyllithium. In some instances, the base comprises sec-butyllithium.

Organic solvents that are useful in the reaction of step ii) comprise alkanes, cyclic alkanes, heterocycles (e.g., THF, 1,4-dioxane, or any combination thereof), ethers, or any combination thereof.

In some implementations, the organic solvent of step ii) comprises pentane, hexane, cyclohexane, heptane, THF, 1,4-dioxane, diethyl ether, petro ether, MTBE, or any combination thereof. For example, the organic solvent of step ii) comprises MTBE.

In other implementations, the organic solvent of step ii) is anhydrous (e.g., anhydrous MTBE).

And, in some implementations, the base of step ii) comprises sec-butyllithium, and the organic solvent of step ii) comprises MTBE.

In some implementations, the compound of Formula 5 has an e.e. of about 98% or greater (e.g., from about 98.0% to about 99.9%). In other implementations, the compound of Formula 5 has a chemical purity of about 95% or greater (e.g., from about 97% to about 99.9%).

In some implementations, the reaction of step ii) is performed at a temperature from about −80° C. to about 30° C. (e.g., from about −78° C. to about room temperature).

In other implementations, the reaction of step ii) is performed under agitation, e.g., stirring.

In some implementations, the reaction of step ii) is performed under an inert gas (e.g., nitrogen gas).

C. Additional Steps

Steps iv)-vii) may optionally be performed with other steps described herein to generate the compound of Formula I.

Some methods further comprise the steps of: iv) refluxing the compound of Formula 1a in the presence of methanol to generate a compound of Formula 1 having an e.e. of greater than about 98%;

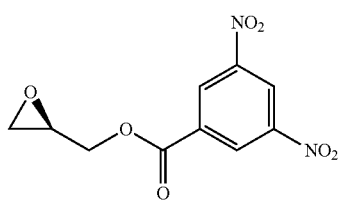

v) reacting the compound of Formula 1 with SiCl(R²)$_3$ under basic conditions to generate the compound of Formula 2;

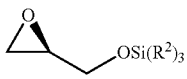

vi) reacting the compound of Formula 2 with 1-TMS-1-propyne to generate the compound of Formula 3; and

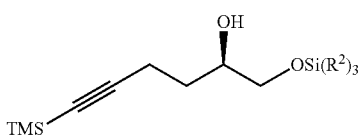

vii) converting the compound of Formula 3 to the compound of Formula 5.

Step iv) is an efficient stereoselective method for generating the compound of Formula 1 having an e.e. of greater than 98% that does not require additional chromatography. Moreover, in some implementations, step iv) generates the compound of Formula 1 with a yield of at least about 90% (e.g., at least about 91%, or about 92%).

In some implementations, the refluxing of the compound of Formula 1a occurs in the presence of an alcohol (e.g., methanol, ethanol, or any combination thereof). In other implementations, the compound of Formula 1a undergoes reflux in the presence of methanol (e.g., anhydrous methanol).

In other implementations, the compound of Formula 1a is heated to reflux under an inert gas (e.g., nitrogen).

And, in some implementations, the compound of Formula 1a is heated to reflux for a period of about 1 to about 3 hrs (e.g., about 2 hrs).

Step v) comprises the protection of the hydroxy functional group of the compound of Formula 1 under basic conditions to generate the alkylsilyl ether compound of Formula 2.

In some implementations, the base of step v) comprises a nitrogen base. In some examples, the nitrogen base comprises Et$_3$N, imidazole, piperidine, piperazine, any combination thereof, or the like. For instance, the base of step v) comprises imidazole.

In some implementations, the SiCl(R$^2$)$_3$ reagent of step v) comprises chloro-tert-butyldimethylsilane (TBS-Cl), tert-butylchlorodiphenyl silane (TBDPS-Cl), chlorotrimethylsilane (TMS-Cl), triisopropylsilyloxymethyl chloride (TOM-Cl), or chlorotriisopropylsilane (TIPS-Cl).

In some implementations, the 1-TMS-1-propyne of step vi) is first reacted with an alkyllithium reagent followed by the reaction with the compound of Formula 2.

The present invention provides a method of generating a compound of Formula 5

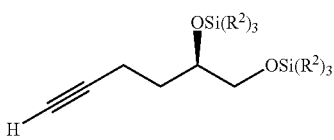

wherein each R$^2$ is independently selected from a C$_{1-6}$ alkyl or phenyl, comprising the steps of: iv) refluxing the compound of Formula 1a in the presence of methanol to generate a compound of Formula 1 having an e.e. of greater than about 98% (e.g., greater than about 98.5%, greater than about 99% or from about 98.5% to about 99.9%);

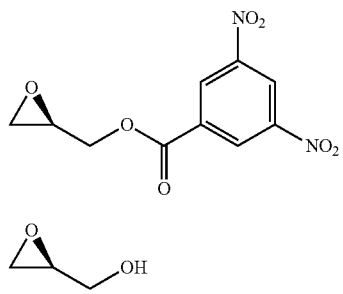

v) reacting the compound of Formula 1 with SiCl(R$^2$)$_3$, wherein each R$^2$ is independently selected from C$_{1-6}$ alkyl or phenyl, under basic conditions to generate the compound of Formula 2;

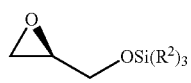

vi) reacting the compound of Formula 2 with 1-TMS-1-propyne to generate the compound of Formula 3;

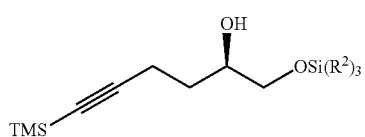

l) deprotecting the compound Formula 3 under basic condition to generate a compound of Formula 4, wherein each of R$^4$ and R$^5$ are H or —OSi(R$^2$)$_3$; and

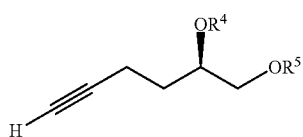

li) reacting the compound of Formula 4 with SiCl(R$^2$)$_3$ under basic conditions to generate the compound of Formula 5, wherein the compound of Formula 5 has a chemical purity of about 98% or greater (e.g., greater than about 98.5%, greater than about 99% or from about 98.5% to about 99.9%) and an e.e. of about 98% or greater (e.g., from about 99% to about 99.99%).

In implementations, the compound of Formula 5 has a chemical purity of about 95% or greater (e.g., from about 97% to about 99.9% or about 99% or greater) and an e.e. of about 98% or greater (e.g., about 99% or greater). In some implementations, the compound of Formula 5 has an e.e. of ~100%, e.g., about 98% or greater, about 99% or greater, or greater than 99%.

Another aspect of the present invention provides a method of generating an N-methyldiethanolamine salt of the compound of Formula I

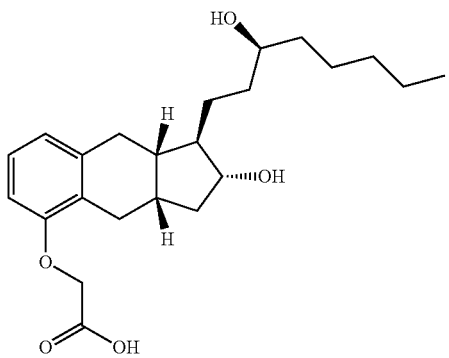

comprising the steps of: viii) reacting a compound of Formula 11 with an oxidizing agent in the presence of an organic solvent to generate a compound of Formula 12

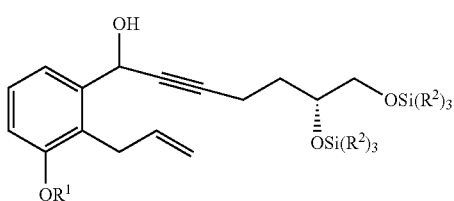

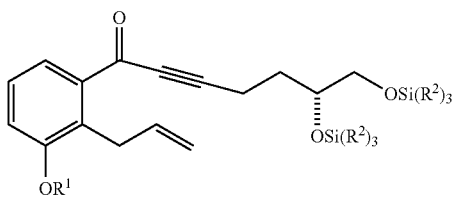

wherein $R^1$ is $C_{1-6}$ alkyl, each $R^2$ is independently selected from $C_{1-6}$ alkyl or phenyl, and the oxidizing agent comprises $MnO_2$; and ix) converting the compound of Formula 12 to the N-methyldiethanolamine salt of the compound of Formula I.

D. Step viii)

The reaction of step viii) accomplishes the oxidation of the compound of Formula 11 to generate the compound of Formula 12 using an oxidizing agent that possesses a reduced toxicity than traditional chromium based oxidation agents (e.g., PCC).

In some implementations, each of the —OSi($R^2$)$_3$ groups in the compounds of Formulae 11 and 12 is independently selected from

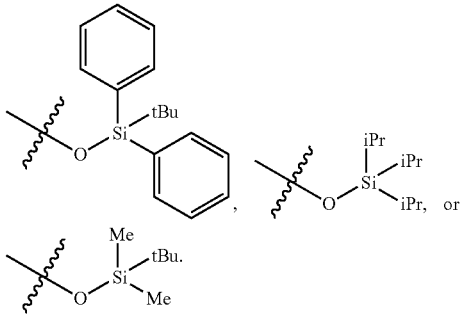

In some implementations, the organic solvent of step viii) comprises a halogenated organic solvent. In some examples, the halogenated organic solvent of step viii) comprises dichloromethane, chloroform, or any combination thereof. In other examples, the organic solvent of step viii) (e.g., dichloromethane) is anhydrous.

Some methods further comprise the steps of: i) reacting a compound of Formula 9 with an oxidizing agent in the presence of an organic solvent to generate a compound of Formula 10

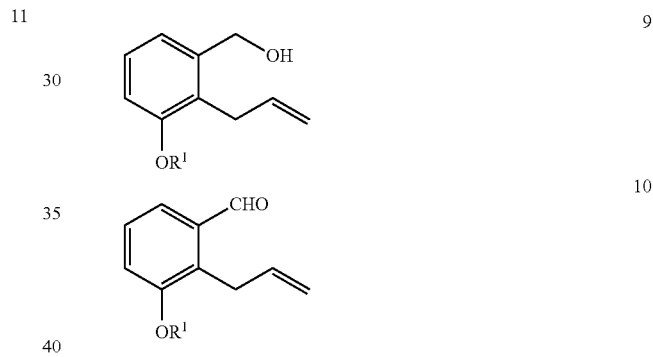

wherein $R^1$ is $C_{1-6}$ alkyl and the oxidizing agent comprises $MnO_2$ or Dess-Martin periodinane; and ii) reacting the compound of Formula 10 with a compound of Formula 5

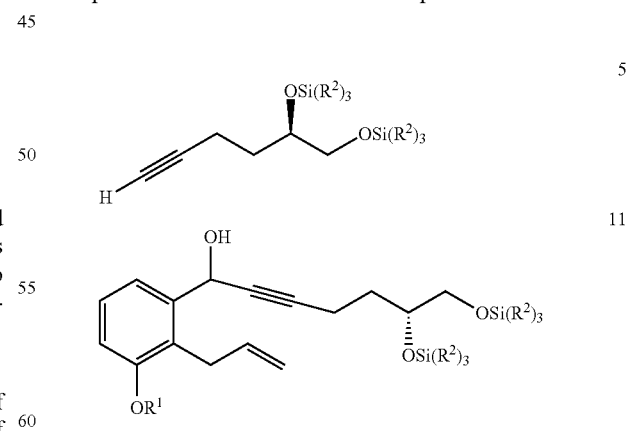

in the presence of a base and an organic solvent to generate a compound of Formula 11.

Steps i) and ii) are described, in detail, above.

Another aspect of the present invention provides a method of generating an N-methyldiethanolamine salt of the compound of Formula I

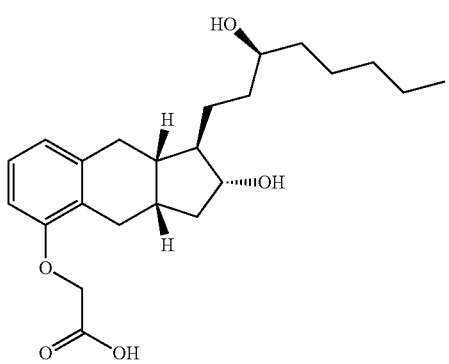

I

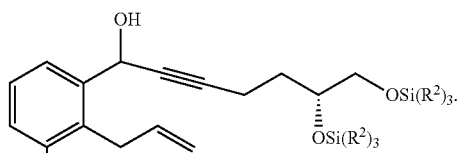

11

Some methods further comprise the steps of: i) reacting a compound of Formula 9 with an oxidizing agent to generate a compound of Formula 10; and comprising the steps of: x) reacting a compound of Formula 12 with a reducing agent in the presence of an organic solvent to generate a compound of Formula 13

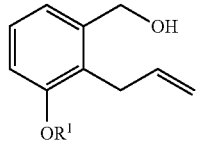

9

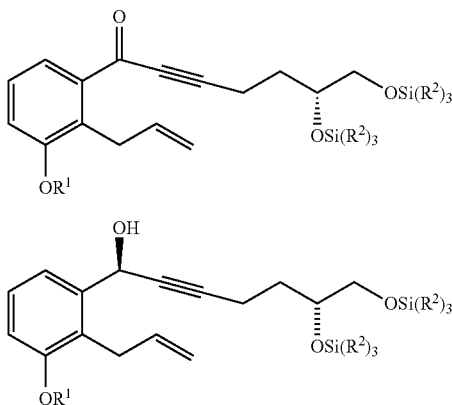

12

13

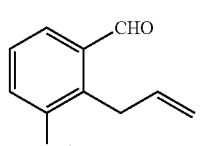

10 ii) reacting the compound of Formula 10 with a compound of Formula 5 in the presence of a base and an organic solvent to generate a compound of Formula 11 wherein the organic solvent comprises THF, $R^1$ is $C_{1-6}$ alkyl, and $R^2$ is independently selected from $C_{1-6}$ alkyl or phenyl; and xi) converting the compound of Formula 13 to the N-methyldiethanolamine salt of the compound of Formula I.

E. Step x)

In some implementations, the reducing agent of step x) comprises a chiral borane compound. In some implementations, the chiral borane compound of step x) reacts with the compound of Formula 12 to generate the compound of Formula 13 with a d.e. of about 97% or greater (e.g., about 97.5% of greater). In other implementations, the chiral borane reducing agent is formed in situ or ex situ. And, in some examples, the chiral borane compound is selected from (R)-1-methyl-3,3-diphenylhexahydropyrrolo[1,2-c][1,3,2]oxazaborole, (R)-3,3-diphenylhexahydropyrrolo[1,2-c][1,3,2]oxazaborole, (R)-1-butyl-3,3-diphenylhexahydropyrrolo[1,2-c][1,3,2]oxazaborole, (R)-tetrahydro-1,3,3-triphenyl-1H,3H-pyrrolo[1,2-c][1,3,2]oxaborole, (4S)-2-methyl-4,5,5-triphenyl-1,3,2-oxazaborolidine, or any combination thereof.

In some implementations, the organic solvent of step x) further comprises toluene.

And, in some implementations, the organic solvent of step x) is anhydrous.

Some methods further comprise the step of: viii) reacting a compound of Formula 11 with an oxidizing agent to generate the compound of Formula 12, wherein the oxidizing agent comprises $MnO_2$

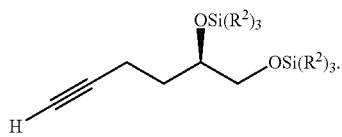

5

Some methods further comprise the steps of: iv) refluxing the compound of Formula 1a in the presence of methanol to generate a compound of Formula 1 having an e.e. of greater than about 98%;

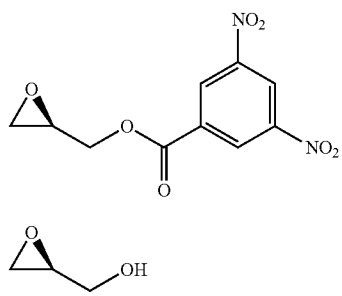

1a

1 v) reacting the compound of Formula 1 with $SiCl(R^2)_3$ under basic conditions to generate the compound of Formula 2;

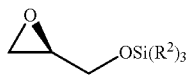 2 vi) reacting the compound of Formula 2 with 1-TMS-1-propyne to generate the compound of Formula 3; and

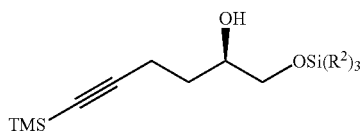 3 vii) converting the compound of Formula 3 to the compound of Formula 5.

Each of steps i), ii), and iv)-viii) is discussed above.

Another aspect of the present invention provides a method of generating an N-methyldiethanolamine salt of the compound of Formula I

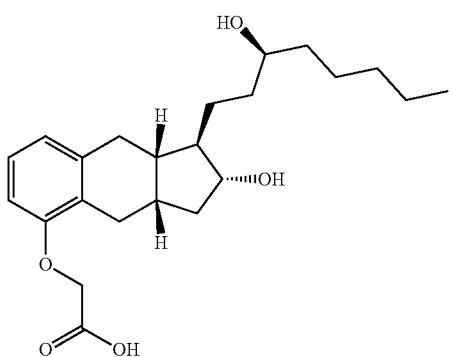 I comprising the steps of: xii) hydrogenating a compound of Formula 15 in the presence of an organic solvent (e.g., an alcohol (e.g., methanol, ethanol, or any combination thereof), an optionally substituted THF (e.g., 2-methyl-THF or THF), EtOAc, or any combination thereof) to generate the compound of Formula 16

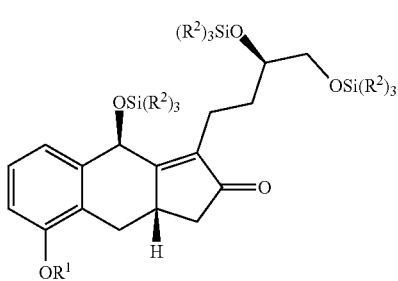 15

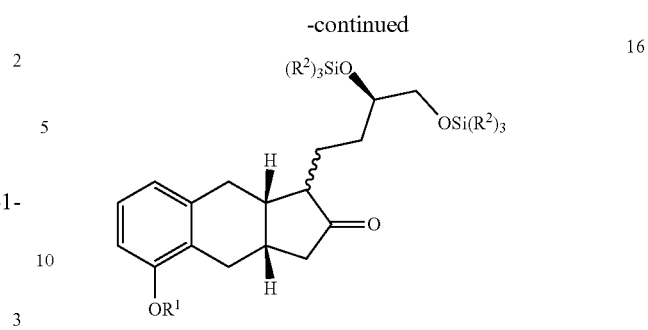 16 wherein $R^1$ is $C_{1-6}$ alkyl and each $R^2$ is independently selected from $C_{1-6}$ alkyl or phenyl; and xiii) converting the compound of Formula 16 to the N-methyldiethanolamine salt of the compound of Formula I.

F. Step xii)

Step xii) comprises the improved hydrogenation of the compound of Formula 15 to generate the compound of Formula 16. Some implementations comprise the hydrogenation of the compound of Formula 15 in the presence of an organic solvent such as an alcohol, optionally substituted THF, EtOAc, or any combination thereof to generate the compound of Formula 16. In other implementations, the hydrogenation of the compound of Formula 15 occurs in the presence of an alcohol (e.g., methanol, ethanol, or any combination thereof) and a base (e.g., potassium carbonate or potassium bicarbonate). In alternative implementations, the hydrogenation of the compound of Formula 15 occurs in the presence of an optionally substituted THF (e.g., THF or 2-methyl-THF) and a base.

The substitution of methanol for the traditional ethanol in step xii) produces an improved yield (e.g., at least about 88%) and improved chemical purity for the compound of Formula 16.

Some methods further comprise the steps of: x) reacting a compound of Formula 12 with a reducing agent in the presence of an organic solvent to generate a compound of Formula 13

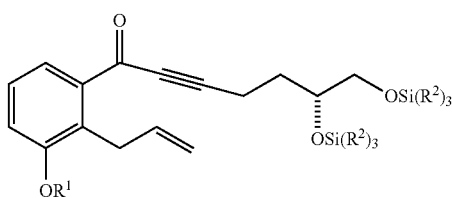 12

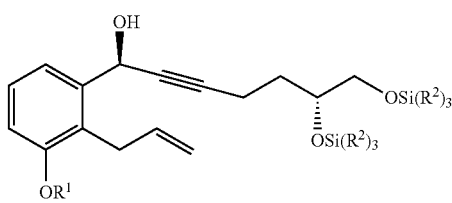 13 wherein the organic solvent comprises THF; and xiv) converting the compound of Formula 13 to the compound of Formula 15.

Some methods further comprise the steps of: viii) reacting a compound of Formula 11 with an oxidizing agent to generate the compound of Formula 12, wherein the oxidizing agent comprises $MnO_2$

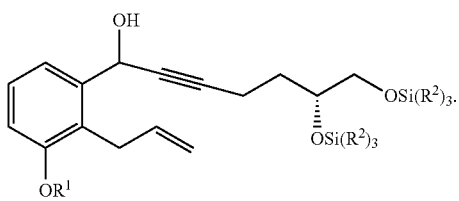

11

Some methods further comprise the steps of: i) reacting a compound of Formula 9 with an oxidizing agent to generate a compound of Formula 10 and

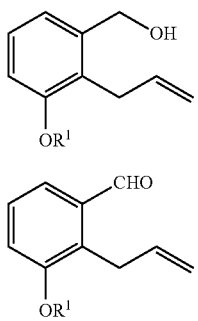

9

10 ii) reacting the compound of Formula 10 with a compound of Formula 5 in the presence of a base and an organic solvent to generate a compound of Formula 11

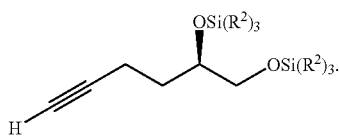

5

In some implementations, the oxidizing agent of step i) comprises MnO$_2$ or Dess-Martin periodinane.

Some methods further comprise the steps of: iv) refluxing the compound of Formula 1a in the presence of methanol to generate a compound of Formula 1 having an e.e. of greater than about 98%;

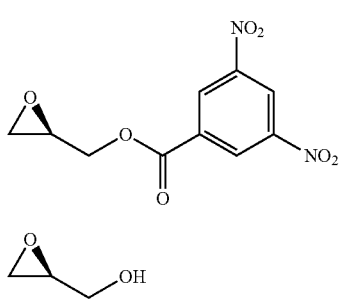

1a

1 v) reacting the compound of Formula 1 with SiCl(R$^2$)$_3$ under basic conditions to generate the compound of Formula 2;

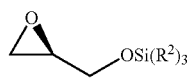

2 vi) reacting the compound of Formula 2 with 1-TMS-1-propyne to generate the compound of Formula 3; and

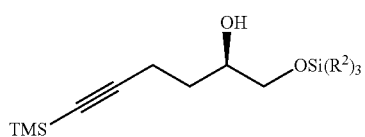

3 vii) converting the compound of Formula 3 to the compound of Formula 5.

Each of steps i), ii), iv), v)-viii), x), and xiv) is discussed above.

Another aspect of the present invention provides a method of generating an N-methyldiethanolamine salt of the compound of Formula I

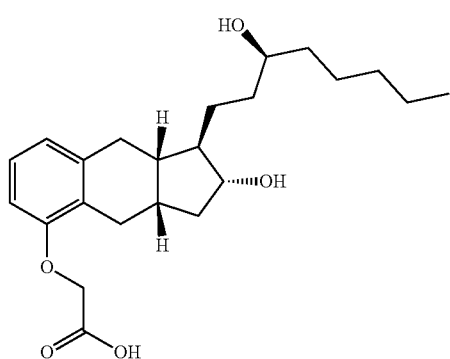

I comprising the steps of: xv) reacting a compound of Formula 21 with n-butyllithium in the presence of an organic solvent and a transition metal catalyst to generate a compound of Formula 22

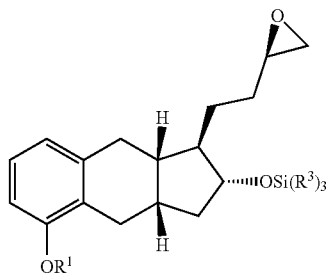

21

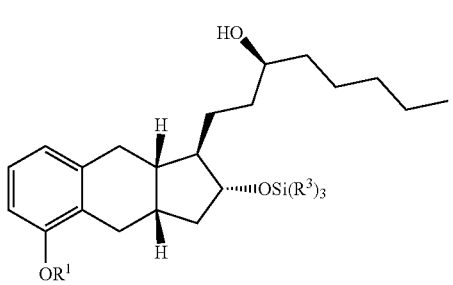

22 wherein R³ is C₁₋₆ alkyl or phenyl; and xvi) converting the compound of Formula 22 to the N-methyldiethanolamine salt of the compound of Formula I.

G. Step xv)

Step xv) generates a yield of at least about 70% (e.g., at least about 75%, at least about 80%, or about 82%) for the compound of Formula 22.

In some implementations, the reaction of step xv) is conducted at a temperature of from about −80° C. to about −20° C. (e.g., from about −78° C. to about −30° C.).

In some implementations, the transition metal catalyst of step xv) comprises copper having a +1 oxidation state. For example, the transition metal catalyst comprises a copper compound or a copper complex wherein the Cu has a +1 oxidation state. In other examples, the transition metal catalyst of step xv) comprises CuX, wherein X is selected from halogen, acetate, benzoate, cyanide, hydroxide, nitrate, or any combination thereof. In other examples, the transition metal catalyst of step xv) comprises CuI.

Some methods further comprise the steps of: xvii) reacting a compound of Formula 19 with R⁴-substituted benzenesulfonyl chloride under basic conditions to generate a compound of Formula 20, wherein each R⁴ is independently selected from —H or C₁₋₃ alkyl; and

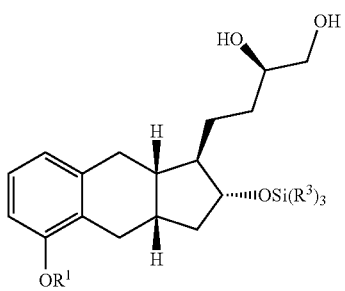

19

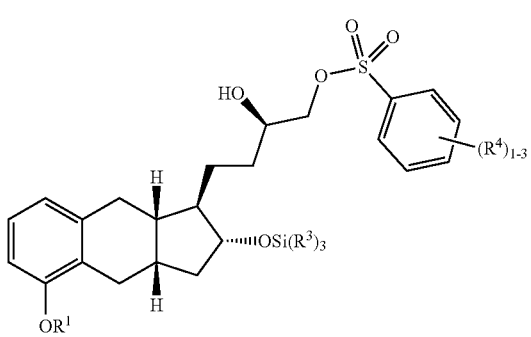

20 xviii) reacting the compound of Formula 20 with methanol under basic conditions to generate the compound of Formula 21.

In some implementations, the R⁴-substituted benzenesulfonyl chloride of step xvii) is 2-mesitylenesulfonyl chloride (2,4,6-trimethylbenzenesulfonyl chloride) or tosyl chloride (TsCl).

Some methods further comprise the steps of: xix) reacting a compound of Formula 16 with a reducing agent to generate a compound of Formula 17;

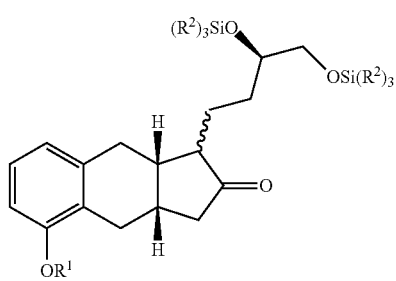

16

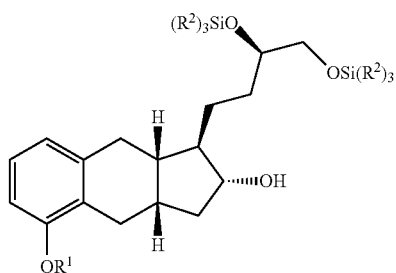

17 xx) reacting the compound of claim 17 with Si(R³)₃Cl under basic conditions to generate a compound of Formula 18; and

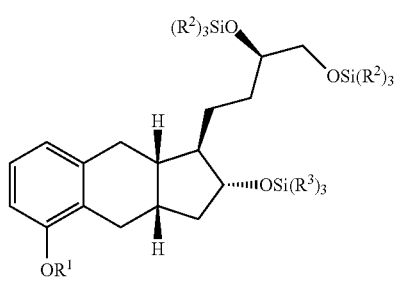

18 xxi) selectively deprotecting the compound of Formula 18 to generate the compound of Formula 19.

Some methods further comprise the steps of: xii) hydrogenating a compound of Formula

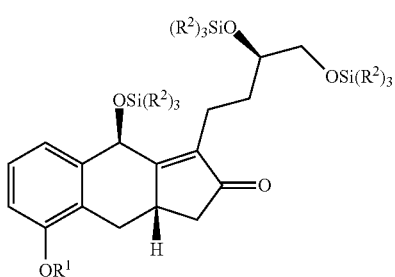

15 in the presence of an organic solvent (e.g., an alcohol (e.g., methanol, ethanol, or any combination thereof), an optionally substituted THF (e.g., 2-methyl-THF or THF), EtOAc, or any combination thereof) to generate the compound of Formula 16.

In some implementations, the hydrogenation of the compound of Formula 15 occurs in the presence of a base (e.g., potassium carbonate or potassium bicarbonate).

Some methods further comprise the steps of: x) reacting a compound of Formula 12 with a reducing agent to generate a compound of Formula 13; and

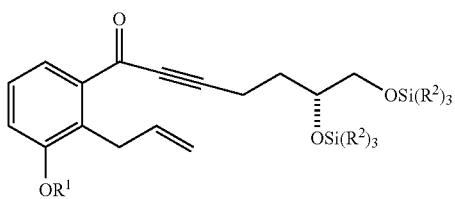

12

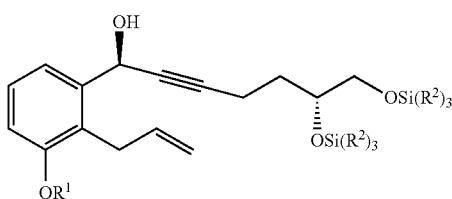

13 xiv) converting the compound of Formula 13 to the compound of Formula 15.

Some methods further comprise the step of: viii) reacting a compound of Formula 11

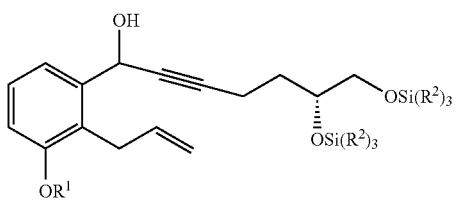

11 with an oxidizing agent to generate the compound of Formula 12, wherein the oxidizing agent comprises MnO$_2$.

Some methods further comprise the steps of: i) reacting a compound of Formula 9 with an oxidizing agent to generate a compound of Formula 10; and

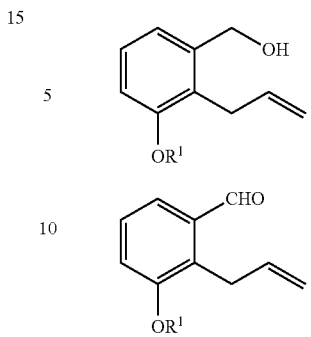

9

10 ii) reacting the compound of Formula 10 with a compound of Formula 5 in the presence of a base and an organic solvent to generate a compound of Formula 11

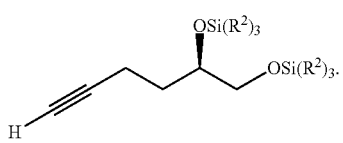

5

Some methods further comprise the steps of: iv) refluxing the compound of Formula 1a in the presence of methanol to generate a compound of Formula 1 having greater than about 99% e.e.;

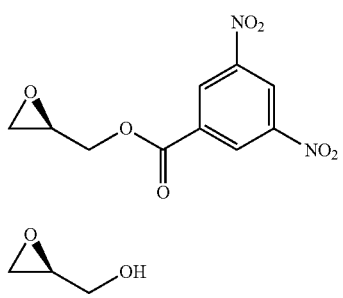

1a

1 v) reacting the compound of Formula 1 with SiCl(R$^2$)$_3$ under basic conditions to generate the compound of Formula 2;

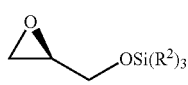

2 vi) reacting the compound of Formula 2 with 1-TMS-1-propyne to generate the compound of Formula 3; and

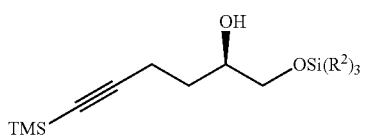

3 vii) converting the compound of Formula 3 to the compound of Formula 5.

Steps i), ii), iv)-viii), x), xii), and xiv) are discussed above.

The present invention also provides a method of generating an N-methyldiethanolamine salt of the compound of Formula I

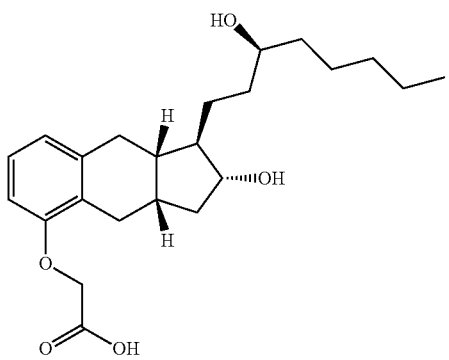

comprising the steps of: xxii) reacting a compound of Formula 7, wherein R¹ is $C_{1-6}$ alkyl and R² is independently selected from $C_{1-6}$ alkyl or phenyl, with a 3-haloprop-1-ene in the presence of a base and an organic solvent to generate a compound of Formula 8;

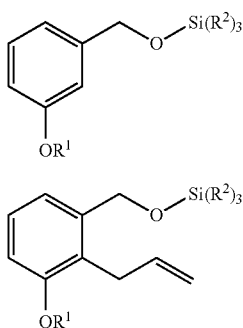

xxiii) deprotecting the compound of Formula 8 to generate the compound of Formula 9, and

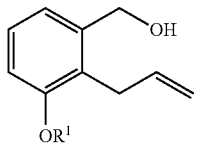

xxiv) converting the compound of Formula 9 to the compound of Formula I, wherein the base of step xxii) comprises sec-butyl lithium.

H. Step xxii)

The reaction of step xxii) generates the compound of Formula 8 with improved chemical purity without additional chromatography steps.

In some implementations, the reaction of step xxii) is conducted at room temperature (e.g., from about 20° C. to about 30° C.) for a period of about 2 hrs (e.g., from about 1.5 to about 2.5 hrs) then cooled to a temperature of about 0° C. (e.g., from about −5° C. to about 5° C.) under stirring.

In some implementations, the organic solvent of step xxii) comprises one or more alkanes. For example, the organic solvent of step xxii) comprises heptanes, cyclohexane, or any combination thereof. In other implementations, the organic solvent of step xxii) comprises MTBE.

Another aspect of the present invention provides a method of generating an N-methyldiethanolamine salt of the compound of Formula I

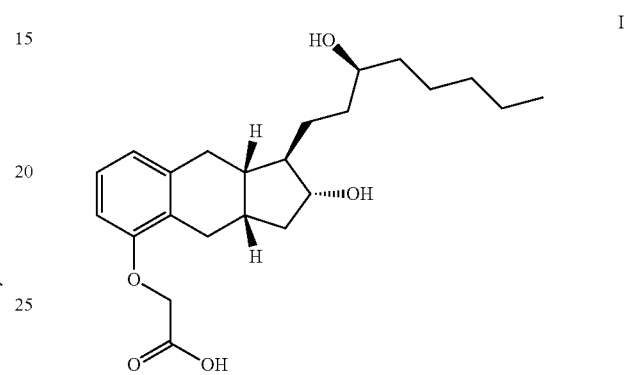

comprising the steps of: i) reacting a compound of Formula 9 with an oxidizing agent in the presence of an organic solvent to generate a compound of Formula 10

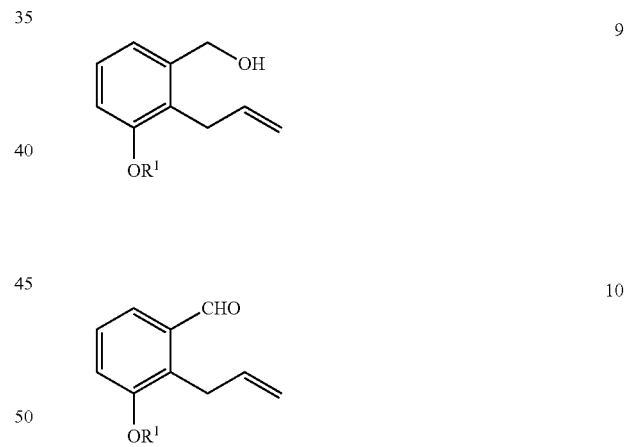

wherein R¹ is $C_{1-6}$ alkyl and the oxidizing agent comprises $MnO_2$ or Dess-Martin periodinane; ii) reacting the compound of Formula 10 with a compound of Formula 5a in the presence of a base and an organic solvent to generate a compound of Formula 11a; and

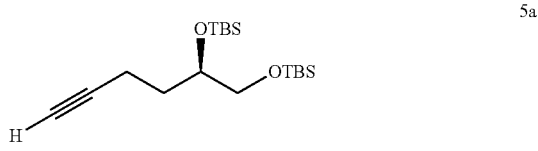 [SMILES: C#CCC[C@H](CO[Si](C)(C)C(C)(C)C)O[Si](C)(C)C(C)(C)C]

-continued

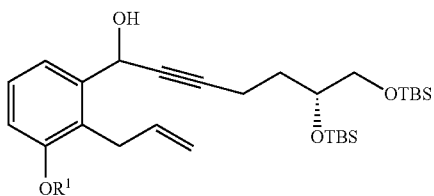
11a

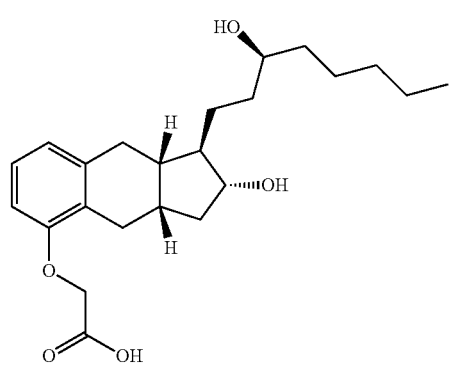
I iii) converting the compound of Formula 11a to the N-methyldiethanolamine salt of the compound of Formula I.

Steps i) and ii) are discussed in detail above.

Some methods further comprise the steps of: iv) refluxing the compound of Formula 1a in the presence of methanol to generate a compound of Formula 1 having an e.e. of greater than about 98%;

comprising the steps of: viii) reacting a compound of Formula IIa with an oxidizing agent in the presence of an organic solvent to generate a compound of Formula 12a

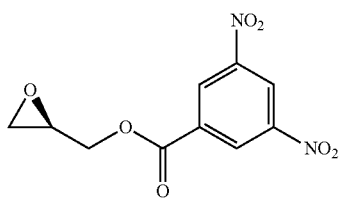
1a

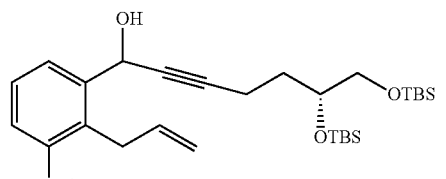
11a

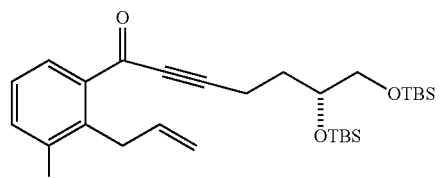
12a

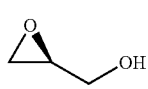
1 wherein $R^1$ is $C_{1-6}$ alkyl and the oxidizing agent comprises $MnO_2$; and ix) converting the compound of Formula 12a to the N-methyldiethanolamine salt of the compound of Formula I.

Step viii) is discussed above.

Some methods further comprise the steps of: i) reacting a compound of Formula 9 with an oxidizing agent in the presence of an organic solvent generate a compound of Formula 10 v) reacting the compound of Formula 1 with TBSCl under basic conditions to generate the compound of Formula 2a;

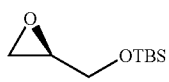
2a vi) reacting the compound of Formula 2a with 1-TMS-1-propyne to generate the compound of Formula 3a; and

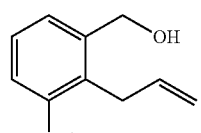
9

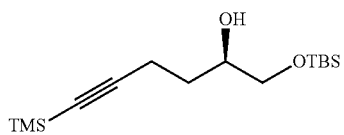
3a

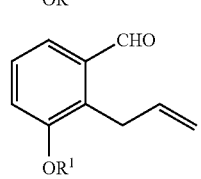
10 vii) converting the compound of Formula 3a to the compound of Formula 5a.

Another aspect of the present invention provides a method of generating an N-methyldiethanolamine salt of the compound of Formula I wherein the oxidizing agent comprises $MnO_2$ or Dess-Martin periodinane; and ii) reacting the compound of Formula 10 with a compound of Formula 5a

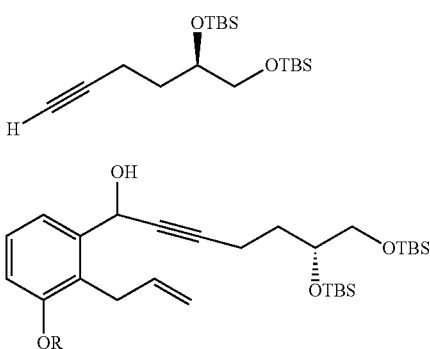

5a

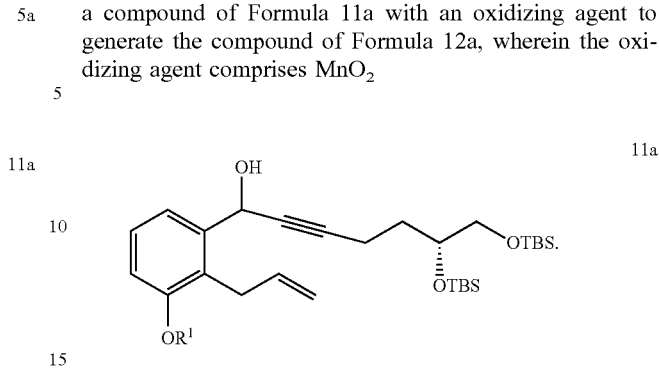

11a

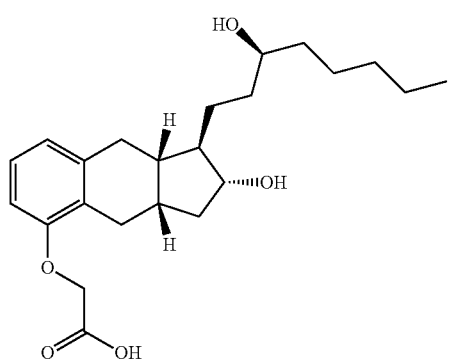

11a in the presence of a base and an organic solvent to generate a compound of Formula 11a.

Steps i) and ii) are discussed in detail above.

Another aspect of the present invention provides a method of generating an N-methyldiethanolamine salt of the compound of Formula I Some methods further comprise the step of: viii) reacting a compound of Formula 11a with an oxidizing agent to generate the compound of Formula 12a, wherein the oxidizing agent comprises $MnO_2$ Some methods further comprise the steps of: i) reacting a compound of Formula 9 with an oxidizing agent to generate a compound of Formula 10; and

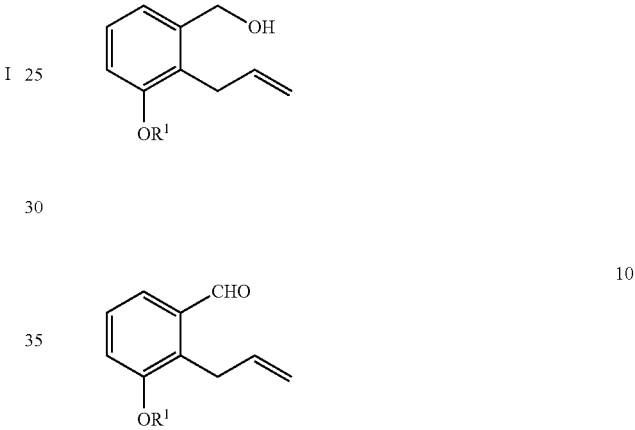

9

10

I

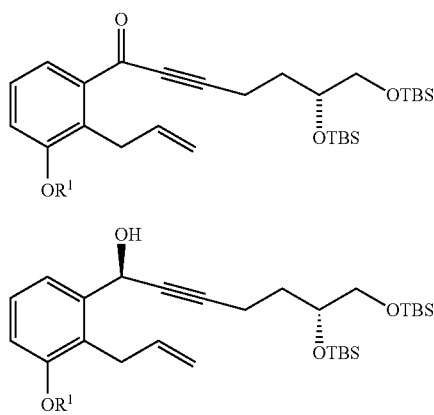

comprising the steps of: x) reacting a compound of Formula 12a with a reducing agent in the presence of an organic solvent to generate a compound of Formula 13a ii) reacting the compound of Formula 10 with a compound of Formula 5a in the presence of a base and an organic solvent to generate a compound of Formula 11a

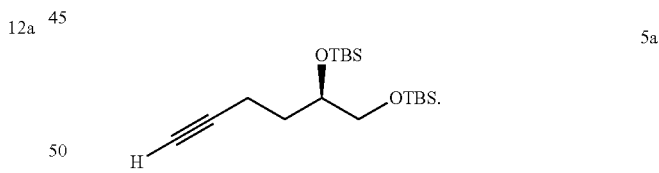

5a

12a

13a wherein the organic solvent comprises THF, $R^1$ is $C_{1-6}$ alkyl, and each $R^2$ is independently selected from $C_{1-6}$ alkyl or phenyl; and xi) converting the compound of Formula 13 to the compound of Formula I.

Steps x) and xi) are discusses in detail above.

In some implementations, the oxidizing agent of step i) comprises $MnO_2$ or Dess-Martin periodinane.

In some implementations, the base of step ii) comprises an alkyllithium reagent. For example, the alkyllithium reagent of step ii) comprises sec-butyllithium.

In some implementations, the organic solvent of step ii) comprises pentane, hexane, cyclohexane, heptane, tetrahydrofuran, 1,4-dioxane, diethyl ether, petro ether, methyl-tert-butylether, or any combination thereof. For example, the organic solvent of step ii) comprises methyl-tert-butylether.

Some methods further comprise the steps of: iv) refluxing the compound of Formula 1a in the presence of methanol to generate a compound of Formula 1 having an e.e. of greater than about 98%;

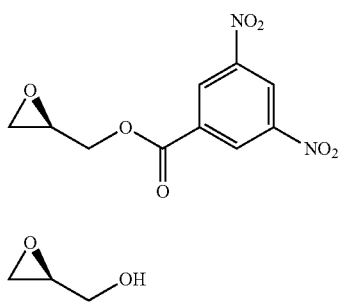

1a

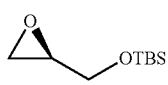

1 v) reacting the compound of Formula 1 with TBSCl under basic conditions to generate the compound of Formula 2a;

2a

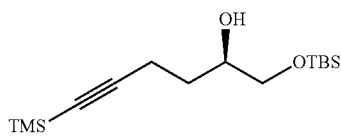

vi) reacting the compound of Formula 2a with 1-TMS-1-propyne to generate the compound of Formula 3a; and 3a

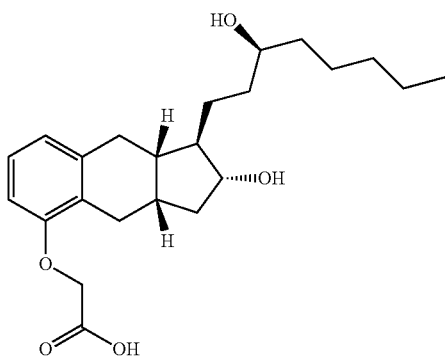

vii) converting the compound of Formula 3a to the compound of Formula 5a.

Another aspect of the present invention provides a method of generating an N-methyldiethanolamine salt of the compound of Formula I

I

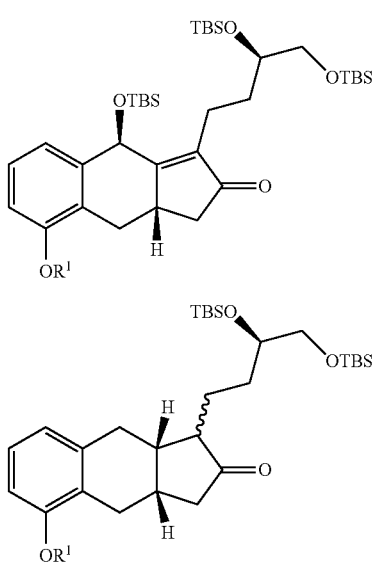

15a

16a wherein $R^1$ is $C_{1-6}$ alkyl; and xiii) converting the compound of Formula 16a to the compound of Formula I.

In some implementations, the hydrogenation of the compound of Formula 15a occurs in the presence of a base (e.g., potassium carbonate or potassium bicarbonate).

Some methods further comprise the steps of: x) reacting a compound of Formula 12a with a reducing agent in the presence of an organic solvent to generate a compound of Formula 13a 12a

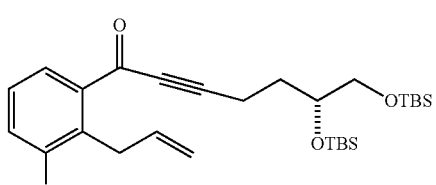

13a

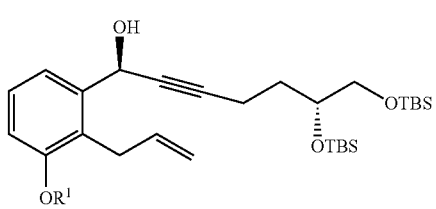

comprising the steps of: xii) hydrogenating a compound of Formula 15a in the presence of an organic solvent (e.g., an alcohol (e.g., methanol, ethanol, or any combination thereof), an optionally substituted THF (e.g., 2-methyl-THF or THF), EtOAc, or any combination thereof) to generate the compound of Formula 16a wherein the organic solvent comprises THF; and xiv) converting the compound of Formula 13a to the compound of Formula 15a.

Some methods further comprise the steps of: viii) reacting a compound of Formula 11a with an oxidizing agent to generate the compound of Formula 12a, wherein the oxidizing agent comprises $MnO_2$

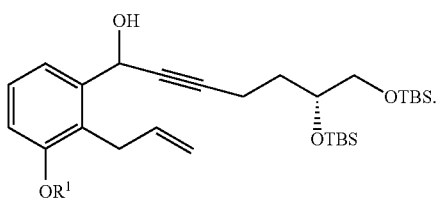
11a

Some methods further comprise the steps of: i) reacting a compound of Formula 9 with an oxidizing agent to generate a compound of Formula 10; and

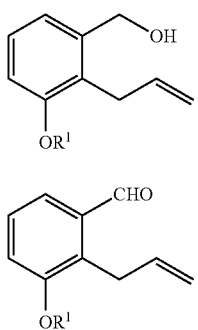

ii) reacting the compound of Formula 10 with a compound of Formula 5a in the presence of a base and an organic solvent to generate a compound of Formula 11a

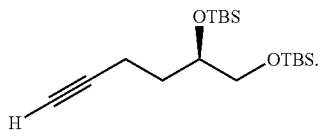
5a

Some methods further comprise the steps of: iv) refluxing the compound of Formula 1a in the presence of methanol to generate a compound of Formula 1 having an e.e. of greater than about 98%;

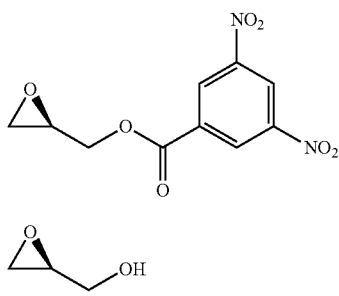

v) reacting the compound of Formula 1 with TBSCl under basic conditions to generate the compound of Formula 2a;

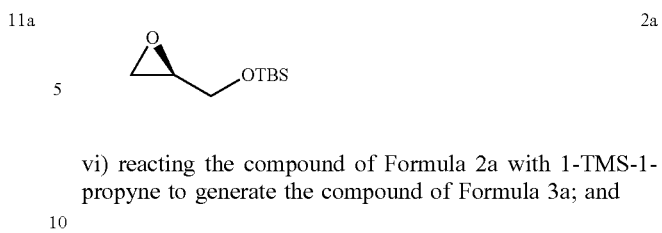

vi) reacting the compound of Formula 2a with 1-TMS-1-propyne to generate the compound of Formula 3a; and

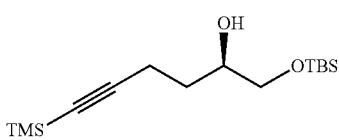
3a vii) converting the compound of Formula 3a to the compound of Formula 5a.

Another aspect of the present invention provides a method of generating an N-methyldiethanolamine salt of the compound of Formula I

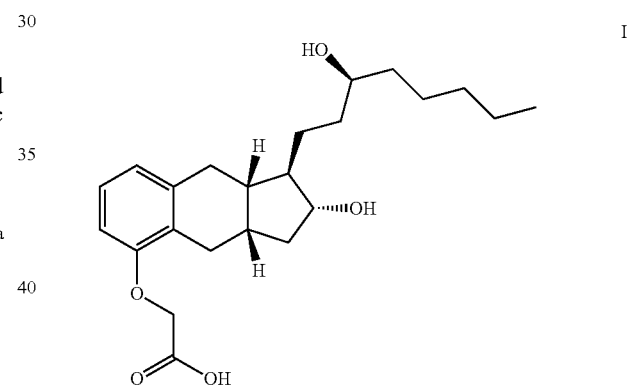
I comprising the steps of: xv) reacting a compound of Formula 21a with n-butyllithium in the presence of an organic solvent and a transition metal catalyst to generate a compound of Formula 22a

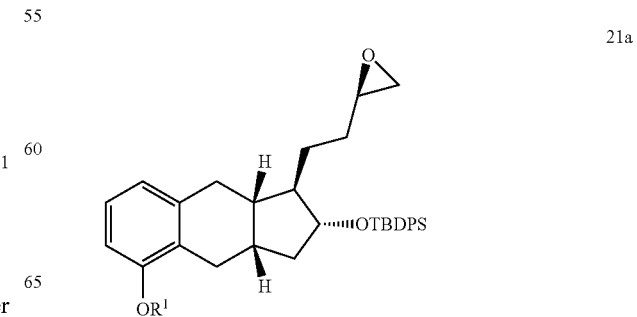
21a

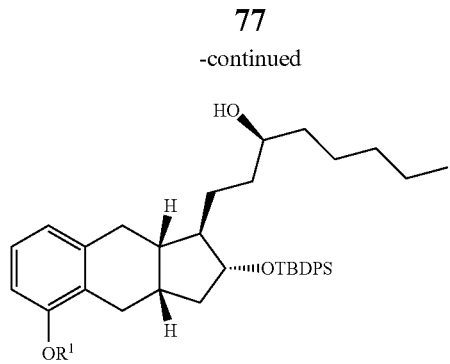

22a wherein $R^1$ is $C_{1-6}$ alkyl; and xvi) converting the compound of Formula 22a to the N-methyldiethanolamine salt of the compound of Formula I.

In some implementations, the transition metal catalyst of step xv) comprises a compound or complex either of which comprises Cu having a +1 oxidation state. For example, the transition metal catalyst of step xv) comprises CuX, wherein X is selected from halogen, acetate, benzoate, cyanide, hydroxide, nitrate, or any combination thereof. In other examples, the transition metal catalyst of step xv) comprises CuI.

Some methods further comprise the steps of: xvii) reacting a compound of Formula 19a with triisopropylbenzenesulfonyl chloride under basic conditions to generate a compound of Formula 20a; and

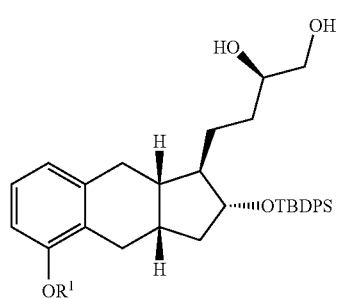

19a

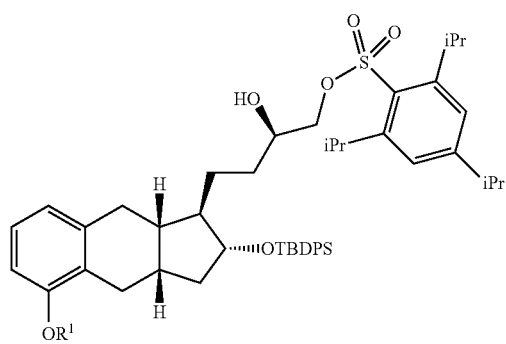

20a xviii) reacting the compound of Formula 20a with methanol under basic conditions to generate the compound of Formula 21a.

Some methods further comprise the steps of: xix) reacting a compound of Formula 16a with a reducing agent to generate a compound of Formula 17a;

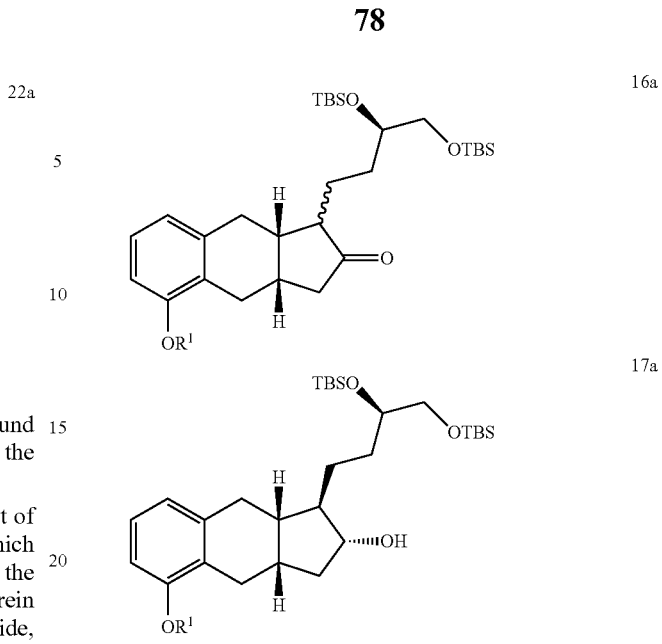

16a

17a xx) reacting the compound of Formula 17a with TBDPSCl under basic conditions to generate a compound of Formula 18a; and 18a xxi) selectively deprotecting the compound of Formula 18a to generate the compound of Formula 19a.

Some methods further comprise the step of: xii) hydrogenating a compound of Formula 15a

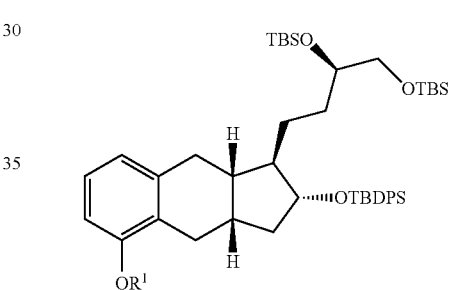

15a in the presence of an organic solvent (e.g., an alcohol (e.g., methanol, ethanol, or any combination thereof), an optionally substituted THF (e.g., 2-methyl-THF or THF), EtOAc, or any combination thereof) to generate the compound of Formula 16a.

In some implementations, the hydrogenation of the compound of Formula 15a occurs in the presence of a base (e.g., potassium carbonate or potassium bicarbonate).

Some methods further comprise the steps of: x) reacting a compound of Formula 12a with a reducing agent to generate a compound of Formula 13a; and

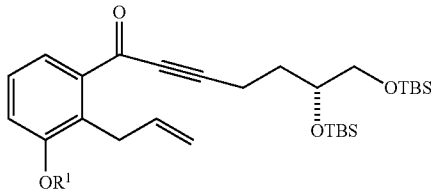

12a

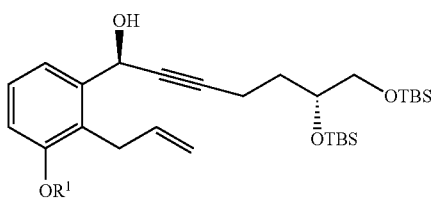

13a xiv) converting the compound of Formula 13a to the compound of Formula 15a.

Some methods further comprise the step of: viii) reacting a compound of Formula 11a

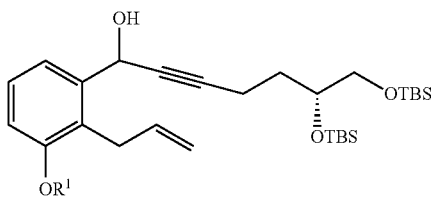

11a with an oxidizing agent to generate the compound of Formula 12a, wherein the oxidizing agent comprises $MnO_2$.

Some methods further comprise the steps of: i) reacting a compound of Formula 9 with an oxidizing agent to generate a compound of Formula 10; and

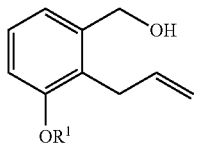

9

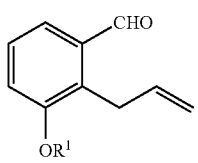

10 ii) reacting the compound of Formula 10 with a compound of Formula 5a in the presence of a base and an organic solvent to generate a compound of Formula 11a

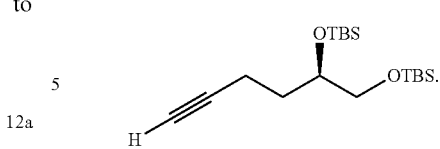

5a

Some methods further comprise the steps of: iv) refluxing the compound of Formula 1a in the presence of methanol to generate a compound of Formula 1 having an e.e. of greater than about 98%;

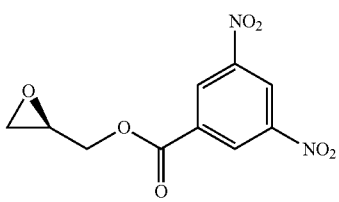

1a

1 v) reacting the compound of Formula 1 with TBSCl under basic conditions to generate the compound of Formula 2a;

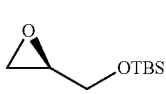

2a vi) reacting the compound of Formula 2a with 1-TMS-1-propyne to generate the compound of Formula 3a; and

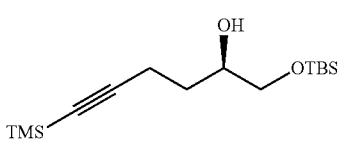

3a vii) converting the compound of Formula 3a to the compound of Formula 5a.

Some methods further comprise the steps of: xxii) reacting a compound of Formula 7a with a 3-haloprop-1-ene in the presence of a base and an organic solvent to generate a compound of Formula 8a; and

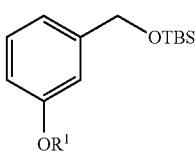

7a

-continued

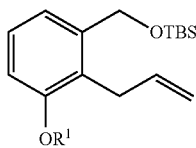
8a xxiii) deprotecting the compound of Formula 8a to generate the compound of Formula 9.

Another aspect of the present invention provides a method of generating an N-methyldiethanolamine salt of the compound of Formula I

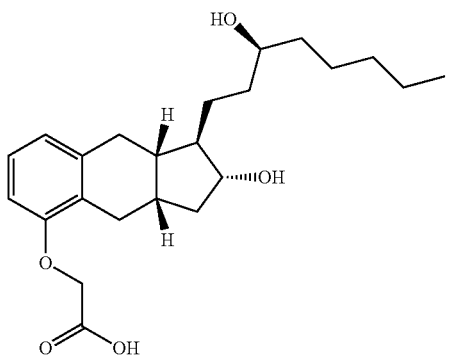
I comprising the steps of: i) reacting a compound of Formula 9 with an oxidizing agent to generate a compound of Formula 10;

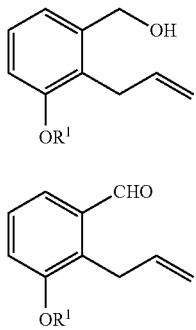
9

10 ii) reacting the compound of Formula 10 with a compound of Formula 5a in the presence of a base and an organic solvent to generate a compound of Formula 11a;

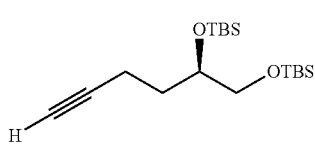
5a

-continued

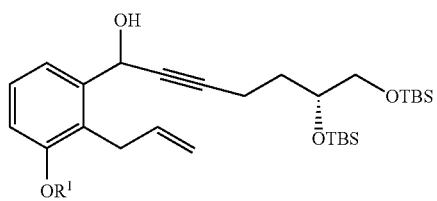
11a iv) refluxing the compound of Formula 1a in the presence of methanol to generate a compound of Formula 1 having an e.e of greater than about 98%;

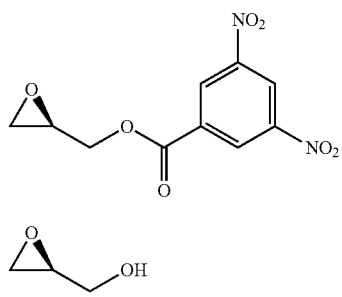
1a

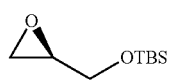
1 v) reacting the compound of Formula 1 with TBSCl under basic conditions to generate the compound of Formula 2a;

2a vi) reacting the compound of Formula 2a with 1-TMS-1-propyne to generate the compound of Formula 3a;

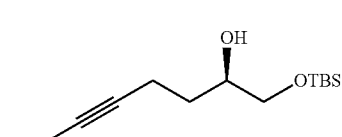
3a vii) converting the compound of Formula 3a to the compound of Formula 5a;
viii) reacting a compound of Formula 11a with an oxidizing agent to generate the compound of Formula 12a, wherein the oxidizing agent comprises $MnO_2$;

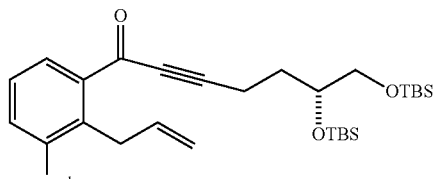
12a x) reacting a compound of Formula 12a with a reducing agent to generate a compound of Formula 13a;

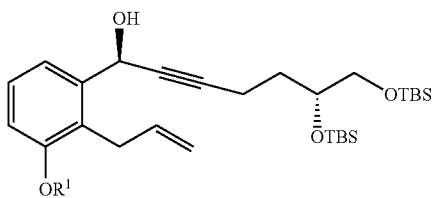

13a xiv) converting the compound of Formula 13a to the compound of Formula 15a;

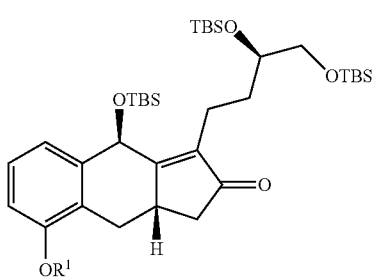

15a xii) hydrogenating a compound of Formula 15a in the presence of an organic solvent (e.g., an alcohol (e.g., methanol, ethanol, or any combination thereof), an optionally substituted THF (e.g., 2-methyl-THF or THF), EtOAc, or any combination thereof) to generate the compound of Formula 16a;

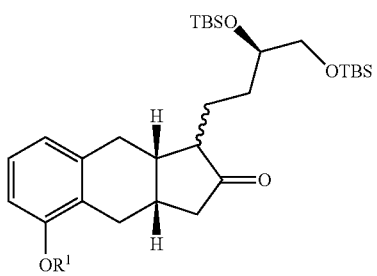

16a xix) reacting a compound of Formula 16a with a reducing agent to generate a compound of Formula 17a;

xx) reacting the compound of Formula 17a with TDPSCl under basic conditions to generate a compound of Formula 18a;

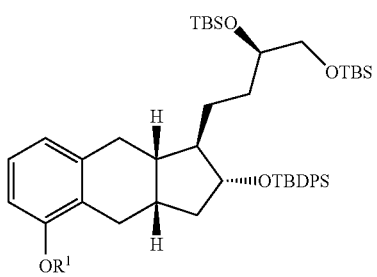

18a xxi) selectively deprotecting the compound of Formula 18a to generate the compound of Formula 19a;

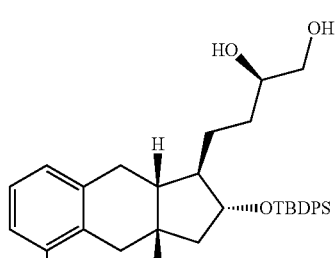

19a xvii) reacting a compound of Formula 19a with triisopropylbenzenesulfonyl chloride under basic conditions to generate a compound of Formula 20a;

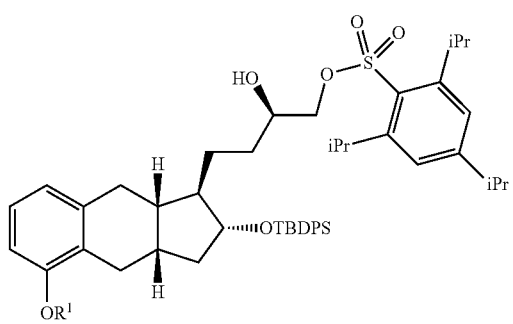

20a xviii) reacting the compound of Formula 20a with methanol under basic conditions to generate the compound of Formula 21a;

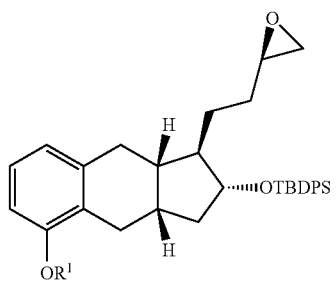

21a xv) reacting a compound of Formula 21a with n-butyllithium in the presence of an organic solvent and a transition metal catalyst to generate a compound of Formula 22a; and

85

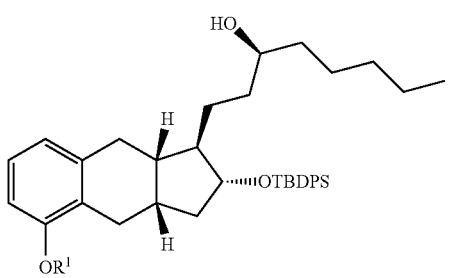

22a xvi) converting the compound of Formula 22a to the N-methyldiethanolamine salt of the compound of Formula I.

In some implementations, the hydrogenation of the compound of Formula 15a occurs in the presence of a base (e.g., potassium carbonate or potassium bicarbonate).

Some methods further comprise the step of: xxiv) reacting the compound of Formula I with diethanolamine in the presence of an organic solvent to generate the diethanolamine salt of the compound of Formula I.

Some methods further comprise the step of: xxva) treating the compound of Formula I with an alkali metal hydroxide (e.g., NaOH, KOH, or like, or any combination thereof) in the presence of an alcohol (e.g., ethanol, methanol, isopropanol, or any combination thereof) to generate the alkali metal salt (e.g., Na salt) of the compound of Formula I.

In some implementations, the alkali metal hydroxide comprises NaOH.

In other implementations, the alcohol comprises ethanol.

Alternatively, some methods further comprise the step of: xxvi) treating the compound of Formula 25

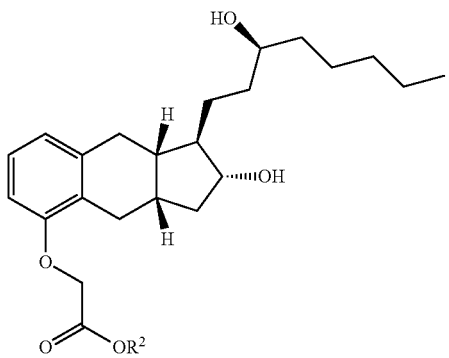

25 wherein $R^2$ is defined above, with an alkali metal hydroxide (e.g., NaOH, KOH, or like, or any combination thereof), in the presence of an alcohol and water to generate the alkali metal salt (e.g., Na salt) of the compound of Formula I.

In some implementations, the alcohol comprises methanol.

Some methods further comprise the step of: xxvii) recrystallizing the N-methyldiethanolamine salt of the compound of Formula I to generate a first pure form of the N-methyldiethanolamine salt of the compound of Formula I. (e.g., about 90% or greater chemical purity, about 95% or greater chemical purity, or about 97.5% or greater chemical purity). Some methods further comprise the step of: xxviii) reacting the first pure form of the N-methyldiethanolamine salt of the compound of Formula I with an acid to generate a second pure form of the compound of Formula I (e.g., about 98% or

86 greater chemical purity, about 98.5% or greater chemical purity, or about 99% or greater chemical purity). And, some methods further comprise the step of: xxvb) converting the second pure form of the compound of Formula I to an alkali metal salt.

V. General Synthetic Schemes

General schemes for generating compounds of Formula I and salts thereof are provided below.

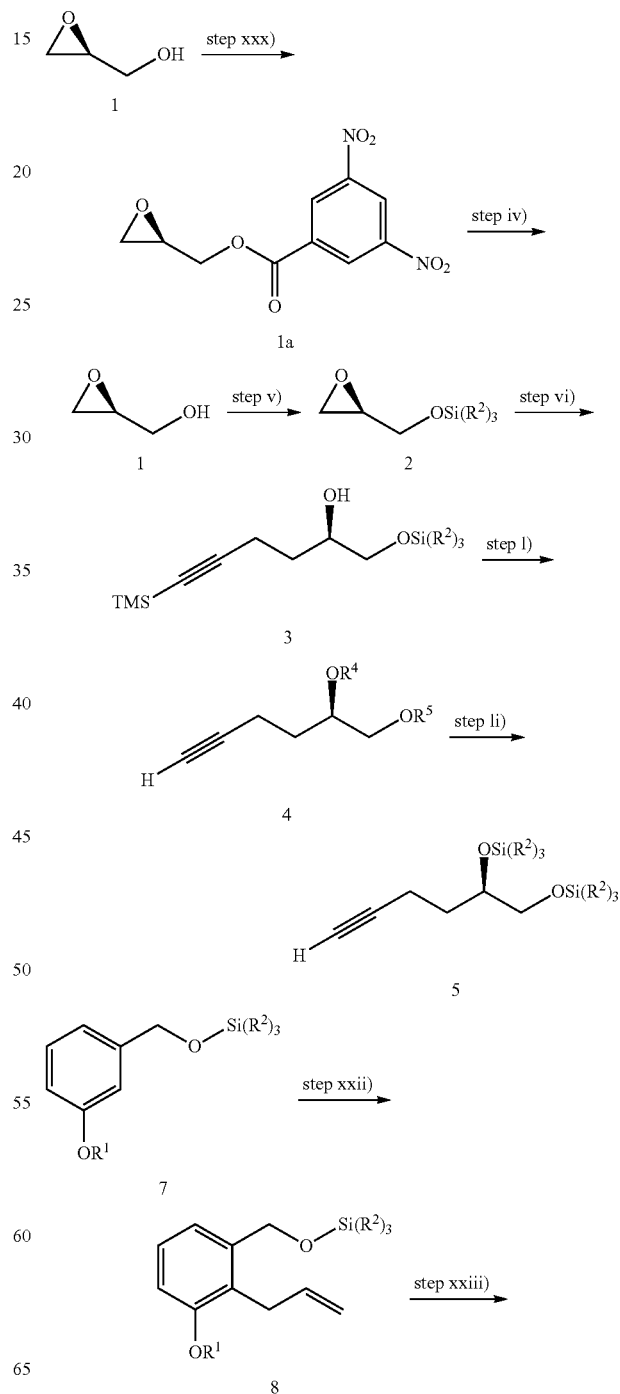

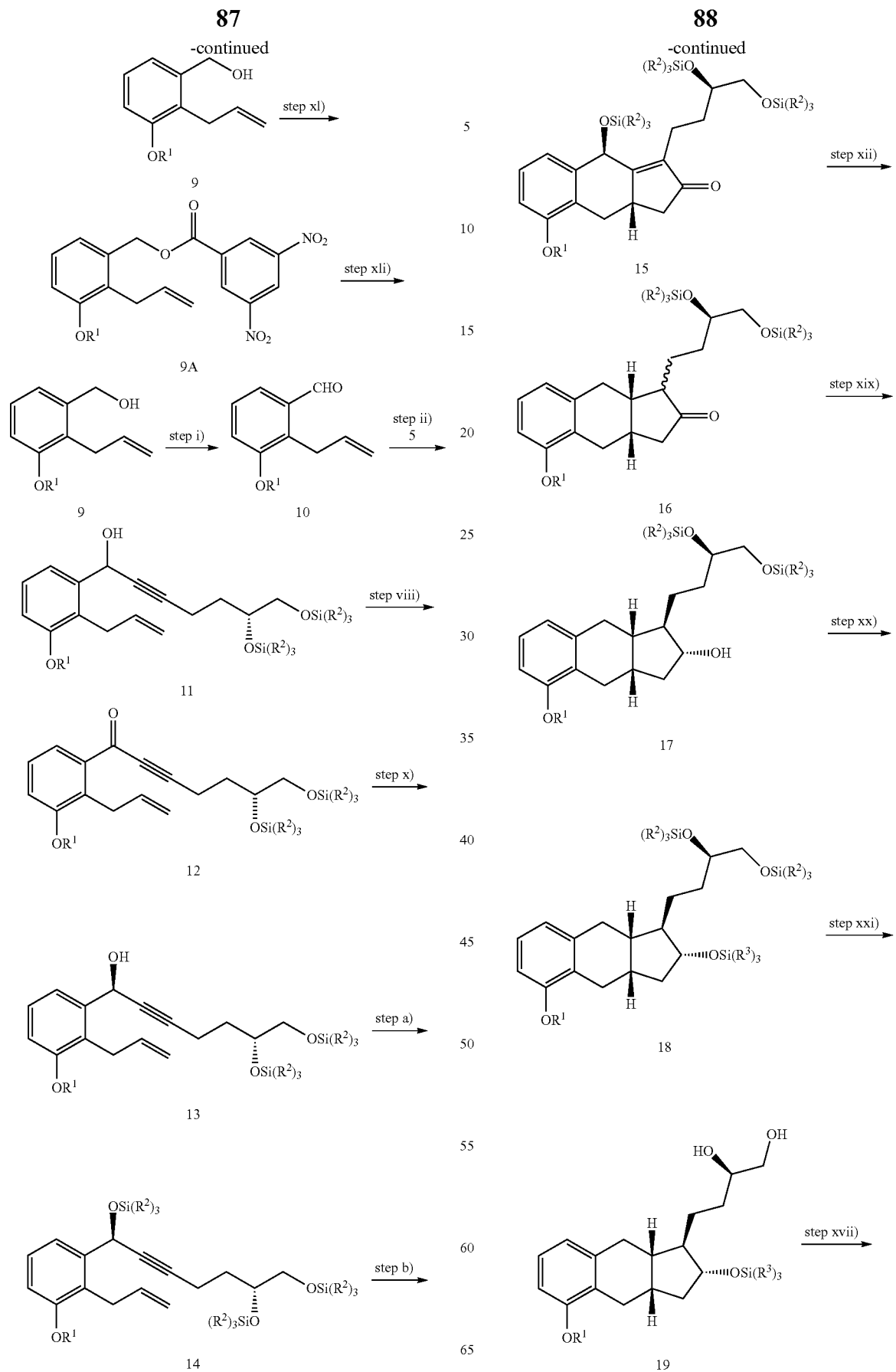

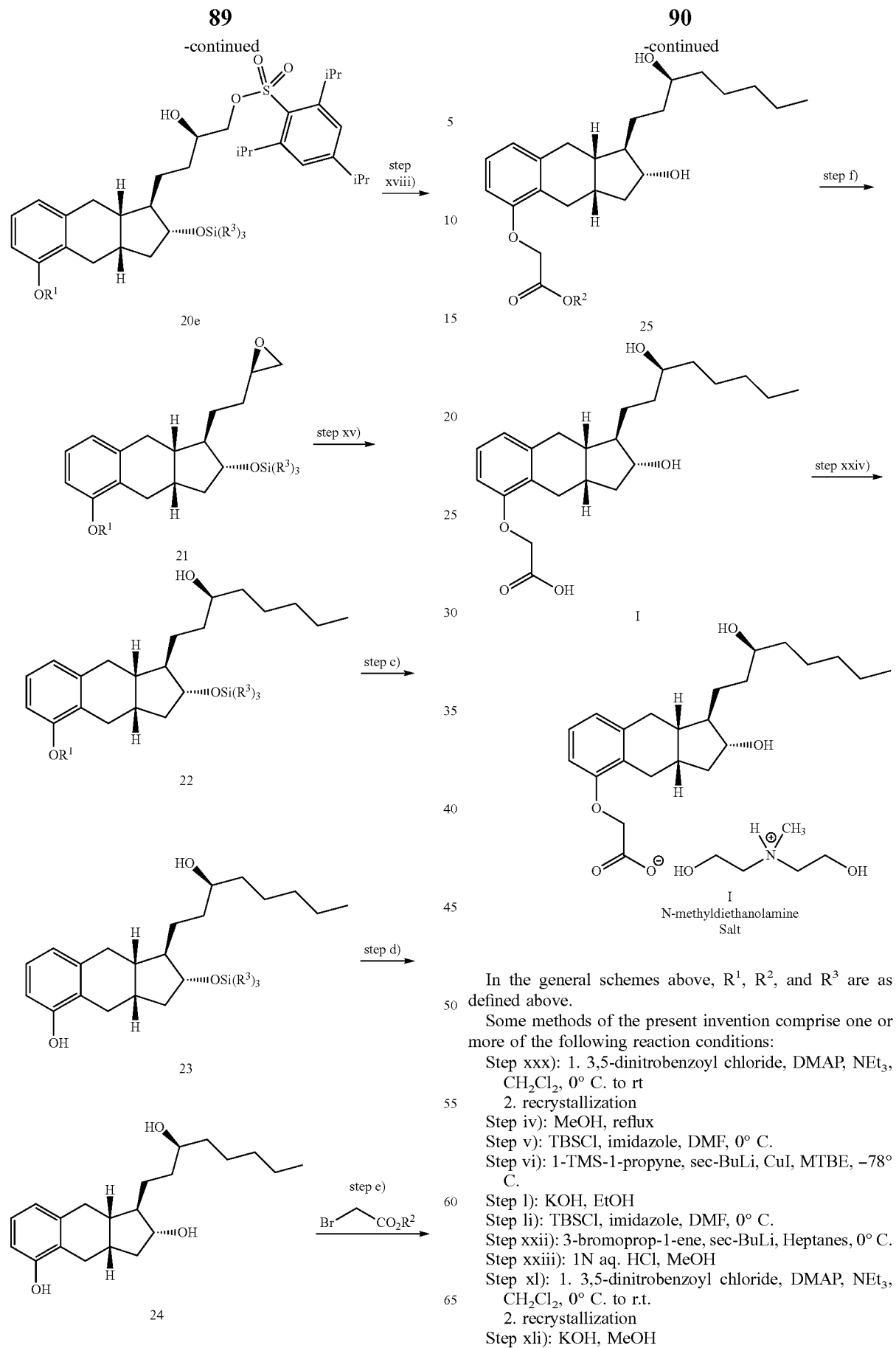

In the general schemes above, $R^1$, $R^2$, and $R^3$ are as defined above.

Some methods of the present invention comprise one or more of the following reaction conditions:

Step xxx): 1. 3,5-dinitrobenzoyl chloride, DMAP, NEt₃, CH₂Cl₂, 0° C. to rt
2. recrystallization
Step iv): MeOH, reflux
Step v): TBSCl, imidazole, DMF, 0° C.
Step vi): 1-TMS-1-propyne, sec-BuLi, CuI, MTBE, −78° C.
Step l): KOH, EtOH
Step li): TBSCl, imidazole, DMF, 0° C.
Step xxii): 3-bromoprop-1-ene, sec-BuLi, Heptanes, 0° C.
Step xxiii): 1N aq. HCl, MeOH
Step xl): 1. 3,5-dinitrobenzoyl chloride, DMAP, NEt₃, CH₂Cl₂, 0° C. to r.t.
2. recrystallization
Step xli): KOH, MeOH Step i): MnO$_2$, CH$_2$Cl$_2$
Step ii): compound of Formula 5, sec-BuLi, THF, −78° C. to r.t.
Step viii): MnO$_2$, CH$_2$Cl$_2$
Step x): (R)-1-methyl-3,3-diphenylhexahydropyrrolo[1,2-c][1,3,2]oxazaborole, BH$_3$, DMS, toluene/THF
Step a): TBSCl, imidazole, DMF, 0° C.
Step b): 1. Co$_2$(CO)$_8$, CH$_2$Cl$_2$, rt
2. CH$_3$CN, reflux
Step xii): H$_2$, 10% Pd/C, K$_2$CO$_3$, (MeOH or THF)
Step xix): NaBH$_4$, aq. NaOH, EtOH, −10° C.
Step xx): TBDPSCl, imidazole, DMF, 50° C.
Step xxi): Aq. HCl, THF/MeOH or TBAF, THF, 0° C.
Step xvii): triisopropylbenzene-sulfonyl chloride, Et$_3$N, DMAP, CH$_2$Cl$_2$, 0° C. to r.t.
Step xviii): K$_2$CO$_3$, MeOH
Step xv): nBuLi, CuI, THF, −78° C. to r.t.
Step c): Ph$_2$PH, nBuLi, THF, −20° C. to reflux
Step d): TBAF, THF, 50° C.
Step e): R$^2$ substituted 2-bromoacetate, K$_2$CO$_3$, KI, acetone
Step f): KOH, MeOH
Step xxiv): N-methyldiethanolamine, EtOAc, EtOH, reflux to r.t.

VI. Alternative Steps

The present invention also provides the following synthetic steps, wherein one or more of the following steps may be optionally substituted for one or more steps described above.

Step A1):

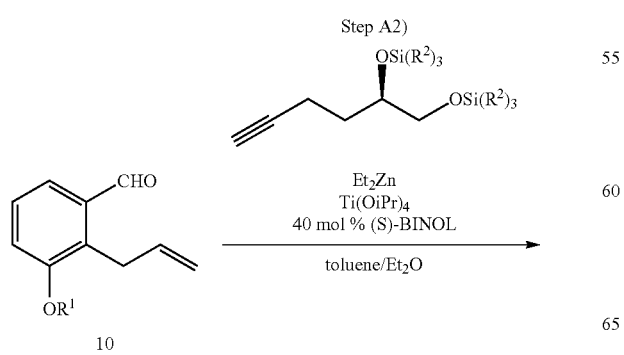

Step A2):

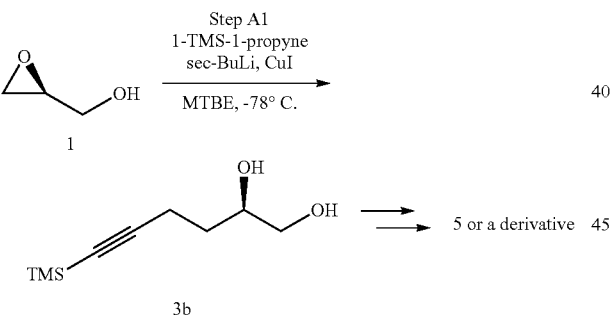

Steps A3) and A4):

Steps A5)-A7):

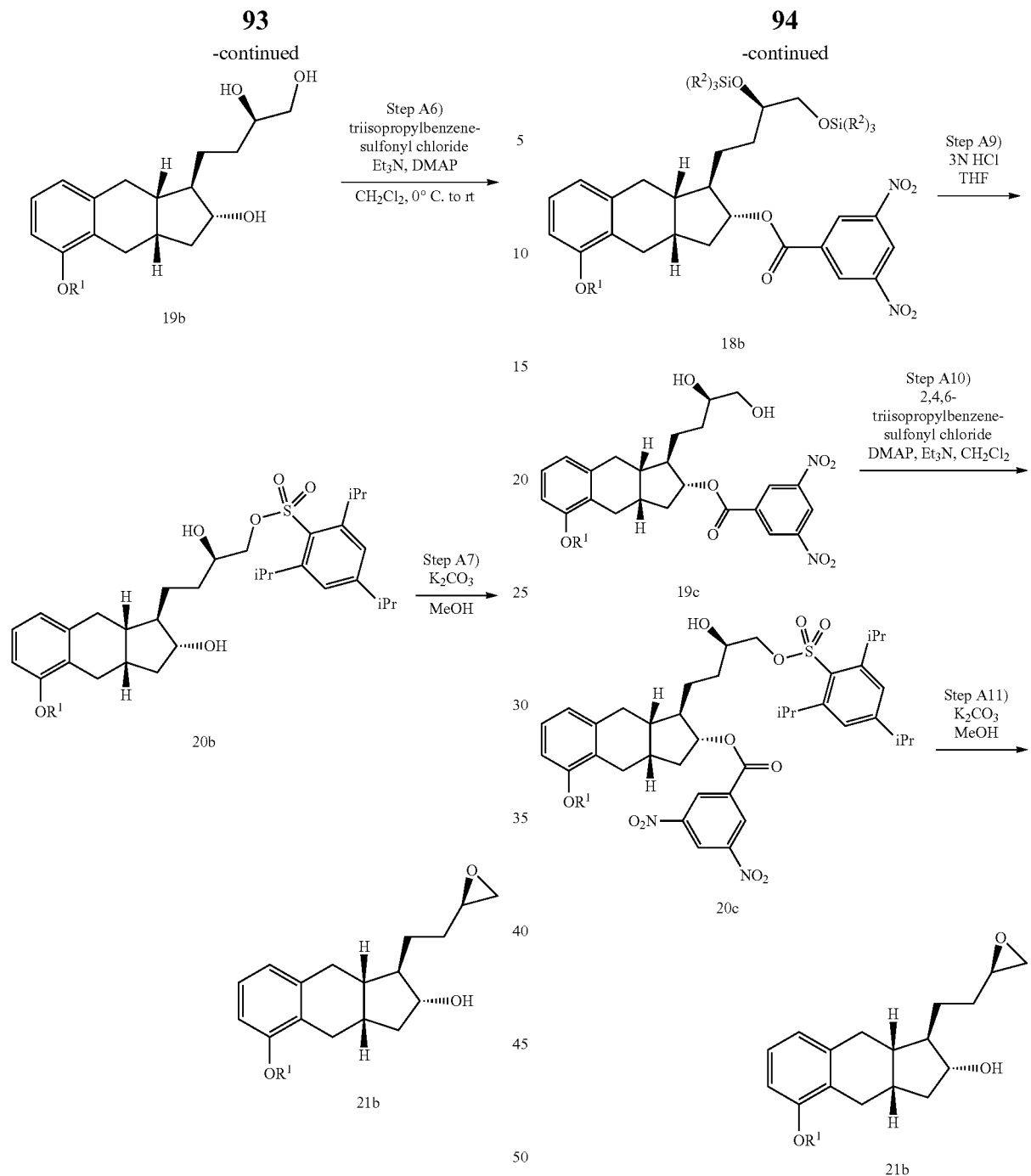
Steps A8)-A11):
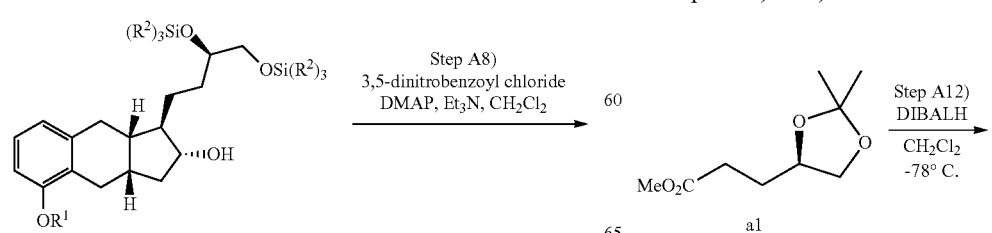
Steps A12)-A23):

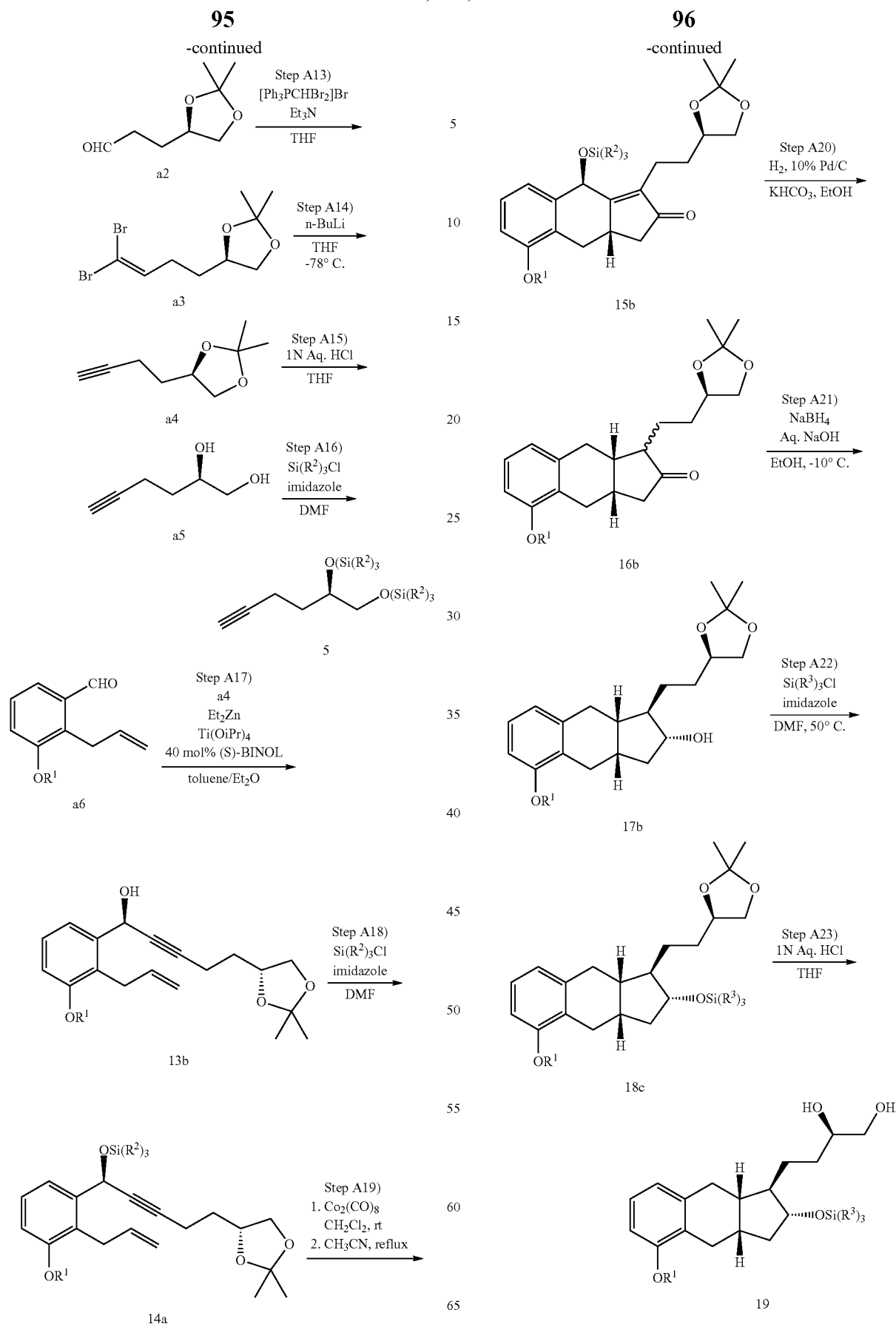

Steps A24)-A30):
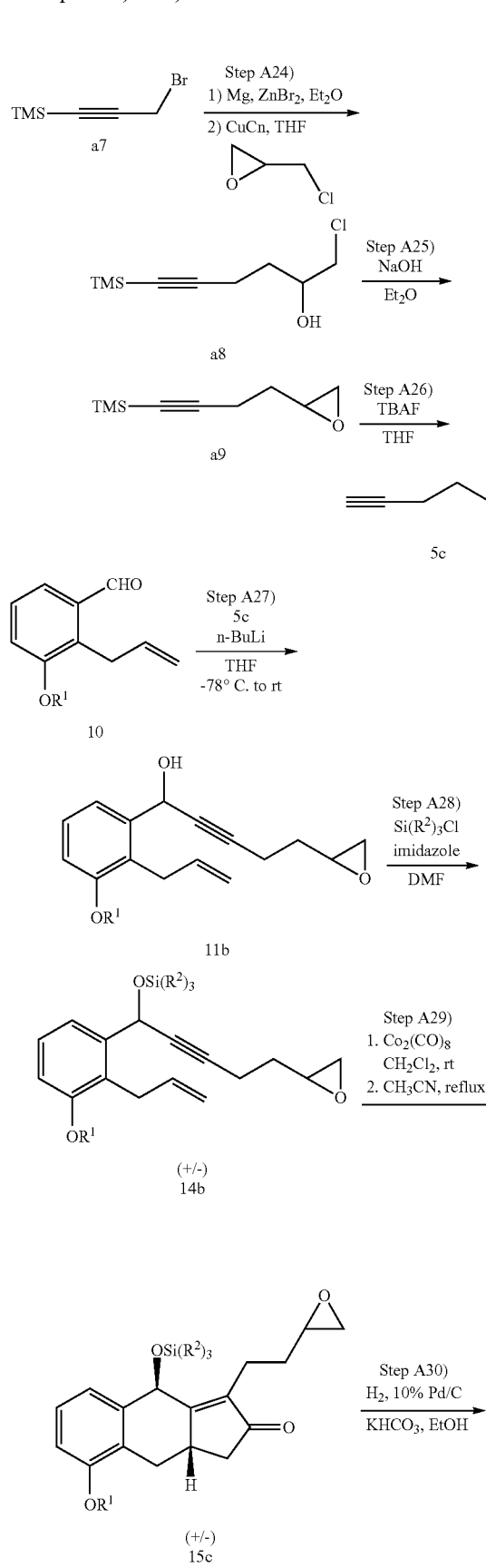
Steps A31) and A32)
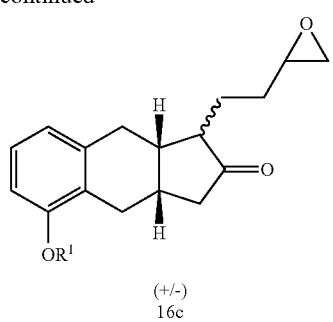
Steps A33)-A36)
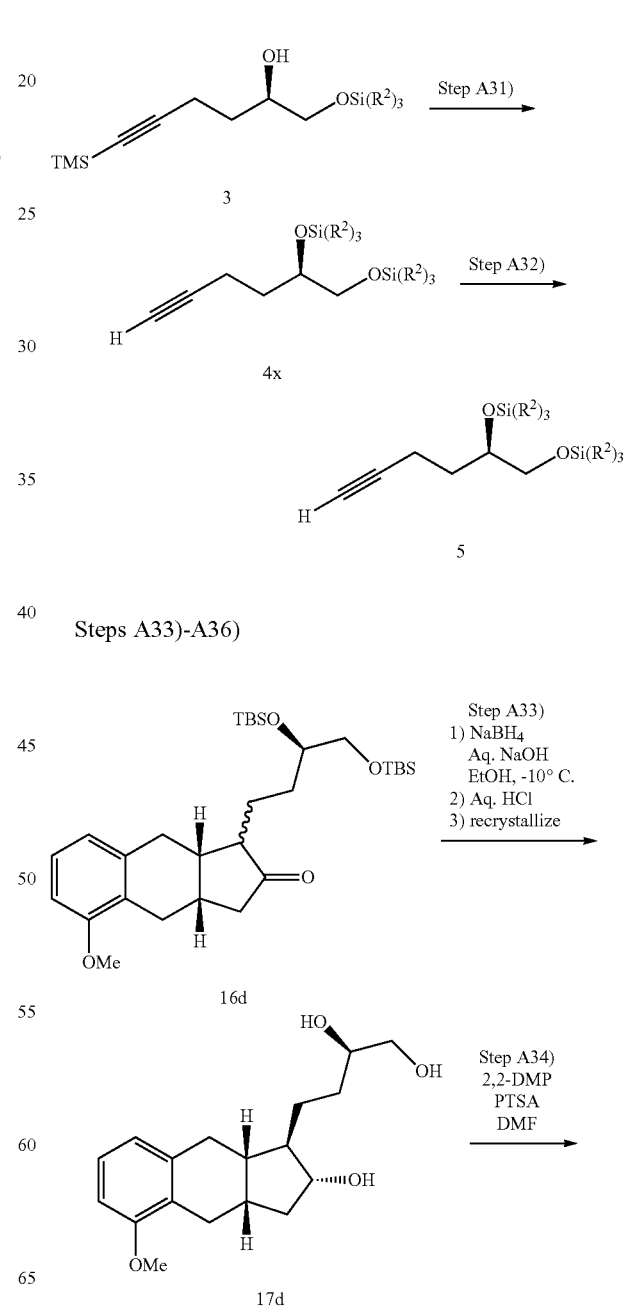

-continued

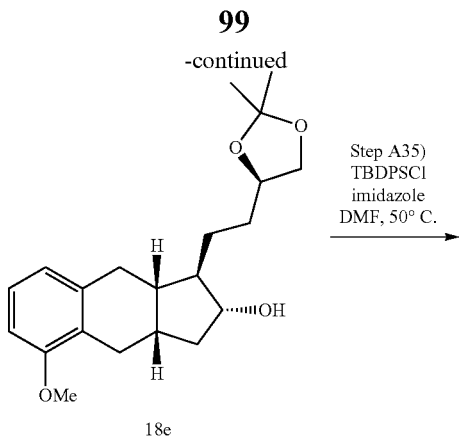

18e

Step A35)
TBDPSCl
imidazole
DMF, 50° C.

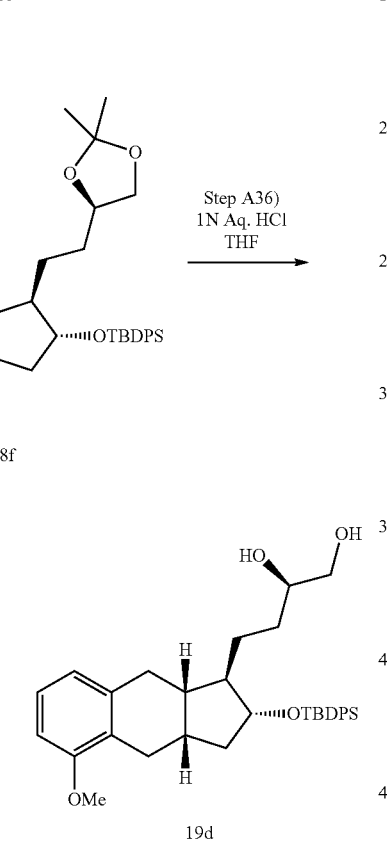

18f

Step A36)
1N Aq. HCl
THF

19d

VII. Examples

The following examples are not intended to limit the scope of the present invention.

Example 1: (R)-oxiran-2-ylmethyl 3,5-dinitrobenzoate (1a)

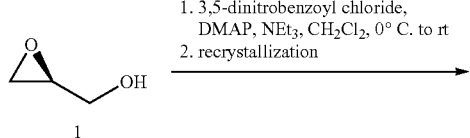

1. 3,5-dinitrobenzoyl chloride, DMAP, NEt₃, CH₂Cl₂, 0° C. to rt
2. recrystallization -continued

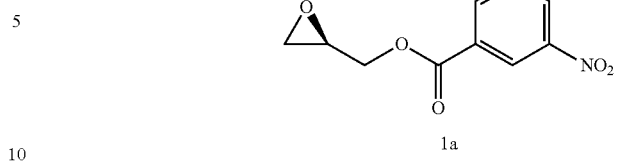

1a

Triethylamine (8.52 g mL, 84.2 mmol, 1.25 equiv) and 4-dimethylaminopyridine (100 mg, 0.818 mmol, 0.01 equiv) were added to a solution of (S)-(−)-glycidol 1 (5.00 g, 67.5 mmol, 1.0 equiv, 99.5% ee) in anhydrous methylene chloride (100 mL) while stirring under nitrogen. The reaction was then warmed to 30° C. and 3,5-dinitrobenzoyl chloride (16.3 g, 70.9 mmol, 1.05 equiv) added drop-wise over 20 minutes as a solution in anhydrous methylene chloride (50 mL). After stirring at this temperature for 30 minutes, the reaction was quenched with addition of 10% aqueous potassium bicarbonate (50 mL) and cooled to room temperature while stirring for an additional 30 minutes. The two phases were separated and the organic phase washed with 10% aqueous citric acid (50 mL). The organic phase was then purified by filtration through a plug of silica gel giving 14.69 g of a white solid that was shown to be 99.4% e.e. by chiral HPLC. Recrystallization (180 mL of 3:2 v/v heptane-dichloromethane) afforded 11.5 g (64%) of the title compound as a white solid. Data for 1a: $R_f$=0.43 (100% methylene chloride); $^1$H NMR (400 MHz, CDCl₃) δ 9.25-9.28 (m, 1H), 9.21 (d, J=2.20 Hz, 2H), 4.82 (dd, J=2.93, 12.45 Hz, 1H), 4.20-4.33 (m, 1H), 3.42 (tdd, J=2.61, 4.07, 6.82 Hz, 1H), 2.92-3.04 (m, 1H), 2.77 (dd, J=2.75, 4.58 Hz, 1H); MS (ESI+) m/z 291.0 (M+Na⁺). HPLC, ChiralPak IA column (4.6×250 mm²), 5 mm; flow rate 1.0 mL/min; 210 nm; mobile phase heptane (80%): ethanol (20%); retention time, 27.0 min, purity (100.0%).

Example 2: (S)-(−)-glycidol (1, ~100% ee)

1a

MeOH reflux 1
100% ee

A solution of dinitrobenzoate 1a (30.06 g, 112.1 mmol, 1.0 equiv) in anhydrous methanol (190 mL) was heated to reflux for 2 hours while stirring, under nitrogen. The reaction was then cooled to 0° C. in an ice bath causing formation of a crystalline solid that was removed by filtration and rinsed with ice cold methanol (15 mL). The filtrate was concentrated under reduced pressure resulting in formation of a white slurry that was dissolved in tert-butyl methyl ether (20 mL) and concentrated to dryness. The residue was again slurried in methanol (15 mL), the solid removed by filtration and rinsed with more methanol (5 mL). The filtrate was concentrated to give 7.6 g (92%) of the title compound as a pale yellow oil. Data for 1: $R_f$=0.12 (20% EtOAc/heptane).

Example 3: (R)-tert-butyldimethyl(oxiran-2-ylmethoxy)silane (2a)

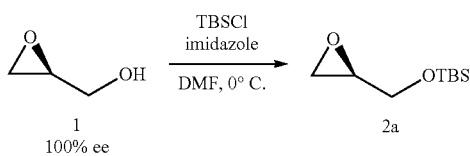 [SMILES: OC[C@H]1CO1 ; CC(C)(C)[Si](C)(C)OC[C@H]1CO1]

To a 0° C. solution of tert-butyl(chloro)dimethylsilane (26.540 g, 176.21 mmol, 1.3 equiv) and imidazole (14.786 g, 217.19 mmol, 1.6 equiv) in dimethylformamide (80 mL) was added (S)-oxiran-2-yl methanol (10.013 g, 135.16 mmol, 1.0 equiv) drop-wise and the resulting mixture stirred at that temperature under nitrogen for 30 minutes. The reaction was then quenched with addition of saturated aqueous ammonium chloride (200 mL) and water (200 mL). The resulting mixture was extracted with heptane (5×200 mL) and the combined organic phases were washed with brine, dried (MgSO$_4$) and concentrated to give 25.142 g (99%) of the title compound as a yellow oil. This material was used in the next step without purification. Data for 2a: $R_f$=0.64 (20% EtOAc/heptane); $^1$H NMR (400 MHz, CDCl$_3$) δ 3.85 (dd, J=3.22, 12.01 Hz, 1H), 3.66 (dd, J=4.69, 12.01 Hz, 1H), 3.05-3.12 (m, 1H), 2.76 (dd, J=4.25, 5.13 Hz, 1H), 2.63 (dd, J=2.64, 4.98 Hz, 1H), 0.90 (s, 9H), 0.08 (s, 3H), 0.07 (s, 3H).

Example 4: (R)-1-((tert-butyldimethylsilyl)oxy)-6-(trimethylsilyl)hex-5-yn-2-ol (3a)

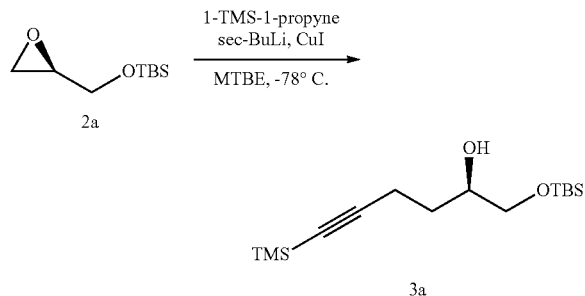

To a 3-neck flask fitted with a mechanical stirrer, a thermocouple and addition funnel was charged 1-(trimethylsilyl)-1-propyne (120.0 g, 1.07 mol, 2.2 equiv) followed by tert-butyl methyl ether (600 mL) while being kept under nitrogen. The solution was cooled to 0±5° C. while stirring and sec-butyllithium (696 mL, mmol, 2.0 equiv, 2 M in cyclohexane) was added slowly while maintaining the reaction temperature below 5° C. After complete addition, the resulting mixture was stirred at 0±5° C. under nitrogen for three hours. In a separate 3-neck flask fitted with a mechanical stirrer, a thermocouple, and addition funnel was charged epoxide 2a (92.5 g, 0.49 mol, 1.0 equiv) followed by tert-butyl methyl ether (1800 mL) and copper iodide (18.6 g, 0.1 mol, 0.2 equiv) while being kept under nitrogen. The resulting mixture was cooled to −78° C.±5° C. and then the 1-(trimethylsilyl)-1-propyne solution was cannulated into the epoxide reaction mixture. The resulting reaction mixture was allowed to slowly warm to room temperature. After stirring for 18 hours, the reaction was judged complete by TLC. The reaction was quenched with addition of 5% aqueous citric acid (1500 mL), the layers were separated and the lower aqueous layer was extracted with heptane (1000 mL). The combined organic phases were filtered through a pad of celite (150 g) and the filtrate was concentrated under reduced pressure to give 147 g (~100%) of the title compound as a dark yellow/brown oil. This material was used in the next step without purification. Data for 3a: $R_f$=0.55 (20% EtOAc/heptane); $^1$H NMR (400 MHz, CDCl$_3$) δ 3.72-3.82 (m, 1H), 3.65 (dd, J=3.81, 9.96 Hz, 1H), 3.45 (dd, J=7.03, 9.96 Hz, 1H), 2.47 (d, J=3.81 Hz, 1H), 2.34-2.42 (m, 2H), 1.63 (q, J=7.13 Hz, 2H), 0.91 (s, 9H), 0.14 (s, 9H), 0.08 (s, 6H); MS (ESI+) m/z 324.4 (M+Na$^+$).

Example 5: (R)-1-((tert-butyldimethylsilyl)oxy)hex-5-yn-2-ol (4a)

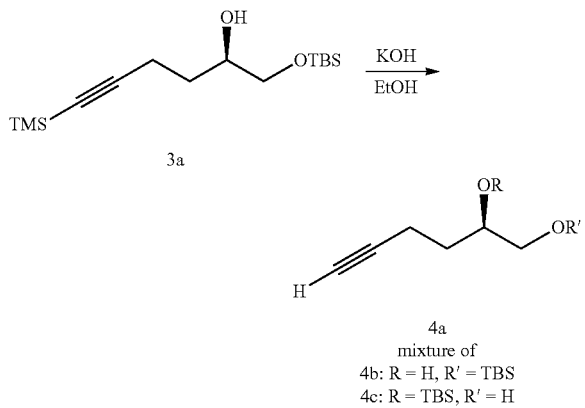

To a 3-neck flask fitted with a mechanical stirrer and thermocouple was charged (R)-1-((tert-butyldimethylsilyl)oxy)-6-(trimethylsilyl)hex-5-yn-2-ol 3a (147 g, 489 mmol, 1 equiv) dissolved in ethanol (1200 mL) under nitrogen. Solid potassium hydroxide pellets (55 g, 980 mmol, 2.0 equiv) was added and the resulting solution was stirred at room temperature for 2 hours. After completion of the reaction as judged by TLC, the reaction mixture was concentrated under reduced pressure. The crude residue was treated with heptane (1000 mL) and 10% citric acid solution (1700 mL) and the resulting mixture was stirred for 5 minutes. The layers were separated and the lower aqueous layer was extracted with heptane (700 mL). The combined organic phases were filtered through a pad of celite (120 g) and concentrated under reduced pressure to give 85 g (77%) of the title compound as a light brown oil. This material was an unquantified mixture of regioisomers due to migration of the silyl protecting group that was used in the next step without further purification. Purification of a small amount of crude 4a by chromatography (0% to 25% ethyl acetate/heptane gradient) provided analytically pure samples of 4b and 4c. Data for 4b: $R_f$=0.50 (20% EtOAc/heptane); $^1$H NMR (400 MHz, CDCl$_3$) δ 3.73-3.84 (m, 1H), 3.60-3.68 (m, 1H), 3.44

(dd, J=7.14, 10.07 Hz, 1H), 2.45 (br. s., 1H), 2.35 (dt, J=2.56, 7.14 Hz, 2H), 1.95 (t, J=2.56 Hz, 1H), 1.59-1.67 (m, 2H), 0.90 (s, 9H), 0.07 (s, 6H); MS (ESI+) m/z 229.2 (M+H⁺). Data for 4c: R$_f$=0.40 (20% EtOAc/heptane); ¹H NMR (400 MHz, CHLOROFORM-d) δ 3.84-3.97 (m, 1H), 3.56-3.66 (m, 1H), 3.43-3.54 (m, 1H), 2.25 (dt, J=2.56, 7.14 Hz, 2H), 1.96 (t, J=2.75 Hz, 1H), 1.89 (br. s., 1H), 1.65-1.81 (m, 2H), 0.78-0.98 (m, 9H), 0.12 (s, 3H), 0.10 (s, 3H); MS (ESI+) m/z 229.2 (M+H⁺).

Example 6: (R)-5-(but-3-yn-1-yl)-2,2,3,3,8,8,9,9-octamethyl-4,7-dioxa-3,8-disiladecane (5a)

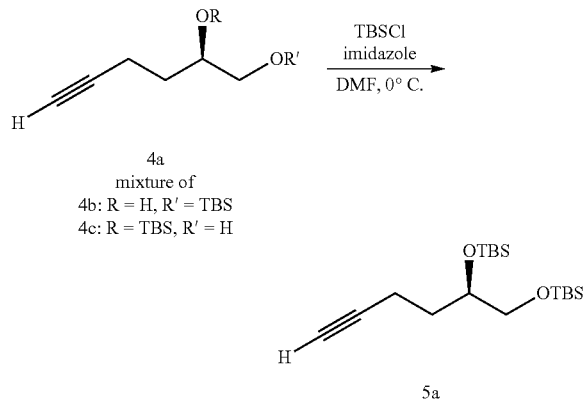

To a 3-neck flask fitted with a mechanical stirrer, a thermocouple and addition funnel was charged tert-butyldimethylsilyl chloride (59.0 g, 391 mmol, 1.05 equiv) and imidazole (40.5 g, 595 mmol, 1.6 equiv) in dimethylformamide (1100 mL). The solution was cooled to 0±5° C. while stirring. Then, a solution of (R)-1-((tert-butyldimethylsilyl)oxy)hex-5-yn-2-ol 4a (85 g, 372 mmol, 1.0 equiv) dissolved in dimethylformamide (200 mL) and added slowly to the reaction while maintaining the temperature below 5° C. Upon complete addition, the resulting mixture was stirred at 0±5° C. under nitrogen for three hours and then was slowly warmed up to room temperature and stir under nitrogen for at least 15 hrs. The reaction mixture was then diluted with methyl tert-butyl ether (1500 mL) and quenched with 5% aqueous citric acid (1500 mL). The layers were separated and the lower aqueous layer was extracted with methyl tert-butyl ether (3×1000 mL). The combined organic phases were washed with 14% aqueous sodium chloride, and concentrated under reduced pressure to give an orange oil. Chromatography (1% to 10% ethyl acetate/heptane gradient) afforded 114 g (90%) of the title compound as a yellow oil. Data for 5a: R$_f$=0.89 (20% EtOAc/heptane); ¹H NMR (400 MHz, CDCl₃) δ 3.72-3.84 (m, 1H), 3.56 (dd, J=5.13, 10.25 Hz, 1H), 3.41 (dd, J=6.59, 9.89 Hz, 1H), 2.19-2.35 (m, 2H), 1.90-1.95 (m, 1H), 1.75-1.89 (m, 1H), 1.54-1.66 (m, 1H), 0.90 (s, 9H), 0.89 (s, 9H), 0.09 (s, 3H), 0.08 (s, 3H), 0.06 (s, 6H); MS (ESI+) m/z 343.2 (M+H⁺). Chiral GC, Restek bDEXm column (30 m×0.32 mm), 65° C. for 40 min, 10° C./min to 130° C., 20° C./min to 200° C., 1 mL injection; retention time, 43.49 min (~100% 5a); Chemical Purity GC, Restek Stabilwax column (30 m×0.32 mm), 60° C. for 2 min, 10° C./min to 230° C., 1 mL injection; retention time, 10.82 min (90.0% 5a).

Example 7: tert-butyl((3-methoxybenzyl)oxy)dimethylsilane (7b)

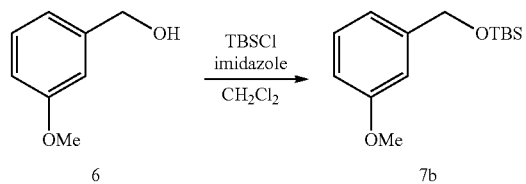 [SMILES: COc1cccc(CO)c1 ; "CH2Cl2" ; "TBSClimidazole" ; COc1cccc(CO[Si](C)(C)C(C)(C)C)c1]

To a solution of 3-methoxybenzyl alcohol 6 (2500 g, 18.09 mol, 1.0 equiv) in dichloromethane (20 L, 8 volumes) was added imidazole (1466 g, 21.53 mol, 1.19 equiv) and the solution cooled to 15° C. while stirring under nitrogen. Once cooled, the solution was charged with tert-butyl(chloro)dimethyl-silane (3164 g, 20.99 mol, 1.16 equiv) over the next 9 minutes during which time an exotherm of 42.9° C. was observed. The reaction was then cooled to room temperature while stirring for 17 hours. The reaction was then quenched with 5% aqueous citric acid (20 L, 8 volumes) and the lower organic phase concentrated to give 4958 g of a pale yellow oil. Vacuum distillation done in two batches (bp ranges 115-120 OC, 132-135° C. at 5 torr) afforded 2336 g and 1964 g of a clear colorless oil, which totaled 4300 g (94%) of the title compound. Data for 7b: R$_f$=0.27 (1% EtOAc/heptane); ¹H NMR (400 MHz, CDCl₃) δ 7.25 (t, J=8.1 Hz, 1H), 6.91 (m, 1H), 6.79 (dd, J=2.4, 8.2 Hz, 2H), 4.74 (s, 2H), 3.82 (s, 3H), 0.96 (s, 9H), 0.11 (s, 6H); MS (ESI+) m/z 275.2 (M+Na⁺).

Example 8: ((2-allyl-3-methoxybenzyl)oxy)(tert-butyl)dimethylsilane (8b)

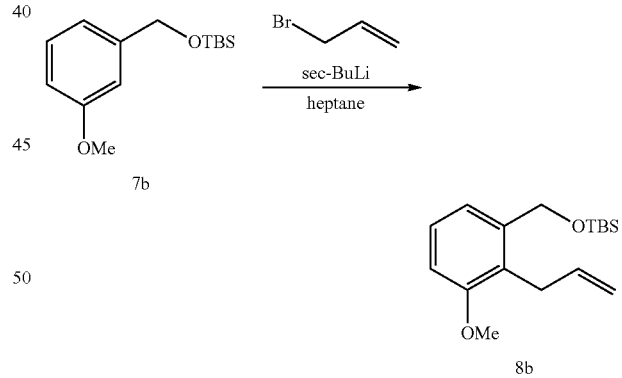

A solution of silane 7b (2660 g, 10.54 mol, 1.0 equiv) in heptane (13.30 L, 5 volumes) was treated drop-wise with sec-butyllithium (15.81 L, 22.13 mol, 2.1 equiv, 1.4 M in cyclohexane) over a period of 2 hours. The reaction was stirred at room temperature for 2 additional hours before cooling to 0° C. Once cooled, the reaction was treated drop-wise with allyl bromide (2805 g, 23.18 mol, 2.2 equiv) over the next 70 minutes. An exotherm of 17.6° C. was observed, and the reaction warmed to room temperature over the next 38 minutes. The reaction was stirred at room temperature for 20 hours and was then quenched with 20% aqueous ammonium chloride (13.30 L, 5 volumes). The organic phase was washed with 14% aqueous sodium chloride (5.32 L, 2 volumes) and was concentrated to give 3274 g of yellow oil. This material was deemed sufficiently pure to be carried forward. Data for 8b: $R_f$=0.64 (5% EtOAc/heptane); $^1$H NMR (400 MHz, CDCl$_3$) δ 7.22 (t, J=8.1 Hz, 1H), 7.11 (d, J=7.7 Hz, 1H), 6.82 (d, J=8.4 Hz, 1H), 5.92 (m, 1H), 4.93 (m, 2H), 4.74 (s, 2H), 3.82 (s, 3H), 3.41 (dt, J=1.6, 6.0 Hz, 2H), 0.95 (s, 9H), 0.10 (s, 6H); MS (ESI+) m/z 315.2 (M+Na$^+$).

Example 9: (2-allyl-3-methoxyphenyl)methanol (9b)

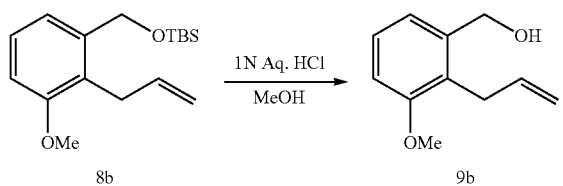 [SMILES: "MeOH" ; C=CCc1c(CO[Si](C)(C)C(C)(C)C)cccc1OC ; "1N Aq. HCl" ; C=CCc1c(CO)cccc1OC]

To a solution of silane 8b (3082 g, 10.54 mol, 1.0 equiv, theoretical weight) in methanol (30.82 L, 10 volumes) was added 6N aqueous hydrochloric acid (8.43 L, 8.431 mol, 0.8 equiv) and the reaction stirred at room temperature for 2 hours. The reaction was quenched with drop-wise addition of 10% aqueous potassium bicarbonate (15.41 L, 5 volumes) and then evaporated until approximately 10 volumes of methanol were removed. The resulting aqueous solution was extracted with ethyl acetate (15.41 L, 10 volumes). The combined organic phases were washed with 7% sodium chloride (15.41 L, 5 volumes) and concentrated to give 2582 g of a brown oil. Vacuum distillation (bp range 132-135° C. at 5 torr) afforded 1558 g (83%, 2 steps) of the title compound as a yellow oil. This material was deemed sufficiently pure to be carried forward. Data for 9b: $R_f$=0.36 (30% EtOAc/heptane); $^1$H NMR (400 MHz, CDCl$_3$) δ 7.24 (t, J=8.1 Hz, 1H), 7.03 (d, J=7.7 Hz, 1H), 6.87 (d, J=8.1 Hz, 1H), 6.01 (m, 1H), 4.97 (dq, J=1.8, 10.0 Hz, 1H), 4.92 (dq, J=1.9, 17.1 Hz, 1H), 4.70 (s, 2H), 3.84 (s, 3H), 3.52 (dt, J=1.7, 5.9 Hz, 2H); MS (ESI+) m/z 201.1 (M+Na$^+$).

Example 10: 2-allyl-3-methoxybenzyl 3,5-dinitrobenzoate (9c)

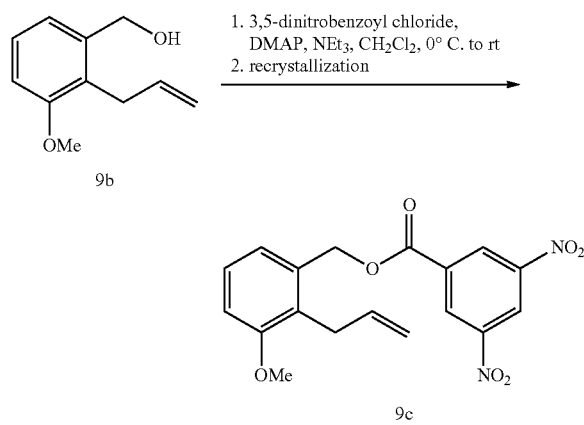

To a 0° C. solution of alcohol 9b (1558 g, 11.28 mol, 1.0 equiv) in dichloromethane (7.789 L, 5 volumes) was added 3,5-dinitrobenzoyl chloride (2860 g, 12.40 mol, 1.1 equiv) and 4-dimethylamino-pyridine (206.6 g, 1.690 mol, 0.15 equiv) resulting in an exotherm of 12.6 OC. The reaction was cooled back to 0° C. and triethylamine (1.729 L, 12.40 mol, 1.1 equiv) was added drop-wise over the next 57 minutes, during which time an exotherm of 17.6° C. was observed. Upon completion of the triethylamine addition, the reaction was quenched with 10% aqueous potassium bicarbonate (7.789 L, 5 volumes) which generated an exotherm of 19.8° C. The lower organic layer was washed with 10% aqueous citric acid (7.789 L, 5 volumes) and concentrated to give 4118 g of a light brown amorphous solid. The crude solid was suspended in methanol (41.18 L, 10 volumes based on crude quantity) and was heated to 65° C. over 94 minutes to fully dissolve the solid. The solution was then cooled back to room temperature and the precipitated solid was isolated by filtration. The solid was vacuum dried at 40° C. for 20 hours to afford 2131 g (65%) of the title compound as a light yellow solid. This material was deemed sufficiently pure to be carried forward. Data for 9c: $R_f$=0.45 (30% EtOAc/heptane); $^1$H NMR (400 MHz, CDCl$_3$) δ 9.22 (t, J=2.2 Hz, 1H), 9.16 (d, J=2.2 Hz, 2H), 7.28 (t, J=8.1 Hz, 1H), 7.08 (dd, J=0.9, 7.5 Hz, 1H), 6.97 (d, J=8.1 Hz, 1H), 5.99 (ddt, J=5.8, 10.1, 17.2 Hz, 1H), 5.49 (s, 2H), 4.98 (dq, J=1.8, 17.2 Hz, 1H), 4.89 (dq, J=1.7, 10.1 Hz, 1H), 3.87 (s, 3H), 3.57 (dt, J=1.8, 5.9 Hz, 2H); MS (ESI+) m/z 395.1 (M+Na$^+$).

Example 11: (2-allyl-3-methoxyphenyl)methanol (9b)

To a slurry of dinitrobenzoate 9c (3463 g, 9.302 mol, 1.0 equiv) in methanol (17.32 L, 5 volumes) was added potassium hydroxide (719.9 g, 11.16 mol, 1.2 equiv) and water (3.463 L, 1 volume), generating an exotherm of 37.7° C. The reaction was cooled to room temperature while stirring over 1 hour and was then concentrated until 5 volumes of methanol was removed. The resulting slurry was dissolved in 10% aqueous citric acid (17.32 L, 5 volumes) and extracted with dichloromethane (17.32 L, 5 volumes). The solid dinitrobenzoic acid byproduct was removed by filtration and the filtrate was washed with 10% aqueous potassium carbonate (9.02 L, 5 volumes) and concentrated to afford 1464 g (88%) of the title compound as a dark green oil. This material was deemed sufficiently pure to be carried forward. Data for 9b: $R_f$=0.36 (30% EtOAc/heptane); $^1$H NMR (400 MHz, CDCl$_3$) δ 7.24 (t, J=8.1 Hz, 1H), 7.03 (d, J=7.3 Hz, 1H), 6.87 (d, J=8.4 Hz, 1H), 6.01 (m, 1H), 4.96 (m, 2H), 4.70 (s, 2H), 3.84 (s, 3H), 3.52 (dt, J=1.6, 6.0 Hz, 2H); MS (ESI+) m/z 201.1 (M+Na$^+$).

Example 12: 2-Allyl-3-Methoxybenzaldehyde (10b)

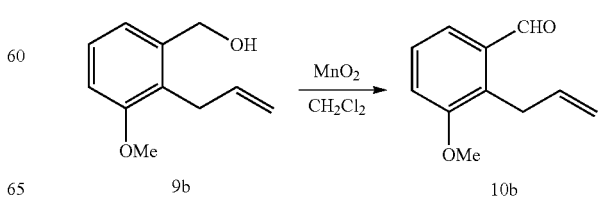

Manganese(IV) oxide (85.00 g, 977.6 mmol, 10.0 equiv) was added to a solution of alcohol 9b (17.424 g, 97.761 mmol, 1.0 equiv) in anhydrous methylene chloride (5 mL) and the mixture stirred under nitrogen for 16 hours. The reaction was then filtered through celite, the solids washed with heptane and the filtrate concentrated to give 534 (99%) of the title compound as a pale oil. Data for 10b: $R_f$=0.64 (30% EtOAc/heptane); $^1$H NMR (400 MHz, CDCl$_3$) δ 10.28 (s, 1H), 7.49 (dd, J=1.1, 7.7 Hz, 1H), 7.36 (t, J=8.1 Hz, 1H), 7.13 (dd, J=0.9, 8.2 Hz, 1H), 6.02 (ddt, J=5.9, 10.0, 17.1 Hz, 1H), 5.02 (dq, J=1.6, 10.1, 5.0 Hz, 1H), 4.93 (dq, J=1.7, 17.2, 4.9 Hz, 1H), 3.88 (s, 3H), 3.86 (dt, J=1.8, 5.9 Hz, 2H); MS (ESI+) m/z 199.1 (M+Na$^+$).

Example 13: (6R)-1-(2-allyl-3-methoxyphenyl)-6,7-bis((tert-butyldimethylsilyl)oxy)hept-2-yn-1-ol (11c)

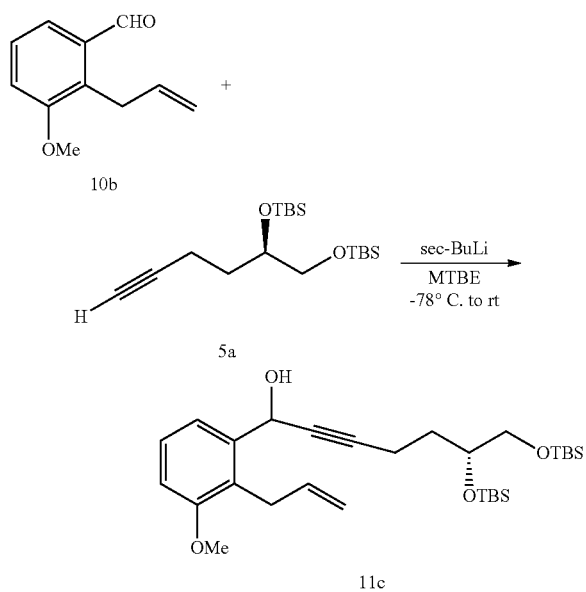

A solution of alkyne 5a (1.070 g, 3.121 mmol, 1.1 equiv) in anhydrous MTBE (11 mL) that had been cooled to −78° C. was treated drop-wise with sec-butyllithium (2.20 mL, 3.12 mmol, 1.1 equiv, 1.4 M solution in cyclohexane) and the resulting mixture stirred at that temperature under nitrogen for 30 minutes. Then, aldehyde 10b (500 mg, 2.83 mmol, 1.0 equiv) was added drop-wise as a solution in MTBE (4 mL) and the reaction allowed to slowly warm to room temperature. After stirring for 17 hours, the reaction was quenched with addition of 10% aqueous citric acid (30 mL) and extracted with heptane (3×30 mL). The combined organic phases were then washed with brine and concentrated to give 1.6 g of a yellow oil. Chromatography (0% to 15% ethyl acetate/heptane gradient) afforded 1.340 g (91%) of the title compound as a pale yellow oil. Data for 11c: $R_f$=0.60 (20% EtOAc/heptane); $^1$H NMR (400 MHz, CDCl$_3$)δ 7.35 (d, J=7.91 Hz, 1H), 7.19-7.29 (m, 1H), 6.87 (dd, J=0.88, 8.20 Hz, 1H), 5.93-6.08 (m, 1H), 5.64 (s, 1H), 4.90-5.03 (m, 2H), 3.83 (s, 3H), 3.71-3.80 (m, 1H), 3.60-3.70 (m, 1H), 3.50-3.60 (m, 2H), 3.40 (dd, J=6.74, 9.96 Hz, 1H), 2.25-2.44 (m, 2H), 2.04 (br. s., 1H), 1.76-1.90 (m, 1H), 1.60 (dtd, J=6.30, 7.67, 13.81 Hz, 1H), 0.90 (s, 9H), 0.88 (s, 9H), 0.05 (s, 12H); MS (ESI+) m/z 541.4 (M+Na$^+$).

Example 14: (R)-1-(2-allyl-3-methoxyphenyl)-6,7-bis((tert-butyldimethylsilyl)oxy)hept-2-yn-1-one (12b)

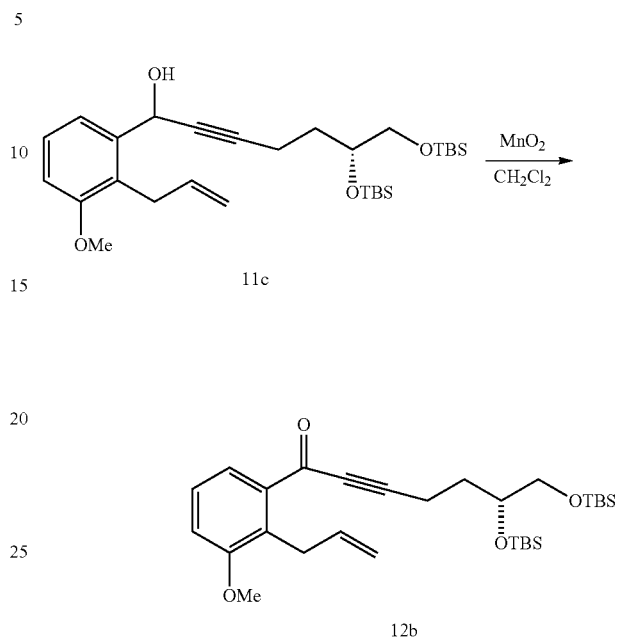

Manganese(IV) oxide (869 mg, 10.0 mmol, 10.0 equiv) was added to a solution of alcohol 11c (540 mg, 1.04 mmol, 1.0 equiv) in anhydrous methylene chloride (5 mL) and the mixture stirred under nitrogen for 16 hours. The reaction was then filtered through celite, the solids washed with heptane and the filtrate concentrated to give 534 (99%) of the title compound as a pale oil. Data for 12b: $R_f$=0.62 (normal phase, 20% EtOAc/heptane); $^1$H NMR (400 MHz, CDCl$_3$) δ 7.74 (dd, J=1.17, 7.81 Hz, 1H), 7.24-7.35 (m, 1H), 7.07 (dd, J=0.78, 8.20 Hz, 1H), 5.90-6.06 (m, 1H), 4.86-5.09 (m, 2H), 3.86 (s, 3H), 3.75-3.84 (m, 3H), 3.58 (dd, J=5.27, 9.96 Hz, 1H), 3.41 (dd, J=6.84, 9.96 Hz, 1H), 2.44-2.66 (m, 2H), 1.87-2.01 (m, 1H), 1.72 (dtd, J=5.86, 7.81, 13.67 Hz, 1H), 0.90 (s, 9H), 0.89 (s, 9H), 0.08 (s, 6H), 0.06 (s, 6H); MS (ESI+) m/z 517.2 (M+H$^+$).

Example 15: (1S,6R)-1-(2-allyl-3-methoxyphenyl)-6,7-bis((tert-butyldimethylsilyl)oxy)hept-2-yn-1-ol (13c)

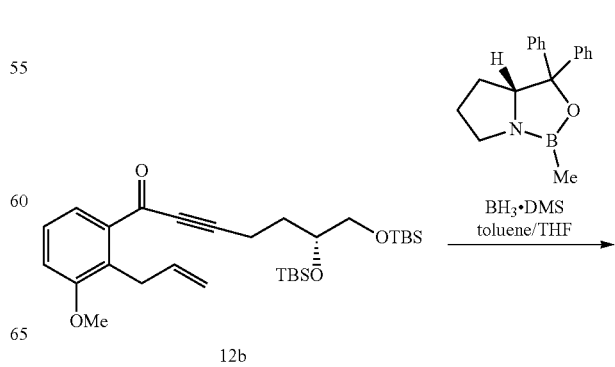

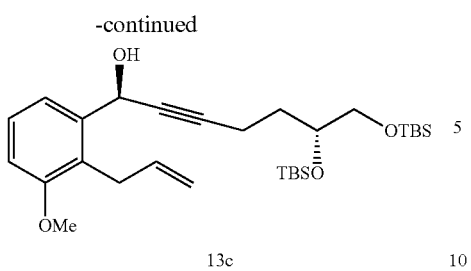

13c

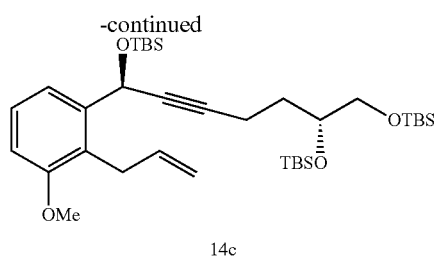

14c

Aryl ketone 12b (95.7 g, 185 mmol, 1.0 equiv) was dissolved in THF (1900 mL) under nitrogen. (R)-(+)-2-methyl-CBS-oxazaborolidine (222 mL, 222 mmol, 1.2 equiv, 1 M solution in toluene) was added and the resulting mixture cooled to −50° C.±5° C. Borane-methyl sulfide complex (370 mL, 370 mmol, 4.0 equiv, 2.0 M solution in THF) was then added drop-wise over 20 minutes. After stirring at −50° C. for 75 minutes, the mixture was cautiously quenched with drop-wise addition of methanol (600 mL) and subsequently warmed to room temperature while stirring overnight. The quenched mixture was cooled to 0° C., diluted with ethyl acetate (2000 mL) and treated with 5% aqueous citric acid (1500 mL). The layers were separated and the aqueous phase was further extracted with ethyl acetate (2×1500 mL). The combined organic phases were washed with 14% sodium chloride solution (1500 mL) and concentrated under reduced pressure. The crude oil was chased with heptane (2×500 mL) to afford 96.35 g of a pale oil. This material was deemed sufficiently pure to be carried forward crude. Data for 13c: $R_f$=0.58 (20% EtOAc/heptane); $^1$H NMR (400 MHz, CDCl$_3$) δ 7.35 (dd, J=1.03, 7.76 Hz, 1H), 7.20-7.29 (m, 1H), 6.87 (dd, J=0.88, 8.20 Hz, 1H), 6.00 (tdd, J=5.64, 10.18, 17.21 Hz, 1H), 5.63 (br. s., 1H), 4.87-5.06 (m, 2H), 3.83 (s, 3H), 3.75 (dddd, J=4.25, 5.27, 6.66, 7.84 Hz, 1H), 3.61-3.69 (m, 1H), 3.51-3.61 (m, 2H), 3.40 (dd, J=6.74, 9.96 Hz, 1H), 2.26-2.42 (m, 2H), 2.06 (br. s., 1H), 1.78-1.90 (m, 1H), 1.60 (dtd, J=5.86, 7.95, 13.70 Hz, 1H), 0.90 (s, 9H), 0.88 (s, 9H), 0.05 (s, 12H); MS (ESI+) m/z 541.2 (M+Na+); HPLC, ChiralPak IA column (4.6×250 mm2), 5 mm; flow rate 1.0 mL/min; 210 nm; mobile phase heptane (99%): 2-propanol (1%): trifluoroacetic acid (0.1%); retention time, 8.66 min (1.2%, (1R,6R)-1-(2-allyl-3-methoxyphenyl)-6,7-bis((tert-butyldimethylsilyl)oxy) hept-2-yn-1-ol), retention time, 9.48 min (98.8%, 13c)

Example 16: (5S,10R)-5-(2-allyl-3-methoxyphenyl)-10-((tert-butyldimethylsilyl)oxy)-2,2,3,3,13,13,14,14-octamethyl-4,12-dioxa-3,13-disilapentadec-6-yne (14c)

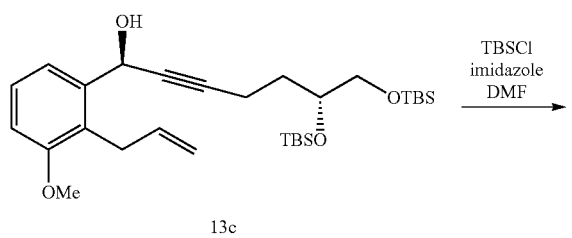

13c

Imidazole (1.732 g, 25.44 mmol, 1.2 equiv) and tert-butyl (chloro)dimethylsilane (3.545 g, 23.32 mmol, 1.1 equiv) were added to a stirred, 0° C. solution of alkynol 13c (11.002 g, 21.20 mmol, 1.0 equiv) in anhydrous DMF under nitrogen and the mixture was then warmed to room temperature. The reaction was then quenched with addition of saturated aqueous ammonium chloride (100 mL) and water (100 mL). The resulting mixture was extracted with heptane (3×200 mL) and the combined organic phases were washed with water, brine, dried (MgSO$_4$) and concentrated to give 13.351 g (99%) of the title compound as a pale yellow oil. This material was deemed sufficiently pure to be carried forward. Data for 14c: $R_f$=0.82 (20% EtOAc/heptane); $^1$H NMR (400 MHz, CDCL$_3$) δ 7.25-7.32 (m, 1H), 7.18-7.25 (m, 1H), 6.82 (d, J=8.20 Hz, 1H), 5.88-6.04 (m, 1H), 5.58 (s, 1H), 4.88-5.03 (m, 2H), 3.82 (s, 3H), 3.67-3.76 (m, 1H), 3.57-3.66 (m, 1H), 3.46-3.57 (m, 2H), 3.37 (dd, J=6.45, 9.96 Hz, 1H), 2.16-2.34 (m, 2H), 1.70-1.85 (m, 1H), 1.47-1.60 (m, 1H), 0.91 (s, 9H), 0.89 (s, 9H), 0.87 (s, 9H), 0.12 (s, 3H), 0.09 (s, 3H), 0.04 (s, 12H); MS (ESI+) m/z 655.5 (M+Na+).

Example 17: (4R,9aS)-3-((R)-3,4-bis((tert-butyldimethylsilyl)oxy)butyl)-4-((tert-butyldimethylsilyl)oxy)-8-methoxy-9,9a-dihydro-1H-cyclopenta[b]naphthalen-2(4H)-one (15d)

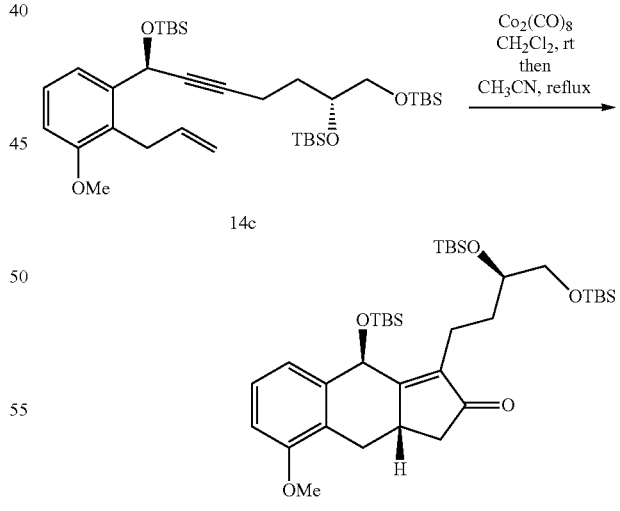

Cobalt carbonyl (7.197 g, 21.05 mmol, 1.0 equiv) was added to a solution of compound 14c (13.326 g, 21.05 mmol, 1.0 equiv) in anhydrous methylene chloride and the reaction stirred at room temperature under nitrogen for 2 hours to allow for formation of the cobalt-alkyne complex. The reaction was then concentrated by rotary evaporation, the residue dissolved in anhydrous acetonitrile and the mixture heated to reflux with stirring for 18 hours. The reaction was then cooled to room temperature, filtered through celite, and the precipitate washed with several portions of acetone. The filtrate was concentrated to give 14.9 g of an amber oil. Chromatography (0% to 20% ethyl acetate/heptane gradient) afforded 13.803 g (99%) of the title compound as a colorless oil. Data for 15d: $R_f$=0.57 (20% EtOAc/heptane); $^1$H NMR (400 MHz, CDCl$_3$) δ 7.24 (t, J=7.91 Hz, 1H), 6.91 (d, J=7.62 Hz, 1H), 6.79 (d, J=7.91 Hz, 1H), 5.51 (s, 1H), 3.83 (s, 3H), 3.61-3.71 (m, 1H), 3.30-3.59 (m, 4H), 2.70 (dd, J=6.45, 18.75 Hz, 1H), 2.35-2.48 (m, 1H), 2.10-2.32 (m, 3H), 1.57 (td, J=7.58, 15.01 Hz, 2H), 0.91 (s, 9H), 0.88 (s, 9H), 0.82 (s, 9H), 0.00-0.14 (m, 18H); MS (ESI+) m/z 683.4 (M+Na$^+$).

Example 18a: (3aS,9aS)-1-((R)-3,4-bis((tert-butyldimethylsilyl)oxy)butyl)-5-methoxy-3a,4,9,9a-tetrahydro-1H-cyclopenta[b]naphthalen-2(3H)-one (16d)

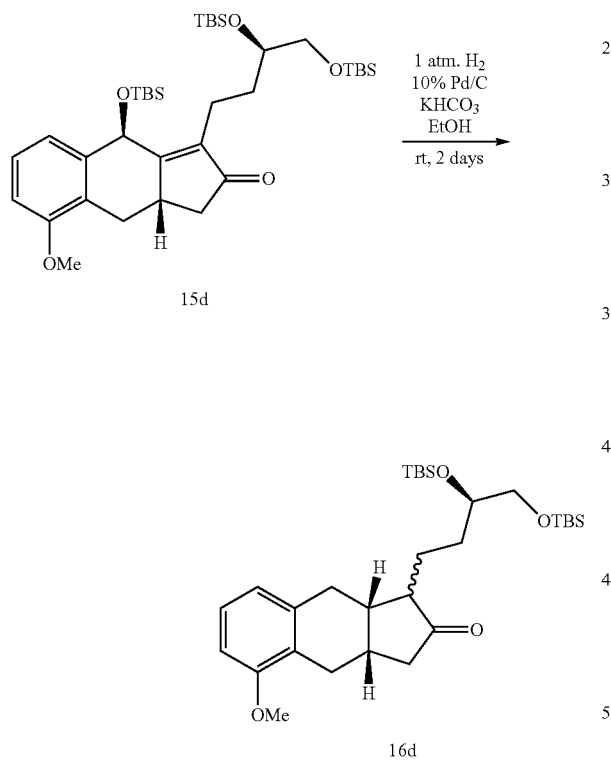

To a solution of tricyclic enone 15d (14.86 g, 22.48 mmol, 1.0 equiv) in absolute methanol (225 mL) was added anhydrous potassium bicarbonate (743 mg, 5% w/w) and 10% Pd/C (3.715 g, 50% wet, 25% w/w) and the mixture was hydrogenated with a balloon of hydrogen gas while stirring at room temperature for 64 hours. The reaction mixture was then filtered through celite, the residue washed with several portions of ethanol, and the filtrate concentrated to give a yellow oil. Triteration with heptane caused formation of a small amount of precipitate that was filtered off, and the filtrate concentrated to give 12.5 g of a viscous, yellow oil. Chromatography (0% to 10% ethyl acetate/heptane gradient) afforded 10.998 g (92%) of the title compound as a pale oil. Data for 16d: $R_f$=0.47 (20% EtOAc/heptane); $^1$H NMR (400 MHz, CDCl$_3$) δ 7.11 (t, J=7.81 Hz, 1H), 6.71 (d, J=8.20 Hz, 2H), 3.84 (s, 3H), 3.62-3.76 (m, 1H), 3.52-3.61 (m, 1H), 3.43 (dd, J=6.84, 9.96 Hz, 1H), 2.10-3.08 (m, 8H), 1.19-2.04 (m, 5H), 0.91 (d, J=8.98 Hz, 18H), 0.01-0.18 (m, 12H); MS (ESI+) m/z 533.2 (M+H$^+$).

Example 18b: (3aS,9aS)-1-((R)-3,4-bis((tert-butyldimethylsilyl)oxy)butyl)-5-methoxy-3a,4,9,9a-tetrahydro-1H-cyclopenta[b]naphthalen-2(3H)-one (16d)

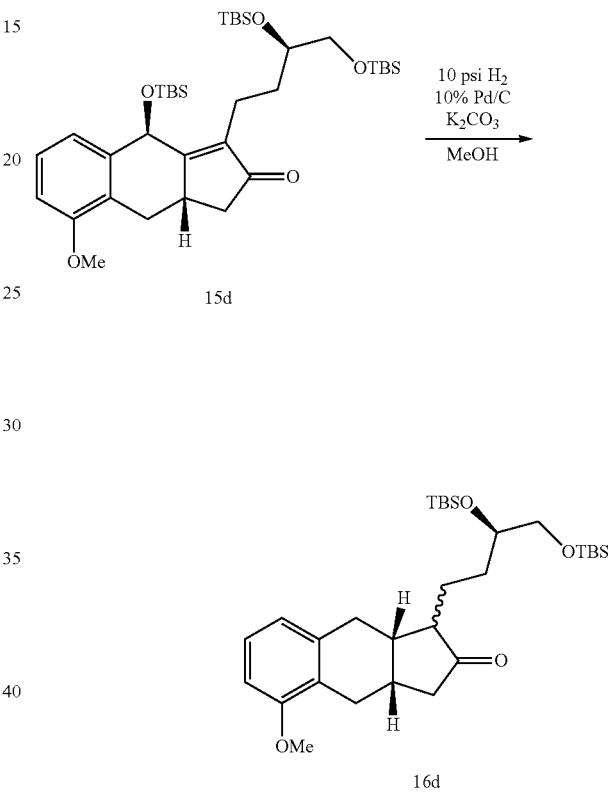

To a solution of tricyclic enone 15d (1.0 g, mmol, 1.0 equiv) in methanol (10 mL) was added anhydrous potassium carbonate (53 mg, 5% w/w) and 10% Pd/C (100 mg, 50% wet, 10% w/w) and the mixture was hydrogenated under 10 psi hydrogen gas while stirring at room temperature for about 18 hours. The reaction mixture was then filtered through celite, the residue was washed with several portions of MTBE, and the filtrate concentrated to give a yellow oil. Triteration with MTBE caused formation of a small amount of precipitate that was filtered off, and the filtrate concentrated to give 0.98 g of viscous, yellow oil. This material was deemed sufficiently pure to be carried forward, but was purified for analytical characterization. Chromatography (0% to 2.5% ethyl acetate/heptane) afforded 0.711 g (88%) of the title compound as a viscous, colorless oil. Data for 16d: $R_f$=0.47 (20% EtOAc/heptane); $^1$H NMR (400 MHz, CDCl$_3$) δ 7.11 (t, J=7.81 Hz, 1H), 6.71 (d, J=8.20 Hz, 2H), 3.84 (s, 3H), 3.62-3.76 (m, 1H), 3.52-3.61 (m, 1H), 3.43 (dd, J=6.84, 9.96 Hz, 1H), 2.10-3.08 (m, 8H), 1.19-2.04 (m, 5H), 0.91 (d, J=8.98 Hz, 18H), 0.01-0.18 (m, 12H); MS (ESI+) m/z 533.2 (M+H$^+$).

Example 18c: (3aS,9aS)-1-((R)-3,4-bis((tert-butyldimethylsilyl)oxy)butyl)-5-methoxy-3a,4,9,9a-tetrahydro-1H-cyclopenta[b]naphthalen-2(3H)-one (16d)

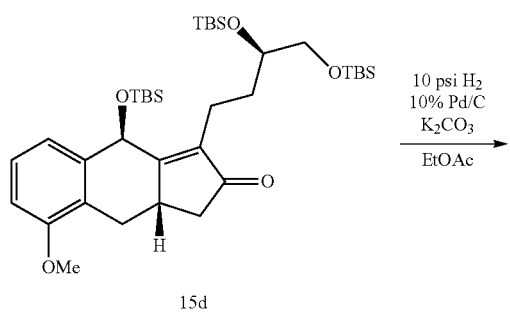

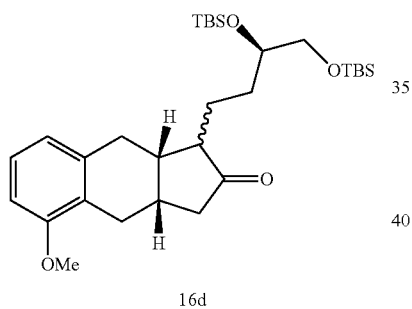

To a solution of tricyclic enone 15d (500 mg, 0.756 mmol, 1.0 equiv) in ethyl acetate (7.5 mL) was added anhydrous potassium carbonate (25 mg, 5% w/w) and 10% Pd/C (75 mg, 50% wet, 15% w/w). The mixture was hydrogenated under 10 psi hydrogen gas while shaking in a Parr flask at room temperature for 24 hours. The reaction was then charged with additional 10% Pd/C (75 mg, 50% wet, 15% w/w), and hydrogenated under 10 psi hydrogen gas while shaking in a Parr flask at room temperature for 24 more hours. At this point the reaction was shown to be complete by TLC and was filtered through celite, the residue was washed with several portions of ethyl acetate, and the filtrate concentrated to give 404 mg of a light yellow oil. Chromatography (0% to 5% ethyl acetate/heptane gradient) afforded 290 mg (72%) of the title compound as a viscous, colorless oil. Data for 16d: $R_f$=0.47 (20% EtOAc/heptane); $^1$H NMR (400 MHz, CHLOROFORM-d) δ 7.11 (t, J=7.81 Hz, 1H), 6.71 (d, J=8.20 Hz, 2H), 3.84 (s, 3H), 3.62-3.76 (m, 1H), 3.52-3.61 (m, 1H), 3.43 (dd, J=6.84, 9.96 Hz, 1H), 2.10-3.08 (m, 8H), 1.19-2.04 (m, 5H), 0.91 (d, J=8.98 Hz, 18H), 0.01-0.18 (m, 12H); MS (ESI+) m/z 533.2 (M+H$^+$).

Example 18d: (3aS,9aS)-1-((R)-3,4-bis((tert-butyldimethylsilyl)oxy)butyl)-5-methoxy-3a,4,9,9a-tetrahydro-1H-cyclopenta[b]naphthalen-2(3H)-one (16d)

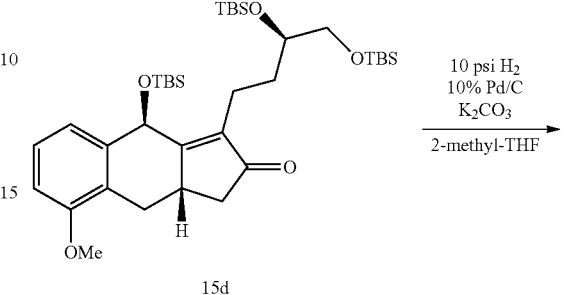

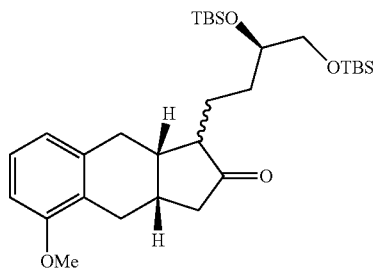

To a solution of tricyclic enone 15d (1.000 g, 1.513 mmol, 1.0 equiv) in 2-methyltetrahydrofuran (15 mL) was added anhydrous potassium carbonate (50 mg, 5% w/w) and 10% Pd/C (150 mg, 50% wet, 10% w/w) and the mixture was hydrogenated under 10 psi hydrogen gas while stirring at room temperature for about 18 hours. The reaction was then charged with additional 10% Pd/C (150 mg, 50% wet, 15% w/w), and hydrogenated under 10 psi hydrogen gas while stirring at room temperature for about 23 hours. At this point the reaction was shown to be complete by TLC and was filtered through celite, the residue was washed with several portions of ethyl acetate, and the filtrate concentrated to give 984 mg of a light yellow oil. Chromatography (0% to 5% ethyl acetate/heptane gradient) afforded 507 mg (63%) of the title compound as a viscous, colorless oil. Data for 16d: $R_f$=0.47 (20% EtOAc/heptane); $^1$H NMR (400 MHz, CHLOROFORM-d) δ 7.11 (t, J=7.81 Hz, 1H), 6.71 (d, J=8.20 Hz, 2H), 3.84 (s, 3H), 3.62-3.76 (m, 1H), 3.52-3.61 (m, 1H), 3.43 (dd, J=6.84, 9.96 Hz, 1H), 2.10-3.08 (m, 8H), 1.19-2.04 (m, 5H), 0.91 (d, J=8.98 Hz, 18H), 0.01-0.18 (m, 12H); MS (ESI+) m/z 533.2 (M+H$^+$).

Example 18e: (3aS,9aS)-1-((R)-3,4-bis((tert-butyldimethylsilyl)oxy)butyl)-5-methoxy-3a,4,9,9a-tetrahydro-1H-cyclopenta[b]naphthalen-2(3H)-one (16d)

Example 18f: (3aS,9aS)-1-((R)-3,4-bis((tert-butyldimethylsilyl)oxy)butyl)-5-methoxy-3a,4,9,9a-tetrahydro-1H-cyclopenta[b]naphthalen-2(3H)-one (16d

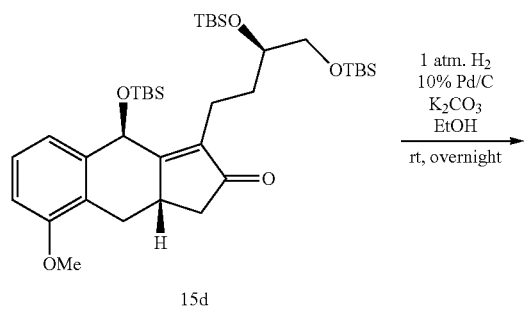

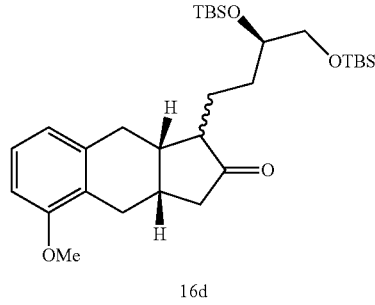

To a solution of tricyclic enone 15d (1.465 g, 2.216 mmol, 1.0 equiv) in absolute ethanol (225 mL) was added anhydrous potassium carbonate (126 mg, 8.5% w/w) and 10% Pd/C (225 mg, 50% wet, 15% w/w) and the mixture was hydrogenated at atmospheric pressure of hydrogen gas while stirring at room temperature overnight. The reaction mixture was then filtered through celite, the residue washed with several portions of ethanol, and the filtrate concentrated to give yellow oil. Triteration with heptane caused formation of a small amount of precipitate that was filtered off, and the filtrate was concentrated to give a viscous, yellow oil. The crude oil was dissolved in ethanol (15 mL) and DI water (7 mL) was added slowly to the stirred solution. The white solid was filtered and washed with a 1:1 mixture of ethanol and DI water. The solid was dried under vacuum overnight to afford 985 mg (83%) of the title compound as a white solid. Data for 16d: $R_f$=0.47 (20% EtOAc/heptane); $^1$H NMR (400 MHz, CHLOROFORM-d) δ 7.11 (t, J=7.81 Hz, 1H), 6.71 (d, J=8.20 Hz, 2H), 3.84 (s, 3H), 3.62-3.76 (m, 1H), 3.52-3.61 (m, 1H), 3.43 (dd, J=6.84, 9.96 Hz, 1H), 2.10-3.08 (m, 8H), 1.19-2.04 (m, 5H), 0.91 (d, J=8.98 Hz, 18H), 0.01-0.18 (m, 12H); MS (ESI+) m/z 533.2 (M+H$^+$).

To a solution of tricyclic enone 15d (1.425 g, 2.155 mmol, 1.0 equiv) in absolute ethanol (225 mL) was added anhydrous potassium carbonate (116 mg, 8% w/w) and 10% Pd/C (220 mg, 50% wet, 15% w/w) and the mixture was hydrogenated under 10 psi of hydrogen gas while stirring at room temperature overnight. The reaction mixture was then filtered through celite, the residue washed with several portions of ethanol, and the filtrate concentrated to give a yellow oil. Triteration with heptane caused formation of a small amount of precipitate that was filtered off, and the filtrate was concentrated to give a viscous, yellow oil. The crude oil was dissolved in ethanol (15 mL) and DI water (7 mL) was added slowly to the stirred solution. The white solid was filtered and washed with a 1:1 mixture of ethanol and DI water. The solid was dried under vacuum overnight to afford 1.51 g (91%) of the title compound as a white solid. Data for 16d: $R_f$=0.47 (20% EtOAc/heptane); $^1$H NMR (400 MHz, CHLOROFORM-d) δ 7.11 (t, J=7.81 Hz, 1H), 6.71 (d, J=8.20 Hz, 2H), 3.84 (s, 3H), 3.62-3.76 (m, 1H), 3.52-3.61 (m, 1H), 3.43 (dd, J=6.84, 9.96 Hz, 1H), 2.10-3.08 (m, 8H), 1.19-2.04 (m, 5H), 0.91 (d, J=8.98 Hz, 18H), 0.01-0.18 (m, 12H); MS (ESI+) m/z 533.2 (M+H$^+$).

Example 18g: (3aS,9aS)-1-((R)-3,4-bis((tert-butyldimethylsilyl)oxy)butyl)-5-methoxy-3a,4,9,9a-tetrahydro-1H-cyclopenta[b]naphthalen-2(3H)-one (16d)

Example 18h: (3aS,9aS)-1-((R)-3,4-bis((tert-butyldimethylsilyl)oxy)butyl)-5-methoxy-3a,4,9,9a-tetrahydro-1H-cyclopenta[b]naphthalen-2(3H)-one (16d)

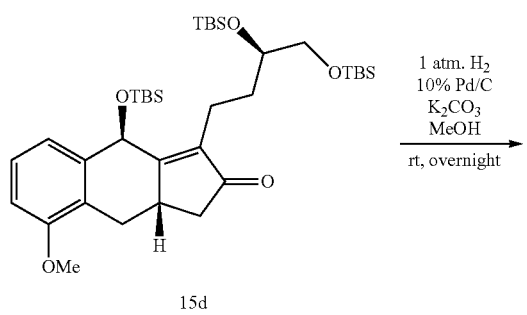

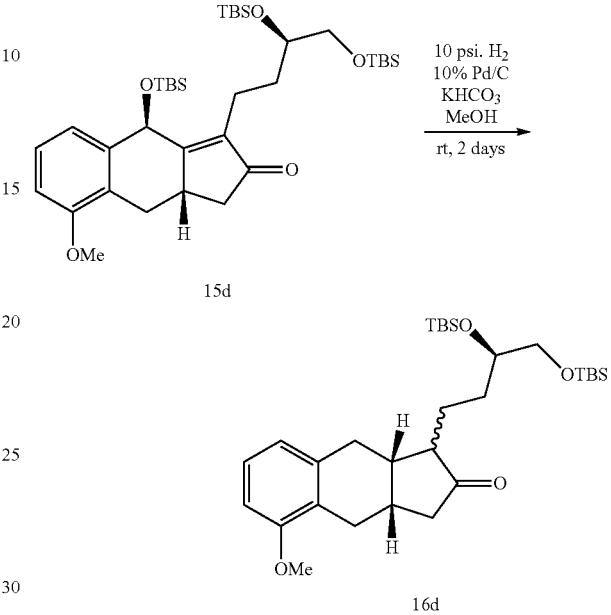

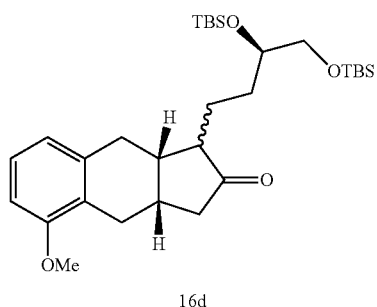

To a solution of tricyclic enone 15d (2.0 g, 3.0 mmol, 1.0 equiv) in methanol (15 mL) was added anhydrous potassium carbonate (141 mg, 7% w/w) and 10% Pd/C (294 mg, 50% wet, 15% w/w) and the mixture was hydrogenated at atmospheric pressure of hydrogen gas while stirring at room temperature overnight. The reaction was then filtered through celite, the residue washed with several portions of methanol, and the filtrate concentrated to give a yellow oil. Triteration with heptane caused formation of a small amount of precipitate that was filtered off. The filtrate was concentrated to give a viscous, yellow oil. Chromatography (0% to 3% ethyl acetate/heptane gradient) afforded 1.51 g (94%) of the title compound as white solid. Data for 16d: $R_f$=0.47 (20% EtOAc/heptane); $^1$H NMR (400 MHz, CHLOROFORM-d) δ 7.11 (t, J=7.81 Hz, 1H), 6.71 (d, J=8.20 Hz, 2H), 3.84 (s, 3H), 3.62-3.76 (m, 1H), 3.52-3.61 (m, 1H), 3.43 (dd, J=6.84, 9.96 Hz, 1H), 2.10-3.08 (m, 8H), 1.19-2.04 (m, 5H), 0.91 (d, J=8.98 Hz, 18H), 0.01-0.18 (m, 12H); MS (ESI+) m/z 533.2 (M+H$^+$).

To a solution of tricyclic enone 15d (1.42 g, 2.15 mmol, 1.0 equiv) in methanol (15 mL) was added anhydrous potassium bicarbonate (110 mg, 8% w/w) and 10% Pd/C (220 mg, 50% wet, 15% w/w) and the mixture was hydrogenated at 10 psi of hydrogen gas while stirring at room temperature for 24 hours. The reaction was then charged with additional anhydrous potassium bicarbonate (110 mg, 8% w/w) and 10% Pd/C (220 mg, 50% wet, 15% w/w) and hydrogenated under 10 psi hydrogen gas while stirring at room temperature for about 24 hours. The reaction was then filtered through celite, the residue washed with several portions of methanol, and the filtrate concentrated to give a yellow oil. Triteration with heptane caused formation of a small amount of precipitate that was filtered off, and the filtrate concentrated to give 12.5 g of a viscous, yellow oil. Chromatography (0% to 10% ethyl acetate/heptane gradient) afforded 722 mg (63%) of the title compound as a pale oil. Data for 16d: $R_f$=0.47 (20% EtOAc/heptane); $^1$H NMR (400 MHz, CHLOROFORM-d) δ 7.11 (t, J=7.81 Hz, 1H), 6.71 (d, J=8.20 Hz, 2H), 3.84 (s, 3H), 3.62-3.76 (m, 1H), 3.52-3.61 (m, 1H), 3.43 (dd, J=6.84, 9.96 Hz, 1H), 2.10-3.08 (m, 8H), 1.19-2.04 (m, 5H), 0.91 (d, J=8.98 Hz, 18H), 0.01-0.18 (m, 12H); MS (ESI+) m/z 533.2 (M+H$^+$).

Examples 18i-18s: (3aS,9aS)-1-((R)-3,4-bis((tert-butyldimethylsilyl)oxy)butyl)-5-methoxy-3a,4,9,9a-tetrahydro-1H-cyclopenta[b]naphthalen-2(3H)-one (16d)

The hydrogenation of tricyclic enone 15d to generate ketone 16d was performed using a 10% Pd/C (50% wet) catalyst and other reaction conditions provided in Table 1:

TABLE 1

Reaction conditions for the hydrogenation of tricyclic enone 15d.

| Ex. # | Catalyst10 | Base (wt %) | Solvent | $H_2$ pressure | % yield 16d |
|---|---|---|---|---|---|
| i | 15 wt % | $K_2CO_3$ (5) | MeOH | 10 psi | 76 |
| j | 15 wt % (×2) | $K_2CO_3$ (5) | EtOAc | 10 psi | 72 |
| k | 15 wt % (×2) | $K_2CO_3$ (5) | THF | 10 psi | 102 |
| l | 15 wt % (×2) | $K_2CO_3$ (5) | THF | 10 psi | 100 |
| m | 15 wt % | $KHCO_3$ (2 × 7.7) | MeOH | 10 psi | 63 |
| n | 15 wt % | $KHCO_3$ (2 × 7.7) | MeOH | atm | 79 |
| o | 15 wt % | $KHCO_3$ (8.2) | EtOH | 10 psi | 83 |
| p | 15 wt % | $KHCO_3$ (7.4) | EtOH | atm | 54 |
| q | 15 wt % (×2) | $K_2CO_3$ (5) | 2-Me-THF | 10 psi | 63 |
| r | 15 wt % | $K_2CO_3$ (5) | EtOH | 10 psi | 64 |
| s | 15 wt % (×2) | $KHCO_3$ (5) | EtOH | 10 psi | 87 |

Example 19a: (1R,2R,3aS,9aS)-1-((R)-3,4-bis((tert-butyldimethylsilyl)oxy)butyl)-5-methoxy-2,3,3a,4,9,9a-hexahydro-1H-cyclopenta[b]naphthalen-2-ol (17c)

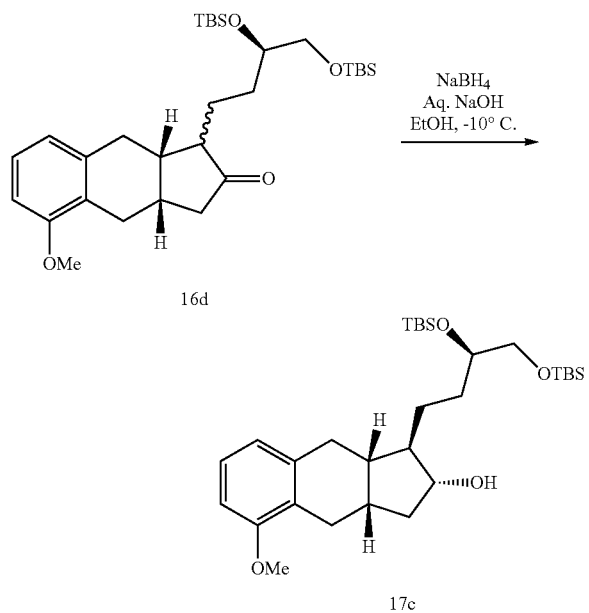

Sodium hydroxide (5.492 g in 28 mL of water, 20% solution in water, 10 equiv) was added to a −10° C. solution of ketone 16d (7.318 g, 13.73 mmol, 1.0 equiv) in absolute ethanol and the reaction was stirred under nitrogen for 30 minutes. Then, sodium borohydride (545 mg, 14.42 mmol, 1.05 equiv) was added in one portion and the reaction maintained at −10° C. for 1 hour with stirring. At that point, an additional portion of sodium borohydride (545 mg, 14.42 mmol, 1.05 equiv) was added and the reaction stirred at −10° C. for 17 hours. The reaction was then cautiously quenched with addition of glacial acetic acid (10 mL), resulting in a pH of 6. This was diluted with brine (200 mL) and warmed to room temperature. The mixture was extracted with heptane (3×200 mL), the combined organic phases dried (MgSO₄) and concentrated to give a yellow oil. Chromatography (0% to 15% ethyl acetate/heptane gradient) afforded 5.359 g (73%) of the title compound as a viscous, colorless oil. Data for 17c: $R_f$=0.44 (20% EtOAc/heptane); ¹H NMR (400 MHz, CDCl₃) δ 7.11 (t, J=7.91 Hz, 1H), 6.76 (dd, J=2.78, 7.76 Hz, 2H), 3.82 (s, 3H), 3.62-3.78 (m, 2H), 3.51-3.60 (m, 1H), 3.39-3.49 (m, 1H), 2.70-2.87 (m, 2H), 2.48 (ddd, J=6.59, 11.35, 14.57 Hz, 2H), 2.12-2.31 (m, 2H), 1.84-1.97 (m, 1H), 1.44-1.80 (m, 5H), 1.22-1.32 (m, 1H), 1.10-1.22 (m, 1H), 0.91 (s, 18H), 0.01-0.16 (m, 12H); MS (ESI+) m/z 557.5 (M+Na⁺).

Example 19b: (R)-4-((1R,2R,3aS,9aS)-2-hydroxy-5-methoxy-2,3,3a,4,9,9a-hexahydro-1H-cyclopenta[b]naphthalen-1-yl)butane-1,2-diol (17d)

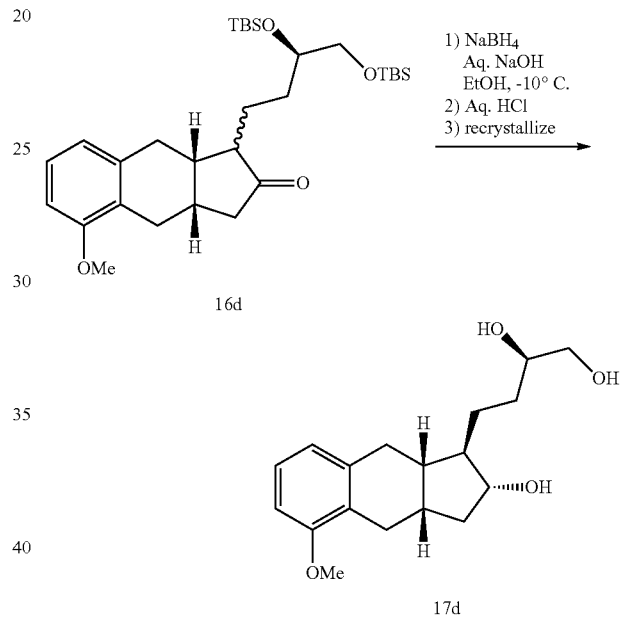

Sodium hydroxide (648 mg in 3.2 mL of water, 20% solution in water, 16.2 mmol, 10 equiv) was added to a −10° C. solution of ketone 16d (864 mg, 1.62 mmol, 1.0 equiv) in absolute ethanol and the reaction was stirred under nitrogen for 30 minutes. Then, sodium borohydride (68 mg, 1.80 mmol, 1.1 equiv) was added in one portion and the reaction maintained at −10° C. for 1 hour with stirring. At that point, an additional portion of sodium borohydride (68 mg, 1.80 mmol, 1.1 equiv) was added and the reaction stirred at −10° C. for 17 hours. The reaction was then cautiously quenched with addition of 3 N aqueous HCl (10 mL) until the pH was about 1, the reaction was warmed to room temperature and stirred 2 hours until homogenous. This was concentrated by rotary evaporation to remove the ethanol, diluted with brine (10 mL) and the resulting white slurry extracted with a solution of 10% ethanol/isopropyl acetate (3×20 mL). The combined organic phases were dried (Na₂SO₄) and concentrated to give 530 mg of an off-white solid. The crude product was recrystallized by dissolving in refluxing ethyl acetate (10 mL) and cooling back to room temperature giving 432 mg (87%) of the title compound as a white solid. Data for 17d: $R_f$=0.18 (100% EtOAc); ¹H NMR (400 MHz, DMSO-d₆) δ 7.07 (t, J=7.87 Hz, 1H), 6.80 (d, J=8.42 Hz, 1H), 6.74 (d, J=7.32 Hz, 1H), 4.48 (d, J=5.49 Hz, 1H), 4.44 (t, J=5.31 Hz, 1H), 4.37 (d, J=4.39 Hz, 1H), 3.74 (s, 3H), 3.40-3.53 (m, 1H), 3.36-3.40 (m, 1H), 3.22-3.32 (m, 2H), 2.64 (ddd, J=6.59, 8.51, 14.56 Hz, 2H), 2.32-2.47 (m, 2H), 2.03-2.19 (m, 1H), 1.87-2.00 (m, 1H), 1.71-1.84 (m, 1H), 1.60-1.71 (m, 1H), 1.46-1.60 (m, 1H), 1.22-1.40 (m, 2H), 1.01-1.14 (m, 1H), 0.84-1.01 (m, 1H); MS (ESI+) m/z 329.2 (M+Na+).

Example 20a: (R)-5-(2-((1R,2R,3aS,9aS)-2-((tert-butyldiphenylsilyl)oxy)-5-methoxy-2,3,3a,4,9,9a-hexahydro-1H-cyclopenta[b]naphthalen-1-yl)ethyl)-2,2,3,3,8,8,9,9-octamethyl-4,7-dioxa-3,8-disiladecane (18d)

Example 20b: (1R,2R,3aS,9aS)-1-(2-((R)-2,2-dimethyl-1,3-dioxolan-4-yl)ethyl)-5-methoxy-2,3,3a,4,9,9a-hexahydro-1H-cyclopenta[b]naphthalen-2-ol (18e)

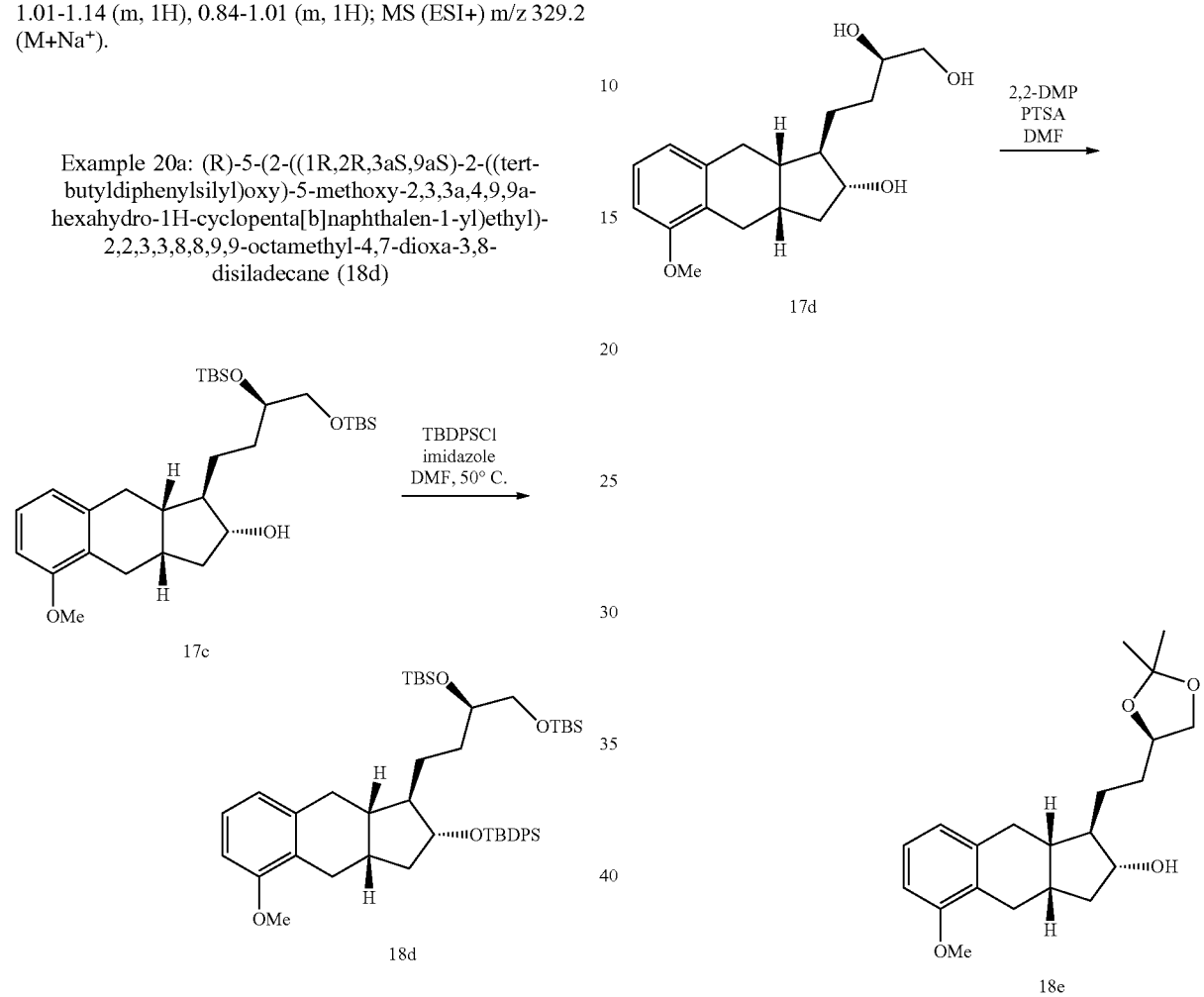

Imidazole (1.017 g, 14.94 mmol, 1.5 equiv) and tert-butyl (chloro)diphenylsilane (3.557 g, 12.94 mmol, 1.3 equiv) were added to a stirred solution of alcohol 17c (5.326 g, 9.957 mmol, 1.0 equiv) in anhydrous DMF, under nitrogen, and the mixture was then warmed to 50° C. for 40 hours. The reaction was then quenched with addition of saturated aqueous ammonium chloride (100 mL) and extracted with heptane (3×100 mL). The combined organic phases were washed with water, brine and concentrated to give a pale yellow oil. Chromatography (0% to 10% ethyl acetate/heptane gradient) afforded 7.186 g (93%) of the title compound as a viscous, colorless oil. Data for 18d: R$_f$=0.74 (20% EtOAc/heptane); $^1$H NMR (400 MHz, CDCl$_3$) δ 7.67 (dd, J=6.77, 14.46 Hz, 4H), 7.30-7.49 (m, 6H), 7.11 (t, J=7.69 Hz, 1H), 6.69-6.83 (m, 2H), 3.73-3.88 (m, 4H, contains s, 3H, 3.79), 3.53-3.65 (m, 1H), 3.43-3.52 (m, 1H), 3.32-3.43 (m, 1H), 2.92 (dd, J=6.23, 14.65 Hz, 1H), 2.77 (dd, J=5.86, 14.28 Hz, 1H), 2.52 (dd, J=8.79, 14.28 Hz, 1H), 2.28 (dd, J=8.42, 14.65 Hz, 1H), 1.96 (sxt, J=8.06 Hz, 1H), 1.48-1.83 (m, 5H), 1.14-1.45 (m, 3H), 1.03 (s, 9H), 0.90 (d, J=4.03 Hz, 18H), 0.06 (t, J=3.30 Hz, 12H).

PTSA.H$_2$O (15 mg, 0.082 mmol, 0.05 equiv) was added to a solution of 17d (500 mg, 1.53 mmol, 1.0 equiv) and 2,2-dimethoxypropane (0.40 mL, 3.2 mmol, 2.0 equiv) in anhydrous DMF (5 mL), under nitrogen, and the mixture was stirred at room temperature for 22 hours. The reaction was then quenched with addition of saturated aqueous sodium bicarbonate (5 mL), diluted with water (5 mL) and extracted with ethyl acetate (3×10 mL). The combined organic phases were washed with brine, dried (MgSO$_4$) and concentrated to give 997 mg of a light brown oil. Chromatography (25% to 60% ethyl acetate/heptane gradient) afforded 529 mg (94%) of the title compound as a colorless oil. Data for 18e: R$_f$=0.32 (50% EtOAc/heptane); $^1$H NMR (400 MHz, CHLOROFORM-d) δ 7.10 (t, J=7.87 Hz, 1H), 6.76 (t, J=8.24 Hz, 2H), 3.96-4.17 (m, 2H), 3.80 (s, 3H), 3.64-3.75 (m, 1H), 3.53 (t, J=7.51 Hz, 1H), 2.76 (ddd, J=6.23, 12.27, 14.46 Hz, 2H), 2.41-2.59 (m, 2H), 2.19-2.33 (m, 1H), 2.09-2.19 (m, 1H), 2.05 (s, 1H), 1.56-1.95 (m, 4H), 1.44-1.55 (m, 1H), 1.42 (s, 3H), 1.37 (s, 3H), 1.21-1.32 (m, 1H), 1.06-1.19 (m, 1H); MS (ESI+) m/z 369.1 (M+Na+).

Example 20c: Tert-butyl(((1R,2R,3aS,9aS)-1-(2-((R)-2,2-dimethyl-1,3-dioxolan-4-yl)ethyl)-5-methoxy-2,3,3a,4,9,9a-hexahydro-1H-cyclopenta[b]naphthalen-2-yl)oxy)diphenylsilane (18f)

Example 21a: (R)-4-((1R,2R,3aS,9aS)-2-((tert-butyldiphenylsilyl)oxy)-5-methoxy-2,3,3a,4,9,9a-hexahydro-1H-cyclopenta[b]naphthalen-1-yl)butane-1,2-diol (19d)

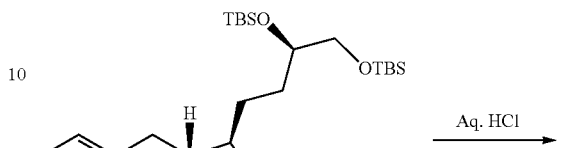

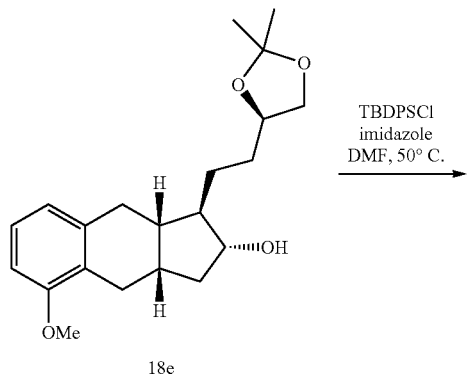

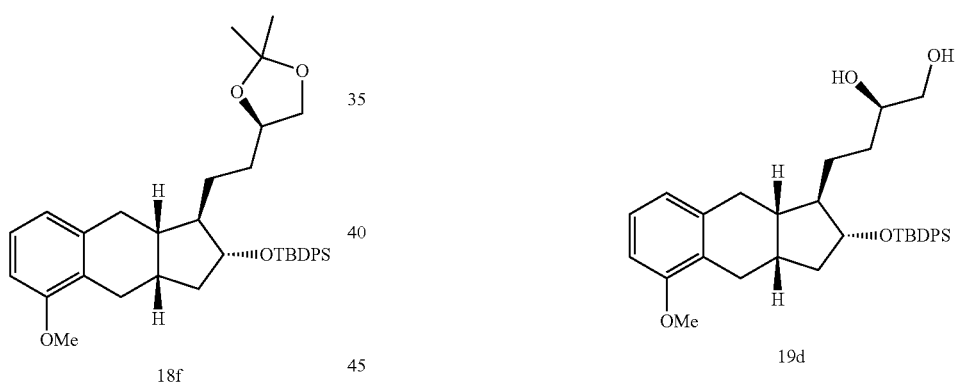

Imidazole (145 mg, 2.13 mmol, 1.4 equiv) and tert-butyl (chloro)diphenylsilane (501 mg, 1.82 mmol, 1.2 equiv) were added to a stirred solution of alcohol 18e (526 mg, 1.52 mmol, 1.0 equiv) in anhydrous DMF (7.5 mL), under nitrogen, and the mixture was then warmed to 50° C. for 19 hours. The reaction was then quenched with water (10 mL) and extracted with heptane (3×10 mL). The combined organic phases were washed with 14% aqueous sodium chloride and concentrated to give 989 mg of a pale yellow oil. Chromatography (0% to 10% ethyl acetate/heptane gradient) afforded 882 mg (99%) of the title compound as a colorless oil. Data for 18f: $R_f$=0.55 (20% EtOAc/heptane); $^1$H NMR (400 MHz, CHLOROFORM-d) δ 7.69 (dt, J=6.59, 17.21 Hz, 4H), 7.32-7.49 (m, 6H), 7.12 (t, J=7.69 Hz, 1H), 6.77 (t, J=8.06 Hz, 2H), 3.89-3.99 (m, 2H), 3.72-3.84 (m, 4H), 3.25-3.43 (m, 1H), 2.89 (dd, J=6.23, 14.65 Hz, 1H), 2.75 (dd, J=6.23, 14.28 Hz, 1H), 2.51 (dd, J=8.24, 14.10 Hz, 1H), 2.34 (dd, J=8.06, 14.65 Hz, 1H), 1.48-2.08 (m, 7H), 1.24-1.46 (m, 7H), 1.18 (td, J=4.94, 9.89 Hz, 1H), 1.04 (s, 9H).

Aqueous 3N hydrochloric acid (10 mL) was added to a solution of TBDMS ether 18d (4.411 g, 5.704 mmol, 1.0 equiv) in THF (30 mL) and MeOH (10 mL) and the reaction stirred at room temperature for 27 hours. The reaction was then concentrated to remove the organic solvents, diluted with water (50 mL), and extracted with EtOAc (3×100 mL). The combined organic phases were washed with saturated aqueous sodium bicarbonate, brine, dried (Na$_2$SO$_4$) and concentrated to give a foamy oil. Chromatography (20% to 80% ethyl acetate/heptane gradient) afforded 1.982 g (64%) of the title compound as a fluffy white solid. Data for 19d: $R_f$=0.26 (40% EtOAc/heptane); $^1$H NMR (400 MHz, CDCl$_3$) δ 7.60-7.76 (m, 4H), 7.32-7.49 (m, 6H), 7.12 (t, J=7.78 Hz, 1H), 6.77 (t, J=7.78 Hz, 2H), 3.72-3.85 (m, 4H, contains s, 3H, 3.80), 3.48-3.59 (m, 2H), 3.27-3.39 (m, 1H), 2.90 (dd, J=6.13, 14.74 Hz, 1H), 2.74 (dd, J=6.04, 14.10 Hz, 1H), 2.50 (dd, J=8.24, 14.10 Hz, 1H), 2.34 (dd, J=7.78, 14.74 Hz, 1H), 1.84-2.08 (m, 2H), 1.80 (s, 2H), 1.72 (td, J=8.03, 16.34 Hz, 1H), 1.48-1.62 (m, 2H), 1.15-1.46 (m, 4H), 1.04 (s, 9H); MS (ESI+) m/z 567.5 (M+Na$^+$).

Example 21b: (R)-4-((1R,2R,3aS,9aS)-2-((tert-butyldiphenylsilyl)oxy)-5-methoxy-2,3,3a,4,9,9a-hexahydro-1H-cyclopenta[b]naphthalen-1-yl)butane-1,2-diol (19d)

Example 21c: (R)-4-((1R,2R,3aS,9aS)-2-((tert-butyldiphenylsilyl)oxy)-5-methoxy-2,3,3a,4,9,9a-hexahydro-1H-cyclopenta[b]naphthalen-1-yl)butane-1,2-diol (19d)

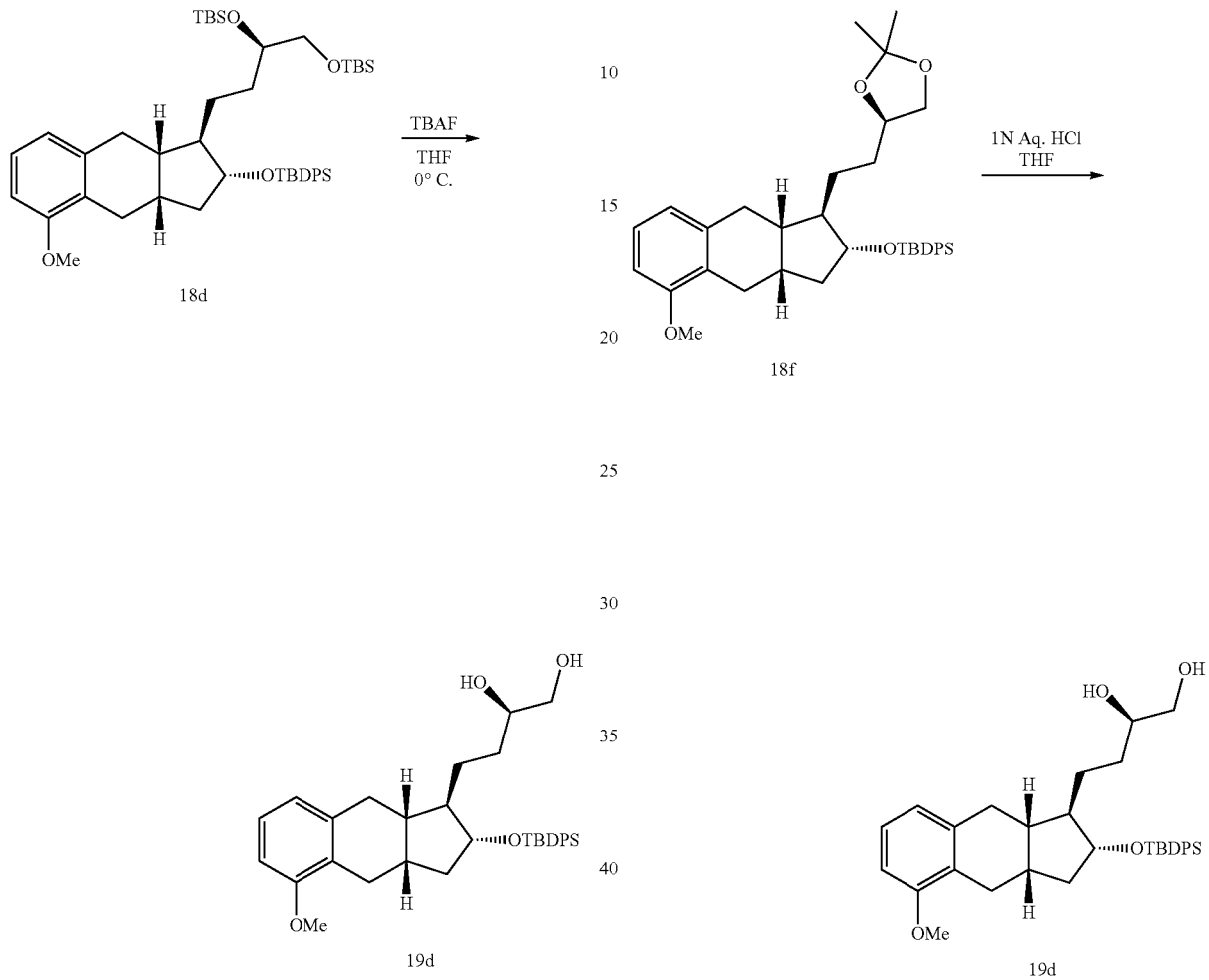

Tetra-n-butylammonium fluoride (2.75 mL, 2.75 mmol, 2.0 equiv, 1.0 M solution in THF) was added to an ice-cold solution of TBDMS ether 18d (1.053 g, 1.362 mmol, 1.0 equiv) in THF (10 mL) and the reaction stirred at 0° C. for 3 hours. The reaction was then quenched with saturated aqueous ammonium chloride (10 mL), diluted with water (10 mL) and extracted with ethyl acetate (3×20 mL). The combined organic phases were dried (Na$_2$SO$_4$) and concentrated to give 1.03 g of a yellow oil. Chromatography (30% to 100% ethyl acetate/heptane gradient) afforded 616 mg (83%) of the title compound as a white, foamy solid. Data for 19d: R$_f$=0.26 (40% EtOAc/heptane); $^1$H NMR (400 MHz, CHLOROFORM-d) δ 7.60-7.76 (m, 4H), 7.32-7.49 (m, 6H), 7.12 (t, J=7.78 Hz, 1H), 6.77 (t, J=7.78 Hz, 2H), 3.72-3.85 (m, 4H, contains s, 3H, 3.80), 3.48-3.59 (m, 2H), 3.27-3.39 (m, 1H), 2.90 (dd, J=6.13, 14.74 Hz, 1H), 2.74 (dd, J=6.04, 14.10 Hz, 1H), 2.50 (dd, J=8.24, 14.10 Hz, 1H), 2.34 (dd, J=7.78, 14.74 Hz, 1H), 1.84-2.08 (m, 2H), 1.80 (s, 2H), 1.72 (td, J=8.03, 16.34 Hz, 1H), 1.48-1.62 (m, 2H), 1.15-1.46 (m, 4H), 1.04 (s, 9H); MS (ESI+) m/z 567.3 (M+Na$^+$).

Aqueous hydrochloric acid (10 mL, 1 N solution) was added to a solution of acetonide 18f (1.015 g, 1.735 mmol, 1.0 equiv) in THF (10 mL) and the reaction stirred at room temperature for 46 hours. It was then diluted with 14% aqueous sodium chloride (20 mL) and extracted with isopropyl acetate (3×20 mL). The combined organic phases were washed with saturated aqueous sodium bicarbonate (40 mL), 14% aqueous sodium chloride (40 mL), dried (Na$_2$SO$_4$) and concentrated to give 1.066 g of a colorless oil. Chromatography (40% to 100% ethyl acetate/heptane gradient) afforded 670 mg (71%) of the title compound as a foamy white solid. Data for 19: R$_f$=0.31 (50% EtOAc/heptane); $^1$H NMR (400 MHz, CHLOROFORM-d) δ 7.58-7.81 (m, 4H), 7.31-7.51 (m, 6H), 7.11 (t, J=7.91 Hz, 1H), 6.77 (t, J=7.62 Hz, 2H), 3.73-3.85 (m, 4H, contains s, 3H, 3.80), 3.47-3.62 (m, 2H), 3.27-3.40 (m, 1H), 2.90 (dd, J=6.15, 14.65 Hz, 1H), 2.74 (dd, J=6.15, 14.06 Hz, 1H), 2.50 (dd, J=8.20, 14.06 Hz, 1H), 2.34 (dd, J=7.91, 14.65 Hz, 1H), 1.83-2.09 (m, 2H), 1.64-1.82 (m, 3H), 1.48-1.62 (m, 2H), 1.14-1.46 (m, 4H), 0.96-1.11 (m, 9H); MS (ESI+) m/z 567.2 (M+Na$^+$).

127

Example 21d: (R)-4-((1R,2R,3aS,9aS)-2-((tert-butyldiphenylsilyl)oxy)-5-methoxy-2,3,3a,4,9,9a-hexahydro-1H-cyclopenta[b]naphthalen-1-yl)butane-1,2-diol (19d)

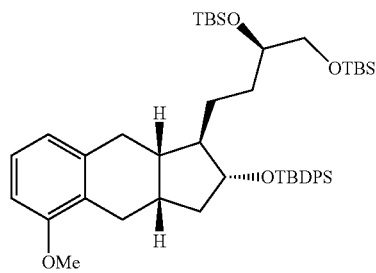

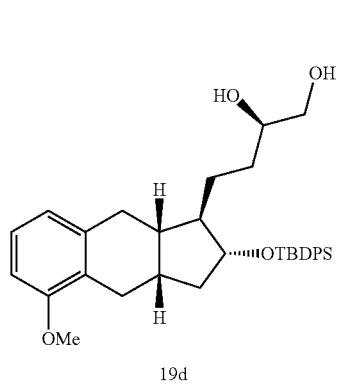

Triethylamine trihydrofluoride (0.16 mL, 0.98 mmol, 3.0 equiv) was added to an ice-cold solution of TBDMS ether 18d (253 mg, 0.327 mmol, 1.0 equiv) in THF (2 mL) with stirring, under nitrogen. The reaction was then warmed to 50° C. for 18 hours at which point it was shown to be complete by TLC. The reaction was quenched with saturated aqueous ammonium chloride (2 mL), diluted with water (2 mL) and extracted with ethyl acetate (3×4 mL). The combined organic phases were dried (Na$_2$SO$_4$) and concentrated to give 172 mg of a yellow oil. Chromatography (30% to 100% ethyl acetate/heptane gradient) afforded 99 mg (58%) of the title compound as a white, foamy solid. Data for 19d: R$_f$=0.26 (40% EtOAc/heptane); $^1$H NMR (400 MHz, CHLOROFORM-d) δ 7.60-7.76 (m, 4H), 7.32-7.49 (m, 6H), 7.12 (t, J=7.78 Hz, 1H), 6.77 (t, J=7.78 Hz, 2H), 3.72-3.85 (m, 4H, contains s, 3H, 3.80), 3.48-3.59 (m, 2H), 3.27-3.39 (m, 1H), 2.90 (dd, J=6.13, 14.74 Hz, 1H), 2.74 (dd, J=6.04, 14.10 Hz, 1H), 2.50 (dd, J=8.24, 14.10 Hz, 1H), 2.34 (dd, J=7.78, 14.74 Hz, 1H), 1.84-2.08 (m, 2H), 1.80 (s, 2H), 1.72 (td, J=8.03, 16.34 Hz, 1H), 1.48-1.62 (m, 2H), 1.15-1.46 (m, 4H), 1.04 (s, 9H).

128

Example 21e: (R)-4-((1R,2R,3aS,9aS)-2-((tert-butyldiphenylsilyl)oxy)-5-methoxy-2,3,3a,4,9,9a-hexahydro-1H-cyclopenta[b]naphthalen-1-yl)butane-1,2-diol (19d)

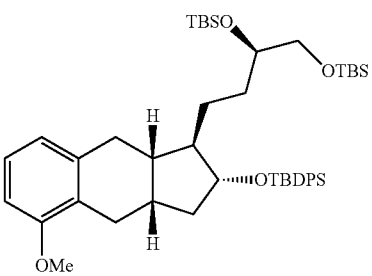

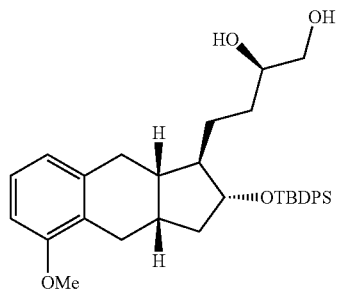

Pyridinium p-toluene sulfonate (5.52 g, 220 mmol) was added to a solution of TBDMS ether 18d (17 g, 221 mmol, 1.0 equiv) in ethanol (170 mL) and the reaction stirred at 40° C. for 56 hours. The reaction was then quenched with 2 mL of pyridine, and the resulting mixture concentrated to remove the organic solvents. Chromatography (15% to 40% ethyl acetate/heptane gradient) afforded 9.48 g (78%) of the title compound as a fluffy white solid. Data for 19d: R$_f$=0.26 (40% EtOAc/heptane); 1H NMR (400 MHz, CHLOROFORM-d) δ ppm 7.60-7.76 (m, 4H), 7.32-7.49 (m, 6H), 7.12 (t, J=7.78 Hz, 1H), 6.77 (t, J=7.78 Hz, 2H), 3.72-3.85 (m, 4H, contains s, 3H, 3.80), 3.48-3.59 (m, 2H), 3.27-3.39 (m, 1H), 2.90 (dd, J=6.13, 14.74 Hz, 1H), 2.74 (dd, J=6.04, 14.10 Hz, 1H), 2.50 (dd, J=8.24, 14.10 Hz, 1H), 2.34 (dd, J=7.78, 14.74 Hz, 1H), 1.84-2.08 (m, 2H), 1.80 (s, 2H), 1.72 (td, J=8.03, 16.34 Hz, 1H), 1.48-1.62 (m, 2H), 1.15-1.46 (m, 4H), 1.04 (s, 9H); MS (ESI+) m/z 567.3 (M+Na$^+$).

Example 22: (R)-4-((1R,2R,3aS,9aS)-2-((tert-butyl-diphenylsilyl)oxy)-5-methoxy-2,3,3a,4,9,9a-hexahydro-1H-cyclopenta[b]naphthalen-1-yl)-2-hydroxybutyl 2,4,6-triisopropylbenzenesulfonate (20d)

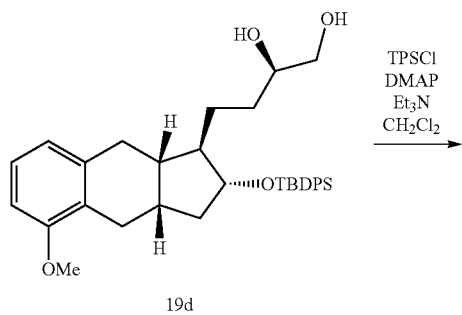

19d

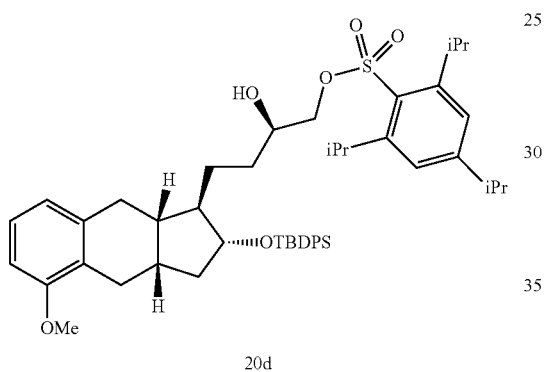

20d

Triethylamine (3.80 mL, 27.5 mmol, 4.0 equiv) and 4-dimethylaminopyridine (168 mg, 1.374 mmol, 0.2 equiv) were added to a solution of diol 19d (3.744 g, 6.872 mmol, 1.0 equiv) in anhydrous methylene chloride (30 mL) while stirring under nitrogen. The reaction was then cooled to 0° C. and 2,4,6-triisopropylbenzenesulfonyl chloride (2.498 g, 8.247 mmol, 1.2 equiv) added drop-wise as a solution in anhydrous methylene chloride (10 mL). After stirring at this temperature for 15 hours, the reaction was quenched with addition of saturated aqueous ammonium chloride (50 mL) and warmed to room temperature. The two phases were separated and the aqueous phase extracted with methylene chloride (3×50 mL). The combined organics were dried (MgSO$_4$) and concentrated to give a dark yellow oil. Chromatography (0% to 20% ethyl acetate/heptane gradient) afforded 4.797 g (86%) of the title compound as a white, foamy solid. Data for 20d: R$_f$=0.46 (20% EtOAc/heptane); $^1$H NMR (400 MHz, CDCl$_3$) δ 7.55-7.73 (m, 4H), 7.29-7.46 (m, 6H), 7.22 (s, 2H), 7.11 (t, J=7.87 Hz, 1H), 6.75 (d, J=8.42 Hz, 2H), 4.15 (quin, J=6.68 Hz, 2H), 3.92 (dd, J=2.56, 9.89 Hz, 1H), 3.58-3.84 (m, 6H, contains s, 3H, 3.80), 2.81-3.03 (m, 2H), 2.71 (dd, J=6.23, 14.28 Hz, 1H), 2.46 (dd, J=8.06, 14.28 Hz, 1H), 2.26-2.40 (m, 1H), 1.81-2.09 (m, 3H), 1.69 (td, J=8.06, 16.11 Hz, 1H), 1.46-1.61 (m, 2H), 1.28 (m, 22H), 1.01 (s, 9H); MS (ESI+) m/z 828.8 (M+NH$_4^+$).

Example 23: tert-butyl(((1R,2R,3aS,9aS)-5-methoxy-1-(2-((R)-oxiran-2-yl)ethyl)-2,3,3a,4,9,9a-hexahydro-1H-cyclopenta[b]naphthalen-2-yl)oxy)diphenylsilane (21c)

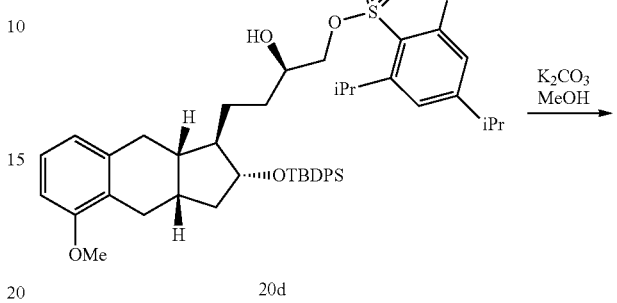

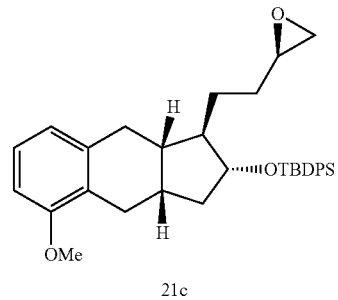

21c

Anhydrous potassium carbonate (1.592 g, 11.52 mmol, 2.0 equiv) was added to a solution of alcohol 20d (4.674 g, 5.762 mmol, 1.0 equiv) in anhydrous methanol (30 mL) and the mixture stirred under nitrogen for 1 hour. The reaction was then concentrated, the residue triterated in methylene chloride and filtered to remove the precipitate. The filtrate was concentrated, and the residue triterated in heptane, filtered to remove the precipitate and the filtrate concentrated to give 3.032 g (99%) of the title compound as a colorless oil. This material was deemed sufficiently pure to be carried forward. Data for 21c: R$_f$=0.50 (20% EtOAc/heptane); $^1$H NMR (400 MHz, CDCl$_3$) δ 7.59-7.77 (m, 4H), 7.32-7.49 (m, 6H), 7.11 (t, J=7.69 Hz, 1H), 6.76 (t, J=8.24 Hz, 2H), 3.72-3.86 (m, 4H, contains s, 3H, 3.80), 2.89 (dd, J=6.23, 14.65 Hz, 1H), 2.66-2.84 (m, 3H), 2.50 (dd, J=8.06, 14.28 Hz, 1H), 2.35-2.44 (m, 1H), 2.32 (dd, J=8.06, 15.01 Hz, 1H), 1.92-2.05 (m, 1H), 1.79-1.90 (m, 1H), 1.22-1.77 (m, 7H), 1.04 (s, 9H); MS (ESI+) m/z 549.5 (M+Na$^+$).

Example 24a: (S)-1-((1R,2R,3aS,9aS)-2-((tert-butyl-diphenylsilyl)oxy)-5-methoxy-2,3,3a,4,9,9a-hexa-hydro-1H-cyclopenta[b]naphthalen-1-yl)heptan-3-ol (22c)

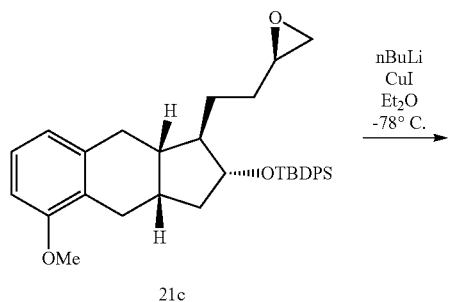

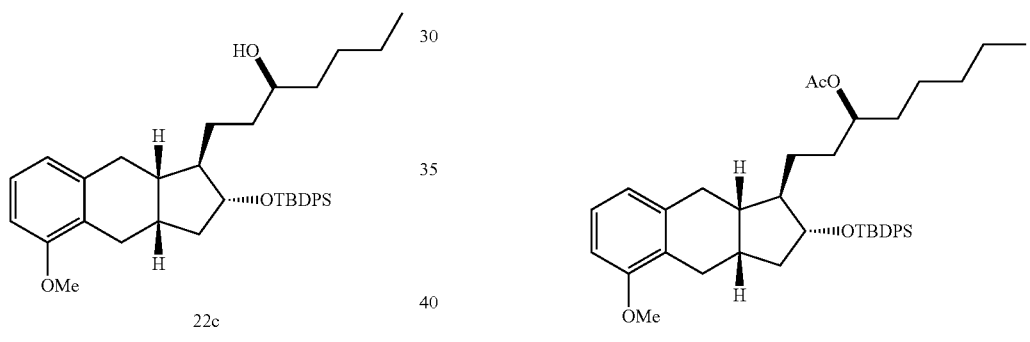

Example 24b: (S)-1-((1R,2R,3aS,9aS)-2-((tert-bu-tyldiphenylsilyl)oxy)-5-methoxy-2,3,3a,4,9,9a-hexa-hydro-1H-cyclopenta[b]naphthalen-1-yl)hexan-3-yl acetate (22a)

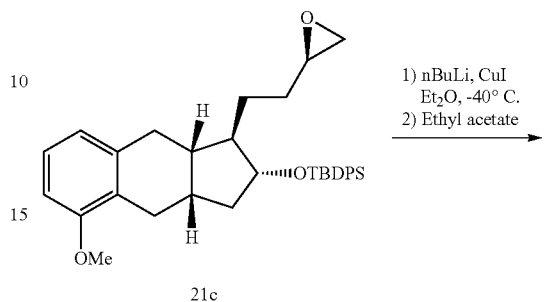

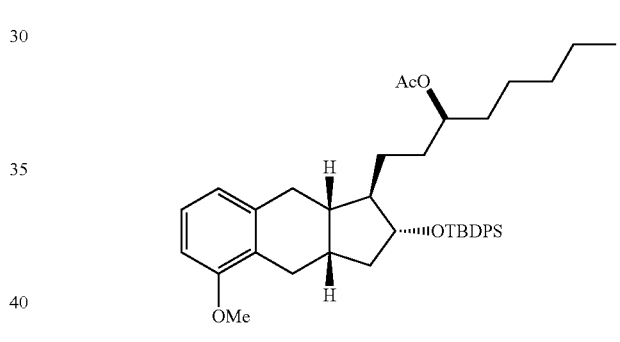

A slurry of epoxide 21c (56 mg, 0.11 mmol, 1.0 equiv) and copper(I) iodide (4.0 mg, 0.021 mmol, 0.2 equiv) in anhydrous ether (1.0 mL) that had been cooled to −78° C. was treated drop-wise with n-butyllithium (0.28 mL, 0.70 mmol, 6.6 equiv, 2.5 M in hexanes) and the resulting mixture slowly warmed to −40° C. over 30 minutes while stirring under nitrogen. The cloudy yellow mixture turned almost black in color during this time and the reaction was shown to be complete by TLC. This was then quenched with addition of saturated aqueous ammonium chloride (5 mL) and warmed to room temperature. The deep blue aqueous layer was extracted with ethyl acetate (3×5 mL). The combined organic phases were washed with brine, dried (MgSO$_4$) and concentrated to give 60 mg of a colorless oil. Chromatography (0% to 20% ethyl acetate/heptane gradient) afforded 52 mg (84%) of the title compound as a colorless oil. Data for 22c: R$_f$=0.42 (20% EtOAc/heptane); $^1$H NMR (400 MHz, CDCl$_3$) δ 7.59-7.77 (m, 4H), 7.31-7.51 (m, 6H), 7.11 (t, J=7.81 Hz, 1H), 6.71-6.81 (m, 2H), 3.73-3.85 (m, 4H, contains s, 3H, 3.80), 3.44 (br. s., 1H), 2.91 (dd, J=6.25, 14.45 Hz, 1H), 2.75 (dd, J=6.25, 14.45 Hz, 1H), 2.50 (dd, J=8.20, 14.06 Hz, 1H), 2.32 (dd, J=8.01, 14.65 Hz, 1H), 1.82-2.05 (m, 2H), 1.65-1.77 (m, 1H), 1.50-1.62 (m, 2H), 1.15-1.47 (m, 13H), 1.04 (s, 9H), 0.92 (t, J=7.03 Hz, 3H); MS (ESI+) m/z 607.2 (M+Na$^+$).

A slurry of epoxide 21c (3.3 g, 6.3 mmol, 1.0 equiv) and copper(I) iodide (148 mg, 0.78 mmol, 0.013 equiv) in methyl tert-butyl ether (35.0 mL) that had been cooled to −40° C. was treated drop-wise with n-butyllithium (11.4 mL, 17.1 mmol, 2.74 equiv, 1.5 M solution in hexanes) and the resulting mixture stirred under nitrogen. The cloudy yellow mixture turned almost black in color during this time and the reaction was shown to be complete by TLC. This was then treated with addition of ethyl acetate and warmed to room temperature then quenched with aqueous ammonium chloride (75 mL). The deep blue aqueous layer was extracted with ethyl acetate (2×75 mL). The combined organic phases were concentrated to give a colorless oil. Chromatography (0% to 2% ethyl acetate/heptane gradient) afforded 3.3 g (88%) of the title compound as a colorless oil. Data for 22c: R$_f$=0.64 (20% EtOAc/heptane); $^1$H NMR (400 MHz, CHLOROFORM-d) δ 7.60-7.73 (m, 4H), 7.31-7.48 (m, 6H), 7.11 (t, J=7.69 Hz, 1H), 6.77 (dd, J=7.87, 16.30 Hz, 2H), 4.80 (d, J=5.86 Hz, 1H), 3.68-3.83 (m, 4H), 2.87 (dd, J=6.23, 14.65 Hz, 1H), 2.73 (dd, J=6.23, 13.92 Hz, 1H), 2.48 (dd, J=8.24, 14.10 Hz, 1H), 2.30 (dd, J=8.06, 15.01 Hz, 1H), 1.89-2.06 (m, 4H), 1.74-1.87 (m, 1H), 1.61-1.74 (m, 1H), 1.13-1.60 (m, 14H), 1.03 (s, 9H), 0.84-0.94 (m, 3H); MS (ESI+) m/z 649.4 (M+Na$^+$).

Example 24c: S)-1-((1R,2R,3aS,9aS)-2-((tert-butyl-diphenylsilyl)oxy)-5-methoxy-2,3,3a,4,9,9a-hexahydro-1H-cyclopenta[b]naphthalen-1-yl)heptan-3-ol (22b)

Example 25: (1R,2R,3aS,9aS)-2-((tert-butyldiphenylsilyl)oxy)-1-((S)-3-hydroxyoctyl)-2,3,3a,4,9,9a-hexahydro-1H-cyclopenta[b]naphthalen-5-ol (23a)

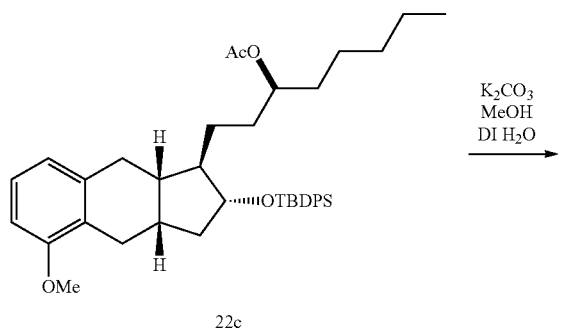

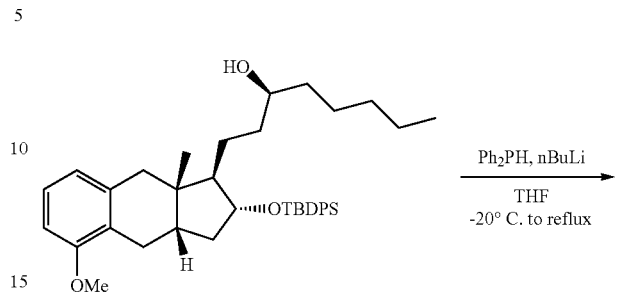

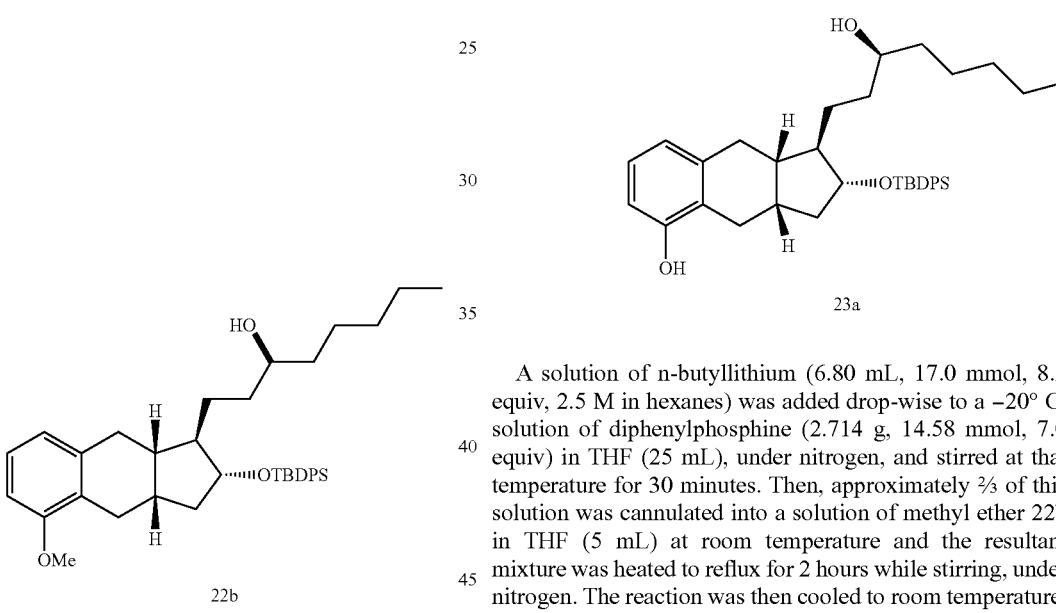

To a solution of acetate 22c (3.3 g, 5.3 mmol, 1 equiv) in methanol (90 mL) was added anhydrous potassium carbonate (3.5 g, 25.4 mmol, 4.8 equiv) and DI water (10 mL). The reaction was stirred at 60° C. for three hours and then cooled to room temperature overnight. At that point the reaction was deemed complete by TLC and the solvent was removed under reduced pressure. The crude residue was extracted with dichloromethane (100 mL), the organic layer passed through filter paper to remove the resulting white solid, and the filtrate was concentrated to give 3.12 g of a pale yellow solid (quantitative). Data for 22b: $R_f$=0.42 (20% EtOAc/heptane); $^1$H NMR (400 MHz, CHLOROFORM-d) δ 7.59-7.77 (m, 4H), 7.31-7.51 (m, 6H), 7.11 (t, J=7.81 Hz, 1H), 6.71-6.81 (m, 2H), 3.73-3.85 (m, 4H, contains s, 3H, 3.80), 3.44 (br. s., 1H), 2.91 (dd, J=6.25, 14.45 Hz, 1H), 2.75 (dd, J=6.25, 14.45 Hz, 1H), 2.50 (dd, J=8.20, 14.06 Hz, 1H), 2.32 (dd, J=8.01, 14.65 Hz, 1H), 1.82-2.05 (m, 2H), 1.65-1.77 (m, 1H), 1.50-1.62 (m, 2H), 1.15-1.47 (m, 13H), 1.04 (s, 9H), 0.92 (t, J=7.03 Hz, 3H).

A solution of n-butyllithium (6.80 mL, 17.0 mmol, 8.2 equiv, 2.5 M in hexanes) was added drop-wise to a −20° C. solution of diphenylphosphine (2.714 g, 14.58 mmol, 7.0 equiv) in THF (25 mL), under nitrogen, and stirred at that temperature for 30 minutes. Then, approximately ⅔ of this solution was cannulated into a solution of methyl ether 22b in THF (5 mL) at room temperature and the resultant mixture was heated to reflux for 2 hours while stirring, under nitrogen. The reaction was then cooled to room temperature, the remainder of the n-butyllithium/diphenylphosphine solution was cannulated over and the reaction was heated back to reflux for 17 hours. At this point, the reaction was cooled in an ice bath and cautiously quenched with addition of 3 M aqueous hydrochloric acid until the pH is acidic. The organic layer was separated and the aqueous phase extracted with ethyl acetate (3×30 mL). The combined organic phases were washed with brine, dried ($Na_2SO_4$) and concentrated to give 4.3 g of a colorless oil. Chromatography (0% to 40% ethyl acetate/heptane gradient) afforded 1.101 g (93%) of the title compound as a white, foamy solid. Data for 23a: $R_f$=0.29 (20% EtOAc/heptane); $^1$H NMR (400 MHz, $CDCl_3$) δ 7.70 (dd, J=7.32, 17.94 Hz, 4H), 7.32-7.51 (m, 6H), 6.96-7.06 (m, 1H), 6.75 (d, J=7.32 Hz, 1H), 6.67 (d, J=8.06 Hz, 1H), 3.82 (q, J=6.84 Hz, 1H), 3.49 (br. s., 1H), 2.84 (dd, J=6.23, 14.65 Hz, 1H), 2.75 (dd, J=5.86, 14.28 Hz, 1H), 2.51 (dd, J=8.24, 14.10 Hz, 1H), 2.34 (dd, J=7.87, 14.46 Hz, 1H), 2.02 (dd, J=7.87, 15.93 Hz, 1H), 1.91 (td, J=6.36, 12.54 Hz, 1H), 1.73 (quin, J=8.06 Hz, 1H), 1.50-1.65 (m, 2H), 1.15-1.49 (m, 13H), 1.07 (s, 9H), 0.87-0.97 (m, 3H); MS (ESI+) m/z 593.3 (M+H$^+$).

Example 26a: (1R,2R,3aS,9aS)-1-((S)-3-hydroxyoctyl)-2,3,3a,4,9,9a-hexahydro-1H-cyclopenta[b]naphthalene-2,5-diol (24a)

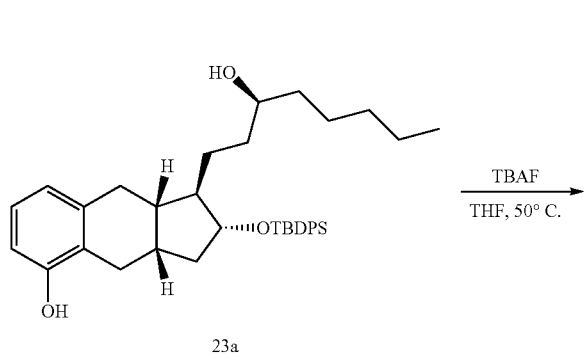

Tetra-n-butylammonium fluoride (2.90 mL, 2.90 mmol, 1.5 equiv, 1.0 M solution in THF) was added to a solution of TBDPS-ether 23a (1.083 g, 1.897 mmol, 1.0 equiv) in anhydrous THF, under nitrogen, and the mixture stirred at room temperature for 22 hours. Analysis by TLC indicated that the reaction was not complete, so it was fitted with a water-cooled condenser and heated to 50° C. for 3.5 hours. The reaction was then quenched with 14% aqueous sodium chloride (20 mL) and extracted with ethyl acetate (3×15 mL). The combined organic phases were dried (Na$_2$SO$_4$) and concentrated to give 1.375 g of an amber oil. Chromatography (12% to 100% ethyl acetate/heptane gradient) afforded 484 mg (77%) of the title compound as a white foam. Data for 24a: R$_f$=0.12 (50% EtOAc/heptane); $^1$H NMR (400 MHz, CHLOROFORM-d) δ 6.95 (t, J=7.51 Hz, 1H), 6.66 (dd, J=7.69, 13.55 Hz, 2H), 6.59 (br. s., 1H), 3.61-3.77 (m, 1H), 3.57 (br. s., 1H), 3.02 (br. s., 1H), 2.58-2.76 (m, 2H), 2.34-2.56 (m, 3H), 2.17-2.30 (m, 1H), 2.03-2.14 (m, 1H), 1.79-1.93 (m, 1H), 1.64 (d, J=7.32 Hz, 2H), 1.38-1.56 (m, 4H), 1.16-1.37 (m, 7H), 1.10 (q, J=10.62 Hz, 1H), 0.85-0.96 (m, 3H); MS (ESI+) m/z 355.2 (M+Na$^+$).

Example 26b: (1R,2R,3aS,9aS)-1-((S)-3-hydroxyoctyl)-2,3,3a,4,9,9a-hexahydro-1H-cyclopenta[b]naphthalene-2,5-diol (24a)

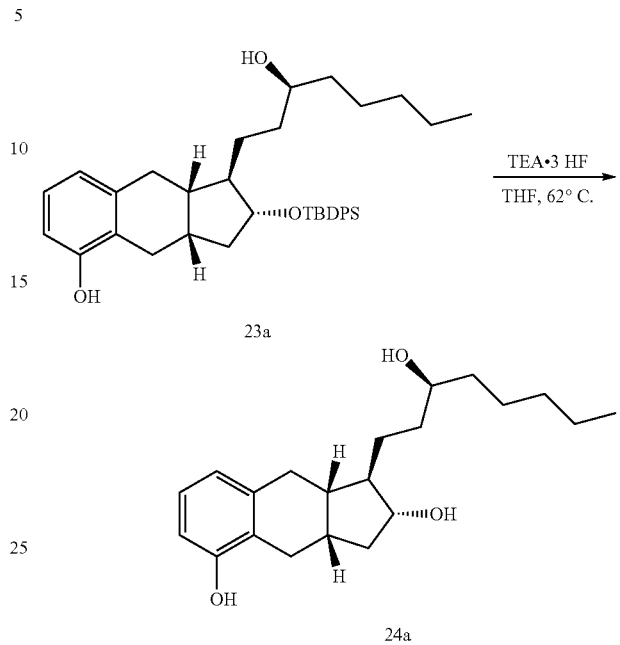

Triethylamine Trihydrofluoride (4.57 g, 28.3 mmol, 3.7 equiv) was added in portions to a solution of TBDPS-ether 23a (4.4 g, 7.7 mmol, 1.0 equiv) in anhydrous THF (45 mL), under nitrogen, and the mixture stirred at 62° C. for 5 days. Analysis by TLC indicated that the reaction was complete. The reaction was then quenched with 10% aqueous potassium bicarbonate (35 mL) and extracted with ethyl acetate (2×35 mL). The combined organic phases were concentrated to give 5.37 g of oil. Chromatography (25% to 100% ethyl acetate/heptane gradient) afforded 1.84 g (72%) of the title compound as white foam. Data for 24a: R$_f$=0.12 (50% EtOAc/heptane); $^1$H NMR (400 MHz, CHLOROFORM-d) δ 6.95 (t, J=7.51 Hz, 1H), 6.66 (dd, J=7.69, 13.55 Hz, 2H), 6.59 (br. s., 1H), 3.61-3.77 (m, 1H), 3.57 (br. s., 1H), 3.02 (br. s., 1H), 2.58-2.76 (m, 2H), 2.34-2.56 (m, 3H), 2.17-2.30 (m, 1H), 2.03-2.14 (m, 1H), 1.79-1.93 (m, 1H), 1.64 (d, J=7.32 Hz, 2H), 1.38-1.56 (m, 4H), 1.16-1.37 (m, 7H), 1.10 (q, J=10.62 Hz, 1H), 0.85-0.96 (m, 3H); MS (ESI+) m/z 355.2 (M+Na$^+$).

Example 26c: (1R,2R,3aS,9aS)-1-((S)-3-hydroxyoctyl)-2,3,3a,4,9,9a-hexahydro-1H-cyclopenta[b]naphthalene-2,5-diol (24a)

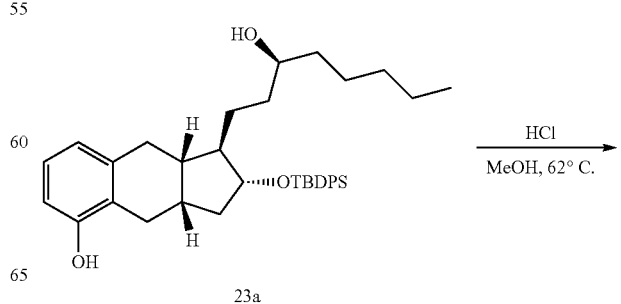

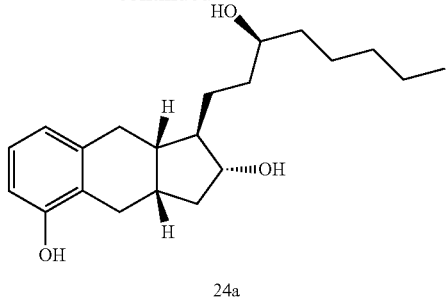

24a

Hydrochloric acid (12 mL, 3 N) was added to a solution of TBDPS-ether 23a (4.4 g, 7.7 mmol) in methanol (40 mL) and the mixture stirred at 62° C. for 22 hrs. Analysis by TLC indicated that the reaction was complete. The reaction was concentrated to give 4.95 g of colorless oil. Chromatography (5% to 40% ethyl acetate/heptane gradient) afforded 1.48 g (58%) of the title compound as white foam. Data for 24a: $R_f$=0.12 (50% EtOAc/heptane); $^1$H NMR (400 MHz, CHLOROFORM-d) δ ppm 6.91-6.99 (m, 1H), 6.66-6.72 (m, 1H), 6.61-6.66 (m, 1H), 3.63-3.73 (m, 1H), 3.53-3.63 (m, 1H), 2.57-2.75 (m, 2H), 2.33-2.51 (m, 2 H), 2.16-2.30 (m, 1H), 2.05-2.15 (m, 1H), 1.79-1.92 (m, 1H), 1.18-1.71 (m, 13H), 1.04-1.15 (m, 1H), 0.83-0.93 (m, 3H); MS (ESI+) m/z 355.2 (M+Na$^+$).

Example 27: ethyl 2-(((1R,2R,3aS,9aS)-2-hydroxy-1-((S)-3-hydroxyoctyl)-2,3,3a,4,9,9a-hexahydro-1H-cyclopenta[b]naphthalen-5-yl)oxy)acetate(25a)

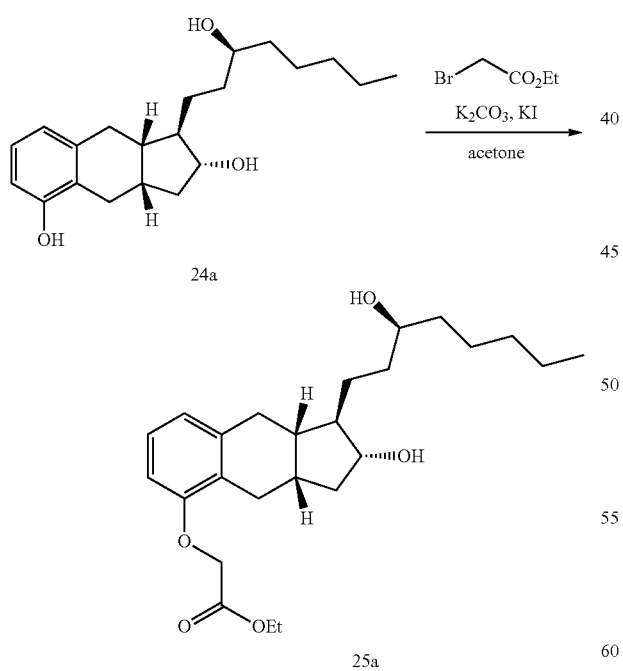

Ethyl bromoacetate was added drop-wise to a slurry of benzindene triol 24a (500 mg, 1.504 mmol, 1.0 equiv), anhydrous potassium carbonate (312 mg, 2.26 mmol, 1.5 equiv) and anhydrous potassium iodide (25 mg, 0.15 mmol, 0.1 equiv) in acetone (20 mL) and the reaction was heated to reflux while stirring, under nitrogen for 16 hours. The reaction was then cooled to room temperature, diluted with heptane (10 mL) and filtered through celite. The celite was rinsed with ethyl acetate (3×30 mL) and the filtrate was concentrated to give a pale oil. Chromatography (10% to 80% ethyl acetate/heptane gradient) afforded 610 mg (96%) of the title compound as a colorless oil. Data for 25a: $R_f$=0.15 (50% EtOAc/heptane); $^1$H NMR $^1$H NMR (400 MHz, CDCl$_3$) δ 7.07 (t, J=7.87 Hz, 1H), 6.81 (d, J=7.32 Hz, 1H), 6.64 (d, J=7.69 Hz, 1H), 4.62 (s, 2H), 4.27 (q, J=7.32 Hz, 2H), 3.76 (dt, J=6.04, 9.61 Hz, 1H), 3.55-3.70 (m, J=4.40 Hz, 1H), 2.89 (dd, J=5.86, 14.65 Hz, 1H), 2.76 (dd, J=6.23, 14.28 Hz, 1H), 2.56 (dd, J=6.59, 15.01 Hz, 1H), 2.46 (dd, J=6.59, 14.28 Hz, 1H), 2.11-2.34 (m, 4H), 1.89 (tt, J=6.50, 9.98 Hz, 1H), 1.24-1.75 (m, 16H), 1.12-1.23 (m, 1H), 0.84-0.99 (m, 3H); MS (ESI+) m/z 419.3 (M+H$^+$).

Example 28: 2-(((1R,2R,3aS,9aS)-2-hydroxy-1-((S)-3-hydroxyoctyl)-2,3,3a,4,9,9a-hexahydro-1H-cyclopenta[b]naphthalen-5-yl)oxy)acetic acid (I)

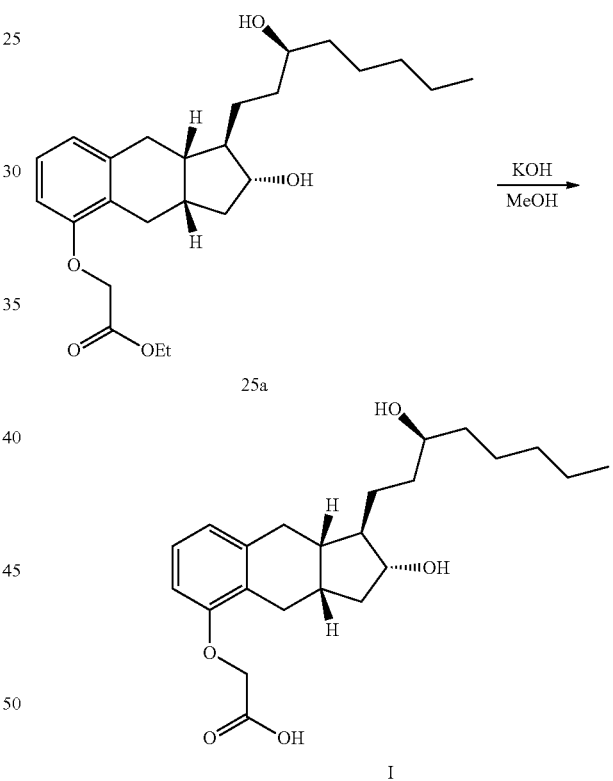

Potassium hydroxide (5.623 g in 19 mL water, 30% solution in water, 100.2 mmol, 5.0 equiv) was added to a solution of ethyl ester 25a (8.390 g, 20.04 mmol, 1.0 equiv) in ethanol (100 mL) and stirred at room temperature, under nitrogen for 90 minutes. The reaction was then concentrated under reduced pressure to remove the ethanol, diluted with water (50 mL) and extracted with ethyl acetate (50 mL) to remove organic impurities. The aqueous layer was acidified to pH 2-3 by addition of 3 N aqueous hydrochloric acid and extracted with ethyl acetate (3×100 mL). The combined organic phases were treated with activated charcoal (800 mg) and heated to reflux for 1 hour, cooled to room temperature, filtered through celite and concentrated to give 8.2 g of the title compound as an off-white solid. This material was moved forward to the next step crude and was not characterized further. Data for I: $R_f$=0.27 (90:10:1 methylene chloride/methanol/acetic acid).

Example 29: 2-hydroxy-N-(2-hydroxyethyl)-N-methylethanaminium 2-(((1R,2R,3aS,9aS)-2-hydroxy-1-((S)-3-hydroxyoctyl)-2,3,3a,4,9,9a-hexahydro-1H-cyclopenta[b]naphthalen-5-yl)oxy)acetate (I, N-methyldiethanolamine salt)

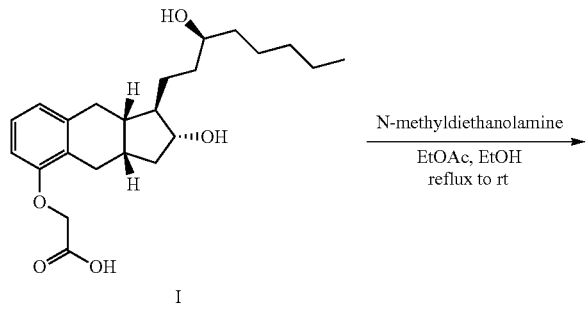

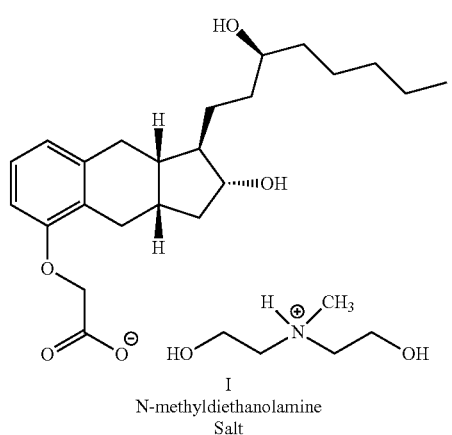

I
N-methyldiethanolamine
Salt

A solution of 2-(((1R,2R,3aS,9aS)-2-hydroxy-1-((S)-3-hydroxyoctyl)-2,3,3a,4,9,9a-hexahydro-1H-cyclopenta[b]naphthalen-5-yl)oxy)acetic acid (I) (50 mg, 0.13 mmol, 1.0 equiv) in ethanol (88 μL) and ethyl acetate (1.6 mL) was warmed to reflux until homogenous and then N-methyldiethanolamine (14.7 μL, 0.128 mmol, 1.0 equiv) was added. This clear solution was then allowed to slowly cool to room temperature overnight resulting in formation of fine white needles as a precipitate. The precipitate was filtered and dried under vacuum to give 60 mg of the title compound as fine white needles. HPLC analysis showed minor enrichment as the free acid had an HPLC purity of 96.47% and the salt had an HPLC purity of 96.98%. These crystals were used as seed crystals for subsequent recrystallizations.

A solution of 2-(((1R,2R,3aS,9aS)-2-hydroxy-1-((S)-3-hydroxyoctyl)-2,3,3a,4,9,9a-hexahydro-1H-cyclopenta[b]naphthalen-5-yl)oxy)acetic acid (I) (500 mg, 1.28 mmol, 1.0 equiv) and N-methyldiethanolamine (429 μL of a 33.3% v/v solution in ethanol, 1.25 mmol, 1.0 equiv) in ethanol (0.45 mL) and ethyl acetate (16 mL) was warmed to reflux until homogenous. An oil formed upon cooling to room temperature, so the mixture was warmed back to reflux until homogenous and the resulting clear mixture cooled to about 50° C. and seeded with 2-hydroxy-N-(2-hydroxyethyl)-N-methylethanaminium 2-(((1R,2R,3 aS,9aS)-2-hydroxy-1-((S)-3-hydroxyoctyl)-2,3,3a,4,9,9a-hexahydro-1H-cyclopenta[b]naphthalen-5-yl)oxy)acetate obtained as previously described. This was then allowed to cool to room temperature over 5 hours. A precipitate of fine white needles was filtered and dried under vacuum to give 551 mg of the title compound as fine white needles. HPLC analysis showed considerable enrichment as the free acid had an HPLC purity of 87.12% and the salt had an HPLC purity of 93.36%.

The 443 mg 2-hydroxy-N-(2-hydroxyethyl)-N-methylethanaminium 2-(((1R,2R,3aS,9aS)-2-hydroxy-1-((S)-3-hydroxyoctyl)-2,3,3a,4,9,9a-hexahydro-1H-cyclopenta[b]naphthalen-5-yl)oxy)acetate obtained above was warmed to reflux as a solution in 0.58 mL ethanol and 10.4 mL ethyl acetate until homogenous and then allowed to cool to room temperature overnight. A precipitate of fine white needles was filtered and dried under vacuum to give 339 mg of the title compound as fine white needles. HPLC purity of this batch was enriched to 98.20%. Data for N-methyldiethanolamine salt of I: mp=83.5-85.5° C.; $[\alpha]^{25}_D$=+30.4 (c 0.514, EtOH); $^1$H NMR (400 MHz, DMSO-$d_6$) δ 6.99 (t, J=7.69 Hz, 1H), 6.64 (dd, J=7.87, 14.83 Hz, 2H), 4.34 (s, 2H), 3.86 (t, J=5.31 Hz, 4H), 3.39-3.60 (m, 2H), 3.29 (br. s., 4H), 2.83-2.95 (m, 3H), 2.75 (dd, J=4.94, 14.46 Hz, 1H), 2.54 (dd, J=5.86, 13.92 Hz, 1H), 2.21-2.42 (m, 2H), 2.03 (d, J=4.03 Hz, 2H), 0.95-1.76 (m, 15H), 0.88 (t, J=6.77 Hz, 3H); $^{13}$C NMR (101 MHz, DMSO-$d_6$) δ 171.25, 155.07, 140.30, 126.58, 125.70, 120.11, 109.39, 75.47, 70.12, 66.14, 58.86, 57.43, 51.50, 41.73, 41.16, 40.52, 37.02, 35.01, 33.42, 32.45, 31.50, 28.33, 25.66, 24.92, 22.14, 13.92; IR (KBr pellet) 3392.1 (s), 3248.9 (m), 3081.7 (m), 2926.6 (s), 2903.8 (s), 2854.7 (m), 1609.9 (vs), 1473.1 (m), 1397.2 (m), 1318.9 (m), 1278.0 (m), 1243.7 (m), 1210.5 (w), 1113.9 (m), 1080.8 (m), 1051.2 (w), 1032.6 (w), 1006.0 (w), 915.2 (w), 902.6 (w), 774.0 (w) cm$^{-1}$; MS (ESI+) m/z 413.2 (M+Na$^+$); HPLC, Synergi Hydro RP column (4.6×250 mm$^2$), 5 μm; flow rate 1.0 mL/min; 277 nm; mobile phase A: 0.1% formic acid in water; mobile phase B: 0.1% formic acid in acetonitrile; 0-45 min (40% B), 45-55 min (40-95% B gradient), 55-65 min (90% B), 65.1 min (40% B); retention time, 37.43 min (98.2%, 27a), retention time, 39.44 min (0.53%, 2-hydroxy-N-(2-hydroxyethyl)-N-methylethan-1-aminium 2-(((1R,2R,3aS,9aS)-2-hydroxy-1-((S)-3-hydroxyoctyl)-2,3,3a,4,9,9a-hexahydro-1H-cyclopenta[b]naphthalen-5-yl)oxy)acetate).

Example 30: 2-(((1R,2R,3aS,9aS)-2-hydroxy-1-((S)-3-hydroxyoctyl)-2,3,3a,4,9,9a-hexahydro-1H-cyclopenta[b]naphthalen-5-yl)oxy)acetic acid (I)

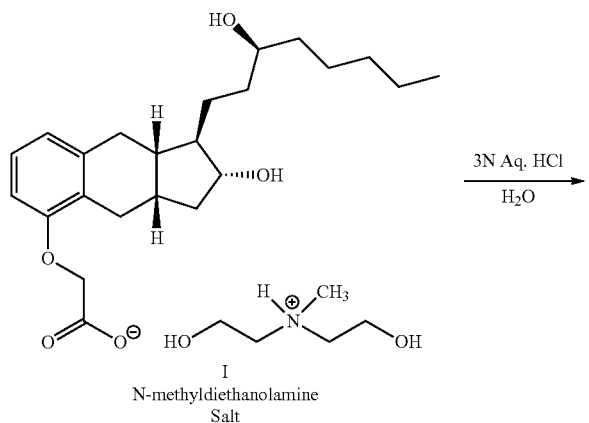

A solution of the N-methyldiethanolamine salt of Formula I (100 mg, 0.196 mmol, 1.0 equiv) in water (1 mL) and isopropyl acetate (2.5 mL) was treated with aqueous hydrochloric acid (0.080 mL, 0.23 mmol, 1.2 equiv, 3.0 M solution in water) and the resulting biphasic slurry was stirred at room temperature until the layers cleared. The layers were separated, and the aqueous phase was extracted with isopropyl acetate (2×2.5 mL). The combined organic phases were washed with water (2×2.5 mL), dried (Na$_2$SO$_4$) and concentrated to give 75 mg (97%) of the title compound as a white powder. The free acid may be recrystallized by methods known in the art to further improve the purity. Data for I: $^1$H NMR (400 MHz, CHLOROFORM-d) δ 7.07 (t, J=7.88 Hz, 1H), 6.82 (d, J=7.69 Hz, 1H), 6.68 (d, J=8.43 Hz, 1H), 4.58-4.72 (m, 2H), 4.40 (br. s., 3H), 3.73 (dt, J=6.23, 9.34 Hz, 1H), 3.64 (d, J=3.66 Hz, 1H), 2.76 (ddd, J=6.23, 14.20, 19.87 Hz, 2H), 2.61 (dd, J=6.04, 14.84 Hz, 1H), 2.48 (dd, J=6.23, 14.29 Hz, 1H), 2.20-2.36 (m, 1H), 2.10-2.20 (m, 1H), 1.82-1.98 (m, 1H), 1.52-1.76 (m, 4H), 1.40-1.52 (m, 3H), 1.21-1.40 (m, 6H), 1.08-1.21 (m, 1H), 0.92 (t, J=6.60 Hz, 3H); MS (ESI+) m/z 413.2 (M+Na$^+$).

Examples 31-41: Amine salts of 2-(((1R,2R,3aS,9aS)-2-hydroxy-1-((S)-3-hydroxyoctyl)-2,3,3a,4,9,9a-hexahydro-1H-cyclopenta[b]naphthalen-5-yl)oxy)acetic acid (I)

A solution of 2-(((1R,2R,3aS,9aS)-2-hydroxy-1-((S)-3-hydroxyoctyl)-2,3,3a,4,9,9a-hexahydro-1H-cyclopenta[b]naphthalen-5-yl)oxy)acetic acid (I) (50 mg, 0.13 mmol, 1.0 equiv) in ethanol (88 μL) and ethyl acetate (1.6 mL) was warmed to reflux until homogenous and then an amine selected from amines A-1 to A-12 (0.128 mmol, 1.0 equiv.) in Table 2 was added. This clear solution was then allowed to slowly cool to room temperature overnight. In the event that a precipitate formed, it was filtered and dried under vacuum and the yield and HPLC purity reported in the table below.

TABLE 2

Amine salts of 2-(((1R,2R,3aS,9aS)-2-hydroxy-1-((S)-3-hydroxyoctyl)-2,3,3a,4,9,9a-hexahydro-1H-cyclopenta[b]naphthalen-5-yl)oxy)acetic acid (I).

| Example | Amine | Name | CAS # | Yield | HPLC Purity |
|---|---|---|---|---|---|
| 31 | A-1 | Ethanolamine | 141-43-5 | Oiled out | n/a |
| 32 | A-2 | N-methyldiethanolamine | 105-59-9 | 92% | 98.02% |
| 33 | A-3 | N-ethyldiethanolamine | 139-87-7 | Oiled out | n/a |
| 34 | A-4 | Serinol | 534-03-2 | 90% | 96.84% |
| 35 | A-5 | 2-(diethylamino)ethanol | 100-37-8 | Oiled out | n/a |
| 36 | A-6 | N,N-diethylethylenediamine | 100-36-7 | Oiled out | n/a |
| 37 | A-7 | N-methylethylenediamine | 109-81-9 | Oiled out | n/a |
| 38 | A-8 | 1,2-Bis(2-aminoethoxy)ethane | 929-59-9 | Oiled out | n/a |
| 39 | A-9 | Tyramine | 51-67-2 | 90% | 97.00% |
| 40 | A-10 | Methylhydrazine | 60-34-4 | Oiled out | n/a |
| 41 | A-11 | Morpholine | 110-91-8 | Oiled out | n/a |

As demonstrated in Table 1, efforts to generate solid form salts of 2-(((1R,2R,3aS,9aS)-2-hydroxy-1-((S)-3-hydroxyoctyl)-2,3,3a,4,9,9a-hexahydro-1H-cyclopenta[b]naphthalen-5-yl)oxy)acetic acid resulted in the generation of only three salts out of the eleven attempted. Thus, the formation of amine salts of 2-(((1R,2R,3aS,9aS)-2-hydroxy-1-((S)-3-hydroxyoctyl)-2,3,3a,4,9,9a-hexahydro-1H-cyclopenta[b]naphthalen-5-yl)oxy)acetic acid is unpredictable.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of generating an N-methyldiethanolamine salt compound of Formula I

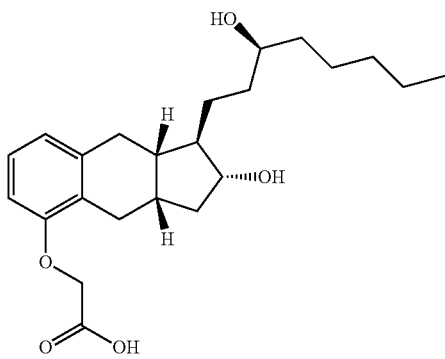

I comprising the steps of:
i) reacting a compound of Formula 11 with an oxidizing agent in the presence of an organic solvent to generate a compound of Formula 12

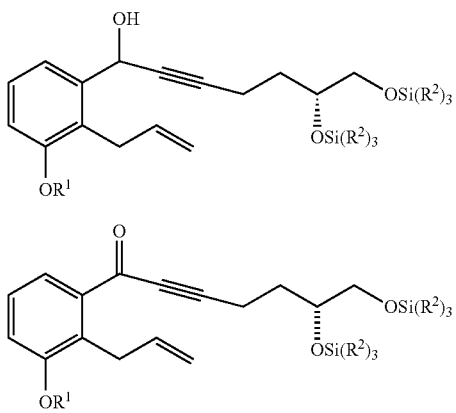

11

12 wherein $R^1$ is $C_{1-6}$ alkyl, each $R^2$ is independently selected from $C_{1-6}$ alkyl or phenyl, and the oxidizing agent comprises $MnO_2$; and ii) converting the compound of Formula 12 to the N-methyldiethanolamine salt of the compound of Formula I.

2. The method of claim 1, wherein each of the $-OSi(R^2)_3$ groups in the compounds of Formulae 11 and 12 is independently selected from

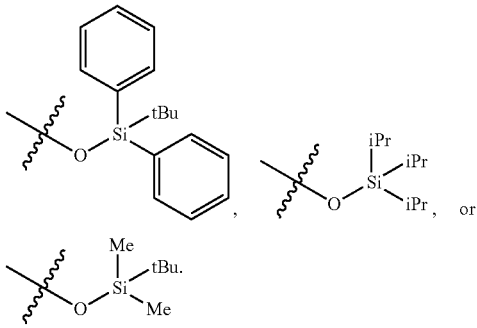 [SMILES: *O[Si](c1ccccc1)(c1ccccc1)C(C)(C)C ; *O[Si](C(C)C)(C(C)C)C(C)C ; *O[Si](C)(C)C(C)(C)C]

3. The method of claim 1, wherein the organic solvent of step viii) comprises a halogenated organic solvent.

4. The method of claim 3, wherein the halogenated organic solvent comprises dichloromethane, chloroform, or any combination thereof.

5. The method of claim 1, further comprising the steps of:
i) reacting a compound of Formula 9 with an oxidizing agent in the presence of an organic solvent to generate a compound of Formula 10

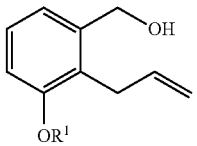

9

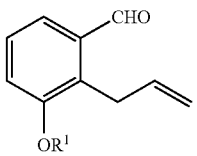

10 wherein $R^1$ is $C_{1-6}$ alkyl and the oxidizing agent comprises $MnO_2$ or Dess-Martin periodinane; and ii) reacting the compound of Formula 10 with a compound of Formula 5

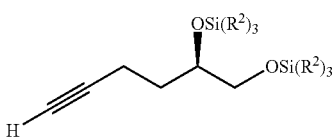

5

-continued

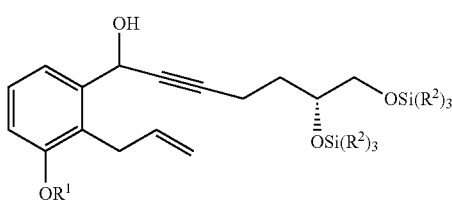
11 in the presence of a base and an organic solvent to generate a compound of Formula 11.

6. The method of claim 5, wherein the base of step ii) comprises an alkyllithium reagent.

7. The method of claim 6, wherein the alkyllithium reagent is sec-butyllithium.

8. The method of claim 5, wherein the organic solvent of step ii) comprises pentane, hexane, cyclohexane, heptane, tetrahydrofuran, 1,4-dioxane, diethyl ether, petro ether, methyl-tert-butylether, or any combination thereof.

9. The method of claim 8, wherein the organic solvent of step ii) comprises methyl-tert-butylether.

10. A method of generating an N-methyldiethanolamine salt of the compound of Formula I

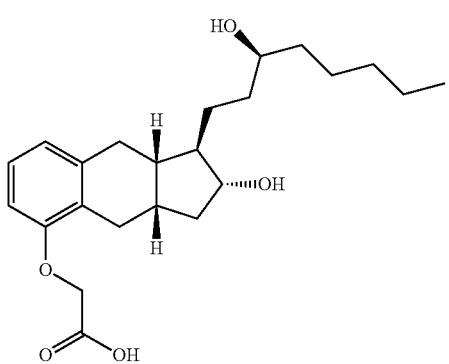
I comprising the steps of:
iii) reacting a compound of Formula 12 with a reducing agent in the presence of an organic solvent to generate a compound of Formula 13

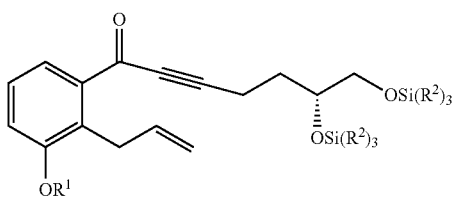
12

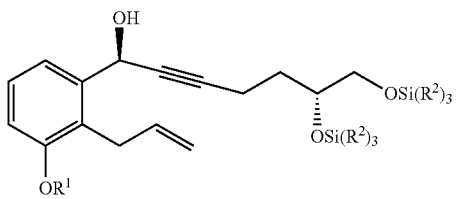
13 wherein the organic solvent comprises THF, $R^1$ is $C_{1-6}$ alkyl, and each $R^2$ is independently selected from $C_{1-6}$ alkyl or phenyl; and iv) converting the compound of Formula 13 to the N-methyldiethanolamine salt of the compound of Formula I.

11. The method of claim 10, wherein the reducing agent of step x) comprises a chiral borane compound.

12. The method of claim 11, wherein the chiral borane compound is selected from (R)-1-methyl-3,3-diphenylhexahydropyrrolo[1,2-c][1,3,2]oxazaborole, (R)-3,3-diphenylhexahydropyrrolo[1,2-c][1,3,2]oxazaborole, (R)-1-butyl-3,3-diphenylhexahydropyrrolo[1,2-c][1,3,2]oxazaborole, (R)-tetrahydro-1,3,3-triphenyl-1H,3H-pyrrolo[1,2-c][1,3,2]oxaborole, (4S)-2-methyl-4,5,5-triphenyl-1,3,2-oxazaborolidine, or any combination thereof.

13. The method of claim 10, wherein the organic solvent of step x) further comprises toluene.

14. The method of claim 10, further comprising the step of:
viii) reacting a compound of Formula 11 with an oxidizing agent to generate the compound of Formula 12, wherein the oxidizing agent comprises $MnO_2$

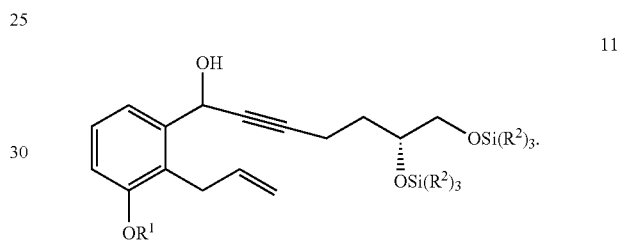
11

15. The method of claim 14, further comprising the steps of:
i) reacting a compound of Formula 9 with an oxidizing agent to generate a compound of Formula 10; and

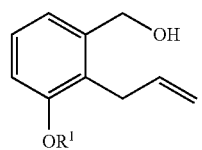
9

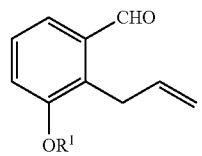
10 ii) reacting the compound of Formula 10 with a compound of Formula 5 in the presence of a base and an organic solvent to generate a compound of Formula 11

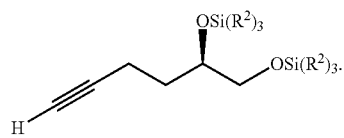
5

16. The method of claim 15, wherein the oxidizing agent comprises MnO$_2$ or Dess-Martin periodinane.

17. The method of claim 16, wherein the base of step ii) comprises an alkyllithium reagent.

18. The method of claim 17, wherein the alkyllithium reagent is sec-butyllithium.

19. The method of claim 15, wherein the organic solvent of step ii) comprises pentane, hexane, cyclohexane, heptane, tetrahydrofuran, 1,4-dioxane, diethyl ether, petro ether, methyl-tert-butylether, or any combination thereof.

20. The method of claim 19, wherein the organic solvent of step ii) comprises methyl-tert-butylether.

21. The method of claim 15, further comprising the steps of:

iv) refluxing the compound of Formula 1a in the presence of methanol to generate a compound of Formula 1 having an e.e. of greater than about 98%;

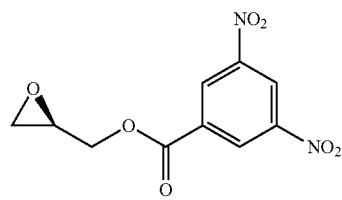

1a

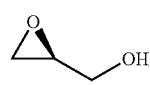

1 v) reacting the compound of Formula 1 with SiCl(R$^2$)$_3$ under basic conditions to generate the compound of Formula 2;

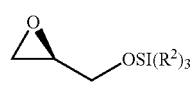

2 vi) reacting the compound of Formula 2 with 1-TMS-1-propyne to generate the compound of Formula 3; and

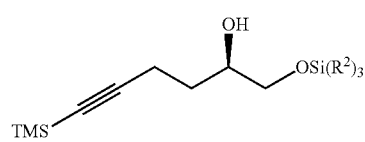

3 vii) converting the compound of Formula 3 to the compound of Formula 5.

22. A method of generating an N-methyldiethanolamine salt of the compound of Formula I

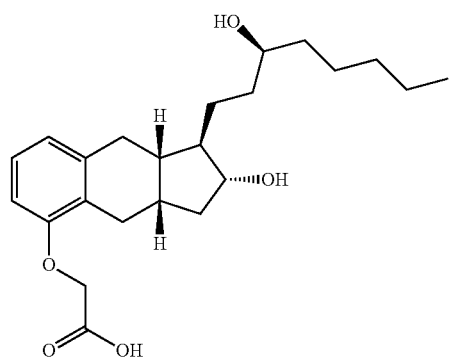

I comprising the steps of:

v) hydrogenating a compound of Formula 15 in the presence of an organic solvent to generate the compound of Formula 16

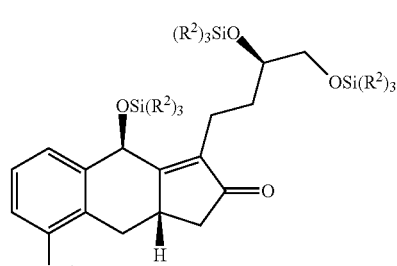

15

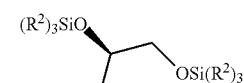

16 wherein R$^1$ is C$_{1-6}$ alkyl, and each R$^2$ is independently selected from C$_{1-6}$ alkyl or phenyl; and vi) converting the compound of Formula 16 to the N-methyldiethanolamine salt of the compound of Formula I.

23. The method of claim 22, wherein the organic solvent of step xii) comprises an alcohol, THF, or any combination thereof.

24. The method of claim 22, further comprising the steps of:

x) reacting a compound of Formula 12 with a reducing agent in the presence of an organic solvent to generate a compound of Formula 13

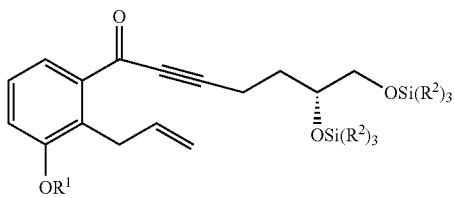

12

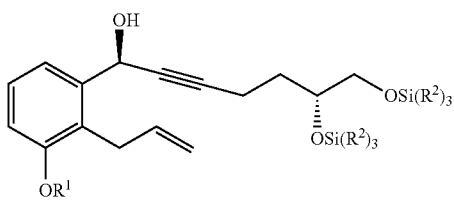

13 wherein the organic solvent comprises THF; and vii) converting the compound of Formula 13 to the compound of Formula 15.

25. The method of claim 24, wherein the reducing agent of step x) comprises a chiral borane compound.

26. The method of claim 25, wherein the chiral borane compound is selected from (R)-1-methyl-3,3-diphenylhexahydropyrrolo[1,2-c][1,3,2]oxazaborole, (R)-3,3-diphenylhexahydropyrrolo[1,2-c][1,3,2]oxazaborole, (R)-1-butyl-3,3-diphenylhexahydropyrrolo[1,2-c][1,3,2]oxazaborole, (R)-tetrahydro-1,3,3-triphenyl-1H,3H-pyrrolo[1,2-c][1,3,2]oxaborole, (4S)-2-methyl-4,5,5-triphenyl-1,3,2-oxazaborolidine, or any combination thereof.

27. The method of claim 24, further comprising the steps of:

viii) reacting a compound of Formula 11 with an oxidizing agent to generate the compound of Formula 12, wherein the oxidizing agent comprises MnO$_2$

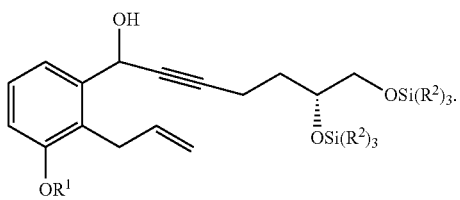

11

28. The method of claim 27, further comprising the steps of:

i) reacting a compound of Formula 9 with an oxidizing agent to generate a compound of Formula 10; and

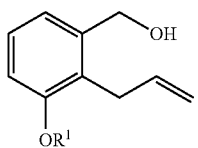

9

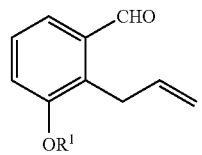

10 ii) reacting the compound of Formula 10 with a compound of Formula 5 in the presence of a base and an organic solvent to generate a compound of Formula 11

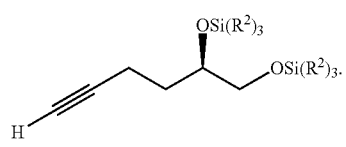

5

29. The method of claim 28, wherein the oxidizing agent of step i) comprises MnO$_2$ or Dess-Martin periodinane.

30. The method of claim 28, wherein the base of step ii) comprises an alkyllithium reagent.

31. The method of claim 30, wherein the alkyllithium reagent is sec-butyllithium.

32. The method of claim 28, wherein the organic solvent of step ii) comprises pentane, hexane, cyclohexane, heptane, tetrahydrofuran, 1,4-dioxane, diethyl ether, petro ether, methyl-tert-butylether, or any combination thereof.

33. The method of claim 32, wherein the organic solvent of step ii) comprises methyl-tert-butylether.

34. The method of claim 28, further comprising the steps of:

iv) refluxing the compound of Formula 1a in the presence of methanol to generate a compound of Formula 1 having an e.e. of greater than about 98%;

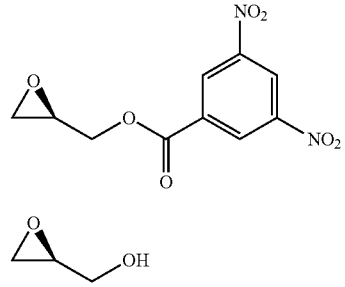

1a

1 v) reacting the compound of Formula 1 with SiCl(R$^2$)$_3$ under basic conditions to generate the compound of Formula 2;

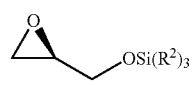

2 vi) reacting the compound of Formula 2 with 1-TMS-1-propyne to generate the compound of Formula 3; and

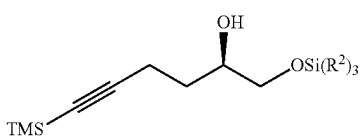

3 vii) converting the compound of Formula 3 to the compound of Formula 5.

35. A method of generating an N-methyldiethanolamine salt of the compound of Formula I

I comprising the steps of:
viii) reacting a compound of Formula 21 with n-butyllithium in the presence of an organic solvent and a transition metal catalyst to generate a compound of Formula 22

21

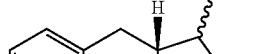

22 wherein $R^3$ is $C_{1-6}$ alkyl or phenyl; and
xvi) converting the compound of Formula 22 to the N-methyldiethanolamine salt of the compound of Formula I.

36. The method of claim 35, wherein the transition metal catalyst of step xv) comprises a compound or complex either of which comprises Cu having a +1 oxidation state.

37. The method of claim 36, wherein the transition metal catalyst of step xv) comprises CuX, wherein X is selected from halogen, acetate, benzoate, cyanide, hydroxide, nitrate, or any combination thereof.

38. The method of claim 37, wherein the transition metal catalyst of step xv) comprises CuI.

39. The method of claim 35, further comprising the steps of:
xvii) reacting a compound of Formula 19 with $R^4$-substituted benzenesulfonyl chloride under basic conditions to generate a compound of Formula 20, wherein each $R^4$ is independently selected from —H or $C_{1-3}$ alkyl; and

19

20 xviii) reacting the compound of Formula 20 with methanol under basic conditions to generate the compound of Formula 21.

40. The method of claim 39, further comprising the steps of:
xix) reacting a compound of Formula 16 with a reducing agent to generate a compound of Formula 17;

16

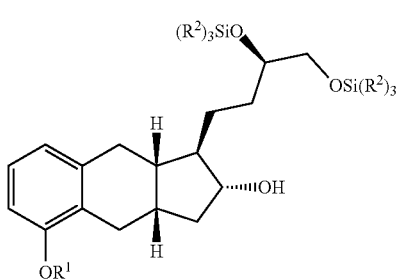

17 xx) reacting the compound of claim 17 with Si(R³)₃Cl under basic conditions to generate a compound of Formula 18; and

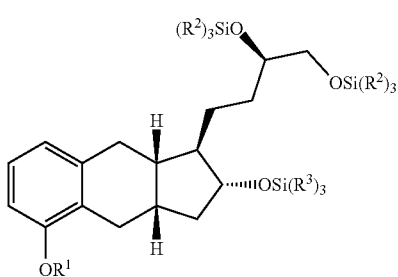

18 xxi) selectively deprotecting the compound of Formula 18 to generate the compound of Formula 19.

41. The method of claim 40, further comprising the steps of:

xii) hydrogenating a compound of Formula 15

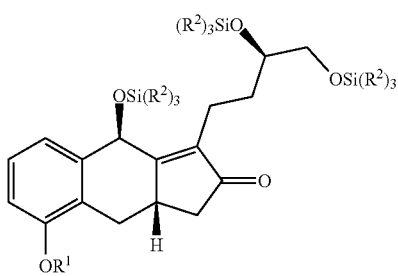

15 in the presence of an organic solvent to generate the compound of Formula 16.

42. The method of claim 41, wherein the organic solvent of step xii) comprises an alcohol, THF, or any combination thereof.

43. The method of claim 42, further comprising the steps of:

x) reacting a compound of Formula 12 with a reducing agent to generate a compound of Formula 13; and

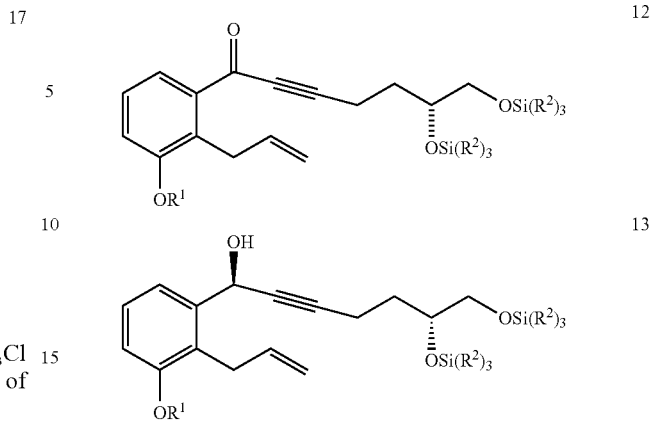

12

13 xiv) converting the compound of Formula 13 to the compound of Formula 15.

44. The method of claim 43, wherein the reducing agent of step x) comprises a chiral borane compound.

45. The method of claim 44, wherein the chiral borane compound is selected from (R)-1-methyl-3,3-diphenylhexahydropyrrolo[1,2-c][1,3,2]oxazaborole, (R)-3,3-diphenylhexahydropyrrolo[1,2-c][1,3,2]oxazaborole, (R)-1-butyl-3,3-diphenylhexahydropyrrolo[1,2-c][1,3,2]oxazaborole, (R)-tetrahydro-1,3,3-triphenyl-1H,3H-pyrrolo[1,2-c][1,3,2]oxaborole, (4S)-2-methyl-4,5,5-triphenyl-1,3,2-oxazaborolidine, or any combination thereof.

46. The method of claim 43, further comprising the step of:

viii) reacting a compound of Formula 11

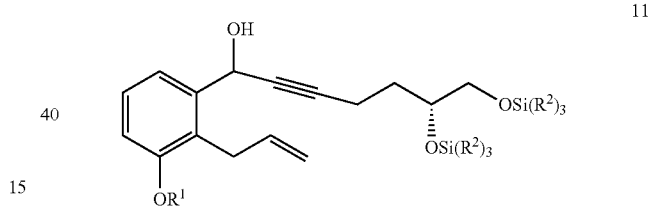

11 with an oxidizing agent to generate the compound of Formula 12, wherein the oxidizing agent comprises MnO₂.

47. The method of claim 46, further comprising the steps of:

i) reacting a compound of Formula 9 with an oxidizing agent to generate a compound of Formula 10; and

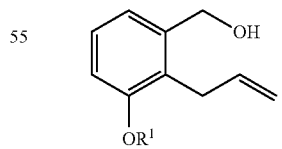

9

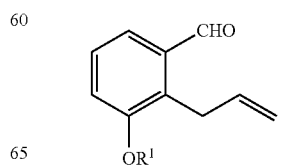

10 ii) reacting the compound of Formula 10 with a compound of Formula 5 in the presence of a base and an organic solvent to generate a compound of Formula 11

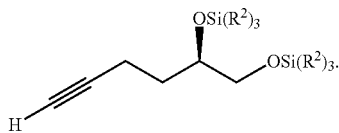

5

48. The method of claim 47, wherein the oxidizing agent of step i) comprises MnO$_2$ or Dess-Martin periodinane.

49. The method of claim 47, wherein the base of step ii) comprises an alkyllithium reagent.

50. The method of claim 49, wherein the alkyllithium reagent is sec-butyllithium.

51. The method of claim 47, wherein the organic solvent of step ii) comprises pentane, hexane, cyclohexane, heptane, tetrahydrofuran, 1,4-dioxane, diethyl ether, petro ether, methyl-tert-butylether, or any combination thereof.

52. The method of claim 51, wherein the organic solvent of step ii) comprises methyl-tert-butylether.

53. The method of claim 47, further comprising the steps of:

iv) refluxing the compound of Formula 1a in the presence of methanol to generate a compound of Formula 1 having greater than about 99% e.e.;

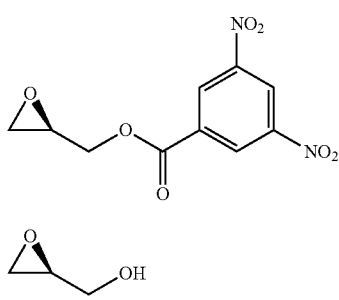

v) reacting the compound of Formula 1 with SiCl(R$^2$)$_3$ under basic conditions to generate the compound of Formula 2;

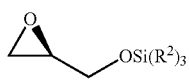

vi) reacting the compound of Formula 2 with 1-TMS-1-propyne to generate the compound of Formula 3; and

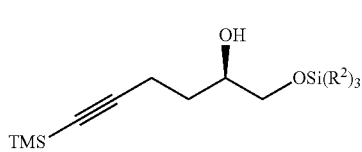

vii) converting the compound of Formula 3 to the compound of Formula 5.

54. The method of claim 53, further comprising the steps of:

xxii) reacting a compound of Formula 7 with a 3-haloprop-1-ene in the presence of a base and an organic solvent to generate a compound of Formula 8; and

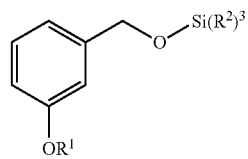

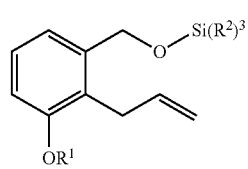

xxiii) deprotecting the compound of Formula 8 to generate the compound of Formula 9.

55. A method of generating an N-methyldiethanolamine salt of the compound of Formula I

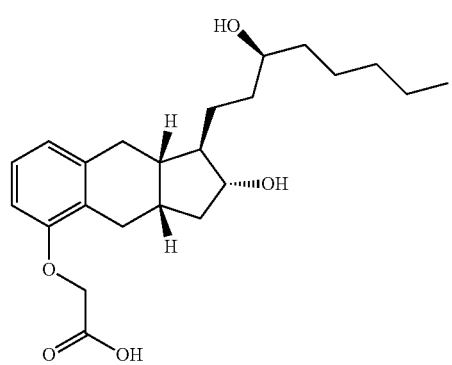

comprising the steps of:

xxii) reacting a compound of Formula 7, wherein R$^1$ is C$_{1-6}$ alkyl and each R$^2$ is independently selected from C$_{1-6}$ alkyl or phenyl, with a 3-haloprop-1-ene in the presence of a base and an organic solvent to generate a compound of Formula 8;

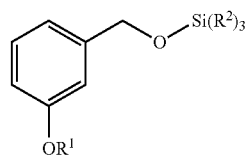

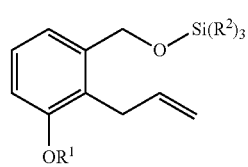

xxiii) deprotecting the compound of Formula 8 to generate the compound of Formula 9, and

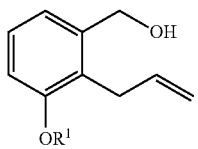

9 xxiv) converting the compound of Formula 9 to the compound of Formula I, wherein the base of step xxii) comprises sec-butyl lithium.

56. A method of generating an N-methyldiethanolamine salt of the compound of Formula I

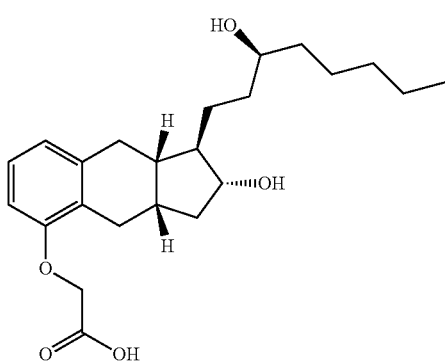

I comprising the steps of:
i) reacting a compound of Formula 9 with an oxidizing agent in the presence of an organic solvent to generate a compound of Formula 10

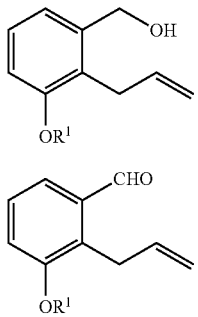

9

10 wherein $R^1$ is $C_{1-6}$ alkyl and the oxidizing agent comprises $MnO_2$ or Dess-Martin periodinane;
ii) reacting the compound of Formula 10 with a compound of Formula 5a in the presence of a base and an organic solvent to generate a compound of Formula 1a and

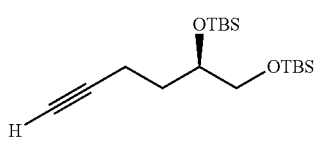

5a

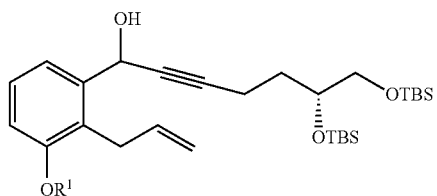

11a iii) converting the compound of Formula IIa to the N-methyldiethanolamine salt of the compound of Formula I.

57. The method of claim 56, wherein the organic solvent of step i) comprises a halogenated organic solvent.

58. The method of claim 57, wherein the halogenated organic solvent comprises dichloromethane, chloroform, or any combination thereof.

59. The method of claim 56, wherein the base of step ii) comprises an alkyllithium reagent.

60. The method of claim 59, wherein the alkyllithium reagent is sec-butyllithium.

61. The method of claim 56, wherein the organic solvent of step ii) comprises pentane, hexane, cyclohexane, heptane, tetrahydrofuran, 1,4-dioxane, diethyl ether, petro ether, methyl-tert-butylether, or any combination thereof.

62. The method of claim 61, wherein the organic solvent of step ii) comprises methyl-tert-butylether.

63. The method of claim 56, further comprising the steps of:
iv) refluxing the compound of Formula 1a in the presence of methanol to generate a compound of Formula 1 having an e.e. of greater than about 98%;

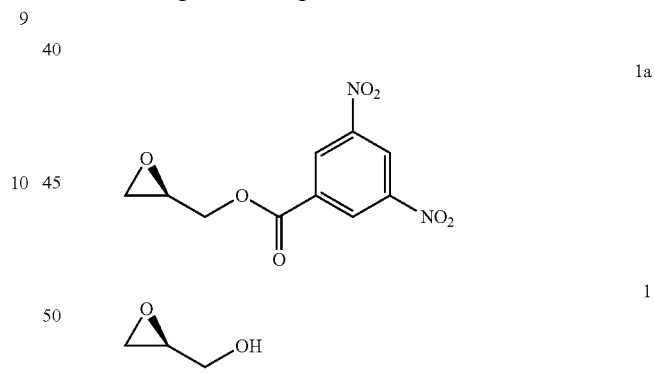

1a

1 v) reacting the compound of Formula 1 with TBSCl under basic conditions to generate the compound of Formula 2a,

2a vi) reacting the compound of Formula 2a with 1-TMS-1-propyne to generate the compound of Formula 3a; and

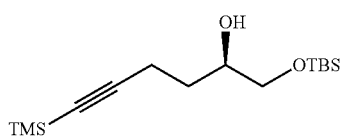

3a vii) converting the compound of Formula 3a to the compound of Formula 5a.

64. A method of generating an N-methyldiethanolamine salt of the compound of Formula I

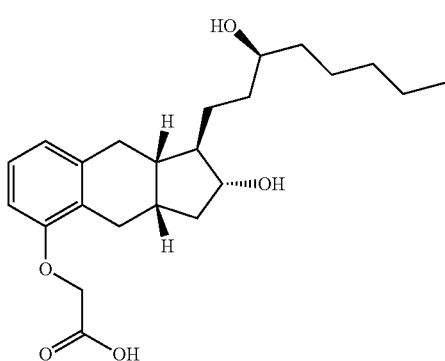

I comprising the steps of:
viii) reacting a compound of Formula 11a with an oxidizing agent in the presence of an organic solvent to generate a compound of Formula 12a

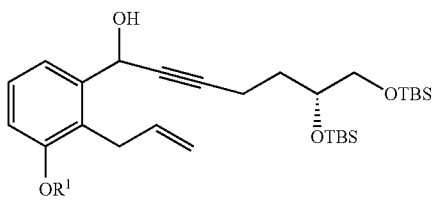

11a

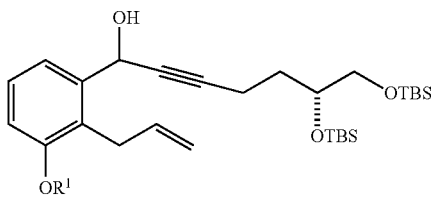

12a wherein $R^1$ is $C_{1-6}$ alkyl and the oxidizing agent comprises $MnO_2$; and
ix) converting the compound of Formula 12a to the N-methyldiethanolamine salt of the compound of Formula I.

65. The method of claim 64, wherein the organic solvent of step viii) comprises a halogenated organic solvent.

66. The method of claim 65, wherein the halogenated organic solvent comprises dichloromethane, chloroform, or any combination thereof.

67. The method of claim 64, further comprising the steps of:
i) reacting a compound of Formula 9 with an oxidizing agent in the presence of an organic solvent to generate a compound of Formula 10

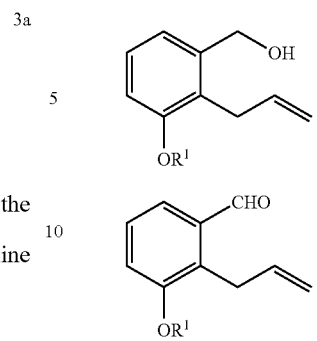

9

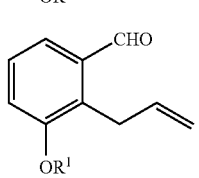

10 wherein the oxidizing agent comprises $MnO_2$ or Dess-Martin periodinane; and
ii) reacting the compound of Formula 10 with a compound of Formula 5a

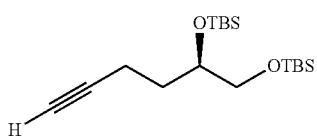

5a

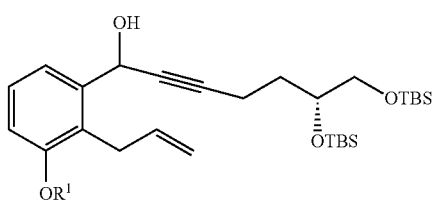

11a in the presence of a base and an organic solvent to generate a compound of Formula 11a.

68. The method of claim 67, wherein the base of step ii) comprises an alkyllithium reagent.

69. The method of claim 68, wherein the alkyllithium reagent is sec-butyllithium.

70. The method of claim 67, wherein the organic solvent of step ii) comprises pentane, hexane, cyclohexane, heptane, tetrahydrofuran, 1,4-dioxane, diethyl ether, petro ether, methyl-tert-butylether, or any combination thereof.

71. The method of claim 70, wherein the organic solvent of step ii) comprises methyl-tert-butylether.

72. A method of generating an N-methyldiethanolamine salt of the compound of Formula I

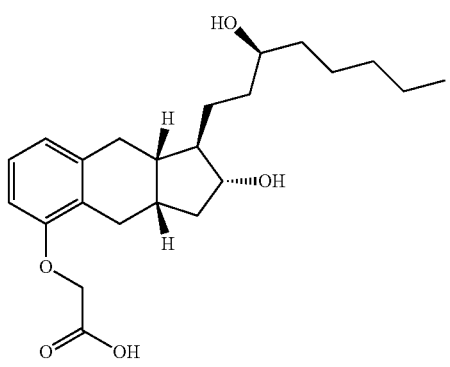

I comprising the steps of:

x) reacting a compound of Formula 12a with a reducing agent in the presence of an organic solvent to generate a compound of Formula 13a

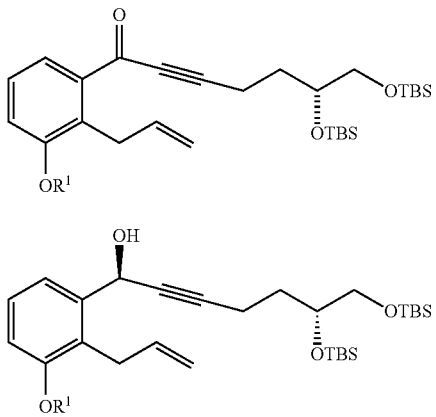

wherein the organic solvent comprises THF, $R^1$ is $C_{1-6}$ alkyl, and each $R^2$ is independently selected from $C_{1-6}$ alkyl or phenyl; and xi) converting the compound of Formula 13 to the N-methyldiethanolamine salt of the compound of Formula I.

73. The method of claim 72, wherein the reducing agent of step x) comprises a chiral borane compound.

74. The method of claim 73, wherein the chiral borane compound is selected from (R)-1-methyl-3,3-diphenylhexahydropyrrolo[1,2-c][1,3,2]oxazaborole, (R)-3,3-diphenylhexahydropyrrolo[1,2-c][1,3,2]oxazaborole, (R)-1-butyl-3,3-diphenylhexahydropyrrolo[1,2-c][1,3,2]oxazaborole, (R)-tetrahydro-1,3,3-triphenyl-1H,3H-pyrrolo[1,2-c][1,3,2]oxaborole, (4S)-2-methyl-4,5,5-triphenyl-1,3,2-oxazaborolidine, or any combination thereof.

75. The method of claim 74, wherein the organic solvent of step x) further comprises toluene.

76. The method of claim 72, further comprising the step of:

viii) reacting a compound of Formula 11a with an oxidizing agent to generate the compound of Formula 12a, wherein the oxidizing agent comprises $MnO_2$

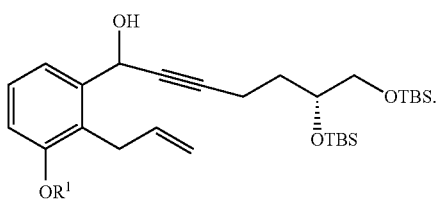

77. The method of claim 76, further comprising the steps of:

i) reacting a compound of Formula 9 with an oxidizing agent to generate a compound of Formula 10; and

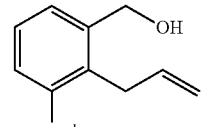

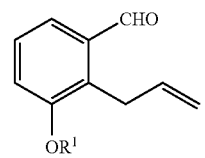

ii) reacting the compound of Formula 10 with a compound of Formula 5a in the presence of a base and an organic solvent to generate a compound of Formula 11a

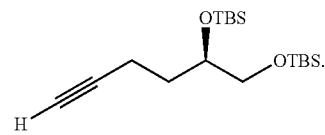

78. The method of claim 77, wherein the oxidizing agent comprises $MnO_2$ or Dess-Martin periodinane.

79. The method of claim 77, further comprising the steps of:

iv) refluxing the compound of Formula 1a in the presence of methanol to generate a compound of Formula 1 having an e.e. of greater than about 98%;

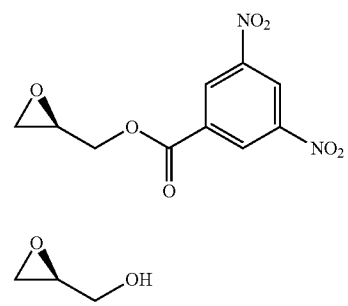

v) reacting the compound of Formula 1 with TBSCl under basic conditions to generate the compound of Formula 2a;

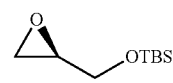

vi) reacting the compound of Formula 2a with 1-TMS-1-propyne to generate the compound of Formula 3a; and

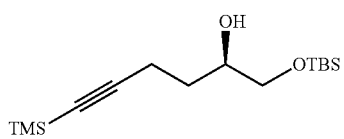

vii) converting the compound of Formula 3a to the compound of Formula 5a.

80. A method of generating an N-methyldiethanolamine salt of the compound of Formula I

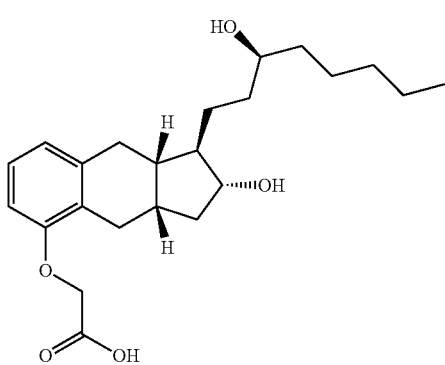

comprising the steps of:
xii) hydrogenating a compound of Formula 15a in the presence of an organic solvent to generate the compound of Formula 162

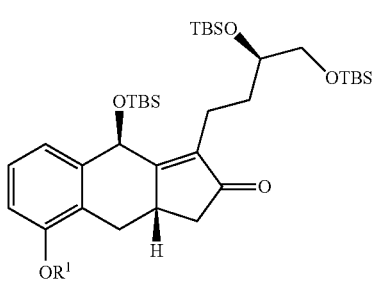

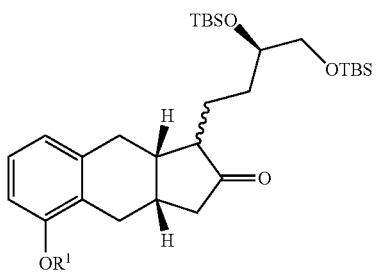

wherein $R^1$ is $C_{1-6}$ alkyl; and
xiii) converting the compound of Formula 16a to the N-methyldiethanolamine salt of the compound of Formula I.

81. The method of claim 80, wherein the organic solvent of step xii) comprises an alcohol, optionally substituted THF, EtOAc, or any combination thereof.

82. The method of claim 81, further comprising the steps of:

x) reacting a compound of Formula 12a with a reducing agent in the presence of an organic solvent to generate a compound of Formula 13a

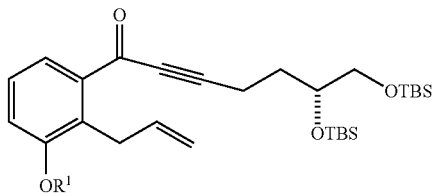

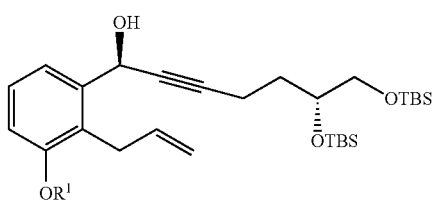

wherein the organic solvent comprises THF; and
xiv) converting the compound of Formula 13a to the compound of Formula 15a.

83. The method of claim 82, further comprising the steps of:
viii) reacting a compound of Formula 11a with an oxidizing agent to generate the compound of Formula 12a, wherein the oxidizing agent comprises $MnO_2$

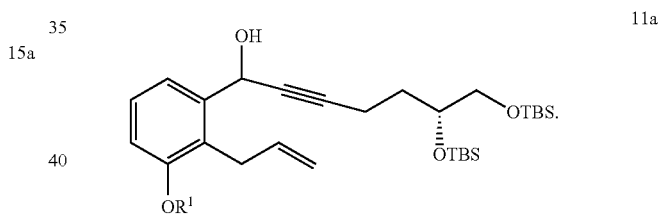

84. The method of claim 83, further comprising the steps of:
i) reacting a compound of Formula 9 with an oxidizing agent to generate a compound of Formula 10; and

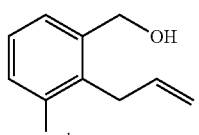

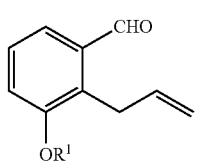

ii) reacting the compound of Formula 10 with a compound of Formula 5a in the presence of a base and an organic solvent to generate a compound of Formula 11a

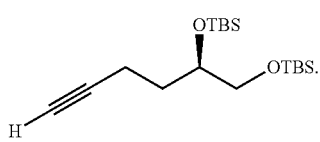
5a

85. The method of claim 84, further comprising the steps of:

iv) refluxing the compound of Formula 1a in the presence of methanol to generate a compound of Formula 1 having an e.e. of greater than about 98%;

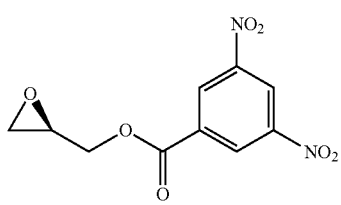
1a

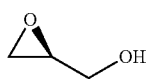
1 v) reacting the compound of Formula 1 with TBSCl under basic conditions to generate the compound of Formula 2a;

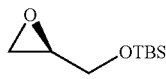
2a vi) reacting the compound of Formula 2a with 1-TMS-1-propyne to generate the compound of Formula 3a; and

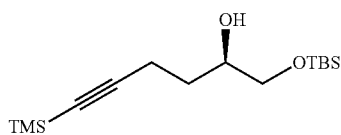
3a vii) converting the compound of Formula 3a to the compound of Formula 5a.

86. A method of generating an N-methyldiethanolamine salt of the compound of Formula I

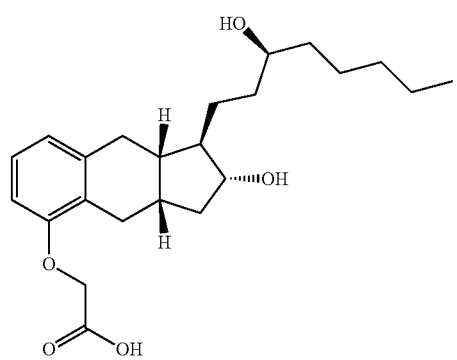
I comprising the steps of:

xv) reacting a compound of Formula 21a with n-butyllithium in the presence of an organic solvent and a transition metal catalyst to generate a compound of Formula 22a

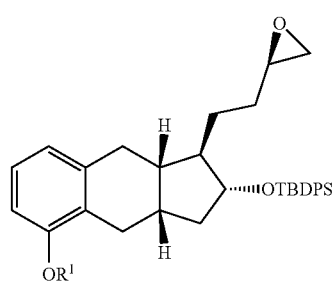
21a

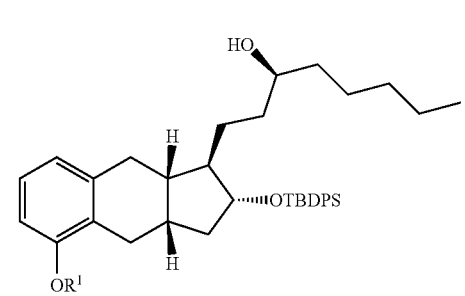
22a wherein $R^1$ is $C_{1-6}$ alkyl; and xvi) converting the compound of Formula 22a to the N-methyldiethanolamine salt of the compound of Formula I.

87. The method of claim 86, wherein the transition metal catalyst comprises a compound or complex either of which comprises copper having a +1 oxidation state.

88. The method of claim 87, wherein the transition metal catalyst comprises CuI.

89. The method of claim 86, further comprising the steps of:

xvii) reacting a compound of Formula 19a with triisopropylbenzenesulfonyl chloride under basic conditions to generate a compound of Formula 20a; and

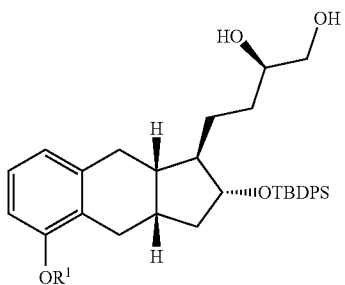

19a

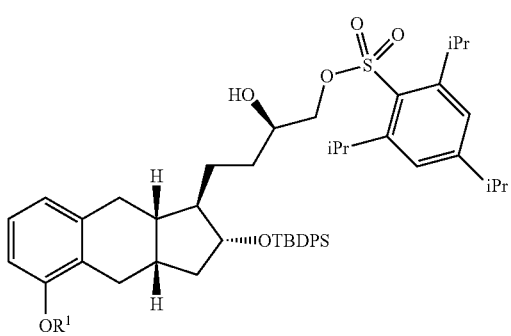

20a xviii) reacting the compound of Formula 20a with methanol under basic conditions to generate the compound of Formula 21a.

90. The method of claim 89, further comprising the steps of:

xix) reacting a compound of Formula 16a with a reducing agent to generate a compound of Formula 17a;

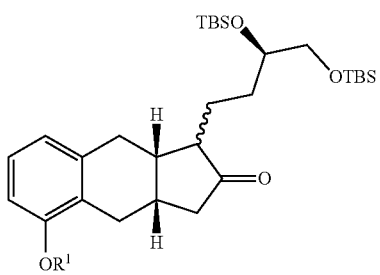

16a

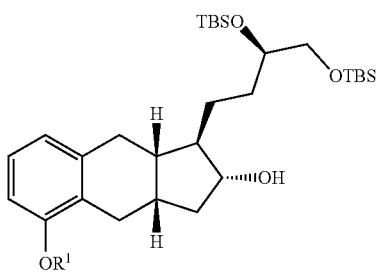

17a xx) reacting the compound of Formula 17a with TBDPSCl under basic conditions to generate a compound of Formula 18a; and

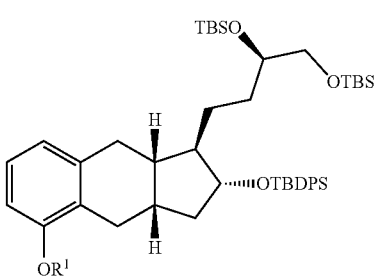

18a xxi) selectively deprotecting the compound of Formula 18a to generate the compound of Formula 19a.

91. The method of claim 90, further comprising the steps of:

xii) hydrogenating a compound of Formula 15a

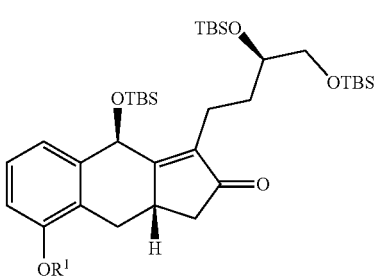

15a in the presence of an organic solvent to generate the compound of Formula 16a.

92. The method of claim 91, wherein the organic solvent of step xii) comprises an alcohol, THF, or any combination thereof.

93. The method of claim 92, further comprising the steps of:

x) reacting a compound of Formula 12a with a reducing agent to generate a compound of Formula 13a; and

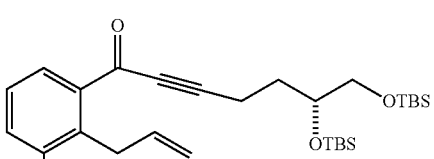

12a

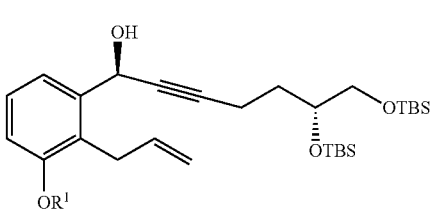

13a xiv) converting the compound of Formula 13a to the compound of Formula 15a.

94. The method of claim 93, further comprising the step of:

viii) reacting a compound of Formula 11a

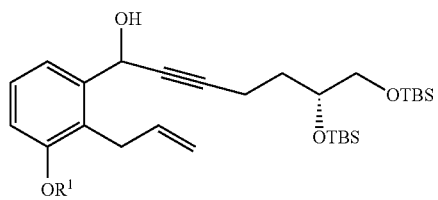

11a with an oxidizing agent to generate the compound of Formula 12a, wherein the oxidizing agent comprises $MnO_2$.

95. The method of claim 94, further comprising the steps of:

i) reacting a compound of Formula 9 with an oxidizing agent to generate a compound of Formula 10; and

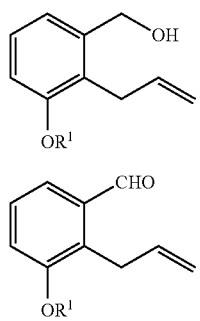

9

10 ii) reacting the compound of Formula 10 with a compound of Formula 5a in the presence of a base and an organic solvent to generate a compound of Formula 11a

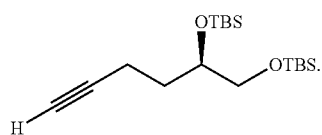

5a

96. The method of claim 95, further comprising the steps of:

iv) refluxing the compound of Formula 1a in the presence of methanol to generate a compound of Formula 1 having an e.e. of greater than about 98%;

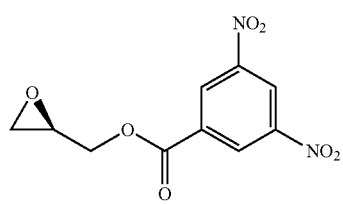

1a

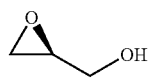

1 v) reacting the compound of Formula 1 with TBSCl under basic conditions to generate the compound of Formula 2a;

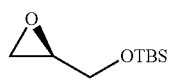

2a vi) reacting the compound of Formula 2a with 1-TMS-1-propyne to generate the compound of Formula 3a; and

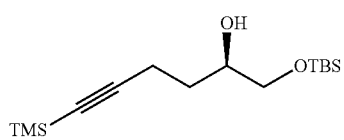

3a vii) converting the compound of Formula 3a to the compound of Formula 5a.

97. The method of claim 96, further comprising the steps of:

xxii) reacting a compound of Formula 7a with a 3-halo-prop-1-ene in the presence of a base and an organic solvent to generate a compound of Formula 8a and

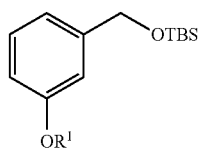

7a

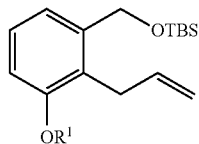

8a xxiii) deprotecting the compound of Formula 8a to generate the compound of Formula 9.

98. A method of generating an N-methyldiethanolamine salt of the compound of Formula I

I

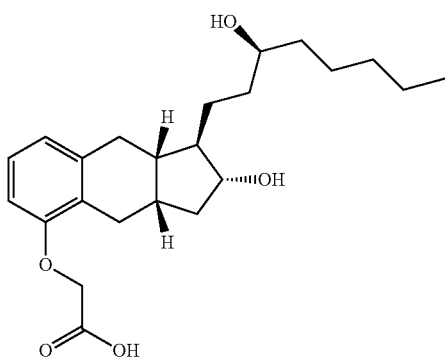

comprising the steps of:
i) reacting a compound of Formula 9 with an oxidizing agent to generate a compound of Formula 10;

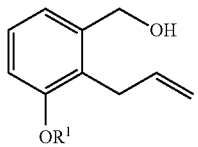

9

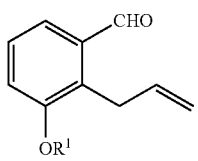

10 ii) reacting the compound of Formula 10 with a compound of Formula 5a in the presence of a base and an organic solvent to generate a compound of Formula 11a;

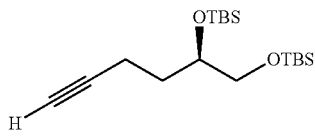

5a

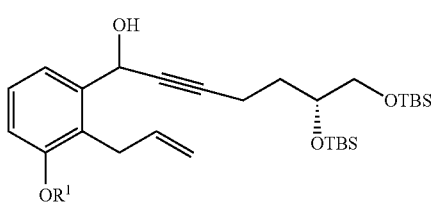

11a iv) refluxing the compound of Formula 1a in the presence of methanol to generate a compound of Formula 1 having an e.e. of greater than about 98%;

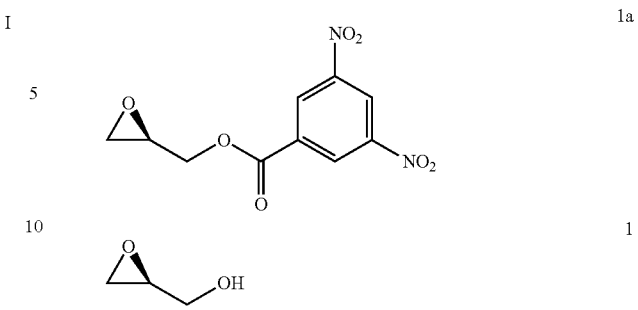

v) reacting the compound of Formula 1 with TBSCl under basic conditions to generate the compound of Formula 2a;

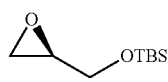

2a vi) reacting the compound of Formula 2a with 1-TMS-1-propyne to generate the compound of Formula 3a;

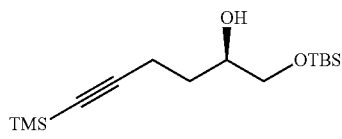

3a vii) converting the compound of Formula 3a to the compound of Formula 5a;
viii) reacting a compound of Formula 11a with an oxidizing agent to generate the compound of Formula 12a, wherein the oxidizing agent comprises $MnO_2$;

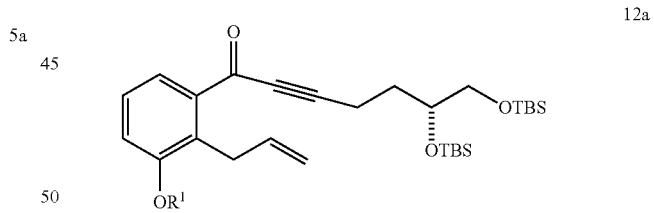

12a x) reacting a compound of Formula 12a with a reducing agent to generate a compound of Formula 13a;

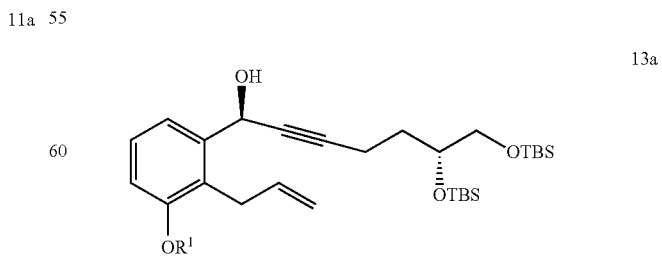

13a xiv) converting the compound of Formula 13a to the compound of Formula 15a;

15a

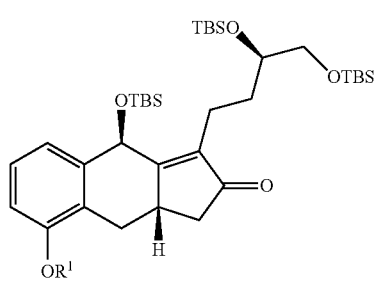

xii) hydrogenating a compound of Formula 15a in the presence of methanol or THF to generate the compound of Formula 16a;

16a

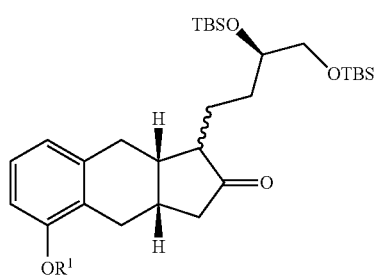

xix) reacting a compound of Formula 16a with a reducing agent to generate a compound of Formula 17a;
xx) reacting the compound of Formula 17a with TDPSCl under basic conditions to generate a compound of Formula 18a;

18a

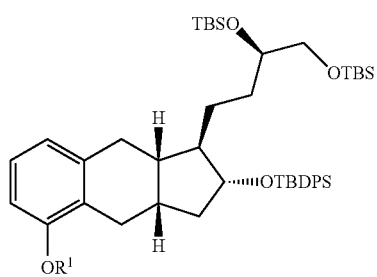

xxi) selectively deprotecting the compound of Formula 18a to generate the compound of Formula 19a;

19a

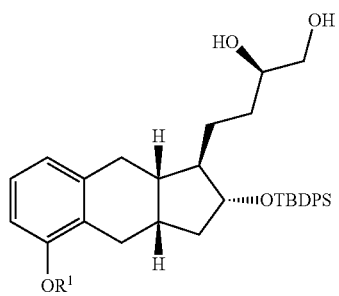

xvii) reacting a compound of Formula 19a with triisopropylbenzenesulfonyl chloride under basic conditions to generate a compound of Formula 20a;

20a

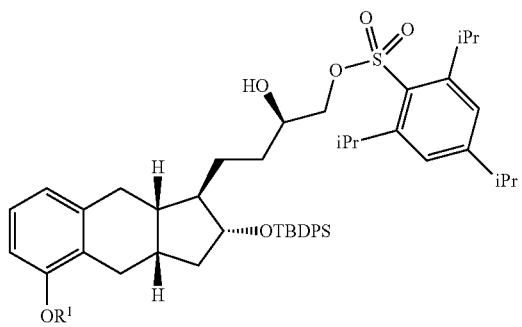

xviii) reacting the compound of Formula 20a with methanol under basic conditions to generate the compound of Formula 21a;

21a

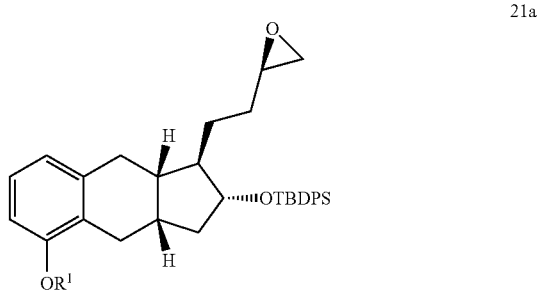

xv) reacting a compound of Formula 21a with n-butyllithium in the presence of an organic solvent and a transition metal catalyst to generate a compound of Formula 22a; and 22a

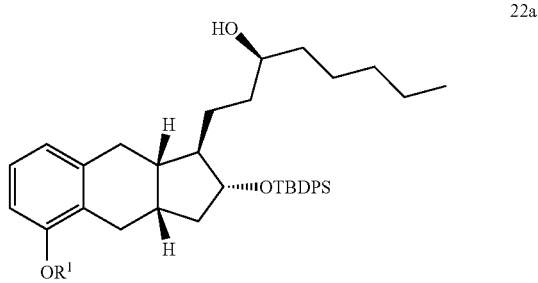

xvi) converting the compound of Formula 22a to the compound of Formula I.

99. The method of claim 98, further comprising the step of:

xxiv) reacting the compound of Formula I with N-methyldiethanolamine in the presence of an organic solvent to generate the N-methyldiethanolamine salt of the compound of Formula I.

* * * * *